US008124744B2

(12) United States Patent
Kashimura et al.

(10) Patent No.: US 8,124,744 B2
(45) Date of Patent: Feb. 28, 2012

(54) MACROLIDE DERIVATIVES

(75) Inventors: Masato Kashimura, Toshima-ku (JP);
Madoka Kawamura, Toshima-ku (JP);
Toshifumi Asaka, Toshima-ku (JP);
Kiyoshi Takayama, Toshima-ku (JP);
Haruhisa Ogita, Toshima-ku (JP)

(73) Assignee: Taisho Pharmaceutical Co., Ltd., Tokyo (JP)

( * ) Notice: Subject to any disclaimer, the term of this patent is extended or adjusted under 35 U.S.C. 154(b) by 558 days.

(21) Appl. No.: 12/299,229

(22) PCT Filed: May 1, 2007

(86) PCT No.: PCT/JP2007/059327
§ 371 (c)(1),
(2), (4) Date: Oct. 31, 2008

(87) PCT Pub. No.: WO2007/129646
PCT Pub. Date: Nov. 15, 2007

(65) Prior Publication Data
US 2009/0076253 A1    Mar. 19, 2009

(30) Foreign Application Priority Data

May 1, 2006   (JP) ................................ 2006-127277
Jan. 6, 2007   (JP) ................................ 2007-000881

(51) Int. Cl.
*C07H 17/08*    (2006.01)
(52) U.S. Cl. ........................................ 536/7.2; 536/7.4
(58) Field of Classification Search .................. 536/7.2, 536/7.4
See application file for complete search history.

(56) References Cited

U.S. PATENT DOCUMENTS 6,833,444 B2 * 12/2004 McMillen et al. ............. 536/7.4
6,900,183 B2 *  5/2005 Andreotti et al. ............. 514/29

FOREIGN PATENT DOCUMENTS

| EP | 0 158 467 A2 | 10/1985 |
| JP | S55-151598 A | 11/1980 |
| JP | 2005-538998 A | 12/2005 |
| WO | WO 02/087596 A2 | 11/2002 |
| WO | 2005/030786 A1 | 4/2005 |
| WO | 2005/075494 A1 | 8/2005 |
| WO | WO 2004/013153 A2 | 12/2005 |
| WO | WO 2006/075255 A | 7/2006 |
| WO | WO 2006/106440 A1 | 10/2006 |

OTHER PUBLICATIONS

Francis G. Spinale, "Matrix Metalloproteinases: Regulation and Dysregulation in the Failing Heart", Circulation Research; 90; p. 520-530, 2002.

Jeffrey J. Atkinson and Robert M. Senior, "Matrix Metalloproteinase-9 in Lung Remodeling", American Journal of Respiratory Cell and Molecular Biology vol. 28, p. 12-24, 2003.
Peter J. Barnes, "New Treatments for COPD", Nature Reviews/Drug Discovery, vol. 1, p. 437-446, 2002.
Richard E. K. Russell, et al., "Release and Activity of Matrix Metalloproteinase-9 and Tissue Inhibitor of Metalloproteinase-1 by Alveolar Macrophages from Patients with Chronic Obstructive Pulmonary Disease", American Journal of Respiratory Cell and Molecular Biology vol. 26, p. 602-609, 2002.
Ken-Ichi Kanai et al., "Suppression of matrix metalloproteinase-9 production from neutrophils by a macrolide antibiotic, roxithromycin, in vitro", Mediators of Inflammation, 13, p. 313-319, 2004.
Shigeo Morimoto et al., "Chemical Modification of Erythromycins (VII). Molecular Rearrangement Observed During Chemical Modification Study of the Desosamine Unit of Erythromycins", Heterocycles, vol. 31, No. 2, p. 305-319, 1990.
Hideo Ono et al., "Drug Resistance in *Staphylococcus aureus*. Induction of Macrolide Resistance by Erythromycin, Oleandomycin and Their Derivatives", Japanese Journal of Microbiology, vol. 19, No. 5, p. 343-347, 1975.
Naozumi Hashimoto et al., "Effect of erythromycin on matrix metalloproteinase-9 and cell migration", Journal of Laboratory and Clinical Medicine, vol. 137, No. 3, p. 176-183, 2001.
Silvio Danese, et al., "Helicobacter pylori Eradication Down-Regulates Matrix Metalloproteinase-9 Expression in Chronic Gastritis and Gastric Ulcer. Comments", Gastroenterology, vol. 126, No. 1, p. 369-371, 2004.
Yoshiaki Watanabe et al., "Chemical Modification of Erythromycins. X. Benzyloxycarbonyl and 2-chlorobenzyl groups of erythromycin derivatives by use of catalytic transfer hydrogenation", Heterocycles, vol. 36, No. 4, p. 761-768, 1993.
Extended European Search Report dated Aug. 18, 2010, as issued in European Application No. 07742762.3.
Chepkwony, H. K., et al., "Isocratic Liquid Chromatographic Method for the Analysis of Roxithromycin and Structurally Related Substances in Bulk Samples", Chomatographia, vol. 54, No. 11/12, pp. 725-729, Dec. 2001.

* cited by examiner

*Primary Examiner* — Elli Peselev
(74) *Attorney, Agent, or Firm* — Sughrue Mion, PLLC

(57) ABSTRACT

Compounds represented by formula (I) and the formula (IV) have an inhibitory activity of MMP-9 production, therefore, are useful as a medicine agent with fewer side effects than conventional MMP enzyme activity inhibitors, as a prophylactic and therapeutic drug for oncogenic angiogenesis, chronic rheumatoid arthritis, vascular intimal thickening after a percutaneous coronary transluminal angioplasty, vascular atherosclerosis, hemorrhagic apoplexy, acute myocardial infarction, chronic heart failure, aneurysm, lung cancer metastasis, adult respiratory distress syndrome, asthma, interstitial pulmonary fibrosis, chronic rhinosinusitis, bronchitis or chronic obstructive pulmonary disease (COPD).

31 Claims, No Drawings

MACROLIDE DERIVATIVES

TECHNICAL FIELD

The present invention relates to novel macrolide derivatives, pharmaceutically acceptable salts and hydrates thereof.

BACKGROUND ART

Matrix metalloproteinase (hereinafter referred to as MMP) is a zinc-dependent endopeptidase which functions extracellularly (see Non-Patent Document 1). MMP degrades extracellular matrix (EMC) (for example, elastin, collagen, gelatine, laminin, and fibronectin), which is essential mainly in maintaining structures of elastic fibers or tissue in vivo under physiological conditions, and functions to facilitate the remodeling of normal tissue or the repair of tissue injury. In addition, under physiological conditions, the amount of mRNA and protein, or enzyme activity of MMP are controlled by various mechanisms so as not to degrade the extracellular matrix excessively. As for the endogenous enzyme inhibitor of MMP, tissue inhibitor of metalloproteinase (TIMP) has been known.

On the other hand, It has been known that, in pathological conditions of oncogenic angiogenesis, chronic rheumatoid arthritis, vascular intimal thickening, vascular atherosclerosis, hemorrhagic apoplexy, acute myocardial infarction, chronic heart failure, aneurysm, cancer metastasis, adult respiratory distress syndrome, asthma, interstitial pulmonary fibrosis, chronic rhinosinusitis, bronchitis or chronic obstructive pulmonary disease (COPD), mechanisms to control the MMP activation fails, and the disease state is exacerbated due to excess EMC degradation (see Non-Patent Documents 1 and 2). Accordingly, if the control mechanisms against the MMP activation can be repaired to a normal state, it would appear to be useful for treating the above-mentioned diseases.

MMP has isozymes of 20 kinds or more. In particular, it is proven that mRNA, protein and the activity of MMP-9 (Gelatinase B) having the molecular weight of 92 kDa are induced in the above-mentioned diseases. MMP-9 is known to not only degrade EMC such as collagen type IV and elastin, but also exacerbate an inflammatory response by degrading cytokines (for example, interleukin (IL)-1β, IL-8, tumor growth factor (TGF)-β) and following by enhancing the said cytokines activity. Furthermore, the MMP degrades endogenous protease inhibitors (e.g. tissue factor protease inhibitor, α 1-antitrypsin, and α 1-antichymorypsin), activates protease cascades, and thereby further exacerbates the disease state.

In general, COPD is a disease characterized by an obstructive ventilator impairment, which is caused by bronchitis, emphysema, or both of them. In GOLD (Global Initiative for Chronic Obstructive Lung Disease) which is an international treatment guideline of COPD, it is defined that "COPD is a disease which is characterized by airflow limitation that is not fully reversible, and the airflow limitation is usually progressive and associated with an abnormal inflammatory response of the lung to noxious particles or gases". This suggests that improvement of inflammatory response can lead to a causal therapy.

Emphysema in COPD is a symptom in which the walls of alveoli are broken down and the microstructure of the alveoli become hollow. Emphysema decreases the gas exchange rate and the elastic recoil of the whole lung, and the lung function is finally depressed. It has been known that the onset of emphysema intimately involves MMP-9 and MMP-12 released from the resident or newly infiltrating inflammatory cells in lung (for example, alveolar macrophage and neutrophil) which are activated by smoking, air pollution, noxious gases or the like (see Non-Patent Document 3).

MMP-9 is produced and activated in cells involved in emphysema such as neutrophils, alveolar macrophages, and epithelial cells by inflammatory stimuli such as TNF α (Tumor Necrosis Factor) and IL-1 (Interleukin-1). It was reported that the amount of MMP-9 increased in correlation with the decrease of lung function in patients with COPD. (See Non-Patent Document 4)

For the present pharmacotherapy, airway dilators (anticholinergic agent, β2 receptor agonist etc.) are widely clinically used which show the effect in improving the patients' QOL, but are still not satisfactory.

As the method of specifically decreasing the functions of MMP-9, a method for inhibiting the enzyme activity, and a method for inhibiting the production of MMP-9 mRNA and protein associated with inflammatory response are considered. With regard to the enzyme inhibitor, several compounds have been found so far in the prior art, which have been tried for oncogenic angiogenesis, metastasis, chronic obstructive pulmonary disease (COPD) or the like. However, it has not been accomplished to launch them as a medicine. In particular, an enzyme inhibitor has not yet been practically used as a medicine out of concern of a side effect on skeletal muscles due to its prolonged administration.

With regard to the antibiotic having a macrolide skeleton (erythromycin, clarithromycin, roxithromycin and azithromycin), anti-inflammatory activity in vitro has been reported.

In addition, roxithromycin has been reported to have an inhibitory effect on MMP-9 production (see Non-Patent Document 3), the 50% inhibitory concentration (IC50) value is 10 μM or more but it is insufficient for a medicine that actively treats the above-mentioned diseases. Further, since roxithromycin has a strong antibacterial activity, there occur problems such as gastrointestinal disorders with changes in intestinal flora by chronic administration, development of resistant bacteria, and the like. From this viewpoint, use of the macrolide derivative which has an antibacterial activity for the above-mentioned diseased is limited. That is, in fact, there is no example of completely separating the antibacterial activity from other required activities (inhibitory activity against MMP-9 production or the like).

Furthermore, the art in which azithromycin is used for the treatment of neutrophil-dominated non-infectious inflammatory diseases including COPD is disclosed (see Patent Document 1), but the antibacterial activity had not been separated.

There are reports about a compound which derivatizes a hydroxy group at the 2'-position of desosamine bonded to the 5-position of erythromycin-based antibiotic (see Patent Document 2 and Non-Patent Document 6), but there is no description on a separation of the antibacterial activity from the inhibitory activity of MMP-9 production.

Patent Document 1: WO 02/087596
Patent Document 2: Japanese Patent Application Laid-Open No. 55-151598
Non-Patent Document 1: Circ. Res., 90:520-530 (2003)
Non-Patent Document 2: Am. J. Respir. Cell Mol. Biol., 28, 12-24 (2003)
Non-Patent Document 3: Nature Reviews/Drug Discovery, Vol. 1, 437-446 (2002)
Non-Patent Document 4: Am. J. Respir. Cell Mol. Biol. 26, 602-609 (2002)
Non-Patent Document 5: Mediator of Inflammation, 13, 313-319 (2004)

Non-Patent Document 6: Heterocycles, Vol. 31, No. 2, 305-319 (1990)

DISCLOSURE OF THE INVENTION

Problems to be Solved by the Invention

It is an object of the invention to provide macrolide derivatives which have a strong MMP-9 production inhibitory activity, and in which an antibacterial activity is separated.

Means for Solving the Problems

The present inventors have carried out various studies to find out macrolide compounds which have a strong MMP-9 production inhibitory activity, and in which an antibacterial activity is separated. In the past, studies for erythromycin-based antibiotic derivatization are focused on enhancement of the antibacterial activity. The inventors' derivatization studies have been conducted focusing on a substituent on desosamine bonded at the 5-position which is considered to be essential for development of the antibacterial activity, particularly, on a hydroxy group at the 2-position of which studies were conducted limitedly mainly for preparing a prodrug or introducing a protective group due to the difficulty of its chemical transformation. Accordingly, they have found compounds which have a strong MMP-9 production inhibitory activity, and in which an antibacterial activity is separated, thereby completing the invention.

That is, the present invention includes:

(1) a compound represented by formula (I) or a pharmaceutically acceptable salt thereof:

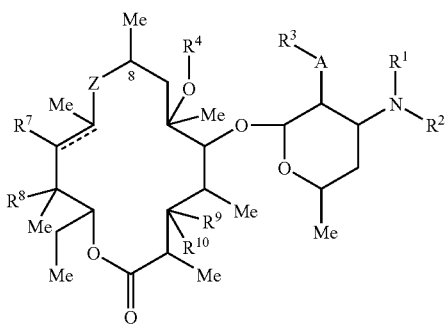

wherein,
the double line including the dashed line represents a single bond or a double bond,
$R^1$ and $R^2$ each independently represents
a hydrogen atom,
an alkyl group having 1 to 6 carbon atom(s) unsubstituted or substituted with 1 to 3 substituent(s) selected from "an aryl group unsubstituted or substituted with 1 to 5 substituent(s) selected from Substituent Group 1, a heteroaryl group unsubstituted or substituted with 1 to 3 substituent(s) selected from Substituent Group 1, a carboxy group, and an alkoxycarbonyl group having 2 to 7 carbon atoms", wherein Substituent Group 1 consists of a halogen atom, an alkyl group having 1 to 6 carbon atom(s), an alkoxy group having 1 to 6 carbon atom(s), a cyano group, a nitro group, a hydroxy group, a cyclic alkyl group having 3 to 6 carbon atoms including 1 to 3 hetero atom(s) on a ring, and an amino group unsubstituted or substituted with 1 or 2 alkyl group(s) having 1 to 6 carbon atom(s), an alkyl group having 2 to 6 carbon atoms substituted with 1 to 5 group(s) selected from "an amino group unsubstituted or substituted with 1 or 2 alkyl group(s) having 1 to 6 carbon atoms, a phthalimide group, an alkoxy group having 1 to 6 carbon atom(s), a morpholino group, an aralkyloxy group having 7 to 12 carbon atoms, an alkanoyloxy group having 2 to 6 carbon atoms, a hydroxy group, and a group represented by the formula:

$$-NHCO_2-(CH_2)_n-R^{31}$$

wherein n is an integer of 0 to 6, $R^{31}$ is a hydrogen atom, an amino group unsubstituted or substituted with 1 or 2 alkyl group(s) having 1 to 6 carbon atom(s), an aryl group, or a heteroaryl group",
a cyclic alkenyl group having 4 to 6 carbon atoms unsubstituted or substituted with 1 to 5 substituent(s) selected from "an oxo group, and an amino group unsubstituted or substituted with 1 or 2 alkyl group(s) having 1 to 6 carbon atom(s)",
a group represented by the formula:

$$-CO_2-(CH_2)_n-R^{31}$$

wherein n and $R^{31}$ have the same meanings as defined above,
a alkanoyl group having 2 to 6 carbon atoms,
a alkylsulfonyl group having 1 to 6 carbon atom(s), or
an aryl group unsubstituted or substituted with 1 to 5 substituent(s) selected from Substituent Group 1, or
$R^1$ and $R^2$ represent a cyclic structure represented by the formula which is formed together with the nitrogen atom to which each is bonded:

$$-(CH_2)_p-Y-(CH_2)_q-$$

wherein p and q each independently represents an integer of 1 to 3, Y represents an oxygen atom, a group represented by the formula:

$$-CR^{39}R^{40}-$$

wherein $R^{39}$ and $R^{40}$ each independently represents a hydrogen atom, a hydroxy group, an alkoxy group having 1 to 6 carbon atom(s), a carboxy group, or an alkoxycarbonyl group having 2 to 7 carbon atoms, or a group represented by the formula:

$$-NR^{21}-$$

wherein $R^{21}$ represents a hydrogen atom, or an alkyl group having 1 to 6 carbon atom(s) unsubstituted or substituted with 1 to 3 substitutent(s) selected from "an aryl group, a carboxy group, an alkoxycarbonyl group having 2 to 7 carbon atoms, and an amino group unsubstituted or substituted with 1 or 2 alkyl group(s) having 1 to 6 carbon atom(s)",
$R^3$ represents
an alkyl group having 1 to 6 carbon atom(s) unsubstituted or substituted with 1 to 3 group(s) selected from "a halogen atom, a cyano group, a carboxy group, an alkoxycarbonyl group having 2 to 7 carbon atoms, an aralkyloxy group having 7 to 12 carbon atoms, an alkanoyloxy group having 2 to 6 carbon atoms, a hydroxy group, a phthalimide group, an alkylsulfonylamino group having 1 to 6 carbon atom(s), a methanesulfonyloxy group, a toluenesulfonyloxy group, an aryl group unsubstituted or substituted with 1 to 5 group(s) selected from Substituent Group 1, a heteroaryl group unsubstituted or substituted with 1 to 3 group(s) selected from Substituent Group 1, a group represented by the formula:

$$-CO-N(-(CH_2)_l-R^{36})-(CH_2)_m-R^{32}$$

wherein l and m each independently represents an integer of 0 to 6, $R^{36}$ and $R^{32}$ each independently represents "a hydrogen atom, an amino group unsubstituted or substituted with 1 or 2 alkyl group(s) having 1 to 6 carbon atom(s), an aryl group, or a heteroaryl group", and a group represented by the formula:

$$-NR^{41}R^{42}$$

wherein $R^{41}$ and $R^{42}$ each independently represents a hydrogen atom, an alkyl group having 1 to 6 carbon atom(s), or $R^{41}$ and $R^{42}$ represent a cyclic structure represented by the formula which is formed together with the nitrogen atom to which each is bonded:

$$-(CH_2)_s-W-(CH_2)_t-$$

wherein s and t each independently represents an integer of 1 to 3, W represents an oxygen atom, a group represented by the formula:

$$-CR^{43}R^{44}-$$

wherein $R^{43}$ and $R^{44}$ each independently represents a hydrogen atom, a hydroxy group, an alkoxy group having 1 to 6 carbon atom(s), a carboxy group, or an alkoxycarbonyl group having 2 to 7 carbon atoms,
or a group represented by the formula:

$$-NR^{45}-$$

wherein $R^{45}$ represents a hydrogen atom, an alkyl group having 1 to 6 carbon atom(s) unsubstituted or substituted with 1 to 3 substituent(s) selected from "an aryl group, a carboxy group, an alkoxycarbonyl group having 2 to 7 carbon atoms, and an amino group unsubstituted or substituted with 1 or 2 alkyl group(s) having 1 to 6 carbon atom(s)",
an alkenyl group having 2 to 6 carbon atoms unsubstituted or substituted with 1 to 3 group(s) selected from "a halogen atom, an alkyl group having 1 to 6 carbon atom(s), an alkoxy group having 1 to 6 carbon atom(s), an alkoxycarbonyl group having 2 to 7 carbon atoms, a cyano group, a nitro group, a hydroxy group, an oxo group, and an amino group unsubstituted or substituted with 1 or 2 alkyl group(s) having 1 to 6 carbon atom(s)",
an aryl group unsubstituted or substituted with 1 to 5 group(s) selected from Substituent Group 1, or
a heteroaryl group unsubstituted or substituted with 1 to 3 group(s) selected from Substituent Group 1,
$R^4$ represents
a hydrogen atom,
an alkyl group having 1 to 6 carbon atom(s) unsubstituted or substituted with 1 to 3 group(s) selected from Substituent Group 2, wherein Substituent Group 2 consists of a halogen atom, a cyclic alkyl group having 3 to 6 carbon atoms, a hydroxy group, a cyano group, an aminosulfonyl group, an aryl group unsubstituted or substituted with 1 to 5 optional substituent(s), and a heteroaryl group unsubstituted or substituted with 1 to 3 optional substituent(s),
an alkenyl group having 2 to 6 carbon atoms unsubstituted or substituted with 1 to 3 group(s) selected from Substituent Group 2,
an alkynyl group having 2 to 6 carbon atoms unsubstituted or substituted with 1 to 3 group(s) selected from Substituent Group 2, or
a alkanoyl group having 2 to 6 carbon atoms, Z represents a group represented by the formula:

$$-CR^5R^6-$$

a group represented by the formula:

$$-C(=O)-$$

a group represented by the formula:

$$-C(=N-NH_2)-$$

a group represented by the formula:

$$-C(=N-OR^{12})-$$

wherein $R^{12}$ is a hydrogen atom, a alkanoyl group having 2 to 6 carbon atoms unsubstituted or substituted with 1 to 3 group(s) selected from "a halogen atom, and an amino group unsubstituted or substituted with 1 or 2 alkyl group(s) having 1 to 6 carbon atom(s)", a vinylcarbonyl group, an alkyl group having 1 to 6 carbon atom(s), a cyclic alkyl group having 3 to 16 carbon atoms, an aryl group unsubstituted or substituted with 1 to 5 optional substituent(s), or an aralkyl group having 7 to 12 carbon atoms unsubstituted or substituted with 1 to 5 optional substituent(s),
a group represented by the formula:

$$-NR^{14}-CH_2-$$

wherein $R^{14}$ represents a hydrogen atom, an alkyl group having 1 to 6 carbon atom(s), an alkanoyl group having 2 to 6 carbon atoms, an alkylsulfonyl group having 1 to 6 carbon atom(s), or a benzyloxycarbonyl group, and the last dash binds to a carbon atom at 8-position of formula (I), or a group represented by the formula:

$$-CH_2-NR^{14}-$$

wherein $R^{14}$ has the same meaning as defined above, and the last dash binds to a carbon atom at 8-position of formula (I),
one of $R^5$ and $R^6$ is a hydrogen atom while the other one is
a group represented by the formula:

$$-NR^{13}R^{15}$$

wherein $R^{13}$ and $R^{15}$ each independently represents a hydrogen atom, an alkyl group having 1 to 6 carbon atom(s), a cyclic alkyl group having 3 to 6 carbon atoms, an alkanoyl group having 2 to 6 carbon atoms, an alkylsulfonyl group having 1 to 6 carbon atom(s), an aryl group unsubstituted or substituted with 1 to 5 optional substituent(s), or an aralkyl group having 7 to 12 carbon atoms unsubstituted or substituted with 1 to 5 optional substituent(s), or $R^{13}$ and $R^{15}$ represent a 5- or 6-membered heterocyclic ring formed together with the nitrogen atom to which each is bonded, or a group represented by the formula:

$$-OR^{12}$$

wherein $R^{12}$ has the same meaning as defined above
$R^7$ represents a hydrogen atom with the proviso that the double line including the dashed line is limited to represent a double bond, a hydroxy group, or a group represented by the formula:

$$-OR^{22}$$

wherein $R^{22}$ represents "an alkyl group having 1 to 6 carbon atom(s), an alkenyl group having 2 to 6 carbon atoms, an alkynyl group having 2 to 6 carbon atoms, or an alkanoyl group having 2 to 6 carbon atoms" unsubstituted or substituted with 1 to 3 group(s) selected from "a halogen atom, an oxo group, an alkyl group having 1 to 6 carbon atom(s), an alkenyl group having 2 to 6 carbon atoms, an alkynyl group having 2 to 6 carbon atoms, a cyano group, an amino group unsubstituted or substituted with 1 or 2 alkyl group(s) having 1 to 6 carbon atom(s), a hydroxy group, a nitro group, a carboxy group, a alkoxy group having 1 to 6 carbon atom(s), an aryl group, and a heteroaryl group", $R^8$ represents a hydrogen atom or a hydroxy group, $R^7$ and $R^8$ may represent a cyclic structure represented by formula (II) which is formed together with carbon atoms to which each is bonded:

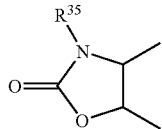

(II)

wherein $R^{35}$ represents a hydrogen atom, an alkyl group having 1 to 6 carbon atom(s), an aryl group, a heteroaryl group, an alkyl group having 1 to 6 carbon atom(s) substituted with 1 to 3 aryl group(s) or heteroaryl group(s), an alkyl group having 1 to 6 carbon atom(s) substituted with 1 to 3 heteroaryl group(s) substituted with 1 to 3 heteroaryl group(s), an alkoxy group having 1 to 6 carbon atom(s), an alkoxy group having 1 to 6 carbon atom(s) substituted with 1 to 3 aryl group(s) or heteroaryl group(s), an amino group substituted with 1 or 2 alkyl group(s) having 1 to 6 carbon atom(s), or an amino group substituted with 1 or 2 alkyl group(s) having 1 to 6 carbon atom(s) substituted with 1 to 3 aryl group(s) or heteroaryl group(S), or a cyclic structure represented by formula (III) which is formed together with carbon atoms to which each is bonded:

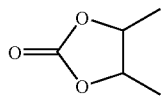

(III)

or $R^7$, $R^8$ and the above-mentioned Z may together represent a cyclic structure represented by formula (IV):

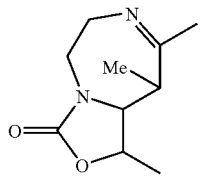

(IV)

$R^9$ represents a hydrogen atom, $R^{10}$ represents a hydroxy group, a group represented by the formula:

—$OR^{23}$ wherein $R^{23}$ represents an aryl group unsubstituted or substituted with 1 to 5 optional substituent(s), or a heteroaryl group unsubstituted or substituted with 1 to 3 optional substituent(s), a group represented by the formula:

—OCO—$R^{24}$ wherein $R^{24}$ represents a cyclic alkyl group having 3 to 6 carbon atoms unsubstituted or substituted with 1 to 5 optional substituent(s), which may include 1 to 3 hetero atom(s) on a ring, or a group represented by the formula:

—$(CH_2)_j$-D-$(CH_2)_k$—$R^{25}$ wherein D represents a bond, a hetero atom, or a group represented by the formula:

—$NHCO_2$—

$R^{25}$ represents a hydrogen atom, an aryl group unsubstituted or substituted with 1 to 5 optional substituent(s), a heteroaryl group unsubstituted or substituted with 1 to 3 optional substituent(s), a cyclic alkyl group having 3 to 6 carbon atoms which may include 1 to 3 hetero atom(s) on a ring and be substituted with 1 to 5 optional group(s), a group represented by the formula:

—$NR^{37}R^{38}$ wherein $R^{37}$ and $R^{38}$ each independently represents a hydrogen atom, an amino group unsubstituted or substituted with 1 or 2 alkyl group(s) having 1 to 6 carbon atom(s), or "an alkyl group having 1 to 6 carbon atom(s), aryl group, or heteroaryl group" unsubstituted or substituted with 1 to 3 group(s) selected from "a halogen atom, an amino group unsubstituted or substituted with 1 or 2 alkyl group(s) having 1 to 6 carbon atom(s), a cyclic alkyl group having 3 to 6 carbon atoms including 1 to 3 hetero atom(s) on a ring, a hydroxy group, an alkyl group having 1 to 6 carbon atom(s), an alkoxy group having 1 to 6 carbon atom(s), and a nitro group", a group represented by the formula:

—$NHCOR^{37}$ wherein $R^{37}$ has the same meaning as defined above, a group represented by the formula:

—$NHSO_2R^{37}$ wherein $R^{37}$ has the same meaning as defined above, or a group represented by the formula:

—$NHCONHR^{37}$ wherein $R^{37}$ has the same meaning as defined above, and j and k each independently represents an integer of 0 to 6, a group represented by the formula:

—$OCO_2R^{24}$ wherein $R^{24}$ has the same meaning as defined above, a group represented by the formula:

—OCO—$NR^{37}R^{38}$ wherein $R^{37}$ and $R^{38}$ have the same meanings as defined above, or a group represented by formula (V):

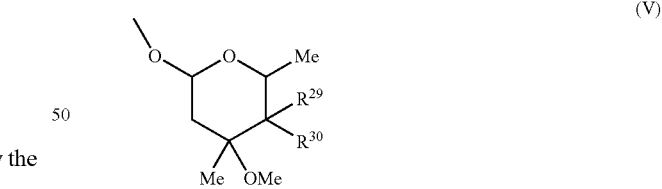

(V)

wherein $R^{29}$ represents a hydrogen atom, $R^{30}$ represents a hydroxy group, an alkoxy group having 1 to 6 carbon atom(s), an alkanoyloxy group having 2 to 6 carbon atoms, an alkanoyloxy group having 2 to 6 carbon atoms substituted with 1 to 3 amino group(s) unsubstituted or substituted with 1 or 2 alkyl group(s) having 1 to 6 carbon atom(s), a cyanomethyloxy group, an aralkyloxy group having 7 to 12 carbon atom(s), an alkoxy group having 1 to 6 carbon atom(s) substituted with 1 to 3 heteroaryl group(s), or a carbamoyloxy group, or $R^{29}$ and $R^{30}$ may together form an oxo group, $R^9$ and $R^{10}$ may together form an oxo group, A represents an oxygen atom, or a group represented by the formula:

—NMe-with the proviso that the following are excluded: a compound in which $R^3$ is a benzyl group or an allyl group and A is an oxygen atom, a compound in which $R^3$ is a methyl group, $R^4$ and $R^9$ are a hydrogen atom, Z is a group represented by the formula —C(=O)—, $R^7$ and $R^8$ are a hydroxy group, $R^{10}$ is a group represented by formula (V), and A is a group represented by the formula —NMe-, a compound in which $R^1$ is a methyl group, $R^2$ is a 2-hydroxyethyl group, $R^3$ is a methyl group, $R^4$ ii a hydrogen atom, Z is a group represented by the formula —NMe-CH$_2$—, $R^7$ and $R^8$ are a hydroxy group, $R^9$ is a hydrogen atom, $R^{10}$ is a hydroxy group, and A is a group represented by the formula —NMe-, a compound in which $R^1$ is a methyl group, $R^2$ is a 2-hydroxyethyl group, $R^3$ is a methyl group, $R^4$ is a hydrogen atom, Z is a group represented by the formula —NMe-CH$_2$—, $R^7$ and $R^8$ are a hydroxy group, $R^9$ is a hydrogen atom, $R^{10}$ is a group represented by formula (V), $R^{29}$ is a hydrogen atom, $R^{30}$ is a hydroxy group, and A is a group represented by the formula —NMe-, a compound in which $R^1$ and $R^2$ are a methyl group, $R^3$ is a methyl group, $R^4$ is a hydrogen atom, Z is a group represented by the formula —C(=O)—, $R^7$ and $R^8$ are a hydroxy group, $R^9$ is a hydrogen atom, $R^{10}$ is a group represented by formula (V), $R^{29}$ is a hydrogen atom, $R^{30}$ is a methoxy group, and A is an oxygen atom, and a compound in which $R^1$ and $R^2$ are a methyl group, $R^3$ is an aminophenyl group, $R^4$ is a hydrogen atom, Z is a group represented by the formula C(=O)—, $R^7$ and $R^8$ are a hydroxy group, $R^9$ is a hydrogen atom, $R^{10}$ is a group represented by formula (V), $R^{29}$ is a hydrogen atom, $R^{30}$ is a methoxy group, and A is an oxygen atom.

(2) The compound or the pharmaceutically acceptable salt thereof as described in the above (1), wherein, the double line including the dashed line is a single bond, $R^4$ represents a hydrogen atom, an alkyl group having 1 to 6 carbon atom(s) unsubstituted or substituted with 1 to 3 group(s) selected from Substituent Group 2, wherein Substituent Group 2 consists of a halogen atom, a cyclic alkyl group having 3 to 6 carbon atoms, a hydroxy group, a cyano group, an aminosulfonyl group, and "an aryl group or a heteroaryl group" unsubstituted or substituted with 1 to 3 group(s) selected from "a halogen atom, an amino group unsubstituted or substituted with 1 or 2 alkyl group(s) having 1 to 6 carbon atom(s), a cyclic alkyl group having 3 to 6 carbon atom(s) including 1 to 3 hetero atom(s) on a ring, a hydroxy group, an alkyl group having 1 to 6 carbon atom(s), an alkoxy group having 1 to 6 carbon atom(s), an aryl group, a heteroaryl group, and a nitro group", an alkenyl group having 2 to 6 carbon atoms unsubstituted or substituted with 1 to 3 group(s) selected from Substituent Group 2, an alkynyl group having 2 to 6 carbon atoms unsubstituted or substituted with 1 to 3 group(s) selected from Substituent Group 2, or an alkanoyl group having 2 to 6 carbon atoms, $R^{12}$ is a hydrogen atom, an alkanoyl group having 2 to 6 carbon atoms unsubstituted or substituted with 1 to 3 group(s) selected from "a halogen atom, and an amino group unsubstituted or substituted with 1 or 2 alkyl group(s) having 1 to 6 carbon atom(s)", a vinylcarbonyl group, an alkyl group having 1 to 6 carbon atom(s), a cyclic alkyl group having 3 to 6 carbon atoms, or "an aryl group, or an aralkyl group having 7 to 12 carbon atoms" unsubstituted or substituted with 1 to 5 group(s) selected from "a halogen atom, an amino group unsubstituted or substituted with 1 or 2 alkyl group(s) having 1 to 6 carbon atom(s), a cyclic alkyl group having 3 to 6 carbon atoms including 1 to 3 hetero atom(s) on a ring, a hydroxy group, an alkyl group having 1 to 6 carbon atom(s), an alkoxy group having 1 to 6 carbon atom(s), and a nitro group", $R^{13}$ and $R^{15}$ each independently represents a hydrogen atom, an alkyl group having 1 to 6 carbon atom(s), a cyclic alkyl group having 3 to 6 carbon atoms, an alkanoyl group having 2 to 6 carbon atoms, an alkylsulfonyl group having 1 to 6 carbon atom(s), or "an aryl group, or an aralkyl group having 7 to 12 carbon atom(s)" unsubstituted or substituted with 1 to 5 group(s) selected from "a halogen atom, an amino group unsubstituted or substituted with 1 or 2 alkyl group(s) having 1 to 6 carbon atom(s), a cyclic alkyl group having 3 to 6 carbon atoms including 1 to 3 hetero atom(s) on a ring, a hydroxy group, an alkyl group having 1 to 6 carbon atom(s), an alkoxy group having 1 to 6 carbon atom(s), and a nitro group", or $R^{13}$ and $R^{15}$ represent a 5- or 6-membered heterocyclic ring formed together with the nitrogen atom to which each is bonded, $R^{23}$ is "an aryl group or a heteroaryl group" unsubstituted or substituted with 1 to 3 group(s) selected from "a halogen atom, an amino group unsubstituted or substituted with 1 or 2 alkyl group(s) having 1 to 6 carbon atom(s), a cyclic alkyl group having 3 to 6 carbon atoms including 1 to 3 hetero atom(s) on a ring, a hydroxy group, an alkyl group having 1 to 6 carbon atom(s), an alkoxy group having 1 to 6 carbon atom(s), and a nitro group", $R^{24}$ represents a cyclic alkyl group having 3 to 6 carbon atoms unsubstituted or substituted with 1 to 5 group(s) selected from "a halogen atom, an amino group unsubstituted or substituted with 1 or 2 alkyl group(s) having 1 to 6 carbon atom(s), a cyclic alkyl group having 3 to 6 carbon atoms including 1 to 3 hetero atom(s) on a ring, a hydroxy group, an alkyl group having 1 to 6 carbon atom(s), an alkoxy group having 1 to 6 carbon atom(s), and a nitro group", which may include 1 to 3 hetero atom(s) on a ring, or a group represented by the formula:

$$-(CH_2)_j\text{-}D\text{-}(CH_2)_k-R^{25}$$

wherein D represents a bond, a hetero atom, or a group represented by the formula:

$$-NHCO_2-$$

$R^{25}$ represents a hydrogen atom, "an aryl group, a heteroaryl group, or a cyclic alkyl group having 3 to 6 carbon atoms which may include 1 to 3 hetero atom(s) on a ring" unsubstituted or substituted with 1 to 3 group(s) selected from "a halogen atom, an amino group unsubstituted or substituted with 1 or 2 alkyl group(s) having 1 to 6 carbon atom(s), a cyclic alkyl group having 3 to 6 carbon atoms including 1 to 3 hetero atom(s) on a ring, a hydroxy group, an alkyl group having 1 to 6 carbon atom(s), an alkoxy group having 1 to 6 carbon atom(s), and a nitro group", a group represented by the formula:

$$-NR^{37}R^{38}$$

wherein $R^{37}$ and $R^{38}$ each independently represents a hydrogen atom, an amino group unsubstituted or substituted with 1 or 2 alkyl group(s) having 1 to 6 carbon atom(s), or "an alkyl group having 1 to 6 carbon atom(s), an aryl group, or a heteroaryl group" unsubstituted or substituted with 1 to 3 group(s) selected from "a halogen atom, an amino group unsubstituted or substituted with 1 or 2 alkyl group(s) having 1 to 6 carbon atom(s), a cyclic alkyl group having 3 to 6 carbon atoms including 1 to 3 hetero atom(s) on a ring, a hydroxy group, an alkyl group having 1 to 6 carbon atom(s), an alkoxy group having 1 to 6 carbon atom(s), and a nitro group", a group represented by the formula:

—NHCOR$^{37}$ wherein R$^{37}$ has the same meaning as defined above, a group represented by the formula:

—NHSO$_2$R$^{37}$ wherein R$^{37}$ has the same meaning as defined above, or a group represented by the formula:

—NHCONHR$^{37}$ wherein R$^{37}$ has the same meaning as defined above, j and k each independently represents an integer of 0 to 6.

(3) The compound or the pharmaceutically acceptable salt thereof as described in the above (1) or (2), wherein
A is a group represented by the formula:

—NMe-.

(4) The compound or the pharmaceutically acceptable salt thereof as described in the above (3), wherein
R$^3$ is an alkyl group having 1 to 6 carbon atom(s) substituted with an amino group unsubstituted or substituted with 1 or 2 alkyl group(s) having 1 to 6 carbon atom(s), or an alkyl group having 1 to 6 carbon atom(s).

(5) The compound or the pharmaceutically acceptable salt thereof as described in the above (3), wherein
R$^3$ is a methyl group.

(6) The compound or the pharmaceutically acceptable salt thereof as described in any one of the above (3) to (5), wherein
R$^1$ and R$^2$ each independently represents
a hydrogen atom,
an alkyl group having 1 to 6 carbon atom(s) unsubstituted or substituted with 1 to 3 substituent(s) selected from "an aryl group unsubstituted or substituted with 1 to 5 substituent(s) selected from Substituent Group 1, a heteroaryl group unsubstituted or substituted with 1 to 3 substituent(s) selected from Substituent Group 1, a carboxy group, and an alkoxycarbonyl group having 2 to 7 carbon atoms",
an alkyl group having 2 to 6 carbon atoms substituted with 1 to 5 group(s) selected from "an amino group unsubstituted or substituted with 1 or 2 alkyl group(s) having 1 to 6 carbon atom(s), a phthalimide group, an alkoxy group having 1 to 6 carbon atom(s), a morpholino group, an aralkyloxy group having 7 to 12 carbon atoms, an alkanoyloxy group having 2 to 6 carbon atoms, a hydroxy group, and a group represented by the formula:

—NHCO$_2$—(CH$_2$)$_n$—R$^{31}$ wherein n and R$^{31}$ have the same meanings as defined above",
an alkanoyl group having 2 to 6 carbon atoms, or
an alkylsulfonyl group having 1 to 6 carbon atom(s) or
R$^1$ and R$^2$ represent a cyclic structure represented by the formula which is formed together with the nitrogen atom to which each is bonded:

—(CH$_2$)$_p$—Y—(CH$_2$)$_q$— wherein p, q and Y have the same meanings as defined above.

(7) The compound or the pharmaceutically acceptable salt thereof as described in any one of the above (3) to (5), wherein
R$^1$ represents an alkyl group having 1 to 6 carbon atom(s),
R$^2$ represents
a hydrogen atom,
an alkyl group having 1 to 6 carbon atom(s) substituted with a substituent selected from "a phenyl group unsubstituted or substituted with a morpholino group, a pyridyl group, and a carboxy group", or an alkyl group having 2 to 6 carbon atoms substituted with a group selected from "an amino group unsubstituted or substituted with 1 or 2 alkyl group(s) having 1 to 6 carbon atom(s), and a hydroxy group" or
R$^1$ and R$^2$ represent a cyclic structure represented by the formula which is formed together with the nitrogen atom to which each is bonded:

—(CH$_2$)$_p$—Y—(CH$_2$)$_q$— wherein p, q and Y have the same meanings as defined above.

(8) The compound or the pharmaceutically acceptable salt thereof as described in the above (1) or (2), wherein
R$^3$ is an alkyl group having 1 to 6 carbon atom(s), with the proviso that a t-butyl group is excluded and
A is an oxygen atom.

(9) The compound or the pharmaceutically acceptable salt thereof as described in the above (1) or (2), wherein
R$^3$ is a methyl group and
A is an oxygen atom.

(10) The compound or the pharmaceutically acceptable salt thereof as described in the above (1) or (2), wherein
R$^3$ is
an alkyl group having 1 to 6 carbon atom(s) substituted with 1 to 3 group(s) selected from "a halogen atom, a cyano group, a carboxy group, an alkoxycarbonyl group having 2 to 7 carbon atoms, an aralkyloxy group having 7 to 12 carbon atoms, an alkanoyloxy group having 2 to 6 carbon atoms, a hydroxy group, a phthalimide group, an alkylsulfonylamino group having 1 to 6 carbon atom(s), a methanesulfonyloxy group, a toluenesulfonyloxy group, an aryl group unsubstituted or substituted with 1 to 5 group(s) selected from Substituent Group 1, a heteroaryl group unsubstituted or substituted with 1 to 3 group(s) selected from Substituent Group 1, a group represented by the formula:

—CO—N(—(CH$_2$)$_l$—R$^{36}$)—(CH$_2$)$_m$—R$^{32}$ wherein l, m, R$^{36}$ and R$^{32}$ have the same meanings as defined above, and a group represented by the formula:

—NR$^{41}$R$^{42}$ wherein R$^{41}$ and R$^{42}$ have the same meanings as defined above", or
an alkenyl group having 2 to 6 carbon atoms substituted with 1 to 3 group(s) selected from "a halogen atom, an alkyl group having 1 to 6 carbon atom(s), an alkoxy group having 1 to 6 carbon atom(s), an alkoxycarbonyl group having 2 to 7 carbon atoms, a cyano is group, a nitro group, a hydroxy group, an oxo group, an amino group unsubstituted or substituted with 1 or 2 alkyl group(s) having 1 to 6 carbon atom(s)", and
A is an oxygen atom.

(11) The compound or the pharmaceutically acceptable salt thereof as described in the above (1) or (2), wherein
R$^3$ is
an alkyl group having 1 to 6 carbon atom(s) substituted with a group selected from a cyano group, a carboxy group, an alkoxycarbonyl group having 2 to 7 carbon atoms, an aralkyloxy group having 7 to 12 carbon atoms, an alkanoyloxy group having 2 to 6 carbon atoms, a hydroxy group, a phthalimide group, an alkylsulfonylamino group having 1 to 6 carbon atom(s), a phenyl group unsubstituted or substituted with a group selected from "an alkoxy group having 1 to 6 carbon atom(s), a nitro group, and an amino group unsubstituted or substituted with 1 or 2 alkyl group(s) having 1 to 6 carbon atom(s)", a pyridyl group, a group represented by the formula:

—CO—NH—(CH$_2$)$_2$—NMe$_2$ and a group represented by the formula:

—NR$^{41}$R$^{42}$ wherein R$^{41}$ and R$^{42}$ have the same meanings as defined above, or
an alkenyl group having 2 to 6 carbon atoms substituted with 1 or 2 group(s) selected from "an alkoxycarbonyl group having 2 to 7 carbon atoms, and an oxo group", and
A is an oxygen atom.

(12) The compound or the pharmaceutically acceptable salt thereof as described in the above (1) or (2), wherein
R$^3$ is
an alkyl group having 2 to 6 carbon atoms substituted with a group selected from "a cyano group, a carboxy group, an alkoxycarbonyl group having 2 to 7 carbon atoms, an alkanoyloxy group having 2 to 6 carbon atoms, a hydroxy group, a phthalimide group, an alkylsulfonylamino group having 1 to 6 carbon atom(s), a phenyl group unsubstituted or substituted with a group selected from "an alkoxy group having 1 to 6 carbon atom(s), a nitro group, and an amino group unsubstituted or substituted with 1 or 2 alkyl group(s) having 1 to 6 carbon atom(s)", a pyridyl group, a group represented by the formula:

—CO—NH—(CH$_2$)$_2$—NMe$_2$ and a group represented by the formula:

—NR$^{41}$R$^{42}$ wherein R$^{41}$ and R$^{42}$ have the same meanings as defined above, or
a an alkenyl group having 2 to 6 carbon atoms substituted with 1 or 2 group(s) selected from "an alkoxycarbonyl group having 2 to 7 carbon atoms, and an oxo group", and
A is an oxygen atom.

(13) The compound or the pharmaceutically acceptable salt thereof as described in any one of the above (8) to (12), wherein
R$^1$ and R$^2$ each independently represents
a hydrogen atom,
an alkyl group having 1 to 6 carbon atom(s) unsubstituted or substituted with 1 to 3 substituent(s) selected from "an aryl group unsubstituted or substituted with 1 to 5 substituent(s) selected from Substituent Group 1, an heteroaryl group unsubstituted or substituted with 1 to 3 substituent(s) selected from Substituent Group 1, a carboxy group, and an alkoxycarbonyl group having 2 to 7 carbon atoms" with the proviso that when R$^3$ is a methyl group, both R$^1$ and R$^2$ do not represent methyl groups, or
an alkyl group having 2 to 6 carbon atoms substituted with 1 to 5 group(s) selected from "an amino group unsubstituted or substituted with 1 or 2 alkyl group(s) having 1 to 6 carbon atom(s), a phthalimide group, an alkoxy group having 1 to 6 carbon atom(s), a morpholino group, an aralkyloxy group having 7 to 12 carbon atoms, an alkanoyloxy group having 2 to 6 carbon atoms, a hydroxy group, and a group represented by the formula:

—NHCO$_2$—(CH$_2$)$_n$—R$^{31}$ wherein n and R$^{31}$ have the same meanings as defined above", or
R$^1$ and R$^2$ are a cyclic structure represented by the formula which is formed together with the nitrogen atom to which each is bonded:

—(CH$_2$)$_p$—Y—(CH$_2$)$_q$— wherein p, q and Y have the same meanings as defined above.

(14) The compound or the pharmaceutically acceptable salt thereof as described in any one of the above (8) to (12), wherein
both R$^1$ and R$^2$ represent hydrogen atoms, or
R$^1$ represents an alkyl group having 1 to 6 carbon atom(s),
R$^2$ represents
a hydrogen atom,
an alkyl group having 1 to 6 carbon atom(s) unsubstituted or substituted with one "phenyl group substituted with an amino group unsubstituted or substituted with 1 or 2 alkyl group(s) having 1 to 6 carbon atom(s)" with the proviso that when R$^3$ is a methyl group, both R$^1$ and R$^2$ do not represent methyl groups, or
an alkyl group having 2 to 6 carbon atoms substituted with 1 or 2 group(s) selected from "an amino group unsubstituted or substituted with 1 or 2 alkyl group(s) having 1 to 6 carbon atom(s), a phthalimide group, an alkoxy group having 1 to 6 carbon atom(s), a morpholino group, an aralkyloxy group having 7 to 12 carbon atoms, an alkanoyloxy group having 2 to 6 carbon atoms, and a hydroxy group", or
R$^1$ and R$^2$ are a cyclic structure represented by the formula which is formed together with the nitrogen atom to which each is bonded:

—(CH$_2$)$_p$—Y—(CH$_2$)$_q$— wherein p, q and Y have the same meanings as defined above.

(15) The compound or the pharmaceutically acceptable salt thereof as described in any one of the above (8) to (12), wherein
R$^1$ and R$^2$ is each a methyl group.

(16) The compound or the pharmaceutically acceptable salt thereof as described in any one of the above (8) to (12), wherein
R$^1$ and R$^2$ is each independently
a hydrogen atom, or
an alkyl group having 1 to 6 carbon atom(s).

(17) The compound or the pharmaceutically acceptable salt thereof as described in any one of the above (1) to (16), wherein
R$^4$ is a methyl group,
Z is a group represented by the formula:

—C(=O)—

R$^7$ is a hydroxy group,
R$^8$ is a hydrogen atom or a hydroxy group, and
R$^9$ is a hydrogen atom.

(18) The compound or the pharmaceutically acceptable salt thereof as described in any one of the above (1) to (16), wherein
R$^4$ is a hydrogen atom, an alkyl group having 1 to 6 carbon atom(s), or an alkanoyl group having 2 to 6 carbon atoms,
Z is a group represented by the formula:

—NR$^{14}$—CH$_2$—

R$^{14}$ is a hydrogen atom, an alkyl group having 1 to 6 carbon atom(s), or an alkanoyl group having 2 to 6 carbon atoms,
R$^7$ is a hydroxy group or an alkanoyloxy group having 2 to 6 carbon atoms,
R$^8$ is a hydroxy group, and
R$^9$ is a hydrogen atom.

(19) The compound or the pharmaceutically acceptable salt thereof as described in any one of the above (1) to (16), wherein
R$^4$ is a hydrogen atom, a methyl group, or an acetyl group,
Z is a group represented by the formula:

—NR$^{14}$—CH$_2$—, $R^{14}$ is a hydrogen atom, a methyl group, or an acetyl group,
$R^7$ is a hydroxy group, or an acetyloxy group,
$R^8$ is a hydroxy group, and
$R^9$ is a hydrogen atom.

(20) The compound or the pharmaceutically acceptable salt thereof as described in any one of the above (1) to (16), wherein
$R^4$ is a methyl group,
Z is a group represented by the formula:

—C(=O)—

$R^7$ and $R^8$ are a cyclic structure represented by formula (II) which is formed together with carbon atoms to which each is bonded,
$R^{35}$ is a hydrogen atom, an alkyl group having 1 to 6 carbon atom(s) substituted with 1 to 3 "aryl group(s) or heteroaryl group(s)", or an alkyl group having 1 to 6 carbon atom(s) substituted with 1 to 3 heteroaryl group(s) substituted with 1 to 3 heteroaryl group(s), and
$R^9$ is a hydrogen atom.

(21) The compound or the pharmaceutically acceptable salt thereof as described in any one of the above (1) to (16), wherein
$R^4$ is a methyl group,
Z is a group represented by the formula:

—C(=O)—

$R^7$ and $R^8$ are a cyclic structure represented by formula (II) which is formed together with carbon atoms to which each is bonded,
$R^{35}$ is a hydrogen atom, or a 4-(4-(pyridin-3-yl)imidazolyl) butyl group, and
$R^9$ is a hydrogen atom.

(22) The compound or the pharmaceutically acceptable salt thereof as described in any one of the above (1) to (16), wherein
$R^4$ is a methyl group,
Z is a group represented by the formula:

—$CR^5R^6$— or a group represented by the formula:

—C(=N—OH)— one of $R^5$ and $R^6$ is a hydrogen atom while the other one is a group represented by the formula:

—$NR^{13}R^{15}$ wherein $R^{13}$ and $R^{15}$ each independently represents a hydrogen atom, an alkyl group having 1 to 6 carbon atom(s), an alkanoyl group having 2 to 6 carbon atoms, or an alkylsulfonyl group having 1 to 6 carbon atom(s), or a group represented by the formula:

—$OR^{12}$ wherein $R^{12}$ is a hydrogen atom, or an alkanoyl group having 2 to 6 carbon atoms unsubstituted or substituted with an amino group unsubstituted or substituted with 1 or 2 alkyl group(s) having 1 to 6 carbon atom(s),
$R^7$ is a hydroxy group or a group represented by the formula:

—$OR^{22}$ wherein $R^{22}$ is "an alkyl group having 1 to 6 carbon atom(s) or an alkanoyl group having 2 to 6 carbon atoms" unsubstituted or substituted with an amino group unsubstituted or substituted with 1 or 2 alkyl group(s) having 1 to 6 carbon atom(s),
$R^8$ is a hydroxy group, and
$R^9$ is a hydrogen atom.

(23) The compound or the pharmaceutically acceptable salt thereof as described in any one of the above (1) to (16), wherein
$R^4$ is a methyl group,
Z is a group represented by the formula:

—$CR^5R^6$— or a group represented by the formula:

—C(=N—OH)— one of $R^5$ and $R^6$ is a hydrogen atom while the other one is a group represented by the formula:

—$NR^{13}R^{15}$ wherein $R^{13}$ and $R^{15}$ each independently represents a hydrogen atom, a methyl group, an acetyl group, or a methanesulfonyl group,
or a group represented by the formula:

—$OR^{12}$ wherein $R^{12}$ is a hydrogen atom, or an alkanoyl group having 2 to 6 carbon atoms substituted with an amino group unsubstituted or substituted with 1 or 2 alkyl group(s) having 1 to 6 carbon atom(s),
$R^7$ is a hydroxy group, or a group represented by the formula:

—$OR^{22}$ wherein $R^{22}$ is an alkanoyl group having 2 to 6 carbon atoms substituted with an amino group unsubstituted or substituted with 1 or 2 alkyl group(s) having 1 to 6 carbon atom(s),
$R^8$ is a hydroxy group, and
$R^9$ is a hydrogen atom.

(24) The compound or the pharmaceutically acceptable salt thereof as described in any one of the above (1) to (23), wherein
$R^{10}$ is a group represented by formula (V),
$R^{29}$ is a hydrogen atom, and
$R^{30}$ is a hydroxy group or an alkanoyloxy group having 2 to 6 carbon atoms.

(25) The compound or the pharmaceutically acceptable salt thereof as described in any one of the above (1) to (23), wherein
$R^{10}$ is a group represented by the formula:

—OCO—$R^{24}$ wherein $R^{24}$ is a group represented by the formula:

—$(CH_2)_j$-D-$(CH_2)_k$—$R^{25}$ wherein D represents a bond, or a group represented by the formula:

—$NHCO_2$—

$R^{25}$ represents a hydrogen atom, "a phenyl group or a pyridyl group" unsubstituted or substituted with 1 to 3 group(s) selected from "a halogen atom, an amino group unsubstituted or substituted with 1 or 2 alkyl group(s) having 1 to 6 carbon atom(s), a cyclic alkyl group having 3 to 6 carbon atoms including 1 to 3 hetero atom(s) on a ring, a hydroxy group, an alkyl group having 1 to 6 carbon atom(s), an alkoxy group having 1 to 6 carbon atom(s), and a nitro group", a group represented by the formula:

—$NR^{37}R^{38}$ wherein $R^{37}$ and $R^{38}$ have the same meanings as defined above, a group represented by the formula:

—$NHCOR^{37}$ wherein $R^{37}$ has the same meaning as defined above, a group represented by the formula:

—NHSO$_2$R$^{37}$ wherein $R^{37}$ has the same meaning as defined above, or a group represented by the formula:

—NHCONHR$^{37}$ wherein $R^{37}$ has the same meaning as defined above, j and k each independently represents an integer of 0 to 2.

(26) The compound or the pharmaceutically acceptable salt thereof as described in any one of the above (1) to (23), wherein
$R^{10}$ is a group represented by the formula:

—OCO—R$^{24}$ wherein $R^{24}$ is a group represented by the formula:

—(CH$_2$)$_j$-D-(CH$_2$)$_k$—R$^{25}$ wherein D represents a bond, or a group represented by the formula:

—NHCO$_2$—

$R^{25}$ is a hydrogen atom, a phenyl group unsubstituted or substituted with an alkoxy group having 1 to 6 carbon atom(s), a pyridyl group, or a group represented by the formula:

—NR$^{37}$R$^{38}$ wherein $R^{37}$ and $R^{38}$ each independently represents a hydrogen atom, or an alkyl group having 1 to 6 carbon atom(s), j and k each independently represents an integer of 0 to 2.

(27) A compound represented by formula (VI) or a pharmaceutically acceptable salt thereof:

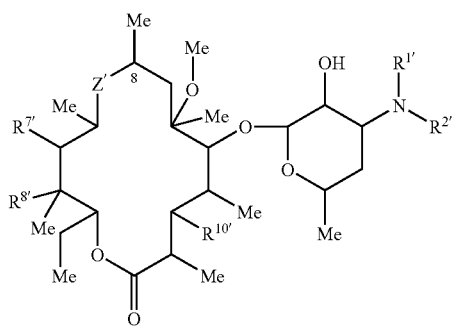

(VI)

wherein
$R^{1'}$ represents a methyl group,
$R^{2'}$ represents
a hydrogen atom,
a methyl group substituted with a substituent selected from "a phenyl group unsubstituted or substituted with a substituent selected from "a halogen atom, a methoxy group, a hydroxy group, and a dimethylamino group", and a pyridyl group,"
"an ethyl group or a propyl group" substituted with a group selected from "an amino group, a dimethylamino group, a phthalimide group, and a benzyloxycarbonylamino group",
a 2-amino-3,4-dioxocyclobut-1-enyl group,
a benzyloxycarbonyl group, or
a phenyl group substituted with a group selected from "a nitro group, an amino group, and a dimethylamino group" or $R^{1'}$ and $R^{2'}$ may identically represent a pyridylmethyl group or a dimethylaminophenylmethyl group,
Z' represents a group represented by the formula:

—C(=O)—

$R^{7'}$ is a hydroxy group,
$R^{8'}$ is a hydrogen atom or a hydroxy group,
$R^{7'}$ and $R^{8'}$ may represent a cyclic structure represented by formula (VII) which is formed together with carbon atoms to which each is bonded:

(VII)

or $R^{7'}$, $R^{8'}$ and the above-mentioned Z' may together represent a cyclic structure represented by formula (IV),

(IV)

$R^{10'}$ represents a hydroxy group, a methoxybenzylcarbonyloxy group, or a group represented by formula (VIII):

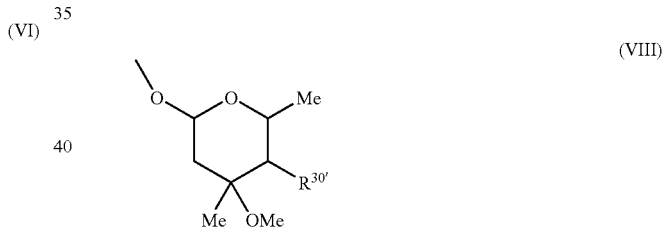

(VIII)

wherein $R^{30'}$ represents a hydroxy group or an acetyloxy group.

Advantage of the Invention

The compounds of the invention have a strong inhibitory activity against MMP-9 production and the antibacterial activity of which is controlled.

BEST MODE FOR CARRYING OUT THE INVENTION

The term "halogen atom" in the present invention refers to fluorine, chlorine, bromine, and iodine.
The term "aryl group" refers to a monocyclic to tetracyclic aromatic carbocyclic group having 6 to 18 carbon atoms, and examples thereof include a phenyl group, a naphthyl group, an anthryl group, a phenanthrenyl group, a tetracenyl group, a pyrenyl group, and the like.
The term "heteroaryl group" refers to a monocyclic aromatic heterocyclic ring group or fused ring aromatic heterocyclic group which includes 1 to 5 atom(s) optionally selected from a nitrogen atom, an oxygen atom and a sulfur atom as a ring constituting atom, and also includes a fused ring heterocyclic group having a partially saturated monocyclic aromatic heterocyclic group and a monocycle in which the aromatic heterocyclic group is partially saturated. In addition, the fused ring heterocyclic group having a monocycle which is partially saturated can be substituted by an oxo group (=O). In the case where a hetero atom is a sulfur atom, a dioxide form is included in the present invention.

The heteroaryl group is preferred to be a heteroaryl group having 2 to 10 carbon atoms in the ring system.

Examples of the heteroaryl group include a pyridyl group, a pyridazinyl group, a pyrimidinyl group, a pyrazinyl group, a quinolyl group, an isoquinolyl group, a thienyl group (for example, 2-thienyl group, 3-thienyl group), a pyrrolyl group (for example, 1-pyrrolyl group, 2-pyrrolyl group, 3-pyrrolyl group), a thiazolyl group (for example, 2-thiazolyl group, 4-thiazolyl group, 5-thiazolyl group), an isothiazolyl group (for example, 3-isothiazolyl group, 4-isothiazolyl group, 5-isothiazolyl group), a pyrazolyl group (for example, 1-pyrazolyl group, 3-pyrazolyl group, 4-pyrazolyl group), an imidazolyl group (for example, 1-imidazolyl group, 2-imidazolyl group, 3-imidazolyl group), a furyl group (for example, 2-furyl group, 3-furyl group), an oxazolyl group (for example, 2-oxazolyl group, 4-oxazolyl group, 5-oxazolyl group), an isoxazolyl group (for example, 3-isoxazolyl group, 4-isoxazolyl group, 5-isoxazolyl group), an oxadiazolyl group (for example, 1,2,3-oxadiazolyl group, 1,3,4-oxadiazolyl group), a thiadiazolyl group (for example, 1,2,3-thiadiazolyl group, 1,3,4-thiadiazolyl group), a triazolyl group (for example, 1,2,4-triazolyl group), a benzofuranyl group (for example, 2-benzofuranyl group, 3-benzofuranyl group, 4-benzofuranyl group, 5-benzofuranyl group), a benzothienyl group (for example, 2-benzothienyl group, 3-benzothienyl group, 4-benzothienyl group, 5-benzothienyl group), an indolyl group (for example, 2-indolyl group, 3-indolyl group, 4-indolyl group, 5-indolyl group), a benzoxazolyl group (for example, 2-benzoxazolyl group, 4-benzoxazolyl group, 5-benzoxazolyl group, 6-benzoxazolyl group), a benzisoxazolyl group (for example, 3-benzo[c]isoxazolyl group, 4-benzo[c]isoxazolyl group, 5-benzo[c]isoxazolyl group, 6-benzo[c]isoxazolyl group, 3-benzo[d]isoxazolyl group, 4-benzo[d]isoxazolyl group, 5-benzo[d]isoxazolyl group, 6-benzo[d]isoxazolyl group), an indazolyl group (for example, 3-indazolyl group, 4-indazolyl group, 5-indazolyl group, 6-indazolyl group), a benzimidazolyl group (for example, 2-benzimidazolyl group, 4-benzimidazolyl group, 5-benzimidazolyl group, 6-benzimidazolyl group), a benzoxadiazolyl group (for example, 4-benzo[1,2,5]oxadiazolyl group, 5-benzo[1,2,5]oxadiazolyl group, 4-benzo[1,2,3]oxadiazolyl group, 5-benzo[1,2,3]oxadiazolyl group), a benzothiadiazolyl group (for example, 4-benzo[1,2,5]thiadiazolyl group, 5-benzo[1,2,5]thiadiazolyl group, 4-benzo[1,2,3]thiadiazolyl group, 5-benzo[1,2,3]thiadiazolyl group), an indolizinyl group (for example, 1-indolizinyl group, 2-indolizinyl group, 3-indolizinyl group, 5-indolizinyl group), a thienopyridyl group (for example, 2-thieno[2,3-b]pyridyl group, 3-thieno[2,3-b]pyridyl group, 5-thieno[2,3-b]pyridyl group, 6-thieno[2,3-b]pyridyl group, 2-thieno[3,2-b]pyridyl group, 3-thieno[3,2-b]pyridyl group, 5-thieno[3,2-b]pyridyl group, 6-thieno[3,2-b]pyridyl group), a pyrazolopyridyl group (for example, 2-pyrazolopyridyl group, 3-pyrazolopyridyl group, 5-pyrazolopyridyl group, 6-pyrazolopyridyl group), an imidazopyridyl group (for example, 1-imidazo[1,5-a]pyridyl group, 3-imidazo[1,5-a]pyridyl group, 5-imidazo[1,5-a]pyridyl group, 7-imidazo[1,5-a]pyridyl group, 2-imidazo[1,2-a]pyridyl group, 3-imidazo[1,2-a]pyridyl group, 5-imidazo[1,2-a]pyridyl group, 7-imidazo[1,2-a]pyridyl group), an imidazopyrazyl group (for example, an 1-imidazo[1,5-a]pyrazyl group, a 3-imidazo[1,5-a]pyrazyl group, 5-imidazo[1,5-a]pyrazyl group, an 8-imidazo[1,5-a]pyrazyl group, a 2-imidazo[1,2-a]pyrazyl group, a 3-imidazo[1,2-a]pyrazyl group, a 5-imidazo[1,2-a]pyrazyl group, an 8-imidazo[1,2-a]pyrazyl group), a pyrazolopyrimidyl group (for example, 2-pyrazolo[1,5-a]pyrimidyl group, 3-pyrazolo[1,5-a]pyrimidyl group, 5-pyrazolo[1,5-a]pyrimidyl group, 6-pyrazolo[1,5-a]pyrimidyl group, 2-pyrazolo[1,5-c]pyrimidyl group, 3-pyrazolo[1,5-c]pyrimidyl group, 4-pyrazolo[1,5-c]pyrimidyl group, 5-pyrazolo[1,5-c]pyrimidyl group,) a triazolopyrimidyl group (for example, 3-[1,2,3]triazolo[1,5-a]pyrimidyl group, 5-[1,2,3]triazolo[1,5-a]pyrimidyl group, 6-[1,2,3]triazolo[1,5-a]pyrimidyl group, 3-[1,2,3]triazolo[1,5-c]pyrimidyl group, 4-[1,2,3]triazolo[1,5-c]pyrimidyl group, 5-[1,2,3]triazolo[1,5-c]pyrimidyl group, 2-[1,2,4]triazolo[1,5-a]pyrimidyl group, 5-[1,2,4]triazolo[1,5-a]pyrimidyl group, 6-[1,2,4]triazolo[1,5-a]pyrimidyl group, 7-[1,2,4]triazolo[1,5-a]pyrimidyl group, 2-[1,2,4]triazolo[1,5-c]pyrimidyl group, 5-[1,2,4]triazolo[1,5-c]pyrimidyl group, 7-[1,2,4]triazolo[1,5-c]pyrimidyl group, 8-[1,2,4]triazolo[1,5-c]pyrimidyl group), a thienothienyl group (for example, 2-thieno[2,3-b]thienyl group, 3-thieno[2,3-b]thienyl group, 2-thieno[3,2-b]thienyl group, 3-thieno[3,2-b]thienyl group,), an imidazothiazolyl group (for example, 2-imidazo[2,1-b]thiazolyl group, 3-imidazo[2,1-b]thiazolyl group, 5-imidazo[2,1-b]thiazolyl group, 2-imidazo[5,1-b]thiazolyl group, 3-imidazo[5,1-b]thiazolyl group, 5-imidazo[5,1-b]thiazolyl group), and the like.

Examples of the fused ring heterocyclic group having a partially saturated monocyclic aromatic heterocyclic group and a monocycle in which the aromatic heterocyclic group is partially saturated include maleimide, a tetrahydrobenzofuranyl group, a tetrahydrobenzothienyl group, a tetrabenzopyrrolyl group, a 2,3-dihydro-1H-benzofuranyl group, a 2,3-dihydro-1H-benzothienyl group, a 2,3-dihydro-1H-indolyl group, a 2,3-dihydro-1H-indazolyl group, a 2,3-dihydro-1H-benzotriazolyl group, a 2,3-dihydro-1H-benzoxazolyl group, a 2,3-dihydro-1H-benzothiazolyl group, a benzo[1,3]oxathiolyl group, a benzo[1,3]dioxolyl group, a 2H-chromenyl group, a chromanyl group, an indolinyl group, an isoindolinyl group, and the like.

Examples of the fused ring heterocyclic group which has a partially saturated monocycle and is substituted with an oxo group include a 2-oxo-1,3-dihydro-1H-indolyl ring, a 3-oxo-1,2-dihydro-1H-indazolyl ring, a 2-oxo-3H-benzoxazolyl ring, a 2-oxo-3H-benzothiazolyl ring, a 2-oxo-benzo[1,3]oxathiolyl ring, a 2-oxo-benzo[1,3]dioxolyl ring, a 2-oxo-chromenyl ring and the like.

The term "alkyl group having 1 to 6 carbon atom(s)" refers to a linear or branched alkyl group having 1 to 6 carbon atom(s), and examples thereof include a methyl group, an ethyl group, a n-propyl group, an isopropyl group, a n-butyl group, a 2-butyl group, a t-butyl group, a 1,1-dimethylethyl group, a n-pentyl group, an isopentyl group, a 1,1-dimethylpropyl group, a n-hexyl group, and the like.

The term "alkyl group having 2 to 6 carbon atoms" refers to a linear or branched alkyl group having 2 to 6 carbon atoms, and examples thereof include an ethyl group, a n-propyl group, an isopropyl group, a n-butyl group, a 2-butyl group, a t-butyl group, a 1,1-dimethylethyl group, a n-pentyl group, an isopentyl group, a 1,1-dimethylpropyl group, a n-hexyl group, and the like.

The term "alkenyl group having 2 to 6 carbon atoms" refers to a linear or branched alkyl group having 2 to 6 carbon atoms which has one or more of double bond(s) at an optional position of the above-mentioned "alkyl group", and examples thereof include a vinyl group, a 1-propenyl group, a 2-propenyl group, a 2-butenyl group, a 1,3-butadienyl group, a 2-pentenyl group, a 3-pentenyl group, a 2-hexenyl group, and the like.

The term "alkynyl group having 2 to 6 carbon atoms" refers to a linear or branched alkynyl group having 2 to 6 carbon atoms which has one or more of triple bond(s) at an optional position of the above-mentioned "alkyl group", and examples thereof include an ethynyl group, a 1-propynyl group, a 2-propynyl group, and the like.

The term "cyclic alkyl group having 3 to 6 carbon atoms" refers to a cycloalkyl group having 3 to 6 carbon atoms, and examples thereof include a cyclopropyl group, a cyclobutyl group, a cyclopentyl group, a cyclohexyl group, and the like.

The term "cyclic alkenyl group having 4 to 6 carbon atoms" refers to a cycloalkenyl group having 4 to 6 carbon atoms, and examples thereof include a cyclobutenyl group, a cyclopentenyl group, a cyclohexenyl group, and the like.

The term "amino group substituted with 1 or 2 alkyl group(s) having 1 to 6 carbon atom(s)" refers to an amino group to which a linear or branched alkyl group having 1 to 6 carbon atom(s) is bonded, and examples thereof include a methylamino group, an ethylamino group, a propylamino group, an isopropylamino group, a butylamino group, a pentylamino group, a hexylamino group, a dimethylamino group, a diethylamino group, a dipropylamino group, a diisopropylamino group, a dibutylamino group, a dipentylamino group, a dihexylamino group, a methylethylamino group, and the like.

The term "alkylsulfonyl group having 1 to 6 carbon atom(s)" refers to a sulfonyl group to which a linear or branched alkyl group having 1 to 6 carbon atom(s) is bonded, and examples thereof include a methylsulfonyl group, an ethylsulfonyl group, a propylsulfonyl group, an isopropylsulfonyl group, a butylsulfonyl group, a pentylsulfonyl group, a hexylsulfonyl group, and the like.

The term "alkylsulfonyloxy group having 1 to 6 carbon atom(s)" refers to a group in which the above-mentioned alkylsulfonyl group having 1 to 6 carbon atom(s) substitutes through an oxygen atom, and examples thereof include a methylsulfonyloxy group, an ethylsulfonyloxy group, a propylsulfonyloxy group, an isopropylsulfonyloxy group, a butylsulfonyloxy group, a pentylsulfonyloxy group, a hexylsulfonyloxy group, and the like.

The term "alkylsulfonylamino group having 1 to 6 carbon atom(s)" refers to a group in which the above-mentioned alkylsulfonyl group having 1 to 6 carbon atom(s) substitutes through an NH group, and examples thereof include a methylsulfonylamino group, an ethylsulfonylamino group, a propylsulfonylamino group, an isopropylsulfonylamino group, a butylsulfonylamino group, a pentylsulfonylamino group, a hexylsulfonylamino group, and the like.

The term "aryloxy group" refers to a group in which the above-mentioned aryl group substitutes through an oxygen atom, and examples thereof include a phenoxy group, a naphthoxy group, and the like.

The term "alkanoyl group having 2 to 6 carbon atoms" refers to a linear or branched alkanoyl group having 2 to 6 carbon atoms, and examples thereof include an acetyl group, a propionyl group, an isopropionyl group, a butyryl group, a pivaloyl group, and the like.

The term "alkanoyloxy group having 2 to 6 carbon atoms" refers to a group in which the above-mentioned alkanoyl group having 2 to 6 carbon atoms substitutes through an oxygen atom, and examples thereof include an acetyloxy group, a propionyloxy group, a pivaloyloxy group, and the like.

The term "alkoxycarbonyl group having 2 to 7 carbon atoms" refers to a group in which an alkoxy group having 1 to 6 carbon atom(s) bonds with a carbonyl group, and examples thereof include a methoxycarbonyl group, an ethoxycarbonyl group, a t-butoxycarbonyl group, a n-hexyloxycarbonyl group, and the like.

The term "aralkyl group having 7 to 12 carbon atoms" refers to a group in which an aryl group and an alkyl group bond, and the number of carbon atom is 7 to 12, and examples thereof include a benzyl group, a phenethyl group, a naphthylmethyl group, and the like.

The term "aralkyloxy group having 7 to 12 carbon atoms" refers to a group in which the above-mentioned aralkyl group having 7 to 12 carbon atoms substitutes through an oxygen atom, and examples thereof include a benzyloxy group, a phenethyloxy group, a naphthylmethyloxy group, and the like.

Examples of the "5- or 6-membered heterocyclic ring formed together with the nitrogen atom to which each is bonded" include a pyrrolidine ring, a piperidine ring, and the like.

Examples of the "cyclic alkyl group having 3 to 6 carbon atoms including 1 to 3 hetero atom(s) on a ring" include a pyrrolidinyl group, a piperidinyl group, a piperazinyl group, a morpholinyl group, and the like.

The term "hetero atom" refers to a nitrogen atom, an oxygen atom, or a sulfur atom.

The term "alkoxy group having 1 to 6 carbon atom(s)" refers to a linear or branched alkoxy group having 1 to 6 carbon atom(s), and examples thereof include a methoxy group, an ethoxy group, a 1-propoxy group, an isopropoxy group, a 1-butoxy group, a 1-methyl-1-propoxy group, a t-butoxy group, a 1-pentyloxy group, and the like.

In the present invention, the pharmaceutically acceptable salt means salts to be used for chemotherapy and prevention. Examples thereof include a salt with an acid such as acetic acid, propionic acid, butyric acid, formic acid, trifluoroacetic acid, maleic acid, tartaric acid, citric acid, stearic acid, succinic acid, ethylsuccinic acid, lactobionic acid, gluconic acid, glucoheptonic acid, benzoic acid, methanesulfonic acid, ethanesulfonic acid, 2-hydroxyethanesulfonic acid, benzenesulfonic acid, p-toluenesulfonic acid, lauryl sulfate, malic acid, aspartic acid, glutamic acid, adipic acid, cysteine, N-acetylcysteine, hydrochloric acid, hydrobromic acid, phosphoric acid, sulfuric acid, hydroiodic acid, nicotinic acid, oxalic acid, picric acid, thiocyanic acid, undecanoic acid, polymer of acrylic acid, and carboxy vinyl polymer; a salt with an inorganic base such as sodium salt, potassium salt, and calcium salt; and a salt with an organic amine such as morpholine and piperidine, or a salt with an amino acid.

In the present invention, the term "optional substituent" refers to a substituent selected from an alkyl group having 1 to 6 carbon atom(s) unsubstituted or substituted with 1 to 5 substituent(s) selected from ["an aryl group, heteroaryl group, or heteroarylthio group" unsubstituted or substituted with 1 to 3 substituent(s) selected from (a halogen atom, an alkyl group having 1 to 6 carbon atom(s), and a nitro group), an aryloxy group, a cyano group, a cyanothio group, a carboxy group, and an alkoxy group having 1 to 6 carbon atom(s)], an alkenyl group having 2 to 6 carbon atoms, an alkynyl group having 2 to 6 carbon atoms, a cyclic alkyl group having 3 to 6 carbon atoms, a cyclic alkyl group having 3 to 6 carbon atoms including 1 to 3 hetero atom(s) on a ring, an alkoxy group having 1 to 6 carbon atom(s), a hydroxyalkoxy group having 1 to 6 carbon atom(s), an alkenyloxy group having 2 to 6 carbon atoms, a carboxy group, a carboxy C1-C6 alkoxy group, a cyano C1-C6 alkoxy group, a hydroxy group, a cyano group, a nitro group, an oxide group, a sulfonic acid group, a halogen atom, an alkylthio group having 1 to 6 carbon atom(s), an alkylsulfonyl group having 1 to 6 carbon atom(s), an arylsulfonyl group unsubstituted or substituted with 1 to 5 substituent(s) selected from "an alkyl group having 1 to 6 carbon atom(s) and a halogen atom", a haloalkylthio group having 1 to 6 carbon atom(s), an alkenylthio group having 2 to 6 carbon atoms, an alkoxy having 1 to 6 carbon atom(s) C1-C6 alkyl group, an alkoxy having 1 to 6 carbon atom(s) C1-C6 alkoxy group, a haloalkyl group having 1 to 6 carbon atom(s), an alkanoyl group having 2 to 6 carbon atoms, a alkanoyloxy group having 2 to 6 carbon atoms, an alkanoyloxy having 2 to 6 carbon atoms C1-C6 alkyl group, a benzoyl group unsubstituted or substituted with 1 to 3 substituent(s) selected from "a halogen atom and a nitro group", an alkanoylamino group having 2 to 6 carbon atoms, an alkylsulfonyl group having 1 to 6 carbon atom(s), an alkylsulfonylamino group having 1 to 6 carbon atom(s), a carbamoyl group, an alkoxycarbonyl group having 2 to 7 carbon atoms, a group represented by the formula:

—$NR^{26}R^{27}$ (wherein $R^{26}$ and $R^{27}$ each represents a hydrogen atom, an alkyl group having 1 to 6 carbon atom(s), a hydroxyalkyl group having 1 to 6 carbon atom(s), an alkoxycarbonyl having 2 to 7 carbon atoms C1-C6 alkyl group, or a cyano C1-C6 alkyl group, or represent a 5- or 6-membered heterocyclic ring formed together with the nitrogen atom to which each is bonded, which may be substituted with "an alkyl group having 1 to 6 carbon atom(s), a cyano C1-C6 alkyl group, a cyclic alkyl group having 3 to 6 carbon atoms, an alkanoyl group having 2 to 6 carbon atoms, a benzoyl group, an aryloxy C2-C6 alkanoyl group which may be substituted with "an alkyl group having 1 to 6 carbon atom(s) or an alkoxy group having 1 to 6 carbon atom(s)", an alkoxy having 1 to 6 carbon atom(s) C1-C6 alkyl group, an alkoxycarbonyl group having 2 to 7 carbon atoms, an oxo group, or a hydroxy group"), a group represented by the formula:

—$CON(R^{26})R^{27}$ wherein $R^{26}$ and $R^{27}$ have the same meanings as defined above, a group represented by the formula:

—$OCON(R^{26})R^{27}$ wherein $R^{26}$ and $R^{27}$ have the same meanings as defined above, a group represented by the formula:

—$O(CH_2)_rN(R^{26})R^{27}$

Wherein r represents an integer of 1 to 6, $R^{26}$ and $R^{27}$ have the same meanings as defined above, and "an aryl group, a heteroaryl group, an aryloxy group, an arylthio group, a heteroaryloxy group, and a heteroarylthio group" unsubstituted or substituted with 1 to 5 group(s) selected from "an alkyl group having 1 to 6 carbon atom(s), a haloalkyl group having 1 to 6 carbon atom(s), a halogen atom, an alkoxy group having 1 to 6 carbon atom(s), an aminosulfonyl group, a carboxy group, a hydroxyalkyl group having 1 to 6 carbon atom(s), a cyano group, and a nitro group".

The term "haloalkyl group having 1 to 6 carbon atom(s)" refers to an alkyl group having 1 to 6 carbon atom(s), which is substituted with one or plural halogen atom(s), and examples thereof include a fluoromethyl group, a difluoromethyl group, a trifluoromethyl group, a 2,2,2-trifluoroethyl group, a 2,2,2-trichloroethyl group, a pentafluoroethyl group, a 4-fluorobutyl group, a 4-chlorobutyl group, a 4-bromobutyl group, a perfluorohexyl group, and the like.

The term "haloalkylthio group having 1 to 6 carbon atom(s)" refers to an alkylthio group having 1 to 6 carbon atom(s), which is substituted with one or plural halogen atom(s), and examples thereof include a fluoromethylthio group, a difluoromethylthio group, a trifluoromethylthio group, a 2,2,2-trifluoroethylthio group, a 2,2,2-trichloroethylthio group, a pentafluoroethylthio group, a 4-fluorobutylthio group, a 4-chlorobutylthio group, a 4-bromobutylthio group, a perfluorohexylthio group, and the like.

The term "alkylthio group having 1 to 6 carbon atom(s)" refers to a linear or branched alkylthio group having 1 to 6 carbon atom(s), and examples thereof include a methylthio group, an ethylthio group, a n-propylthio group, an isopropylthio group, a n-butylthio group, a 2-butylthio group, a n-pentylthio group, a n-hexylthio group, and the like.

The term "alkenylthio group having 2 to 6 carbon atoms" refers to a linear or branched alkenylthio group having 2 to 6 carbon atoms, and examples thereof include a vinylthio group, an allylthio group, a n-propenylthio group, an isopropenylthio group, a n-butenylthio group, a 2-butenylthio group, a n-pentenylthio group, a n-hexenylthio group, and the like.

The term "alkenyloxy group having 2 to 6 carbon atoms" refers to a linear or branched alkenyloxy group having 2 to 6 carbon atoms.

The term "alkoxy having 1 to 6 carbon atom(s) C1-C6 alkyl group" refers to an alkyl group having 1 to 6 carbon atom(s), which is substituted with an alkoxy group having 1 to 6 carbon atom(s).

The term "alkoxy having 1 to 6 carbon atom(s) C1-C6 alkoxy group" refers to an alkoxy group having 1 to 6 carbon atom(s), which is substituted with an alkoxy group having 1 to 6 carbon atom(s)

The term "alkanoyloxy having 2 to 6 carbon atoms C1-C6 alkyl group" refers to an alkyl group having 1 to 6 carbon atom(s), which is substituted with an alkanoyloxy group having 2 to 6 carbon atoms.

Examples of the term "alkanoylamino group having 2 to 6 carbon atoms" include an acetylamino group, a propionylamino group, a pivaloylamino group, and the like.

The term "cyano C1-C6 alkyl group" refers to an alkyl group having 1 to 6 carbon atom(s), which is substituted with a cyano group.

The term "cyano C1-C6 alkoxy group" refers to an alkoxy group having 1 to 6 carbon atom(s), which is substituted with a cyano group.

The term "carboxy C1-C6 alkoxy group" refers to an alkoxy group having 1 to 6 carbon atom(s), which is substituted with a carboxy group.

The term "alkoxycarbonyl having 2 to 7 carbon atoms C1-C6 alkyl group" refers to an alkyl group having 1 to 6 carbon atom(s), which is substituted with an alkoxycarbonyl group having 2 to 7 carbon atoms.

The term "aryloxy C2-C6 alkanoyl group" refers to an alkanoyl group having 2 to 6 carbon atoms, which is substituted with an aryloxy group.

The term "hydroxyalkyl group having 1 to 6 carbon atom(s)" means an alkyl group having 1 to 6 carbon atom(s), which is substituted with 1 or 2 hydroxy group(s), and examples thereof include a hydroxymethyl group, a 2-hydroxyethyl group, a 4-hydroxybutyl group, and the like.

The term "hydroxyalkoxy group having 1 to 6 carbon atom(s)" means an alkoxy group having 1 to 6 carbon atom(s), which is substituted with 1 or 2 hydroxy group(s), and examples thereof include a hydroxymethoxy group, a 2-hydroxyethoxy group, a 4-hydroxybutoxy group, and the like.

The term "arylsulfonyl group" refers to a group in which an aryl group substitutes through a sulfonyl group.

The term "arylthio group" refers to a group in which an aryl group substitutes through a sulfur atom.

The term "heteroaryloxy group" refers to a group in which a heteroaryl group substitutes through an oxygen atom.

The term "heteroarylthio group" refers to a group in which a heteroaryl group substitutes through a sulfur atom.

In context, unless otherwise specified, the base means organic bases (e.g., amines such as triethylamine, diisopropylethylamine, pyridine or 4-dimethylaminopyridine; or metal alkoxides such as sodium methoxide), or inorganic bases (e.g., alkali metal carbonates such as sodium carbonate or potassium carbonate; alkaline earth metal carbonates such as calcium carbonate; metal hydroxides such as sodium hydroxide, or potassium hydroxide; metal hydrides such as sodium hydride; etc.).

Unless otherwise specified, the solvent means polar solvents (e.g., water or alcoholic solvents such as methanol; etc.), inert solvents (e.g., halogenated hydrocarbon solvents such as chloroform or methylene chloride; ethereal solvents such as diethyl ether, tetrahydrofuran or 1,4-dioxane; aprotic solvents such as dimethylformamide, dimethylsulfoxide or acetonitrile; aromatic hydrocarbons such as toluene; hydrocarbons such as cyclohexane; etc.), or mixed solvents thereof.

Unless otherwise specified, the condensing agent means, for example, chloroformate esters (e.g., isobutyl chloroformate, ethyl chloroformate, methyl chloroformate, etc.), acid chlorides (e.g., pivaloyl chloride, oxalyl chloride, 2,4,6-trichloro benzoyl chloride, etc.), dehydration condensing agents (carbodiimide reagents such as 1-ethyl-3-[3-(N,N-dimethylamino)propyl]carbodiimide•hydrochloride, or dicyclohexylcarbodiimide; carbonyldiimidazole; 2-chloro-1-methylpyridinium iodide salt; etc), or the like.

Compounds of the present invention, for example, can be synthesized by methods as follows.

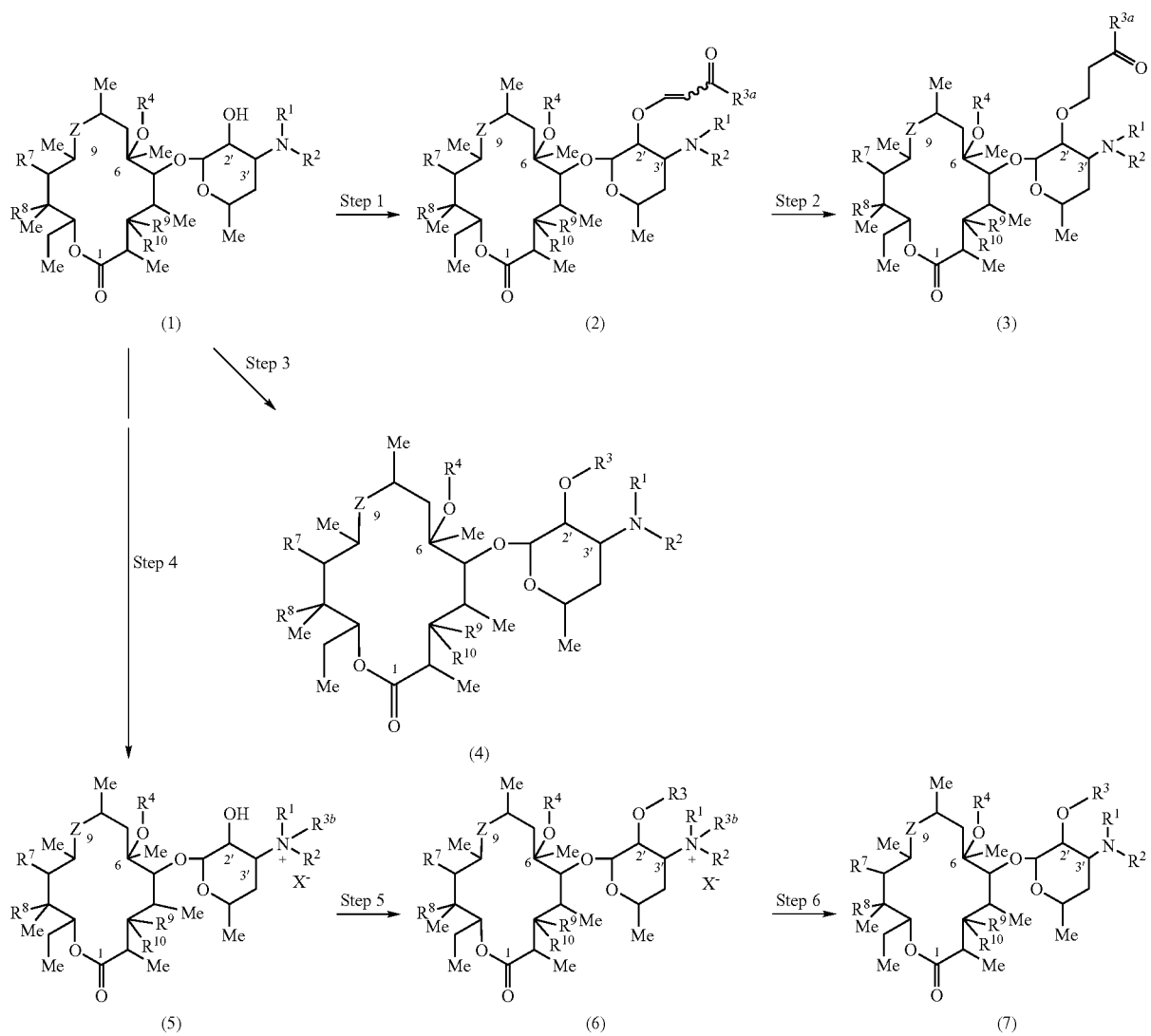

wherein $R^{3a}$ represents a remaining group in which a part having the structure represented by the formula:

—CH=CHCO— or a part having the structure represented by the formula:

—CH$_2$CH$_2$CO—;

is subtracted from the above-mentioned $R^3$
$R^{3b}$ represents an allyl group or a benzyl group, X represents a group capable of taking an anion (e.g., a chloro group, a bromo group, an iodo group, and a methanesulfonyloxy group), and other symbols have the same meanings as defined above.

[Step 1]

A compound represented by formula (2) can be synthesized by reacting a compound represented by formula (1) which can be synthesized by the methods described for example in Patent Document (Japanese Patent Application Laid-Open No. 57-8:2400, WO 9321199 etc.), Non-Patent Document (Journal of Organic Chemistry, Vol. 53, No. 10, p. 2340-2345, 1988, The Journal of Antibiotics, Vol. 54, No. 8, p. 664-678, 2001), and the like with a compound represented by the formula:

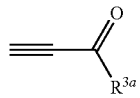

wherein $R^{3a}$ has the same meaning as defined above, in a solvent, if needed in the presence of a base, at room temperature.

[Step 2]

By hydrogenating the compound obtained in Step 1 using hydrogen source in a solvent (preferably tetrahydrofuran, or N,N-dimethylformamide) in the presence of a palladium catalyst (preferably 5 to 10% palladium carbon, palladium black, or palladium hydroxide carbon) at room temperature, a compound represented by formula (3) can be synthesized. For the hydrogen source, for example, hydrogen gas, ammonium formate, sodium formate, or triethylammonium formate can be used.

[Step 3]

By reacting a compound represented by formula (I) with slightly excessive amount of base (preferably sodium hydride) and a compound represented by the formula:

$R^3$—X wherein $R^3$ and X have the same meanings as defined above, in a solvent (aprotic polar solvent such as preferably N,N-dimethylformamide, dimethylsulfoxide, or ethereal solvent such as preferably tetrahydrofuran), a compound represented by formula (4) can be synthesized.

[Step 4]

By reacting the compound represented by formula (I) with a compound represented by the formula:

$R^{3b}$—X wherein $R^{3b}$ and X have the same meanings as defined above, in a solvent (preferably N,N-dimethylformamide, or dimethylsulfoxide) at 0 to 100° C. (preferably from room temperature to 80° C.), a compound represented by formula (5) can be synthesized.

[Step 5]

By reacting the compound obtained in Step 4 with a compound represented by the formula:

$R^3$—X wherein $R^3$ and X have the same meanings as defined above, and base (preferably sodium hydride, potassium hydroxide, or sodium hydroxide), in the presence or absence of crown ether (e.g., 18-crown-6), in a solvent (preferably N,N-dimethylformamide or dimethylsulfoxide, or mixed solvent of these solvents and an inert solvent (preferably tetrahydrofuran)), at 0 to 100° C. (preferably from 0° C. to room temperature), a compound represented by formula (6) can be synthesized.

[Step 6]

By hydrogenating the compound represented by formula (6) in which $R^{3b}$ is a benzyl group, using hydrogen source in a solvent (preferably alcoholic solvent, more preferably methanol or ethanol) in the presence of a palladium catalyst (preferably 5 to 10% palladium carbon, palladium black, or palladium hydroxide carbon) at room temperature, a compound represented by formula (7) can be synthesized. For the hydrogen source, for example, hydrogen gas, ammonium formate, sodium formate, or triethylammonium formate can be used.

Meanwhile, in the case of using the compound represented by formula (6) in which $R^{3b}$ is an allyl group, by deprotecting in a solvent (preferably ethereal solvent (e.g., tetrahydrofuran or dioxane) or mixed solvent of those solvents and water) using palladium acetate, triphenylphosphine, a formic acid, and triethylamine at room temperature to 100° C. (preferably from room temperature to 80° C.), a compound represented by formula (7) can be synthesized.

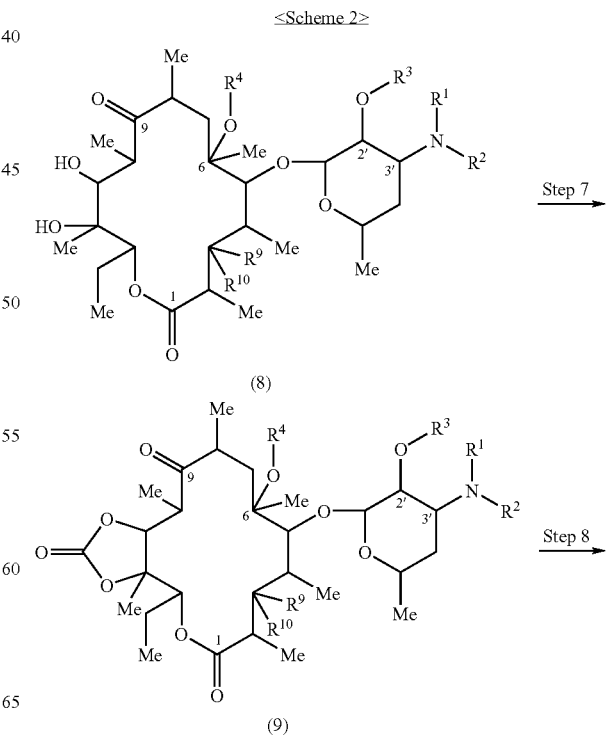

-continued

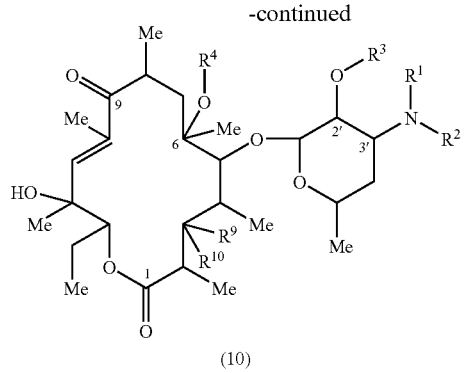

(10)

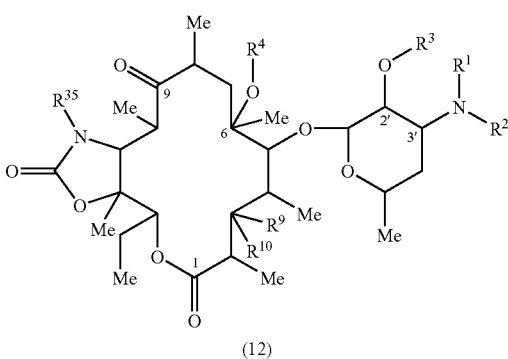

(11)

(12)

(symbols in the formula have the same meanings as defined above)

A compound represented by formula (12) can be synthesized by the method described in a literature (Journal of Medicinal Chemistry, Vol. 41, p. 4180-4190, 1998), using the compound represented by formula (8). That is, the compound can be synthesized through the following steps.

[Step 7]

A compound represented by formula (9) can be synthesized by reacting the compound represented by formula (8) in a solvent (preferably dichloromethane or chloroform) with triphosgene in the presence of a base (preferably pyridine).

[Step 8]

A compound represented by formula (10) can be synthesized by reacting the compound represented by formula (9) in a solvent (aprotic polar solvent, preferred is N,N-dimethylformamide or dimethylsulfoxide) in the presence of a base (preferably 1,1,3,3-tetramethylguanidine) at 0 to 120° C. (preferably 90 to 100° C.).

[Step 9]

A compound represented by formula (11) can be synthesized by reacting a compound that is obtained by reacting the compound represented by formula (10) with 1,1'-carbonyldiimidazole in a solvent (preferably N,N-dimethylformamide or dimethylsulfoxide, or a mixed solvent of these solvent and an inert solvent (preferably tetrahydrofuran)) in the presence of a base (preferably sodium hydride), with a compound represented by

$R^{35}$—$NH_2$ wherein $R^{35}$ has the same meaning as defined above, in a solvent (preferably acetonitrile or tetrahydrofuran) in the presence or absence of a base.

[Step 10]

A compound represented by formula (12) can be synthesized by reacting the compound represented by formula (11) in a solvent (preferably N,N-dimethylformamide, or dimethylsulfoxide, or a mixed solvent of these solvent and an inert solvent (preferably, tetrahydrofuran)) in the presence of a base (preferably sodium hydride).

≤Scheme 3≥

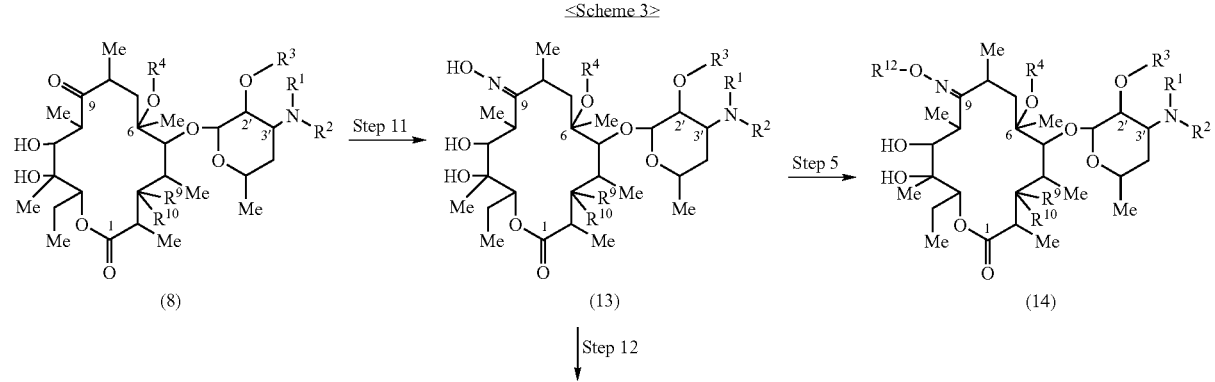

(8)　　　　(13)　　　　(14)

↓ Step 12

-continued

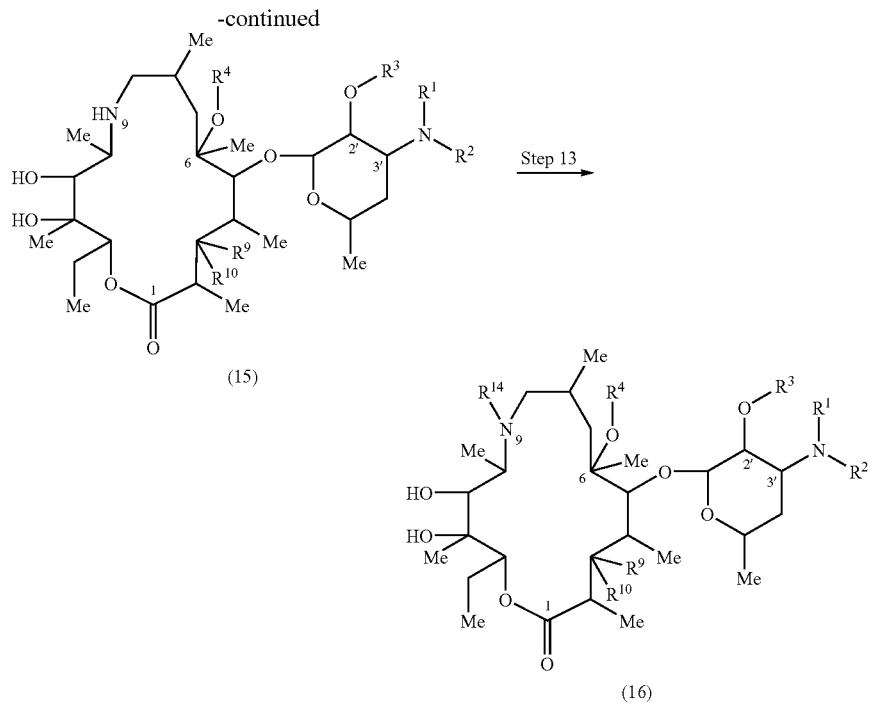

(symbols in the formula have the same meanings as defined above)

[Step 11]

A compound represented by formula (13) can be synthesized by reacting hydroxylamine hydrochloride or hydroxylamine with the compound represented by formula (8) in a solvent (preferably methanol) in the presence or absence of base (preferably imidazole).

Subsequently, a compound represented by formula (14) can be synthesized via the similar process as in Step 5. That is, the formula:

$$R^{12}—X$$

wherein $R^{12}$ and X have the same meanings as defined above, is used instead of the compound represented by the formula $R^3$—X in Step 5.

[Step 12]

According to a method described in the literature (Bioorganic & Medicinal Chemistry Letters, Vol. 8, p. 2427-2432, 1998), that is, by reducing a compound obtained by reacting the compound represented by formula (13) with substituted sulfonyl chloride (preferably, p-toluenesulfonylchloride) in a solvent (preferably a mixed solvent of pyridines and diethyl- ether) at −10° C. to room temperature, with a reducing agent (e.g., sodium borohydride) in a solvent (preferably ethylene glycol), or by reacting the compound in a solvent (preferably acetic acid) in the presence of a catalyst (preferably platinum oxide) in a hydrogen atmosphere at 1 to 10 atm., a compound represented by formula (15) can be synthesized.

[Step 13]

A compound represented by formula (16) in which $R^{14}$ is a methyl group can be synthesized by reacting the compound represented by formula (15) with formaldehyde in a solvent (preferably chloroform) in the presence of a formic acid.

Alternatively, a compound represented by formula (16) can be synthesized by reacting the compound represented by Formula (15) with a compound represented by the formula:

$$R^{14}—X$$

wherein $R^{14}$ has the same meaning as defined above, but is preferably a alkylsulfonyl group having 1 to 6 carbon atom(s), a alkanoyl group having 2 to 6 carbon atoms, or a benzyloxycarbonyl group; and X has the same meaning as defined above, in a proper solvent (preferably methanol, ethanol, dimethylformamide, dimethylsulfoxide, tetrahydrofuran, dichloromethane, or chloroform), if needed in the presence of a base (e.g., triethylamine, or diisopropylethylamine).

<Scheme 4>

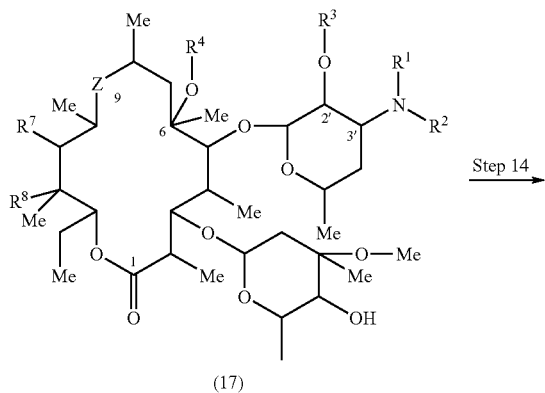

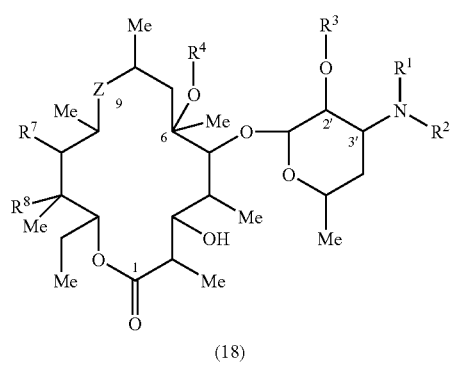

(18)

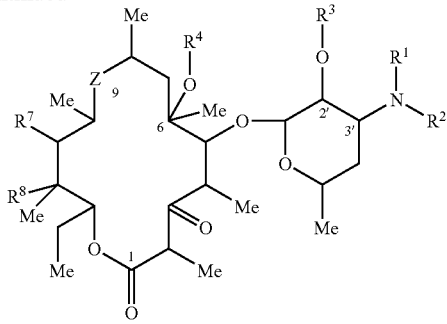

(19)

-continued

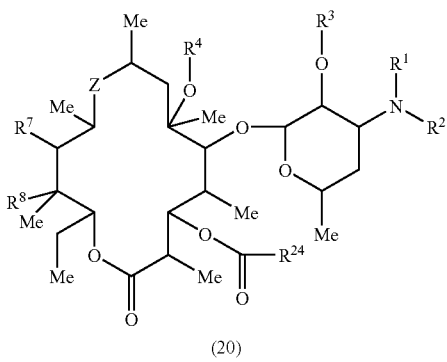

(20)

(symbols in the formula have the same meanings as defined above)

[Step 14]
A compound represented by formula (18) can be synthesized by reacting a compound represented by formula (17) with an acid (preferably hydrochloric acid) in a solvent (preferably methanol or ethanol).

[Step 15]
A compound represented by formula (19) can be synthesized by oxidizing the compound represented by formula (18) according to the method known in the art (e.g., Dess-Martin oxidation, Corey-Kim oxidation, Swern oxidation, and Jones oxidation, preferably Corey-Kim oxidation).

[Step 16]
A compound represented by formula (20) can be synthesized by the method described in a literature (Journal of Medicinal Chemistry, Vol. 44, p. 4027-4030, 2001), using the compound represented by formula (18), that is, by reacting the compound represented by formula (18) in a solvent (preferably dichloromethane) in the presence of a compound represented by the formula:

$R^{24}$—$CO_2H$ wherein $R^{24}$ has the same meaning as defined above, a base (preferably 4-dimethylaminopyridine) and a condensing agent (preferably, 1-(dimethylaminopropyl)-3-ethylcarbodiimide hydrochloride).

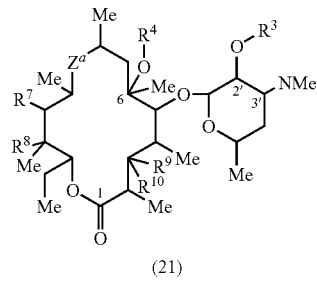

(21)

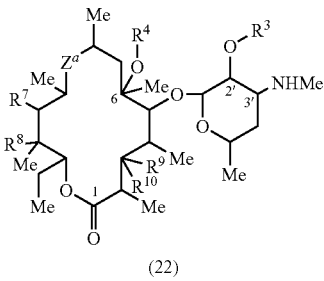

(22)

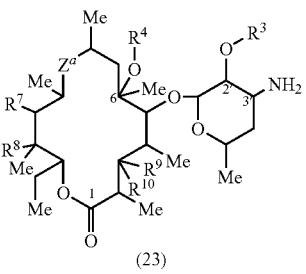

(23)

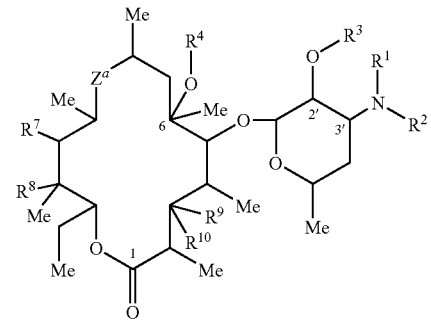

(40)

wherein $Z^a$ represents a group represented by the formula:

—$CR^5R^6$— or a group represented by the formula:

—C(=O)— other symbols have the same meanings as defined above.

[Step 17]

A compound represented by formula (22) can be synthesized by reacting a compound represented by formula (21) with a halogenating agent (e.g., iodine or N-bromosuccinimide), and if needed an alkali metal salt of an organic acid (e.g., sodium acetate) in a solvent (preferably methanol) at room temperature.

[Step 18]

A compound represented by formula (23) can be synthesized by the similar method described in a Patent Document (Japanese Patent Application Laid-Open No. 47-9129), that is, by reacting the compound represented by formula (22) with an alkali metal salt of alcohol (preferably sodium methoxide) and a halogenating agent (preferably iodine) in a solvent (preferably methanol) at room temperature.

[Step 19]

A compound represented by formula (40) can be synthesized by reacting the compound represented by formula (22) or formula (23) with a compound represented by the formula:

$R^{3c}$—CHO wherein $R^{3c}$ represents a group excluding a methylene group from $R^1$ or $R^2$, and a reducing agent (e.g., sodium triacetoxyborohydride, sodium cyanoborohydride, or sodium borohydride) in a proper solvent (preferably chloroform, dichloromethane, methanol, or ethanol) if needed an acid (e.g., acetic acid or formic acid). In the case that the compound represented by formula (23) is a starting material, 3'-N-monosubstitution compound and 3'-N-disubstitution compound can be produced separately by adjusting the amount of an aldehyde reagent to be used.

Alternatively, a compound represented by formula (40) can be synthesized by reacting the compound represented by formula (22) or formula (23) with a compound represented by the formula:

$R^1$—X, $R^2$—X wherein $R^1$ and $R^2$ have the same meanings as defined above, but are preferably an alkyl group having 1 to 6 carbon atom(s) which may have a substituent, an alkylsulfonyl group having 1 to 6 carbon atom(s), an alkanoyl group having 2 to 6 carbon atoms, or a benzyloxycarbonyl group, and X has the same meaning as defined above, in a proper solvent (preferably methanol, ethanol, dimethylformamide, dimethylsulfoxide, tetrahydrofuran, dichloromethane, or chloroform), if needed in the presence of a base (e.g., triethylamine, and diisopropylethylamine). In the case that the compound represented by formula (23) is a starting material, 3'-N-monosubstitution compound and 3'-N-disubstitution compound can be produced separately by adjusting the amount of a reagent to be used.

And when $R^1$ and $R^2$ form a ring together with the nitrogen atom to which each is bonded, a compound represented by formula (40) can be synthesized by reacting the compound represented by formula (23), with a compound by represented by the formula:

X—$R^{3d}$—X wherein $R^{3d}$ represents the formula:

—$(CH_2)_p$—Y—$(CH_2)_q$— p, q, Y and X have the same meanings as defined above, and if needed a base (e.g., triethylamine or diisopropylethylamine), or with a reducing agent (e.g., sodium triacetoxyborohydride, sodium cyanoborohydride, or sodium borohydride) and a compound represented by the formula:

OHC—$R^{3e}$—CHO wherein $R^{3e}$ represents a group in which an integer of 1 is subtracted from p and q of the structure represented by the formula:

—$(CH_2)_p$—Y—$(CH_2)_q$— with the proviso that p and q each independently represents an integer of 2 or 3, and Y has the same meanings as defined above, if needed in the presence of an acid (e.g., acetic acid or formic acid).

<Scheme 6>

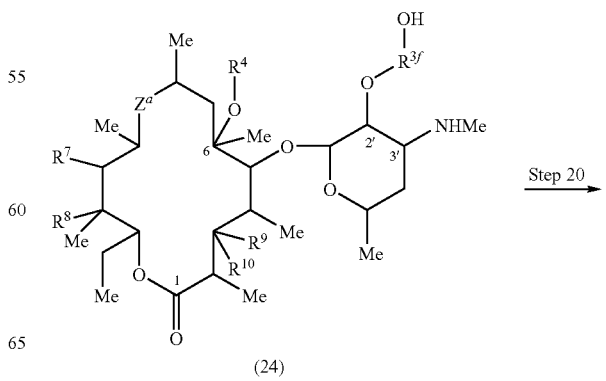

(24)

Step 20

-continued

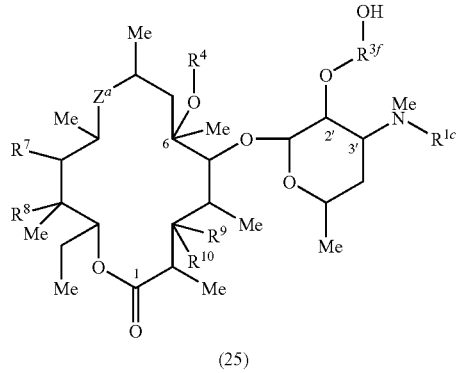

(25)

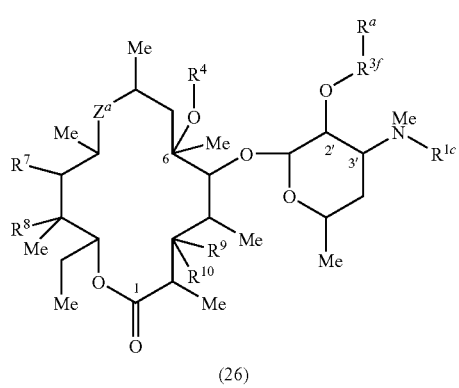

(26)

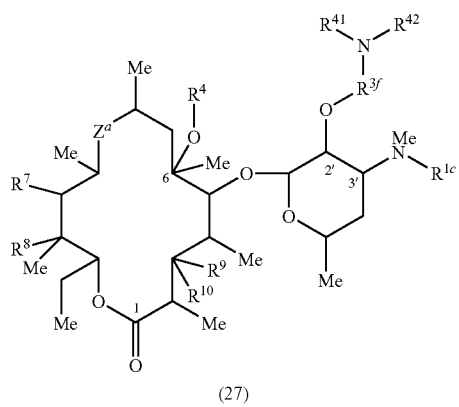

(27)

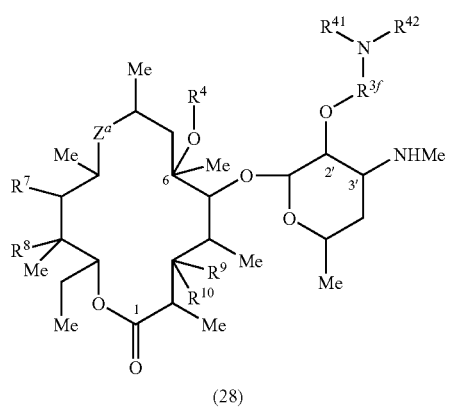

(28)

-continued

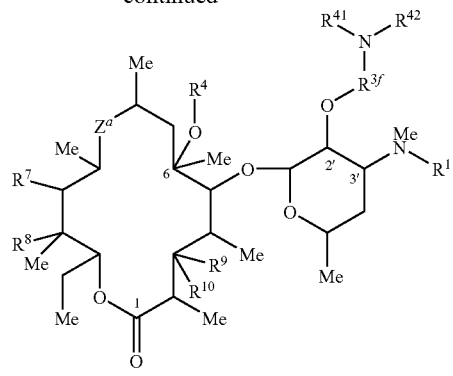

(29)

($R^{3f}$, $R^a$, and $R^{1c}$ are as defined below, and other symbols have the same meanings as defined above)

[Step 20]

A compound represented by formula (25) can be synthesized by reacting a compound represented by formula (24) wherein $R^{3f}$ represents a group excluding a hydroxy group from the group having a hydroxy group as a substituent in the above-mentioned $R^3$, preferably an unsubstituted alkyl group having 2 to 6 carbon atoms, with a compound represented by the formula:

$R^{1c}$—X wherein $R^{1c}$ is a group bonding with the nitrogen atom through a carbonyl group in the above-mentioned $R^1$, preferably a benzyloxycarbonyl group, X has the same meaning as defined above, in a solvent (preferably diethylether or chloroform) in the presence of a base (e.g., triethylamine, diisopropylamine, or saturated aqueous sodium bicarbonate solution) at room temperature.

[Step 21]

A compound represented by formula (26) can be synthesized by reacting the compound represented by formula (25) with a compound represented by the formula:

$R^a$—$X^a$ wherein $R^a$ represents a substituted sulfonyl group, or phosphoryl group (preferably a methanesulfonyl group); $X^a$ is a halogen atom, preferably a chlorine atom, in a proper solvent (preferably tetrahydrofuran) at room temperature, if needed in the presence of a base (preferably triethylamine). In the formula, when $R^a$ is a substituted sulfonyl group (preferably a methanesulfonyl group), a compound in which $R^a$ is substituted with a halogen atom (preferably a bromine atom) can be synthesized by reacting with a corresponding salt (preferably lithium bromide).

[Step 22]

A compound represented by formula (27) can be synthesized by reacting the compound represented by formula (26) with a compound represented by the formula:

$R^{41}R^{42}$NH wherein $R^{41}$ and $R^{42}$ have the same meanings as defined above, but preferably primary amine or secondary amine as $R^{41}R^{42}$NH, in a proper solvent (preferably methanol or ethanol), if needed in the presence of a base (e.g., triethylamine).

[Step 23]

When $R^{1c}$ of the compound represented by formula (27) is a benzyloxycarbonyl group, a compound represented by formula (28) can be synthesized by hydrogenating the compound represented by formula (27) using hydrogen source in the presence of a palladium catalyst (e.g., palladium black, palladium hydroxide carbon, or 5 to 10% palladium carbon, preferably 5% palladium carbon) in a solvent (preferably tetrahydrofuran) at room temperature. For the hydrogen source, for example, hydrogen gas, ammonium formate, sodium formate, or triethylammonium formate can be used.

Subsequently, the compound represented by formula (29) can be synthesized via Step 19.

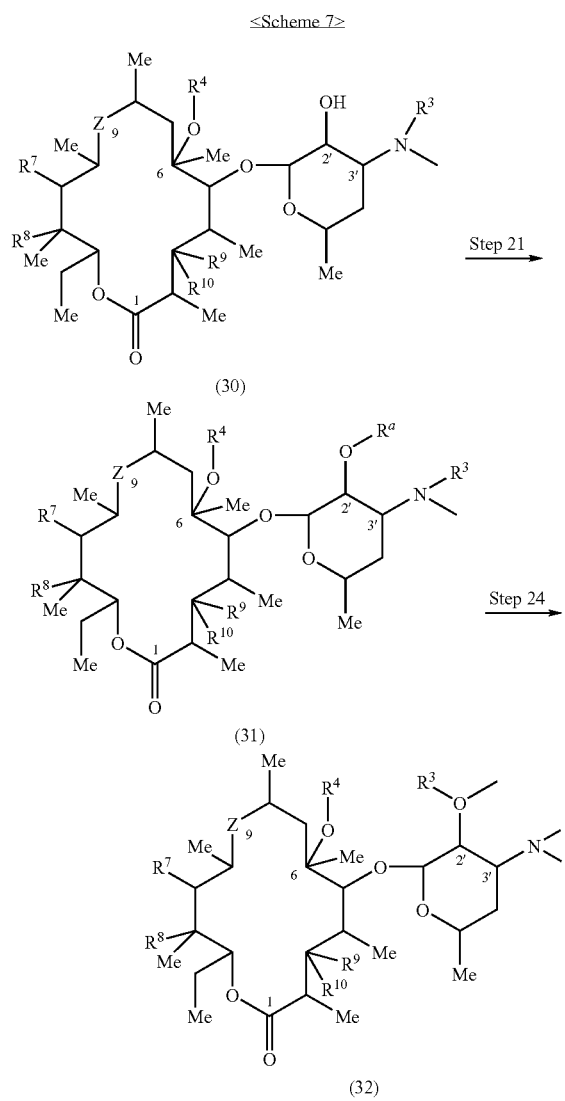

(symbols in the formula have the same meanings as defined above)

A compound (32) can be synthesized by the method described in a literature (Heterocycles, Vol. 31, No. 2, p. 305-319, 1990), using the compound represented by formula (30) wherein $R^3$ has the same meaning as defined above, but preferably a alkyl group having 1 to 6 carbon atom(s) which may have a substituent(s).

[Step 24]

A compound represented by formula (31) can be synthesized via Step 21 using the compound represented by formula (30). Herein, $R^a$—$X^a$ is preferred to be methanesulfonyl chloride.

At this time, when there are hydroxy groups or amino groups in formula (30), it is preferred to introducing a protecting group thereto by the law of the art. In particular, it is preferred to protect with acetyl groups when there are hydroxy groups. A compound represented by formula (32) can be synthesized by reacting the compound represented by formula (31) obtained in the above step with a compound represented by the formula:

$R^1R^2NH$ wherein $R^1$ and $R^2$ have the same meanings as defined above, under heating (preferably in the range of 70 to 100° C.) in a solvent (preferably N,N-dimethylformamide), if needed in the presence of a base, at room temperature.

Further, when there are protected hydroxy groups or amino groups in formula (30), a compound represented by formula (32) which has hydroxy groups or amino groups can be synthesized by deprotecting by the law of the art.

Besides, the compound represented by formula (32) can be also synthesized with the use of an amine whose protecting group is a benzyl group or an allyl group, instead of the formula:

$R^1R^2NH$ by conducting the same process as in Step 24, thereafter, deprotecting the benzyl group or the allyl group in accordance with Step 6, thereby conducting Step 19.

(symbols in the formula have the same meanings as defined above)

A compound represented by formula (35) can be synthesized by the method described in a patent (WO 03070174), using the compound represented by formula (33), that is, by conducting the following steps.

[Step 25]

A compound represented by formula (34) can be synthesized by reacting the compound represented by formula (33) with acetic anhydride as a solvent in the presence of a base (preferably triethylamine), followed by reacting in a solvent (preferably methanol or ethanol) at room temperature to 100° C. (preferably from room temperature to a boiling point).

The compound represented by formula (35) can be synthesized using the compound represented by formula (34) obtained in the above step, via Step 21 and Step 24.

[Step 28]

A compound represented by formula (38) can be synthesized by the method described in a literature (Tetrahedron Letters, Vol. 1, p. 29-30, 1972), using the compound represented by formula (41), that is, by converting to an amino group from an oxo group via a hydrazonyl group or an imino group.

In addition, a compound represented by formula (39) wherein $R^{13}$ and $R^{15}$ have the same meanings as defined above, can be synthesized using the compound represented by formula (38) via the similar process as in Step 19.

All of the compounds of the present invention are novel, and have not been described in a literature. However, they can be produced by the known methods which have been

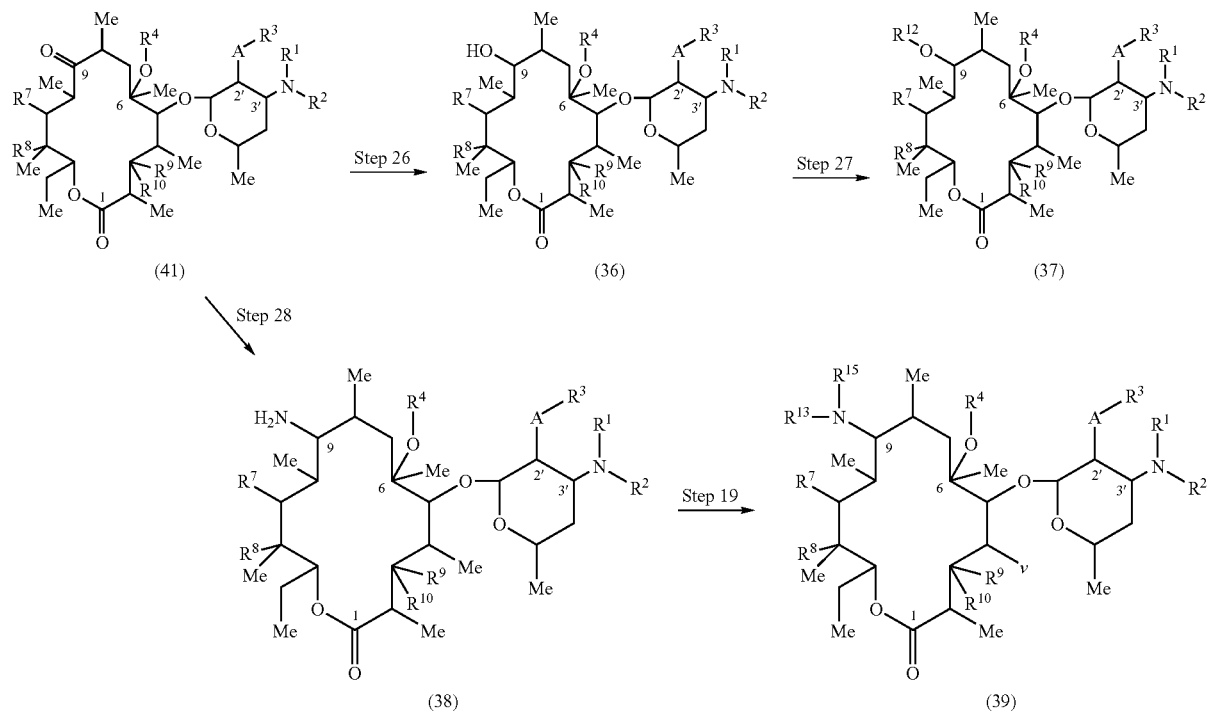

(symbols in the formula have the same meanings as defined above)

[Step 26]

A compound represented by formula (36) can be synthesized by reacting a compound represented by formula (41) with a reducing agent (preferably sodium triethylborohydride) in a solvent (preferably tetrahydrofuran).

[Step 27]

A compound represented by formula (37) can be synthesized by reacting the compound represented by formula (36) in a proper solvent (preferably chloroform or toluene) with a compound represented by the formula:

$R^{12}$—$X^a$ wherein $R^{12}$ has the same meaning as defined above, but preferably an alkanoyl group having 2 to 6 carbon atoms substituted with an amino group unsubstituted or substituted with 1 or 2 alkyl group(s) having 1 to 6 carbon atom(s); an $X^a$ has the same meaning as defined above, in the presence of a base (preferably triethylamine).

described in literatures, or by an analogous method thereof. Examples of the literature include Organic Functional Group Preparations, S. R. Sandler, et al.; Academic Press Inc., New York and London, 1968; Synthetic Organic Chemistry, S. R. Wagner, et al., John Wiley, 1961; Comprehensive Organic Transformations, R. C. Larock, 1989; Encyclopedia of Reagents for Organic Synthesis, L. A. Paquette, et al., 1995; Compendium of Organic Synthetic Methods; and the like.

Hydroxy groups, amino groups, carboxy groups and oxime groups in the compounds represented by formulae (1) to (41) of the present synthetic methods may be protected by known protecting groups in the field capable of selective removal. Deprotection at a desired stage provides a compound represented by formula (I) and an intermediate for the synthesis thereof. Examples of the known protecting group include silyl type protecting groups such as a trimethylsilyl group, a triethylsilyl group, and a tert-butyldimethylsilyl group; acyl type protecting groups such as an acetyl group, a propionyl group, and a benzoyl group; ether type protecting groups such as a benzyl group, a p-methoxybenzyl group, and a 2-chlorobenzyl group; and carbonate type protecting groups such as a benzyloxycarbonyl group, a tert-butyloxycarbonyl group. In addition, other protecting groups, which have been described in Protective Groups in Organic Synthesis (3$^{rd}$ ed., 1999, P. G. M. Wuts, T. Green) or the like, can be employed.

Moreover, some compounds of the present invention can lead to novel derivatives as synthetic intermediates.

Intermediates and target compounds in each production method mentioned above can be isolated and purified by a common purification method in organic synthetic chemistry field, for example, neutralization, filtration, extraction, washing, drying, concentration, recrystallization using a solvent such as ethyl acetate, ethyl acetate-hexane, isopropyl alcohol, ethanol, aqueous ethanol, acetone, and aqueous acetone, various chromatography, and the like. Intermediates can be used in the next reaction without purifying particularly.

Some compounds in Compound (I) may have an isomer, but the present invention includes its isomers and all possible isomers and their mixture.

Compounds and pharmaceutically acceptable salts thereof according to the present invention may exist in the form of an adduct with various solvents or water, and these adducts are included in the present invention.

Since compounds of the present invention have an inhibitory activity of MMP-9 production, and do not have an antibacterial activity, they are considered to be useful as a prophylactic and therapeutic drug against oncogenic angiogenesis, chronic rheumatoid arthritis, vascular intimal thickening after a percutaneous coronary transluminal angioplasty, vascular atherosclerosis, hemorrhagic apoplexy, acute myocardial infarction, chronic heart failure, aneurysm, lung cancer metastasis, adult respiratory distress syndrome, asthma, interstitial pulmonary fibrosis, chronic rhinosinusitis, bronchitis or chronic obstructive pulmonary disease (COPD).

The Process of the present invention is described in detail by the following examples and test examples which are not limiting the scope of the invention in any matter.

EXAMPLE 1

2'-O-(3-oxobut-1-enyl)-9-deoxo-9a-aza-9a-methyl-9a-homoerythromycin A 1.0 g of 9-deoxo-9a-aza-9a-methyl-9a-homoerythromycin A was dissolved in 4 ml of chloroform, 136 μl of 3-butyn-2-one was added, and the mixture was stirred at room temperature for 15 hours. The reaction solution was evaporated under reduced pressure, and the resulting residue was purified by silica gel chromatography (chloroform:methanol:ammonia water solution=49:1:0.1 to 24:1:0.1) to give 717 mg of the titled compound.

MS (ESI) m/z=817.7 [M+H]$^+$

13C NMR (126 MHz, CHLOROFORM-d) δ ppm 8.72, 11.33, 14.75, 16.22, 18.38, 21.26, 21.72, 22.19, 26.75, 27.65, 32.08, 34.80, 36.41, 40.93, 42.01, 42.44, 45.32, 49.57, 63.36, 65.64, 68.35, 70.05, 73.17, 74.35, 77.30, 77.51, 78.21, 83.22, 83.92, 94.52, 100.69, 108.54, 164.85, 197.54

EXAMPLE 2

11-amino-11-deoxy-2'-O— (3-oxobut-1-enyl)-6-O-methylerythromycin A 11,12-cyclic carbamate Using 500 mg of 11-amino-11-deoxy-6-O-methylerythromycin A 11,12,-cyclic carbamate described in a literature (Journal of Organic Chemistry, 1988, Vol. 53, No. 10, p. 2340-2345), a reaction was carried out in a similar manner described in Example 1 to give 330 mg of the titled compound.

MS (ESI) m/z=839.5 [M+H]$^+$

13C NMR (126 MHz, CHLOROFORM-d) δ ppm 8.76, 10.55, 13.51, 13.77, 15.74, 18.14, 18.75, 19.94, 21.3, 21.60, 22.08, 28.09, 34.81, 37.61, 39.43, 40.14, 40.83, 45.03, 45.54, 49.58, 50.12, 57.86, 63.33, 65.96, 68.45, 72.91, 75.89, 77.52, 77.84, 78.48, 80.40, 84.0, 95.68, 100.68, 158.44, 176.83, 197.60, 218.06

EXAMPLE 3

11-amino-11-deoxy-2'-O-(2-methoxycarbonylvinyl)-6-O-methylerythromycin A 11,12-cyclic carbamate Using 500 mg of 11-amino-11-deoxy-6-O-methylerythromycin A 11,12,-cyclic carbamate and using 70 μl of methyl propionate instead of 3-butyn-2-one, a reaction was carried out in a similar manner described in Example 1 to give 452 mg of the titled compound.

MS (ESI) m/z=857.6 [M+H]$^+$

1H NMR (600 MHz, CHLOROFORM-d) δ ppm 0.85 (t, J=7.57 Hz, 3H) 0.89 (d, J=7.79 Hz, 3H) 1.10-1.15 (m, 6H) 1.19 (d, J=7.34 Hz, 3H) 1.21 (d, J=5.96 Hz, 3H) 1.26 (s, 1H) 1.25 (s, 3H) 1.27 (d, J=6.42 Hz, 3H) 1.34 (s, 3H) 1.42 (s, 3H) 1.47-1.79 (m, 6H) 1.84-1.92 (m, 1H) 2.13-2.17 (m, 1H) 2.24-2.36 (m, 1H) 2.30 (s, 6H) 2.49-2.58 (m, 1H) 2.65-2.78 (m, 2H) 2.81-2.87 (m, 1H) 2.91 (s, 3H) 2.99-3.05 (m, 1H) 3.32 (s, 3H) 3.45-3.51 (m, 1H) 3.52-3.57 (m, 1H) 3.57-3.61 (m, 1H) 3.64-3.67 (m, 1H) 3.69 (s, 3H) 3.73-3.81 (m, 1H) 3.88-3.95 (m, 1H) 4.49-4.53 (m, 1H) 4.86-4.90 (m, 1H) 5.04-5.08 (m, 1H) 5.27 (d, J=11.92 Hz, 1H) 5.77 (s, 1H) 7.47 (d, J=12.38 Hz, 1H)

EXAMPLE 4

11-amino-11-deoxy-2'-O-(2-methoxycarbonylethyl)-6-O-methylerythromycin A 11,12-cyclic carbamate 452 mg of the compound obtained in Example 3 was dissolved in methanol, 45 mg of 5% palladium-carbon was added, and the mixture was stirred in a hydrogen atmosphere at 1 atm at room temperature for 15 hours. After filtering the reaction mixture, the filtrate was evaporated under reduced pressure, and the resulting residue was purified by silica gel chromatography (chloroform:methanol:ammonia water solution=49:1:0.1 to 24:1:0.1) to give 170 mg of the titled compound.

MS (ESI) m/z=857.6 [M+H]$^+$

13C NMR (126 MHz, CHLOROFORM-d) δ ppm 8.64, 10.57, 13.49, 13.78, 15.79, 18.18, 18.82, 20.02, 21.47, 21.6, 22.12, 32.49, 34.80, 35.42, 37.61, 39.65, 40.62, 41.23, 45.03, 45.78, 49.52, 50.11, 51.66, 57.86, 64.45, 65.83, 67.65, 68.29, 72.75, 75.82, 77.99, 78.75, 79.74, 84.00, 95.71, 102.81, 172.24, 177.00

EXAMPLE 5

2'-O-(2-methoxycarbonylvinyl)-9-deoxo-9a-aza-9a-methyl-9a-homoerythromycin A

Using 11.0 g of 9-deoxo-9a-aza-9a-methyl-9a-homoerythromycin A, a reaction was carried out in a similar manner described in Example 3 to give 628 mg of the titled compound.

MS (ESI) m/z=833.6 [M+H]$^+$

1H NMR (600 MHz, CHLOROFORM-d) δ ppm 0.85-0.90 (m, 6H) 0.92 (d, J=6.88 Hz, 3H) 1.06 (s, 3H) 1.08 (d, J=6.88 Hz, 3H) 1.18 (d, J=7.34 Hz, 3H) 1.20-1.36 (m, 14H) 1.40-1.51 (m, 1H) 1.54-1.61 (m, 1H) 1.62-1.67 (m, 1H) 1.70-1.78 (m, 1H) 1.82-2.12 (m, 5H) 2.31 (s, 6H) 2.41 (s, 3H) 2.49-2.54 (m, 1H) 2.64-2.76 (m, 3H) 2.79-2.83 (m, 1H) 3.00-3.06 (m, 1H) 3.33 (s, 3H) 3.49-3.56 (m, 1H) 3.57-3.68 (m, 3H) 3.67 (s, 3H) 3.98-4.05 (m, 1H) 4.24-4.28 (m, 1H) 4.40-4.45 (m, 1H) 4.51-4.55 (m, 1H) 4.64-4.70 (m, 1H) 5.07-5.10 (m, 1H) 5.27 (d, J=12.15 Hz, 1H) 7.48 (d, J=12.15 Hz, 1H) 8.92 (br. s., 1H)

EXAMPLE 6

2'-O-(2-methoxycarbonylethyl)-9-deoxo-9a-aza-9a-methyl-9a-homoerythromycin A

Using 628 mg of the compound obtained in Example 5, a reaction was carried out in a similar manner described in Example 4 to give 372 mg of the titled compound.
MS (ESI) m/z=835.6 [M+H]$^+$
13C NMR (126 MHz, CHLOROFORM-d) δ ppm 7.89, 10.36, 13.46, 15.42, 18.24, 19.45, 21.12, 22.20, 28.14, 32.14, 35.77, 37.42, 39.22, 40.92, 44.27, 45.39, 49.65, 58.33, 63.05, 69.04, 75.88, 77.86, 78.03, 81.51, 83.28, 84.01, 99.72, 108.21, 158.56, 164.30, 217.68

EXAMPLE 7

11-amino-11-deoxy-3'-N-demethyl-3'-N-(2-(1,3-dioxo-1,3-dihydroisoindol-2-yl)ethyl)-6-O-methyl-erythromycin A 11,12-cyclic carbamate (1) 2.5 g of 11-amino-11-deoxy-6-O-methylerythromycin A 11,12-cyclic carbamate was dissolved in methanol, to which 2.65 g of sodium acetate and 2.46 g of iodine were added, and the mixture was stirred at room temperature for 4 hours. To the reaction solution were added a 2N aqueous sodium thiosulfate solution and a 2N aqueous sodium hydroxide solution, and the mixture was extracted with ethyl acetate. The organic layer was washed with water and saturated brine, dried over anhydrous magnesium sulfate, and filtered. The filtrate was evaporated under reduced pressure, and the resulting residue was purified by silica gel column chromatography (chloroform:methanol:ammonia water solution-91:9:0.9 to 90:10:1) to give 2.0 g of 3'-N-demethylated compound.

(2) 400 mg of the compound obtained in the above (1) was dissolved in chloroform. 129 mg of phthalimideacetaldehyde prepared by the procedure described in a literature (Tetrahedron Letters, 2001, Vol. 42, p. 315) and 134 mg of sodium triacetoxyborohydride were added in this order, and then the mixture was stirred at room temperature for 14 hours.

A saturated aqueous sodium bicarbonate solution was added to the reaction mixture, and the mixture was extracted with chloroform. After post-treating by the common method, the resulting residue was purified by silica gel column chromatography (acetone:hexane:triethylamine=10:10:0.2) to give 510 mg of the titled compound.
MS (ESI) m/z=932.6 [M+H]$^+$
13C NMR (126 MHz, CHLOROFORM-d) δ ppm 9.02, 10.52, 13.36, 13.79, 15.86, 18.23, 18.70, 19.89, 21.48, 21.59, 22.06, 30.41, 34.86, 36.81, 36.98, 37.49, 39.66, 40.22, 45.17, 45.53, 49.54, 50.22, 52.27, 57.81, 65.36, 65.84, 68.74, 71.02, 72.75, 75.72, 77.89, 78.06, 78.63, 80.60, 84.00, 95.96, 103.02, 123.41, 132.08, 134.12, 158.47, 168.54, 176.82, 218.28

EXAMPLE 8

11-amino-11-deoxy-3'-N-demethyl-3'-N-(2-aminoethyl)-6-O-methylerythromycin A 11,12-cyclic carbamate 510 mg of the compound obtained in Example 7 was dissolved in methanol, 80 µl of hydrazine was added, and the mixture was stirred at room temperature for 14 hours. The reaction solution was evaporated under reduced pressure, and the resulting residue was purified by silica gel column chromatography (chloroform:methanol:ammonia water solution=10:1:0.1) to give 280 mg of the titled compound.
MS (ESI) m/z=802.6 [M+H]$^+$
1H NMR (600 MHz, CHLOROFORM-d) δ ppm 0.85 (t, J=7.34 Hz, 3H) 1.03-1.31 (m, 22H) 1.34-1.43 (m, 6H) 1.47-1.60 (m, 2H) 1.62-1.94 (m, 5H) 2.28 (s, 3H) 2.32-2.43 (m, 2H) 2.44-2.65 (m, 3H) 2.73-2.89 (m, 4H) 2.93 (s, 3H) 2.99-3.04 (m, 1H) 3.19-3.24 (m, 1H) 3.31 (s, 3H) 3.42-3.50 (m, 1H) 3.58-3.62 (m, 1H) 3.67-3.68 (m, 1H) 3.75-3.80 (m, 1H) 3.95-4.02 (m, 1H) 4.38-4.42 (m, 1H) 4.87-4.91 (m, 1H) 5.06-5.11 (m, 1H) 5.77 (s, 1H)

EXAMPLE 9

11-amino-11-deoxy-3'-N-demethyl-3'-N-(2-dimethylaminoethyl)-6-O-methylerythromycin A 11,12-cyclic carbamate 270 mg of the compound obtained in Example 8 was dissolved in chloroform. 100 µl of 37% aqueous formaldehyde solution and 220 mg of sodium triacetoxyborohydride were added in this order, and then the mixture was stirred at room temperature for 14 hours. To the reaction solution was added a saturated aqueous sodium bicarbonate solution, and the mixture was extracted with chloroform. The organic layer was washed with saturated brine, dried over anhydrous magnesium sulfate, and filtered. The filtrate was evaporated under reduced pressure, and the resulting residue was purified by silica gel column chromatography (acetone:hexane:triethylamine=10:10:0.2) to give 199 mg of the titled compound.
MS (ESI) m/z=830.6 [M+H]$^+$
13C NMR (126 MHz, CHLOROFORM-d) δ ppm 7.89, 10.36, 13.46, 15.42, 18.24, 19.45, 21.12, 22.20, 28.14, 32.14, 35.77, 37.42, 39.22, 40.92, 44.27, 45.39, 49.65, 58.33, 63.05, 69.04, 75.88, 77.86, 78.03, 81.51, 83.28, 84.01, 99.72, 108.21, 158.56, 164.30, 217.68

EXAMPLE 10

3'-N-demethyl-3'-N-(2-aminoethyl)-9-deoxo-9a-aza-9a-methyl-9a-homoerythromycin A (1) Using 780 mg of 9-deoxo-9a-aza-9a-methyl-9a-homoerythromycin A, a reaction was carried out in a similar manner described in Example 7 (1) and (2) to give 294 mg of a 3'-N-ethyl phthalimide compound.
(2) Using 261 mg of the compound obtained in the above (1), a reaction was carried out in a similar manner described in Example 8 to give 96 mg of the titled compound.
1H NMR (600 MHz, CHLOROFORM-d) δ ppm 0.65-0.78 (m, 3H) 0.82-0.93 (m, 3H) 0.95-1.38 (m, 32H) 1.38-1.55 (m, 1H) 1.60-2.10 (m, 8H) 2.16 (s, 3H) 2.20-3.07 (m, 11H) 3.15-3.37 (m, 5H) 3.38-3.50 (m, 1H) 3.50-3.61 (m, 1H) 4.00-4.19 (m, 1H) 4.26-4.51 (m, 2H) 4.60-4.71 (m, 1H) 4.95-5.09 (m, 1H)

EXAMPLE 11

3'-N-demethyl-3'-N-(2-dimethylaminoethyl)-9-deoxo-9a-aza-9a-methyl-9a-homoerythromycin A Using 96 mg of the compound obtained in Example 10, a reaction was carried out in a similar manner described in Example 9 to give 60 mg of the titled compound.

MS (ESI) m/z=806.6 [M+H]$^+$

13C NMR (126 MHz, CHLOROFORM-d) δ ppm 6.70, 8.98, 11.44, 14.89, 18.26, 21.51, 21.67, 22.17, 26.88, 30.62, 34.77, 37.51, 42.83, 45.50, 46.19, 49.57, 65.61, 68.79, 70.98, 73.05, 73.79, 77.80, 78.36, 103.28

EXAMPLE 12

11-amino-11-deoxy-5-O-(2'-O-(2-methoxycarbonyl-ethyl)desosaminyl)-6-O-methylerythronolide A 11,12-cyclic carbamate 80 mg of the compound obtained in Example 4 was dissolved in methanol, 1N aqueous hydrochloride solution was added, and the mixture was stirred at 60° C. for 5 hours. The reaction solution was evaporated under reduced pressure. To the resulting residue were added water and ethyl acetate followed by separation A 2N aqueous sodium hydroxide solution was added to the aqueous layer to be adjusted to be basic, and the mixture was extracted with ethyl acetate. The organic layer was washed with saturated brine, dried over anhydrous magnesium sulfate, and filtered. The filtrate was evaporated under reduced pressure, and the resulting residue was purified by silica gel column chromatography (acetone:hexane:triethylamine=10:10:0.2) to give 44 mg of the titled compound.

MS (ESI) m/z=701.4 [M+H]$^+$

13C NMR (126 MHz, CHLOROFORM-d) δ ppm 7.89, 10.36, 13.46, 15.42, 18.24, 19.45, 21.12, 22.20, 28.14, 32.14, 35.77, 37.42, 39.22, 40.92, 44.27, 45.39, 49.65, 58.33, 63.05, 69.04, 75.88, 77.86, 78.03, 81.51, 83.28, 84.01, 99.72, 108.21, 158.56, 164.30, 217.68

EXAMPLE 13

11-amino-11-deoxy-3'-N-demethyl-3'-N-benzyl-6-O-methylerythromycin A 11,12-cyclic carbamate 300 mg of the compound obtained in Example 7 (1) was dissolved in chloroform. 48 μl of benzaldehyde and 101 mg of sodium triacetoxyborohydride were added in this order, and the mixture was stirred at room temperature for 14 hours. To the reaction solution was added a saturated aqueous sodium bicarbonate solution, and the mixture was extracted with chloroform. The organic layer was washed with saturated brine, then dried over anhydrous magnesium sulfate, and filtered. The filtrate was evaporated under reduced pressure, and the resulting residue was purified by silica gel column chromatography (acetone:hexane:triethylamine=10:10:0.2) to give 130 mg of the titled compound.

MS (ESI) m/z=849.5 [M+H]$^+$

13C NMR (126 MHz, CHLOROFORM-d) δ ppm 9.04, 10.52, 13.36, 13.79, 15.86, 18.23, 18.62, 19.93, 21.54, 21.57, 22.07, 29.30, 34.80, 36.85, 37.49, 39.61, 40.11, 45.18, 45.50, 49.50, 50.22, 57.82, 58.07, 63.70, 65.76, 68.85, 70.69, 72.60, 75.72, 77.81, 77.96, 78.56, 80.69, 84.00, 95.80, 103.00, 127.41, 128.55, 128.94, 138.80, 158.47, 176.74, 218.28

EXAMPLE 14

11-amino-11-deoxy-5-O-(2'-O-(3-oxobut-1-enyl) desosaminyl)-6-O-methylerythronolide A 11,12-cyclic carbamate (1) 20 g of 11-amino-11-deoxy-2'-O-acetyl-5-O-desosaminyl-6-O-methylerythronolide A 11,12-cyclic carbamate described in a literature (Journal of Medicinal Chemistry, 2003, Vol. 46, No. 13, p. 2706-2715) was dissolved in 600 ml of methanol, and the mixture was stirred under reflux for 8 hours. The reaction solution was evaporated under reduced pressure, a saturated aqueous sodium bicarbonate solution was added to the resulting residue, and the mixture was extracted with ethyl acetate. The organic layer was washed with saturated brine, dried over anhydrous magnesium sulfate, and filtered. The filtrate was evaporated under reduced pressure to give 24 g of a 2'-OH compound.

(2) Using 2.0 g of the compound obtained in the above (1), a reaction was carried out in a similar manner described in Example 1 to give 1.8 g of the titled compound.

MS (ESI) m/z=683.4 [M+H]$^+$

13C NMR (126 MHz, CHLOROFORM-d) δ ppm 7.89, 10.36, 13.46, 15.42, 18.24, 19.45, 21.12, 22.20, 28.14, 32.14, 35.77, 37.42, 39.22, 40.92, 44.27, 45.39, 49.65, 58.33, 63.05, 69.04, 75.88, 77.86, 78.03, 81.5, 83.28, 84.01, 99.72, 108.21, 158.56, 164.30, 217.68

EXAMPLE 15

11-amino-11-deoxy-3-O-(2-pyridyl)acetyl-5-O-(2'-O-(3-oxobut-1-enyl)desosaminyl)-6-O-methylerythronolide A 11,12-cyclic carbamate (1) 6.1 g of 11-amino-11-deoxy-2'-O-acetyl-5-O-desosaminyl-6-O-methylerythronolide A 11,12-cyclic carbamate described in a literature (Journal of Medicinal Chemistry, 2003, Vol. 46, No. 13, p. 2706-2715) was dissolved in 60 ml of chloroform, 3.2 g of 2-pyridyl acetate hydrochloride, 3.57 g of 1-[3-(dimethylamino)propyl]-3-ethylcarbodiimide hydrochloride and 1.14 g of 4-dimethylaminopyridine were added in this order, and the mixture was stirred at room temperature for 1 hour. The reaction solution was evaporated under reduced pressure, a 2N aqueous sodium hydroxide solution was added to the resulting residue, and the mixture was extracted with ethyl acetate. The organic layer was washed with saturated aqueous ammonium chloride solution and then saturated brine, dried over anhydrous magnesium sulfate, and filtered. The filtrate was evaporated under reduced pressure to give 7.26 g of a 3-O-(2-pyridyl)acetyl compound.

(2) 7.26 g of the compound obtained in the above (1) was dissolved in 500 ml of methanol, and the mixture was stirred at room temperature for 62 hours. The reaction solution was evaporated under reduced pressure, and the resulting residue was purified by silica gel column chromatography (chloroform:methanol:ammonia water solution=20:1:0.1) to give 6.8 g of a 2'-OH compound.

(3) Using 1.0 g of the compound obtained in the above (2), a reaction was carried out in a similar manner described in Example 1 to give 739 mg of the titled compound.

MS (ESI) m/z=802.4 [M+H]$^+$

13C NMR (126 MHz, CHLOROFORM-d) δ ppm 8.86, 10.30, 13.43, 13.87, 15.43, 18.24, 19.52, 20.80, 22.03, 27.96, 31.88, 36.25, 37.42, 38.99, 40.90, 43.25, 44.03, 45.15, 49.91, 58.12, 62.74, 69.01, 76.15, 77.92, 78.47, 79.97, 83.37, 83.88, 100.10, 108.33, 122.48, 124.31, 136.71, 149.44, 153.84, 158.44, 164.44, 170.06, 174.18, 197.42, 217.62

EXAMPLE 16

3'-N-demethyl-3'-N-benzyl-9-deoxo-9a-aza-9a-methyl-9a-homoerythromycin A (1) Using 5.0 g of 9-deoxo-9a-aza-9a-methyl-9a-homoerythromycin A, a reaction was carried out in a similar manner described in Example 7 (1) to give 2.5 g of 3'-N-demethyl-9-deoxo-9a-aza-9a-methyl-9a-homoerythromycin A.

(2) Using 500 mg of the compound obtained in the above (1), a reaction was carried out in a similar manner described in Example 13 to give 200 mg of the titled compound.

MS (ESI) m/z=824.5 [M+H]$^+$

13C NMR (126 MHz, CHLOROFORM-d) δ ppm 6.56, 8.86, 11.06, 15.05, 15.95, 18.15, 21.46, 21.53, 21.60, 22.05, 26.34, 27.36, 29.67, 34.58, 35.3, 36.9, 41.75, 42.57, 45.72, 49.52, 58.13, 64.28, 65.89, 68.86, 70.64, 72.79, 73.58, 78.12, 78.27, 78.41, 79.56, 80.95, 83.82, 94.73, 103.29, 127.31, 128.51, 128.90, 138.95, 179.68

EXAMPLE 17

3-O-(3-pyridyl)acetyl-5-O-(2'-O-(3-oxobut-1-enyl)desosaminyl)-9-deoxo-9a-aza-9a-methyl-9a-homoerythronolide A (1) Using 10 g of 9-deoxo-9a-aza-9a-methyl-9a-homoerythromycin A, a reaction was carried out in a similar manner described in Example 12 to give 8.8 g of a 3-OH compound.

(2) 8.8 g of the compound obtained in the above (1) was suspended in 100 ml of acetone, 1.4 ml of acetic anhydride was added, and the mixture was stirred at room temperature for 17 hours. The reaction solution was evaporated under reduced pressure, a saturated aqueous sodium bicarbonate solution was added to the resulting residue, and the mixture was extracted with chloroform. The organic layer was dried over anhydrous sodium sulfate, and filtered. The filtrate was evaporated under reduced pressure to give 9.6 g of a 2'-O-acetyl compound.

(3) Using the compound obtained in the above (2) and using 3-pyridyl acetate hydrochloride instead of 2-pyridyl acetate hydrochloride, a reaction was carried out in a similar manner described in Example 15 (1) and (2) to give 3.9 g of a 3-O-(3-pyridyl)acetyl compound.

(4) Using 1.0 g of the compound obtained in the above (3), a reaction was carried out in a similar manner described in Example 1 to give 410 mg of the titled compound.

MS (ESI) m/z=778.5 [M+H]$^+$

13C NMR (126 MHz, CHLOROFORM-d) δ ppm 7.91, 9.15, 11.10, 15.86, 16.02, 20.82, 21.71, 26.43, 26.53, 27.75, 31.63, 36.25, 36.86, 38.92, 40.96, 42.17, 43.21, 62.43, 63.45, 69.18, 70.81, 73.04, 74.23, 75.78, 78.36, 80.00, 83.32, 84.98, 100.29, 108.57, 123.60, 129.40, 137.06, 149.02, 150.44, 164.55, 169.68, 176.06, 197.41

EXAMPLE 18

2'-O-(3-oxobut-1-enyl)-6-O-methylerythromycin B

Using 1.0 g of 6-O-methylerythromycin B described in a literature (The Journal of Antibiotics, 1990, Vol. 43, No. 5, p. 544-549), a reaction was carried out in a similar manner described in Example 1 to give 995 mg of the titled compound.

MS (ESI) m/z=800.5 [M+H]$^+$

13C NMR (126 MHz, CHLOROFORM-d) δ ppm 8.99, 9.25, 9.96, 10.56, 15.97, 18.46, 18.84, 20.13, 21.37, 21.60, 25.79, 28.08, 35.12, 37.99, 38.62, 38.76, 40.29, 40.83, 44.90, 45.32, 49.54, 50.92, 63.51, 68.26, 69.67, 72.96, 75.00, 77.3, 77.85, 78.65, 78.72, 80.71, 96.07, 100.41, 176.06, 197.53, 219.57

EXAMPLE 19

3'-N-demethyl-3'-N-benzyl-6-O-methylerythromycin B

Using 5.0 g of 6-O-methylerythromycin B, a reaction was carried out in a similar manner described in Example 7 (1) and Example 13 to give 690 mg of the titled compound.

MS (ESI) m/z=822.4 [M+H]$^+$

13C NMR (126 MHz, CHLOROFORM-d) δ ppm 8.63, 8.71, 9.44, 10.07, 15.57, 17.97, 18.23, 19.57, 21.01, 21.09, 25.31, 28.86, 34.54, 36.37, 37.32, 38.20, 38.26, 39.80, 44.44, 45.01, 48.97, 50.48, 57.51, 63.21, 65.29, 68.14, 69.11, 70.35, 72.12, 74.33, 77.52, 78.24, 78.30, 80.30, 95.60, 102.18, 126.86, 128.02, 128.44, 138.33, 175.54, 219.28

EXAMPLE 20

5-O-(3'-N-demethyl-3'-N-benzyl)desosaminyl-9-deoxo-9a-aza-9a-methyl-9a-homoerythronolide A Using 200 mg of the compound obtained in Example 16, a reaction was carried out in a similar manner described in Example 12 to give 175 mg of the titled compound.

MS (ESI) m/z=667.3 [M+H]$^+$

1H NMR (600 MHz, CHLOROFORM-d) δ ppm 0.84-0.93 (m, 6H) 1.01-1.14 (m, 9H) 1.20-1.81 (m, 15H) 1.84-1.94 (m, 2H) 2.00-2.08 (m, 1H) 2.14 (s, 3H) 2.23-2.32 (m, 1H) 2.36 (s, 3H) 2.48-2.54 (m, 1H) 2.58-2.77 (m, 4H) 3.36-3.44 (m, 2H) 3.52-3.60 (m, 2H) 3.61-3.73 (m, 3H) 3.75-3.81 (m, 1H) 3.92-4.02 (m, 2H) 4.46 (d, J=7.34 Hz, 1H) 4.67-4.72 (m, 1H) 7.20-7.35 (m, 5H)

EXAMPLE 21

5-O-(3'-N-demethyl-3'-N-benzyl)desosaminyl-6-O-methylerythronolide B

Using 350 mg of the compound obtained in Example 19, a reaction was carried out in a similar manner described in Example 12 to give 181 mg of the titled compound.

MS (ESI) m/z=650.3 [M+H]$^+$

13C NMR (126 MHz, CHLOROFORM-d) δ ppm 8.34, 9.28, 10.07, 10.50, 15.19, 18.03, 19.02, 21.35, 26.29, 36.04, 36.56, 38.33, 38.39, 40.35, 44.62, 45.62, 49.80, 58.20, 70.20, 74.75, 78.66, 79.16, 128.65, 175.42, 219.68

EXAMPLE 22

11-amino-11-deoxy-5-O-(3'-N-demethyl-3'-N-benzyl)desosaminyl-6-O-methylerythronolide A 11,12-cyclic carbamate (1) Using 5.17 g of the compound obtained in Example 14 (1), a reaction was carried out in a similar manner described in Example 7 (1) to give 2.0 g of a 3'-N-demethyl compound.

(2) Using 1.0 g of the compound obtained in the above (1), a reaction was carried out in a similar manner described in Example 13 to give 690 mg of the titled compound.

MS (ESI) m/z=691.3 [M+H]$^+$

13C NMR (126 MHz, CHLOROFORM-d) δ ppm 8.47, 10.33, 13.46, 14.00, 15.35, 18.15, 18.74, 21.35, 22.27, 29.15, 36.10, 36.56, 37.45, 39.20, 44.74, 45.52, 49.46, 58.16, 58.48, 65.08, 70.50, 70.77, 75.68, 78.11, 79.11, 84.12, 89.30, 107.18, 127.08, 127.52, 128.64, 128.73, 128.77, 138.63, 158.63, 175.50, 217.72,

EXAMPLE 23

11-amino-11-deoxy-3-O-(4-methoxyphenyl)acetyl-5-O-(3'-N-demethyl-3'-N-benzyl)desosaminyl-6-O-methylerythronolide A 11,12-cyclic carbamate 115 mg of the titled compound was prepared from 1.5 g of the compound obtained in Example 22 in a similar manner described in Ex. 17(2) (obtained 2'-acetyl compound), successively in a similar manner described in Ex15(1) (2) using 721 mg of 4-methoxyphenylacetic acid instead of 2-pyridyl acetate hydrochloride.

MS (ESI) m/z=839.4 [M+H]$^+$

13C NMR (126 MHz, CHLOROFORM-d) δ ppm 9.11, 10.25, 13.90, 15.07, 18.26, 19.45, 21.20, 22.04, 29.22, 36.47, 36.90, 37.37, 39.16, 40.73, 43.39, 45.29, 49.84, 55.34, 58.10, 58.16, 64.24, 69.57, 70.23, 75.97, 78.03, 78.31, 82.17, 83.92, 103.64, 113.99, 125.71, 127.45, 128.76, 130.58, 138.76, 158.49, 158.89, 171.49, 174.26, 217.78

EXAMPLE 24

2'-O-(3-phenylpropyl)-6-O-methylerythromycin A (1) 5.0 g of 6-O-methylerythromycin was suspended in 25 ml of N,N-dimethylformamide, 2.91 ml of allyl bromide was added, and the mixture was stirred at room temperature for 75 minutes. Under stirring, to the reaction solution 90 ml of ethyl acetate and 90 ml of hexane were added, and the mixture was stirred at room temperature for 30 minutes. The produced solid substance was collected by filtration to give 5.77 g of a 6-O-methylerythromycin A 3'-N-allyl quaternary salt.

(2) 11.0 g of the compound obtained in the above (1) was dissolved in 10 ml of N,N-dimethylformamide, 0.26 ml of 1-bromo-3-phenylpropane and 69 mg of sodium hydride were added in this order, and the mixture was stirred at room temperature for 45 minutes. Water and ethyl acetate were added to the reaction solution followed by separation, and the aqueous layer was extracted with chloroform. The organic layer was evaporated under reduced pressure to give 1.0 g of a 2'-O-(3-phenylpropyl) compound.

(3) 1.0 g of the compound obtained in the above (2) was dissolved in a mixed solution of 4 ml of THF and 1 ml of water, 23 mg of palladium acetate (II), 107 mg of triphenylphosphine, 0.27 ml of formic acid and 0.99 ml of triethylamine were added, and the mixture was stirred under reflux for 3 hours. A 2N aqueous sodium hydroxide solution was added to the reaction solution, and the mixture was extracted with ethyl acetate. The organic layer was washed with saturated brine, dried over anhydrous magnesium sulfate, and filtered. The filtrate was evaporated under reduced pressure, and the resulting residue was purified by silica gel chromatography (chloroform:methanol:ammonia water solution=20:1:0.1). The resulting residue was recrystallized from 2-propanol to give 210 mg of the titled compound.

MS (ESI) m/z=866.4 [M+H]$^+$

13C NMR (126 MHz, CHLOROFORM-d) δ ppm 8.68, 10.73, 12.38, 16.02, 16.21, 18.01, 18.90, 20.05, 21.17, 21.55, 21.61, 31.90, 32.58, 34.96, 37.48, 39.33, 39.76, 41.35, 45.08, 45.42, 49.54, 50.55, 64.62, 65.87, 68.13, 69.17, 71.86, 72.74, 74.32, 76.70, 78.00, 78.04, 78.56, 79.95, 80.12, 95.89, 102.89, 125.79, 128.36, 128.47, 135.25, 142.46, 176.20, 220.99

EXAMPLE 25

2'-O-(3-oxobut-1-enyl)-6-O-methylerythromycin A

Using 2.0 g of 6-O-methylerythromycin A, a reaction was carried out in a similar manner described in Example 1 to give 1.55 g of the titled compound.

MS (ESI) m/z=815.5 [M−H]$^+$

13C NMR (126 MHz, CHLOROFORM-d) δ ppm 10.70, 12.38, 15.97, 16.17, 18.02, 18.81, 19.94, 21.12, 21.34, 21.59, 28.13, 31.39, 34.96, 37.43, 39.20, 39.24, 40.79, 45.17, 49.56, 50.60, 63.41, 65.99, 68.33, 69.20, 72.91, 74.30, 77.88, 78.15, 80.80, 83.72, 95.91, 100.55, 107.86, 164.49, 175.98, 197.63, 220.99

EXAMPLE 26

2'-O-(3-oxobut-1-enyl)-3'-N-demethyl-6-O-methyl-erythromycin A

Using 1.0 g of the compound obtained in Example 25, a reaction was carried out in a similar manner described in Example 7 (1) to give 140 mg of the titled compound.

MS (ESI) m/z=824.3 [M+H]$^+$

13C NMR (126 MHz, CHLOROFORM-d) δ ppm 10.67, 12.41, 16.17, 18.71, 19.83, 21.12, 21.57, 29.36, 31.02, 31.83, 35.01, 37.42, 38.77, 39.27, 45.08, 45.17, 49.58, 50.68, 53.89, 66.35, 68.14, 69.21, 73.00, 74.29, 77.68, 78.26, 78.61, 81.83, 96.19, 102.73, 175.60, 195.74, 220.80

EXAMPLE 27

5-O-(2'-O-(2-methoxycarbonylvinyl)desosaminyl)-9-deoxo-9a-aza-9a-methyl-9a-homoerythronolide A Using 2.0 g of the compound obtained in Example 17 (1), a reaction was carried out in a similar manner described in Example 3 to give 1.34 g of the titled compound.

MS (ESI) m/z=675.2 [M+H]$^+$

1H NMR (600 MHz, CHLOROFORM-d) δ ppm 0.81-1.37 (m, 26H) 1.47-1.57 (m, 2H) 1.69-1.75 (m, 1H) 1.78-1.93 (m, 2H) 1.98-2.06 (m, 1H) 2.20-2.27 (m, 1H) 2.30 (s, 6H) 2.35 (s, 3H) 2.44-2.60 (m, 3H) 2.61-2.75 (m, 2H) 2.75-2.82 (m, 1H) 3.46-3.54 (m, 2H) 3.57-3.72 (m, 4H) 3.66 (s, 3H) 4.60-4.65 (m, 1H) 4.74 (d, J=7.34 Hz, 1H) 5.28 (d, J=12.15 Hz, 1H) 7.20 (br. s., 1H) 7.49 (d, J=12.15 Hz, 1H)

EXAMPLE 28

5-O-(2'-O-(2-methoxycarbonylethyl)desosaminyl)-9-deoxo-9a-aza-9a-methyl-9a-homoerythronolide A Using 1.34 g of the compound obtained in Example 27, a reaction was carried out in a similar manner described in Example 4 to give 1.07 g of the titled compound.

MS (ESI) m/z=677.3 [M+H]$^+$

13C NMR (126 MHz, CHLOROFORM-d) δ ppm 7.78, 11.05, 16.09, 16.24, 20.95, 21.17, 21.37, 26.35, 31.91, 35.40, 35.93, 41.13, 42.12, 44.34, 51.67, 62.56, 64.94, 67.53, 68.92, 73.15, 76.01, 77.30, 77.74, 78.95, 79.58, 172.21, 177.76

EXAMPLE 29

3'-N-demethyl-3'-N-benzyl-6-O-methylerythromycin A

Using 6-O-methylerythromycin A, a reaction was carried out in a similar manner described in Example 7 (1) and Example 13 to give 690 mg of the titled compound.

MS (ESI) m/z=824.4 [M+H]$^+$

13C NMR (126 MHz, CHLOROFORM-d) δ ppm 9.16, 10.69, 12.40, 16.04, 18.09, 18.72, 19.90, 21.12, 21.53, 29.37, 34.95, 36.89, 37.30, 39.20, 39.35, 45.16, 45.36, 49.50, 50.71, 58.03, 63.74, 65.77, 68.75, 69.15, 70.80, 72.61, 74.35, 76.68, 78.02, 78.37, 81.00, 96.02, 102.86, 127.40, 128.55, 128.96, 175.89

EXAMPLE 30

2'-O-cyanomethyl-6-O-methylerythromycin A (Compound A) and 11,2'-bis-O-cyanomethyl-6-O-methylerythromycin A (Compound B)

(1) 200 g of 6-O-methylerythromycin A was dissolved in 1,000 ml of tetrahydrofuran, 106 g of pyridine and 145 g of trimethylchlorosilane were added in this order, and the mixture was stirred at room temperature for 3 hours. A saturated aqueous sodium bicarbonate solution was added to the reaction solution, and the mixture was extracted with ethyl acetate. The organic layer was washed with saturated brine, dried over anhydrous magnesium sulfate, and filtered. The filtrate was evaporated under reduced pressure, and to the residue were added ethyl acetate and hexane, and the reaction mixture was stirred at room temperature overnight. The resulting solid substance was collected by filtration to give 139 g of 4"-O-trimethylsilyl compound.

(2) 94.5 g of the compound obtained in the above (1) was dissolved in 1,000 ml of tetrahydrofuran, and 4.2 g of sodium hydride was added under ice cooling. The mixture was stirred under ice cooling for 15 minutes, 13.8 g of bromoacetonitrile was added, and the mixture was stirred for 30 minutes. Thereafter, the said operation (adding the said amount of sodium hydride and bromoacetonitrile) was repeated 2 times. Water was added to the reaction solution under ice cooling, and the mixture was extracted with ethyl acetate. The organic layer was washed with saturated brine, dried over anhydrous magnesium sulfate, and filtered. The filtrate was evaporated under reduced pressure, and the resulting residue was purified by silica gel column chromatography (hexane:acetone=5:1) to give 55 g of a mixture of a 4"-O-trimethylsilyl-2'-O-cyanomethyl compound and a 4"-O-trimethylsilyl-11,2'-bis-O-cyanomethyl compound.

(3) 39.8 g of the mixture obtained in the above (2) was dissolved in 232 ml of tetrahydrofuran, 51 ml of tetra-n-butyl ammonium fluoride (1M tetrahydrofuran solution) was added, and the mixture was stirred at room temperature for 20 minutes. Water was added to the reaction solution, and the mixture was extracted with ethyl acetate. The organic layer was washed with saturated brine, dried over anhydrous magnesium sulfate, and filtered. The filtrate was evaporated under reduced pressure, and the resulting residue was purified by silica gel column chromatography (hexane:acetone=2:1 to 1:2). The resulting residue was recrystallized from ethyl acetate to give 24.5 g of 2'-O-cyanomethyl-6-O-methylerythromycin A (compound A).

(4) 1 g of the mixture obtained in the above (2) was crystallized from ethyl acetate, the filtrate was concentrated, and then purified by silica gel chromatography (acetone:hexane:triethylamine=1:10:0.1 to 3:10:0.2) to give 110 mg of a 4"-O-trimethylsilyl-11,2'-bis-O-cyanomethyl compound and then a reaction was carried out in a similar manner as in the above (3), to give 80 mg of 1',2'-bis-O-cyanomethyl-6-O-methylerythromycin A (Compound B).

2'-O-cyanomethyl-6-O-methylerythromycin A (Compound A)

MS (ESI) m/z=787.5 [M+H]$^+$

13C NMR (126 MHz, CHLOROFORM-d) δ ppm 9.04, 10.72, 12.37, 16.01, 16.19, 17.97, 18.87, 19.94, 21.15, 21.44, 21.59, 29.95, 34.97, 37.44, 39.26, 39.45, 40.90, 45.19, 45.29, 49.55, 50.58, 57.49, 65.02, 65.92, 68.26, 69.21, 72.84, 74.30, 76.76, 77.95, 78.11, 78.45, 79.58, 80.58, 95.89, 100.01, 101.73, 116.93, 176.01, 221.10, 11,2'-bis-O-cyanomethyl-6-O-methylerythromycin A (Compound B)

MS (ESI) m/z=826.6 [M+H]$^+$

13C NMR (126 MHz, CHLOROFORM-d) δ ppm 9.16, 10.51, 12.86, 16.20, 18.87, 18.94, 20.47, 21.34, 21.46, 21.57, 35.09, 37.71, 37.80, 38.38, 40.88, 45.02, 45.58, 49.51, 50.72, 57.55, 57.61, 65.25, 66.14, 68.16, 72.81, 76.32, 77.83, 78.30, 79.47, 79.54, 79.68, 96.21, 101.34, 117.13, 175.92, 217.54

EXAMPLE 31

6,2'-di-O-methylerythromycin A (1) 10 g of (6-O-methylerythromycin A was suspended in 15 ml of N,N-dimethylformamide, 2 ml of benzyl bromide was added, and the mixture was stirred at room temperature for 3 hours. Ethyl acetate and water were added to the reaction solution, and the mixture was stirred at room temperature for 1 hour. The resulting solid substance was collected by filtration to give 9.88 g of a 6-O-methylerythromycin A 3'-N-benzyl quaternary salt.

(2) 2.0 g of the compound obtained in the above (1) was dissolved in a mixed solution of 5 ml of N,N-dimethylformamide and 5 ml of tetrahydrofuran, and 0.15 ml of methyl iodide and 87 mg of sodium hydride were added. After stirring at room temperature for 90 minutes, 0.15 ml of methyl iodide and 87 mg of sodium hydride were added, and the mixture was stirred at room temperature for 90 minutes. Water was added to the reaction solution, and the mixture was extracted with chloroform. The organic layer was washed with water and saturated brine, dried over anhydrous magnesium sulfate, and filtered. The filtrate was evaporated under reduced pressure, and the resulting residue was purified by silica gel chromatography (chloroform:methanol=5:1) to give 1.4 g of a 2'-O-methyl compound.

(3) 950 mg of the compound obtained in the above (2) was dissolved in 10 ml of N,N-dimethylformamide, 1.0 g of 5% palladium-carbon and 1.28 g of ammonium formate were added, and the mixture was stirred at 50° C. for 45 minutes. After filtering the reaction solution, the filtrate was evaporated under reduced pressure, a 2N aqueous sodium hydroxide solution and water were added to the resulting residue, and the mixture was extracted with ethyl acetate. The organic layer was washed with water, subsequently saturated brine, dried over anhydrous magnesium sulfate, and filtered. The filtrate was evaporated under reduced pressure, and the resulting residue was purified by silica gel chromatography (chloroform:methanol:ammonia water solution-30:1:0.1). The resulting residue was recrystallized from chloroform and heptane to give 320 mg of the titled compound.

MS (ESI) m/z=762.4 [M+H]$^+$

13C NMR (126 MHz, CHLOROFORM-d) δ ppm 8.39, 10.72, 12.38, 16.03, 16.17, 18.07, 18.90, 19.98, 21.14, 21.53, 21.59, 34.95, 37.48, 39.36, 39.70, 41.08, 45.11, 45.35, 49.57, 50.61, 60.40, 64.18, 65.79, 68.19, 69.16, 72.74, 74.33, 76.70, 78.06, 78.56, 80.23, 81.63, 95.94, 103.20, 176.16, 220.95

EXAMPLE 32

3'-N-demethyl-3'-N-(2-aminoethyl)-6-O-methyl-erythromycin A (1) Using 10 g of 6-O-methylerythromycin A, a reaction was carried out in a similar manner described in Example 7 (1) to give 6.5 g of 3'-N-demethyl-6-O-methylerythromycin A.

(2) 5.14 g of the compound obtained in the above (1) was dissolved in 35 ml of acetone, 2.53 g of N-benzyloxycarbonyl-2-bromoethylamine obtained by the method described in a literature (Journal of Organic Chemistry, 2000, Vol. 65, p. 3979-8987), 880 mg of sodium bicarbonate, and 100 mg of sodium iodide were added, and the mixture was stirred under reflux for 22 hours, and stirred at room temperature for 87.5 hours. The reaction solution was evaporated under reduced pressure, water was added to the resulting residue, and the mixture was extracted with chloroform. The organic layer was washed with saturated brine, dried over anhydrous magnesium sulfate, and filtered. The filtrate was evaporated under reduced pressure, and the resulting residue was purified by column chromatography (chloroform:methanol=100:2 to 100:3). The resulting residue was crystallized from ethyl acetate and hexane to give 3.61 g of a 3'-N-benzyloxycarbonylaminoethyl compound.

(3) 1.82 g of the mixture obtained in the above (2) was dissolved in a mixed solution of 18 ml of ethanol and 2 ml of water, 360 mg of 10% palladium-carbon was added, and the mixture was stirred at room temperature for 20 hours under a hydrogen atmosphere at 1 atm. After filtering the reaction solution, the filtrate was evaporated under reduced pressure, and the resulting residue was crystallized by methanol and isopropyl ether to give 878 mg of the titled compound.

MS (ESI) m/z=777.5 [M+H]$^+$

13C NMR (126 MHz, CHLOROFORM-d) δ ppm 9.15, 10.69, 12.38, 16.05, 18.10, 18.81, 19.84, 21.10, 21.53, 21.58, 30.22, 34.99, 37.31, 37.42, 39.31, 39.43, 39.83, 45.16, 45.33, 49.60, 50.73, 55.36, 65.56, 65.79, 68.86, 69.15, 71.28, 72.81, 74.35, 76.72, 78.08, 78.50, 78.58, 81.09, 96.24, 103.07, 176.00, 221.17

EXAMPLE 33

3'-N-demethyl-3'-N-(2-dimethylaminoethyl)-6-O-methylerythromycin A 800 mg of the compound obtained in Example 32 was dissolved in 13 ml of ethanol.

2 ml of water, 300 mg of 10% palladium-carbon and 1 ml of 37% aqueous formaldehyde solution were added in this order, and the mixture was stirred at room temperature for 19 hours under a hydrogen atmosphere at 1 atm. After filtering the reaction solution, the filtrate was evaporated under reduced pressure, and the resulting residue was purified by silica gel chromatography (chloroform:methanol=25:1 to 100:7). The resulting residue was crystallized with methanol to give 165 mg of the titled compound.

MS (ESI) m/z=805.5 [M+H]$^+$

13C NMR (126 MHz, CHLOROFORM-d) δ ppm 9.05, 10.70, 12.38, 16.02, 18.08, 18.84, 19.86, 21.10, 21.57, 30.55, 34.98, 37.29, 37.63, 39.43, 45.19, 45.36, 45.58, 49.59, 50.72, 51.00, 58.13, 64.80, 65.75, 68.79, 69.15, 71.24, 72.78, 74.35, 76.67, 78.12, 78.43, 78.53, 80.73, 96.13, 103.14, 176.05, 221.24

EXAMPLE 34

2'-O-(2-methoxycarbonylvinyl)-6-O-methylerythromycin A 10 g of 6-O-methylerythromycin A was dissolved in 35 ml of methylene chloride. 1.45 ml of methylpropiolate was added, and the mixture was stirred at room temperature for 21 hours. The reaction solution was evaporated under reduced pressure, and the resulting residue was purified by column chromatography (chloroform:methanol=100:3 to 25:1). The resulting residue was crystallized from ethyl acetate and hexane to give 4.62 g of the titled compound.

MS (ESI) m/z=832.5 [M+H]$^+$

13C NMR (126 MHz, CHLOROFORM-d) δ ppm 8.88, 10.72, 12.38, 15.98, 16.15, 17.98, 18.82, 19.93, 21.13, 21.35, 21.59, 31.61, 34.98, 37.39, 39.22, 39.28, 40.84, 45.16, 45.20, 49.56, 50.62, 51.05, 63.42, 65.94, 68.34, 69.19, 72.88, 74.32, 76.78, 77.93, 78.20, 78.35, 80.74, 83.50, 95.95, 96.79, 100.66, 164.37, 168.79, 175.96, 221.04

EXAMPLE 35

2'-O-(2-methoxycarbonylethyl)-6-O-methylerythromycin A

Using 3.7 g of the compound obtained in Example 34, a reaction was carried out in a similar manner described in Example 4 to give 0.56 g of the titled compound.

MS (ESI) m/z=834.5 [M+H]$^+$

13C NMR (126 MHz, CHLOROFORM-d) δ ppm 8.70, 10.73, 12.37, 16.01, 16.19, 18.03, 18.88, 20.04, 21.15, 21.59, 32.40, 34.95, 35.38, 37.47, 39.38, 39.68, 41.17, 45.12, 45.41, 49.50, 50.58, 51.65, 64.44, 65.88, 67.62, 68.17, 69.19, 72.76, 74.33, 78.02, 78.56, 80.14, 80.32, 95.92, 100.01, 102.68, 172.27, 176.20, 221.05

EXAMPLE 36

2'-O-(3-aminobutyl)-6-O-methylerythromycin A 1.0 g of the compound obtained in Example 25 was suspended in a mixed solution of 10 ml of methanol and 2 ml of N,N-dimethylformamide, 200 mg of 5% palladium-carbon and 772 mg of ammonium formate were added, and the mixture was stirred at room temperature for 16 hours. After filtering the reaction solution, the filtrate was evaporated under reduced pressure, a 2N aqueous sodium hydroxide solution and water were added to the resulting residue, and the mixture was extracted with ethyl acetate. The organic layer was washed with water, subsequently saturated brine, dried over anhydrous magnesium sulfate, and filtered. The filtrate was evaporated under reduced pressure, and the resulting residue was purified by silica gel chromatography (chloroform:methanol:ammonia water solution=20:1:0.1 to 10:1:0.1). The resulting residue was crystallized from chloroform and hexane to give 340 mg of the titled compound.

MS (ESI) m/z=819.4 [M+H]+

13C NMR (126 MHz, CHLOROFORM-d) δ ppm 8.61, 10.72, 12.35, 16.04, 16.18, 18.10, 19.04, 19.92, 21.13, 21.52, 21.62, 30.06, 35.01, 37.47, 39.44, 39.61, 40.42, 45.07, 45.35, 49.59, 50.63, 64.49, 65.75, 68.34, 69.14, 72.00, 72.78, 74.33, 76.76, 77.31, 78.13, 78.57, 80.04, 80.79, 96.29, 103.00, 176.16, 220.88

EXAMPLE 37

2'-O-(2-carboxyethyl)-6-O-methylerythromycin A 83 mg of the compound obtained in Example 35 was suspended in 0.2 ml of water and 0.2 ml of methanol, 0.05 ml of 2N aqueous sodium hydroxide solution was added, and the mixture was stirred at room temperature for 20 hours. Thereafter, 0.2 ml of methanol was added to the reaction solution, and the mixture was stirred at 40° C. for 10 hours. The reaction solution was evaporated under reduced pressure, and the resulting residue was purified by silica gel chromatography (chloroform:methanol:ammonia water solution=10:1:0.1) to give 55 mg of the titled compound.

MS (ESI) m/z=820.3 [M+H]+

13C NMR (126 MHz, CHLOROFORM-d) δ ppm 8.45, 10.71, 12.40, 16.01, 16.25, 18.09, 18.85, 20.03, 21.14, 21.47, 21.59, 29.71, 34.98, 37.01, 37.55, 39.1, 39.36, 40.30, 45.12, 45.27, 49.65, 50.56, 64.91, 66.12, 67.75, 68.94, 69.21, 72.93, 74.32, 76.79, 77.82, 78.01, 78.08, 78.32, 80.75, 95.81, 102.47, 174.43, 176.01, 220.78

EXAMPLE 38

3-O-(2-nitro-4-fluorophenyl)-5-O-(2'-O-(2-nitro-4-fluorophenyl)desosaminyl)-6-O-methylerythronolide A 11,12-cyclic carbonate (1) Using 14.4 g of 2'-O-acetyl-5-O-desosaminyl-6-O-methylerythronolide A 11,12-cyclic carbonate obtained by the method described in a literature (Journal of Medicinal Chemistry, 2003, Vol. 46, No. 13, p. 2706), a reaction was carried out in a similar manner described in Example 15 (2) to give 7.03 g of a 2'-OH compound.

(2) 3.0 g of the compound obtained in the above (1) was dissolved in 30 ml of tetrahydrofuran, 1.6 ml of 2,5-difluoronitrobenzene was added, and then 296 mg of sodium hydride was added under ice cooling. After stirring at room temperature for 20 hours, 296 mg of sodium hydride and 1.6 ml of 2,5-difluoronitrobenzene were added, and the mixture was stirred for another 23 hours. Under ice cooling, water was added to the reaction solution, and the mixture was extracted with ethyl acetate. The organic layer was washed with saturated brine, dried over anhydrous magnesium sulfate, and filtered. The filtrate was evaporated under reduced pressure, and the resulting residue was purified by silica gel chromatography (chloroform:methanol:ammonia water solution=20:1:0.1) to give 4.42 g of the titled compound.

MS (ESI) m/z=894.3 [M+H]+

13C NMR (126 MHz, CHLOROFORM-d) δ ppm 7.94, 10.17, 12.89, 13.22, 15.50, 18.32, 19.79, 20.62, 21.99, 31.02, 37.28, 37.86, 38.84, 44.34, 44.69, 50.2, 68.99, 76.06, 78.23, 78.69, 80.76, 82.79, 84.85, 99.85, 112.41, 112.62, 112.82, 113.04, 114.60, 114.67, 119.77, 119.95, 120.52, 120.70, 139.89, 148.35, 154.23, 156.18, 174.89, 211.73

EXAMPLE 39

11-amino-11-deoxy-5-O-(3'-N-demethyl-3'-N-(3-fluorobenzyl)desosaminyl)-6-O-methylerythronolide A 11,12-cyclic carbamate Using 250 mg of the compound obtained in Example 22 (1) and 3-fluorobenzaldehyde instead of benzaldehyde, a reaction was carried out in a similar manner described in Example 13 to give 230 mg of the titled compound.

MS (ESI) m/z=709.3 [M+H]+

13C NMR (126 MHz, CHLOROFORM-d) δ ppm 8.42, 10.32, 13.46, 13.99, 15.32, 18.15, 18.79, 21.32, 22.27, 29.32, 36.07, 36.64, 37.45, 39.21, 44.72, 45.52, 57.68, 58.48, 65.27, 70.37, 70.78, 75.68, 78.09, 79.11, 84.12, 89.08, 106.92, 114.34, 114.51, 115.49, 124.17, 130.16, 141.21, 158.62, 175.49, 217.72,

EXAMPLE 40

2',4"-bis-O-cyanomethyl-6-O-methylerythromycin A

Using 100 g of 6-O-methylerythromycin A, a reaction was carried out in a similar manner described in Example 30 (2) to give 130 mg of the titled compound.

MS (ESI) m/z=826.4 [M+H]+

13C NMR (126 MHz, CHLOROFORM-d) δ ppm 9.03, 10.70, 12.39, 16.00, 16.20, 17.97, 19.17, 19.90, 21.14, 21.88, 35.32, 37.44, 39.21, 45.18, 49.63, 50.58, 58.41, 64.62, 69.24, 74.28, 101.37, 116.03,

EXAMPLE 41

4"-O-acetyl-2'-O-cyanomethyl-6-O-methylerythromycin A (1) 200 g of 6-O-methylerythromycin A was suspended in 800 ml of acetone, 81.9 g of acetic anhydride and 32.7 g of 4-dimethylaminopyridine were added in this order, and the mixture was stirred at room temperature for 4 hours. The reaction solution was evaporated under reduced pressure, saturated aqueous ammonium chloride was added to the resulting residue, and the mixture was extracted with ethyl acetate. The organic layer was evaporated under reduced pressure, the resulting residue was dissolved in 1.5 L of methanol, and the resultant solution was stirred under reflux for 4.5 hours. The resulting crystal in evaporating methanol under heating at normal pressure was collected by filtration to give 202 g of a 4"-O-acetyl compound.

(2) 5 g of the compound obtained in the above (1) was dissolved in 30 ml of tetrahydrofuran, 910 mg of bromoacetonitrile and 304 mg of sodium hydride were added in this order under ice cooling, and the mixture was stirred for 2 hours. Saturated brine was added to the reaction solution, and the mixture was extracted with ethyl acetate. The organic layer was evaporated under reduced pressure, and the resulting residue was purified by column chromatography (chloroform:methanol:ammonia water solution=9:1:0.1). The resulting residue was crystallized from acetonitrile to give 1.46 g of the titled compound.

MS (ESI) m/z=829.5 [M+H]+

13C NMR (126 MHz, CHLOROFORM-d) δ ppm 9.03, 10.70, 12.42, 16.00, 16.21, 18.00, 18.52, 19.85, 21.02, 21.18, 21.72, 35.23, 37.41, 39.10, 39.18, 40.93, 45.09, 45.26, 49.57, 50.63, 57.49, 63.13, 64.69, 67.40, 69.23, 72.77, 74.32, 76.74, 77.73, 78.36, 78.71, 79.79, 80.36, 95.82, 101.23, 116.99, 170.55, 175.87, 221.08

EXAMPLE 42

3'-N-demethyl-3'-N-(2-nitrophenyl)-6-O-methylerythromycin A 2.0 g of the compound obtained in Example 32 (1) was dissolved in 15 ml of N,N-dimethylformamide. 0.86 ml of 2-fluoronitrobenzene and 144 mg of sodium carbonate were added, and the mixture was stirred at 90° C. for 13 hours. Ethyl acetate and saturated brine were added to separate the solution. The organic layer was washed with saturated brine, dried over anhydrous magnesium sulfate, and filtered. The filtrate was evaporated under reduced pressure, and the resulting residue was purified by silica gel chromatography (acetone:hexane 1:3 to 1:1). The resulting residue was crystallized from methylene chloride and isopropyl ether, to give 1.68 g of the titled compound.
MS (ESI) m/z=853.3 [M−H]$^+$
13C NMR (126 MHz, CHLOROFORM-d) δ ppm 9.59, 10.67, 12.40, 16.11, 18.09, 18.68, 19.89, 21.12, 21.25, 21.55, 32.68, 34.84, 34.98, 37.36, 39.00, 39.28, 45.09, 45.26, 49.46, 50.70, 64.73, 65.96, 68.15, 69.17, 72.10, 72.80, 74.32, 76.73, 77.96, 78.24, 78.32, 81.39, 96.05, 102.57, 120.14, 121.91, 126.24, 133.32, 141.76, 146.78, 175.73, 220.97

EXAMPLE 43

3'-N-didemethyl-3'-N-bis(3-pyridylmethyl)-6-O-methylerythromycin A (1) After dissolving 0.62 g of sodium in 100 ml of methanol, 2.0 g of the compound obtained in Example 32 (1) and 1.70 g of iodine were added, and the mixture was stirred for 6 hours. A saturated aqueous sodium thiosulfate solution was added to the reaction solution, and subsequently a saturated aqueous ammonium chloride solution was added, and the mixture was extracted with ethyl acetate. The combined organic layer was dried over anhydrous magnesium sulfate, and then concentrated. The resulting residue was purified by silica gel column chromatography (hexane:acetone:triethylamine=50:10:0.2 to 10:10:0.2) to give 1.08 g of 3'-N-didemethyl-6-O-methylerythromycin A.

(2) Using 500 mg of the compound obtained in the above (1) and using 0.16 ml of 3-pyridinecarboxyaldehyde instead of benzaldehyde, a reaction was carried out in a similar manner described in Example 13 to give 130 mg of the titled compound.
MS (ESI) m/z=902.4 [M+H]$^+$
13C NMR (126 MHz, CHLOROFORM-d) δ ppm 9.46, 10.66, 12.40, 16.08, 18.09, 18.63, 19.89, 21.12, 21.43, 21.51, 31.67, 34.92, 37.34, 38.92, 39.26, 45.09, 45.27, 49.26, 50.69, 51.33, 59.73, 65.79, 68.48, 69.16, 71.60, 72.65, 74.32, 76.71, 77.91, 78.22, 78.27, 81.40, 95.88, 102.76, 123.63, 134.49, 136.56, 149.03, 150.35, 175.66, 220.99,

EXAMPLE 44

3'-N-demethyl-3'-N-(2-aminophenyl)-6-O-methylerythromycin A 500 mg of the compound obtained in Example 42 was dissolved in 15 ml of methanol, 1.5 ml of water and 250 mg of 10% palladium-carbon were added in this order, and the mixture was stirred at room temperature for 2.5 hours in a hydrogen atmosphere at 1 atm. After filtering the reaction solution, the filtrate was evaporated under reduced pressure, and the resulting residue was purified by silica gel chromatography (benzene:acetone=9:1 to 7:1). The resulting residue was crystallized from isopropyl ether to give 324 mg of the titled compound.
MS (ESI) m/z=825.4 [M+H]$^+$
13C NMR (126 MHz, CHLOROFORM-d) δ ppm 9.74, 10.67, 12.43, 16.03, 16.15, 18.10, 18.75, 19.72, 21.14, 21.26, 21.60, 35.13, 37.35, 38.79, 39.37, 45.03, 45.25, 49.42, 50.73, 60.81, 66.11, 68.79, 69.20, 72.37, 72.90, 74.32, 76.79, 77.91, 78.35, 78.80, 82.58, 96.36, 103.91, 115.65, 117.81, 122.75, 124.58, 137.69, 142.09, 175.62, 220.96

EXAMPLE 45

3'-N-demethyl-3'-N-(2-dimethylaminophenyl)-6-O-methylerythromycin A

Using 500 mg of the compound obtained in Example 44, and methanol instead of ethanol, a reaction was carried out in a similar manner described in Example 33 to give 165 mg of the titled compound.
MS (ESI) m/z=853.4 [M+H]$^+$
13C NMR (126 MHz, CHLOROFORM-d) δ ppm 9.11, 10.72, 12.38, 16.02, 18.07, 18.90, 19.87, 21.12, 21.48, 31.90, 33.14, 34.95, 37.28, 39.51, 39.61, 44.64, 45.21, 45.35, 49.41, 50.71, 65.69, 66.60, 68.17, 69.15, 71.32, 72.71, 74.36, 76.65, 78.10, 78.34, 78.61, 80.46, 96.06, 103.76, 120.59, 124.41, 125.00, 147.12, 176.09, 221.28

EXAMPLE 46

3'-N-demethyl-3'-N-(2-benzyloxycarbonylaminoethyl)-6-O-methylerythromycin A 5.14 g of the compound obtained in the Example 32 (1) was dissolved in 35 ml of acetone, 2.53 g of N-benzyloxycarbonyl-2-bromoethylamine obtained by the method, described in a literature (Journal of Organic Chemistry, 2000, Vol. 65, No. 26, p. 8979), 100 mg of sodium iodine and 880 mg of sodium bicarbonate were added, and the mixture was stirred under reflux for 22 hours, and stirred at room temperature for 4 days. Water was added to the reaction solution, and the mixture was extracted with chloroform. The organic layer was evaporated under reduced pressure, and the resulting residue was purified by silica gel column chromatography (chloroform:methanol=50:1). The resulting residue was crystallized from ethyl acetate and hexane to give 3.61 g of the titled compound.
MS (ESI) m/z=911.5 [M+H]$^+$
13C NMR (126 MHz, CHLOROFORM-d) δ ppm 9.40, 10.69, 12.39, 16.09, 18.08, 18.7%, 19.84, 21.12, 21.57, 31.02, 34.97, 37.33, 39.39, 45.14, 45.28, 49.56, 50.72, 52.45, 65.01, 65.86, 66.77, 68.73, 69.16, 71.43, 72.82, 74.33, 76.75, 78.02, 78.42, 78.465, 81.12, 96.17, 102.93, 128.17, 128.60, 175.85, 221.06

EXAMPLE 47

3'-N-demethyl-3'-N-(3-benzyloxycarbonylaminopropyl)-6-O-methylerythromycin A 7.34 g of the compound obtained in the Example 32 (1) was dissolved in 50 ml of acetone, 2.76 g of potassium carbonate, and 3.81 g of N-benzyloxycarbonyl-3-bromopropylamine obtained by the method described in a literature (Journal of Organic Chemistry, 2000, Vol. 65, No. 26, p. 8979), were added in this order, and the mixture was stirred at room temperature for 2 days. The reaction solution was evaporated under reduced pressure, and ethyl acetate was added to the resulting residue. After washing with saturated brine, the mixture was dried over anhydrous magnesium sulfate, and filtered. The filtrate was evaporated under reduced pressure, and the resulting residue was purified by silica gel chromatography (chloroform:methanol=50:1 to 20:1). The resulting residue was crystallized from ethyl acetate and hexane, to give 4.83 g of the titled compound.

MS (ESI) m/z=925.5 [M+H]$^+$

13C NMR (126 MHz, CHLOROFORM-d) δ ppm 9.29, 10.70, 12.39, 16.07, 18.08, 18.80, 19.83, 21.58, 28.01, 29.94, 34.97, 37.31, 39.22, 45.32, 49.56, 50.73, 65.83, 68.83, 69.15, 71.15, 72.80, 74.34, 78.04, 78.45, 81.04, 96.18, 102.99, 128.12, 128.59, 156.59, 175.89, 221.10

EXAMPLE 48

2'-O-(3-(2-dimethylaminoethylamino)carbonylpropyl)-6-O-methylerythromycin A 540 mg of the compound obtained in Example 35 was dissolved in 15 ml of tetrahydrofuran, 0.35 ml of N,N-dimethylethylenediamine was added, and the mixture was stirred under reflux for 3 hours. The reaction solution was evaporated under reduced pressure to decrease the said tetrahydrofuran, and then 1.5 ml of N,N-dimethylethylenediamine was added hereto, and the mixture was stirred under reflux for 5 hours. Ethyl acetate was added to the reaction solution, and the mixture was washed with saturated brine, dried over anhydrous magnesium sulfate, and filtered. The filtrate was evaporated under reduced pressure, and the resulting residue was purified by silica gel chromatography (chloroform:methanol=10:1 to 6:1). The resulting residue was crystallized from ethyl acetate to give 140 mg of the titled compound.

MS (ESI) m/z=890.5 [M+H]$^+$

13C NMR (126 MHz, CHLOROFORM-d) δ ppm 8.50, 10.72, 12.38, 16.01, 16.25, 18.04, 18.85, 20.03, 21.14, 21.53, 28.86, 34.95, 37.16, 37.53, 37.93, 39.22, 39.58, 40.77, 45.11, 45.36, 45.75, 49.55, 50.53, 59.02, 64.57, 65.98, 68.18, 68.38, 69.19, 72.84, 74.30, 76.78, 77.92, 78.09, 78.45, 79.06, 80.42, 95.89, 102.80, 172.25, 176.10, 220.92

EXAMPLE 49

3'-N-demethyl-3'-N—(N-methylcarbamoyl)-6-O-methylerythromycin A 1.0 g of the compound obtained in Example 32 (1) was dissolved in 10 ml of tetrahydrofuran, 0.08 ml of methyl isocyanate was added, and the mixture was stirred at room temperature for 20 minutes. Ethyl acetate was added to the reaction solution, and the mixture was washed with saturated brine, dried over anhydrous magnesium sulfate, and filtered. The filtrate was evaporated under reduced pressure, and the resulting residue was crystallized from ethyl acetate and hexane to give 386 mg of the titled compound.

MS (ESI) m/z=790.5 [M+H]$^+$

13C NMR (126 MHz, CHLOROFORM-d) δ ppm 9.54, 10.66, 12.40, 16.08, 18.08, 18.73, 19.77, 21.11, 21.24, 21.60, 27.82, 28.43, 35.09, 36.58, 37.36, 38.99, 39.34, 45.08, 45.23, 49.55, 50.72, 55.47, 65.91, 68.41, 69.17, 72.45, 72.92, 74.34, 76.73, 78.04, 78.36, 78.68, 82.22, 96.31, 103.79, 160.44, 175.80, 220.98

EXAMPLE 50

3'-N-demethyl-3'-N-(2-amino-3,4-dioxocyclobut-1-enyl)-6-O-methylerythromycin 367 mg of the compound obtained in Example 42 (1) was dissolved in methanol, 3-amino-4-ethoxy-3-cyclobutene-1,2-dione obtained by the method described in a literature (Bioorganic & Medicinal Chemistry Letters, 2005, Vol. 15, p. 4243), was added and the mixture was stirred at room temperature for 8 days. The reaction solution was evaporated under reduced pressure, and the resulting residue was crystallized from ethanol to give 254 mg of the titled compound.

MS (ESI) m/z=851.4 [M+H]$^+$

13C NMR (126 MHz, CHLOROFORM-d) δ ppm 10.66, 12.38, 16.16, 18.07, 18.68, 19.95, 21.08, 21.51, 35.10, 36.09, 37.43, 38.93, 39.27, 45.13, 49.39, 50.67, 65.82, 69.20, 74.31, 78.27, 78.57, 82.26, 96.24, 170.34, 175.65, 220.84

EXAMPLE 51

11-amino-11-deoxy-3-O-(2-nitro-4-fluorophenyl)-5-O-(2'-O-(2-nitro-4-fluorophenyl)desosaminyl)-6-O-methylerythronolide A 11,12-cyclic carbamate (compound C) and 11-amino-11-deoxy-3-O, 11-N-bis(2-nitro-4-fluorophenyl)-5-O-(2'-O-(2-nitro-4-fluorophenyl)desosaminyl)-6-O-methylerythronolide A 11,12-cyclic carbamate (compound D)

3.0 g of the compound obtained in Example 14 (1) was dissolved in 30 ml of tetrahydrofuran, 2.66 ml of 2,5-difluoronitrobenzene was added, and 290 mg of sodium hydride was added under ice cooling. After stirring the mixture at room temperature for 5 hour, 290 mg of sodium hydride was added, the mixture was stirred for another 20 hours. 390 mg of sodium hydroxide and 2.7 ml of 2,5-difluoronitrobenzene were added, and stirred for another 25 hours. Then, 15 ml of N,N-dimethylformamide was added, and the mixture was stirred for 3.5 hours. Water was added to the reaction solution under ice cooling, and the mixture was extracted with ethyl acetate. The organic layer was washed with saturated brine, dried over anhydrous magnesium sulfate, and filtered. The filtrate was evaporated under reduced pressure, and the resulting residue was purified by silica gel chromatography (chloroform:methanol:ammonia water solution=50:1:0.1) to give 1.3 g of 11-amino-11-deoxy-3-O-(2-nitro-4-fluorophenyl)-5-O-(2'-O-(2-nitro-4-fluorophenyl)desosaminyl)-6-O-methylerythronolide A 11,12-cyclic carbamate (compound C) and 0.17 g of 11-amino-11-deoxy-3-O, 11-N-bis(2-nitro-4-fluorophenyl)-5-O-(2'-O-(2-nitro-4-fluorophenyl)desosaminyl)-6-O-methylerythronolide A 11,12-cyclic carbamate (compound D)

11-amino-11-deoxy-3-O-(2-nitro-4-fluorophenyl)-5-O-(2'-O-(2-nitro-4-fluorophenyl)desosaminyl)-6-O-methylerythronolide A 11,12-cyclic carbamate (compound C)

MS (ESI) m/z=893.3 [M+H]$^+$

13C NMR (126 MHz, CHLOROFORM-d) δ ppm 7.98, 10.31, 13.44, 13.88, 15.59, 18.23, 19.58, 20.62, 21.98, 33.16, 37.17, 37.50, 39.15, 40.99, 44.36, 45.11, 50.09, 58.21, 63.35, 68.99, 76.47, 78.06, 78.81, 79.36, 82.86, 99.82, 112.41, 112.62, 112.80, 113.02, 114.59, 117.97, 119.91, 120.48, 139.82, 140.82, 143.37, 149.19, 154.19, 156.14, 158.40, 175.05, 217.36

11-amino-11-deoxy-3-O, 11-N-bis(2-nitro-4-fluorophenyl)-5-O-(2'-O-(2-nitro-4-fluorophenyl)desosaminyl)-6-O-methylerythronolide A 11,12-cyclic carbamate (compound D)

MS (ESI) m/z=1032.4 [M+H]$^+$

1H NMR (500 MHz, CHLOROFORM-d) δ ppm 0.76 (d, J=6.12 Hz, 3H) 0.85 (t, J=7.45 Hz, 3H) 2.15 (br. s., 6H) 2.94 (s, 3H) 3.71 (d, J=3.44 Hz, 1H) 4.10 (s, 1H) 4.45 (d, J=7.26

Hz, 1H) 4.50-4.57 (m, 1H) 5.12-5.23 (m, 1H) 7.09-7.37 (m, 5H) 7.52-7.57 (m, 2H) 7.74-7.80 (m, 1H) 7.81-7.87 (m, 1H)

EXAMPLE 52

3'-N-demethyl-6-O-methylerythromycin B

Using 5.0 g of 6-O-methylerythromycin B, a reaction was carried out in a similar manner described in Example 7 (1) to give 2.78 g of the titled compound.

MS (ESI) m/z=560.2 [M+H]+
1H NMR (600 MHz, CHLOROFORM-d) δ ppm 0.83-0.90 (m, 6H) 0.94-0.99 (m, 3H) 1.32-1.36 (m, 3H) 1.43-1.52 (m, 2H) 1.60-1.74 (m, 2H) 1.87-1.98 (m, 2H) 2.18-2.25 (m, 1H) 2.39 (s, 6H) 2.44-2.51 (m, 1H) 2.54-2.61 (m, 1H) 2.62-2.70 (m, 1H) 2.85-2.94 (m, 2H) 2.99 (s, 3H) 3.08-3.13 (m, 1H) 3.52-3.59 (m, 2H) 3.72-3.75 (m, 1H) 3.82 (d, J=10.09 Hz, 1H) 4.42 (d, J=7.79 Hz, 1H) 5.46-5.50 (m, 1H)

EXAMPLE 53

5-O-(3'-N-demethyl)desosaminyl-6-O-methylerythronolide B

Using 840 mg of the compound obtained in Example 52, a reaction was carried out in a similar manner described in Example 12 to give 580 mg of the titled compound.

MS (ESI) m/z 718.3 [M+H]+
1H NMR (600 MHz, CHLOROFORM-d) δ ppm 0.77 (d, J=7.34 Hz, 3H) 0.80 (t, J=7.57 Hz, 3H) 0.90 (d, J=6.88 Hz, 3H) 0.98 (d, J=7.34 Hz, 3H) 1.03 (d, J=6.88 Hz, 3H) 1.18 (s, 3H) 1.23 (d, J=6.42 Hz, 3H) 1.34 (s, 3H) 1.72-1.78 (m, 1H) 1.84-1.90 (m, 1H) 1.95-2.01 (m, 1H) 2.15-2.23 (m, 1H) 2.25-2.30 (m, 1H) 2.34 (s, 3H) 2.37-2.42 (m, 1H) 2.81-2.87 (m, 2H) 2.92-2.98 (m, 1H) 3.01 (s, 3H) 3.03-3.09 (m, 2H) 3.25 (s, 3H) 3.44-3.52 (m, 1H) 3.92-3.98 (m, 3H) 4.36 (d, J=7.79 Hz, 1H) 4.85-4.88 (m, 1H) 5.30-5.34 (m, 1H)

EXAMPLE 54

5-O-(3'-N-demethyl-3'-N-benzyloxycarbonyl)desosaminyl-6-O-methylerythronolide B 580 mg of the compound obtained in Example 53 was dissolved in 6 ml of chloroform, 174 mg of sodium bicarbonate was added, and 163 μl of benzyl chloroformate was added under ice cooling. The mixture was stirred at room temperature for 7 hours, water was added to the reaction solution, and the mixture was extracted with chloroform. The organic layer was washed with a 2N aqueous sodium hydride solution and saturated brine in this order, dried over anhydrous magnesium sulfate, and filtered. The resulting filtrate was purified by silica gel column chromatography (chloroform:methanol:ammonia water solution=50:1:0.1) to give 668 mg of the titled compound.

MS (ESI) m/z=716.2 [M+Na]+
13C NMR (126 MHz, CHLOROFORM-d) δ ppm 8.43, 9.28, 10.09, 10.50, 15.09, 18.11, 19.15, 21.02, 26.25, 28.58, 35.78, 38.26, 38.42, 40.32, 44.24, 45.58, 49.91, 56.78, 67.56, 69.18, 70.14, 71.62, 74.94, 78.53, 78.82, 85.85, 104.90, 127.96, 128.12, 128.58, 175.10, 219.61

EXAMPLE 55

3-O-(4-methoxyphenyl)acetyl-5-O-(2'-O-(2-methoxycarbonylethyl)desosaminyl)-9-deoxo-9a-aza-9a-methyl-9a-homoerythronolide A Using 450 mg of the compound obtained in Example 28 and using 221 mg of 4-methoxyphenylacetic acid instead of 2-pyridyl acetate hydrochloride, a reaction was carried out in a similar manner described in Example 15 (1) to give 35 mg of the titled compound.

MS (ESI) m/z=825.4 [M+H]+
13C NMR (126 MHz, CHLOROFORM-d) δ ppm 7.83, 9.09, 11.07, 15.69, 16.01, 20.85, 20.94, 21.67, 26.42, 26.48, 35.55, 36.30, 36.82, 41.21, 42.20, 43.35, 51.68, 55.35, 62.48, 64.53, 67.44, 68.80, 70.95, 73.18, 74.24, 75.78, 78.13, 79.16, 83.88, 114.05, 130.59, 158.89, 170.77, 172.21, 176.34

EXAMPLE 56

5-O-(2'-O—(3-oxobut-1-enyl)desosaminyl)-6-O-methylerythronolide A

Using 1 g of 5-O-desosaminyl-6-O-methylerythronolide A obtained by the method described in a literature (Journal of Medicinal Chemistry, 2001, Vol. 44, No. 24, p. 4027), a reaction was carried out in a similar manner described in Example 1 to give 1.3 g of the titled compound.

MS (ESI) m/z=658.3 [M+H]+
13C NMR (126 MHz, CHLOROFORM-d) δ ppm 7.86, 10.53, 11.58, 12.69, 15.39, 16.31, 17.94, 19.49, 21.12, 21.43, 28.15, 32.19, 35.69, 37.51, 38.89, 40.92, 44.20, 45.54, 46.29, 49.83, 63.08, 68.96, 69.75, 74.23, 76.95, 77.90, 78.02, 81.35, 83.26, 99.68, 108.12, 164.31, 174.77, 197.43, 220.77

EXAMPLE 57

3-O-(4-methoxyphenyl)acetyl-5-O-(2'-O-(3-oxobut-1-enyl)desosaminyl)-6-O-methylerythronolide A Using 24 mg of 3-O-(4-methoxyphenyl)acetyl-5-O-desosaminyl-6-O-methylerythronolide A obtained by the method described in a literature (Journal of Medicinal Chemistry, 2003, Vol. 46, No. 13, p. 2706-2715), a reaction was carried out in a similar manner described in Example 1 to give 16 mg of the titled compound.

MS (ESI) m/z=806.4 [M+H]+
13C NMR (126 MHz, CHLOROFORM-d) δ ppm 8.94, 10.50, 12.57, 15.23, 16.27, 18.02, 19.55, 20.77, 21.22, 28.09, 36.03, 37.44, 38.70, 40.74, 43.12, 45.29, 50.24, 55.38, 63.14, 69.52, 74.24, 77.21, 77.93, 78.48, 79.77, 114.16, 130.61, 159.05, 171.27, 173.67, 220.61

EXAMPLE 58

5-O-(3'-N-demethyl-3'-N-benzyl desosaminyl)-6-O-methylerythronolide A (1) Using 3.0 g of 5-O-desosaminyl-6-O-methylerythronolide A, a reaction was carried out in a similar manner described in Example 7 (1) to give 1.35 g of a 3'-N-demethyl compound.

(2) Using 600 mg of the compound obtained in the above (1), a reaction was carried out in a similar manner described in Example 13 to give 572 mg of the titled compound.

MS (ESI) m/z=666.3 [M+H]+
13C NMR (126 MHz, CHLOROFORM-d) δ ppm 8.36, 10.52, 12.74, 15.32, 16.30, 17.84, 18.85, 21.35, 21.53, 36.01, 36.56, 37.64, 38.85, 44.66, 45.62, 49.66, 58.18, 65.15, 69.88, 70.35, 70.74, 74.30, 76.75, 78.16, 79.13, 88.81, 106.92, 128.64, 175.10, 220.78

EXAMPLE 59

5-O-(3'-N-demethyl-3'-N-(2-(1,3-dioxo-1,3-dihydroisoindol-2-yl)-ethyl)desosaminyl)-6-O-methylerythronolide A Using 300 mg of the compound obtained in Example 58 (1), a reaction was carried out in a similar manner described in Example 7 (2) to give 331 mg of the titled compound.
MS (ESI) m/z=749.3 [M+H]$^+$
1H NMR (600 MHz, CHLOROFORM-d) δ ppm 0.80-0.85 (m, 3H) 0.99-1.03 (m, 3H) 1.08-1.14 (m, 6H) 1.15-1.18 (m, 3H) 1.20-1.31 (m, 7H) 1.31-1.35 (m, 3H) 1.44-1.67 (m, 3H) 1.84-1.97 (m, 2H) 2.04-2.10 (m, 1H) 2.30 (s, 3H) 2.46-2.68 (m, 4H) 2.79-2.88 (m, 1H) 2.94 (s, 3H) 2.96-3.01 (m, 1H) 3.16-3.22 (m, 1H) 3.24-3.26 (m, 1H) 3.27-3.34 (m, 1H) 3.45-3.53 (m, 2H) 3.61-3.64 (m, 1H) 3.64-3.69 (m, 1H) 3.69-3.84 (m, 3H) 3.90-3.91 (m, 1H) 4.32 (d, J=7.34 Hz, 1H) 5.13-5.18 (m, 1H) 7.70-7.72 (m, J=5.50, 3.21 Hz, 2H) 7.83-7.85 (m, 2H)

EXAMPLE 60

5-O-(3'-N-demethyl-3'-N-(2-aminoethyl)desosaminyl)-6-O-methylerythronolide A

Using 331 mg of the compound obtained in Example 59, a reaction was carried out in a similar manner described in Example 8 to give 196 mg of the titled compound.
MS (ESI) m/z=619.3 [M+H]$^+$
1H NMR (600 MHz, CHLOROFORM-d) δ ppm 0.82 (t, J=7.57 Hz, 3H) 1.17 (s, 3H) 1.36 (s, 3H) 1.43-1.58 (m, 2H) 1.64-1.69 (m, 1H) 1.83 (s, 3H) 1.87-1.96 (m, 2H) 2.00 (s, 3H) 2.06-2.12 (m, 1H) 2.26 (s, 3H) 2.36-2.42 (m, 1H) 2.50-2.67 (m, 4H) 2.71-2.81 (m, 2H) 2.96 (s, 3H) 2.97-3.02 (m, 1H) 3.22-3.31 (m, 2H) 3.47-3.60 (m, 2H) 3.65-3.68 (m, 1H) 3.83-3.86 (m, 1H) 4.35 (d, J=7.34 Hz, 1H) 5.14-5.18 (m, 1H)

EXAMPLE 61

5-O-(3'-N-dimethyl-3'-N-(2-dimethylaminoethyl)desosaminyl)-6-O-methylerythronolide A Using 331 mg of the compound obtained in Example 60, a reaction was carried out in a similar manner described in Example 9 to give 186 mg of the titled compound.
MS (ESI) m/z=647.4 [M+H]$^+$
13C NMR (126 MHz, CHLOROFORM-d) δ ppm 8.49, 10.52, 12.74, 15.30, 16.30, 17.81, 18.74, 21.35, 21.57, 30.98, 36.03, 37.66, 37.73, 38.83, 44.85, 45.03, 45.65, 49.57, 50.25, 57.62, 63.59, 69.90, 70.32, 71.65, 74.32, 76.58, 78.24, 79.03, 90.05, 108.36, 175.36, 220.84

EXAMPLE 62

5-O-(3'-N-demethyl-3'-N-(2-dimethylaminoethyl)desosaminyl)-6-O-methylerythronolide B (1) Using 300 mg of the compound obtained in Example 53, a reaction was carried out in a similar manner described in Example 7 (2) to give 408 mg of a 3'-N-phthalimide ethyl compound.
(2) Using 368 mg of the compound obtained in the above (1), a reaction was carried out in a similar manner described in Example 8 and Example 9 to give 238 mg of the titled compound.
MS (ESI) m/z=631.4 [M+H]$^+$
13C NMR (126 MHz, CHLOROFORM-d) δ ppm 8.45, 9.27, 10.06, 10.50, 15.16, 17.99, 18.92, 21.35, 26.31, 30.94, 36.05, 38.38, 40.34, 44.80, 45.03, 45.64, 49.71, 50.27, 57.60, 63.66, 70.21, 71.60, 74.56, 78.74, 79.05, 89.79, 108.21, 175.70, 219.73

EXAMPLE 63

3-O-(2-nitrophenyl)-5-O-(2'-O-(3-oxobut-1-enyl) desosaminyl)-6-O-methylerythronolide A Using 300 mg of 3-O-(2-nitrophenyl)-5-O-desosaminyl-6-O-methylerythronolide A obtained by the method described in a literature (Journal of Medicinal Chemistry, 2001, Vol. 44, No. 24, p. 4027), a reaction was carried out in a similar manner described in Example 1 to give 270 mg of the titled compound.
MS (ESI) m/z=779.4 [M+H]$^+$
13C NMR (126 MHz, CHLOROFORM-d) δ ppm 8.20, 10.51, 12.67, 15.61, 16.29, 17.85, 19.53, 20.52, 21.24, 28.50, 36.65, 37.49, 38.66, 41.00, 44.18, 45.44, 50.28, 68.68, 69.78, 74.22, 77.50, 78.11, 82.45, 99.00, 113.49, 120.47, 125.50, 133.80, 140.34, 174.31, 220.90

EXAMPLE 64

2'-O-(1,2-di(ethoxycarbonyl)vinyl)-6-O-methylerythromycin A

Using 10 g of 6-O-methylerythromycin A and using 2.46 ml of diethylacetylene dicarboxylate instead of 3-butyn-2-one, a reaction was carried out in a similar manner described in Example 1 to give 4.95 g of the titled compound.
MS (ESI) m/z=918.4 [M+H]$^+$
13C NMR (126 MHz, CHLOROFORM-d) δ ppm 8.72, 10.76, 12.39, 13.94, 16.18, 17.84, 18.80, 20.04, 21.17, 21.61, 34.98, 35.58, 37.52, 39.38, 45.09, 49.57, 50.47, 60.34, 61.94, 68.35, 69.25, 72.96, 74.28, 77.99, 78.26, 80.64, 95.73, 101.01, 163.75, 176.22, 221.01

EXAMPLE 65

11-amino-11-deoxy-5-O-(3'-N-demethyl-3'-N-(3-methoxybenzyl)desosaminyl)-6-O-methylerythronolide A 11,12-cyclic carbamate Using 500 mg of the compound obtained in Example 22 (1) and using 3-methoxybenzaldehyde instead of benzaldehyde, and methylene chloride instead of chloroform, a reaction was carried out in a similar manner described in Example 13 to give 490 mg of the titled compound.
MS (ESI) m/z=721.3 [M+H]$^+$
13C NMR (126 MHz, CHLOROFORM-d) δ ppm 8.45, 10.33, 13.47, 14.00, 15.33, 18.15, 18.76, 21.35, 22.28, 29.14, 31.02, 36.09, 36.58, 37.46, 39.21, 44.75, 45.53, 49.46, 55.32, 58.17, 58.49, 65.00, 70.47, 70.75, 75.67, 78.11, 79.11, 84.12, 89.25, 107.12, 112.52, 119.18, 129.65, 140.16, 158.62, 175.50, 217.72

EXAMPLE 66

2'-O-(4-methoxybenzyl)-6-O-methylerythromycin A

Using 1 g of the compound obtained in Example 24 (1) as a starting material and using 4-methoxybenzyl chloride instead of 1-bromo-3-phenylpropane, a reaction was carried out in a similar manner described in Example 24 (2) and (3) to give 0.39 g of the titled compound.

MS (ESI) m/z=868.5 [M+H]+

13C NMR (126 MHz, CHLOROFORM-d) δ ppm 8.72, 10.65, 12.30, 15.92, 16.12, 18.08, 18.88, 19.98, 21.07, 21.47, 21.52, 32.47, 34.88, 37.42, 39.59, 39.77, 41.14, 45.04, 45.32, 49.51, 50.56, 55.27, 64.45, 65.78, 68.21, 69.07, 72.65, 73.40, 74.26, 76.63, 77.90, 77.96, 78.54, 78.71, 79.90, 95.87, 103.08, 113.51, 129.67, 158.97, 176.14, 220.81

EXAMPLE 67

3'-N-demethyl-3'-N-benzyloxycarbonyl-9-deoxo-9a-aza-9a-methyl-9a-homoerythromycin A (1) Using 50 g of 9-deoxo-9a-aza-9a-methyl-9a-homoerythromycin A, a reaction was carried out in a similar manner described in Example 7 (1) to give 2.5 g of a 3'-N-demethyl compound.

(2) 250 mg of the compound obtained in the above (1) was dissolved in a mixed solution of chloroform, N,N-dimethylformamide, acetone and triethylamine. 143 mg of sodium bicarbonate was added and 0.06 ml of benzyl chloroformate was added under ice cooling. After stirring for 3 hours, water was added to the reaction solution, and the mixture was extracted with ethyl acetate. The organic layer was washed with a 2N aqueous sodium hydroxide solution and saturated brine in this order, dried over anhydrous magnesium sulfate, and filtered. The resulting filtrate was purified by silica gel column chromatography (acetone:hexane:triethylamine=6:10:0.2) to give 189 mg of the titled compound.

MS (ESI) m/z=869.6 [M+H]+

1H NMR (500 MHz, CHLOROFORM-d) characteristic peak δ ppm 2.33 (s, 3H) 2.88 (s, 3H) 7.24-7.39 (m, 5H)

EXAMPLE 68

11-amino-3'-N-demethyl-3'-N-benzyl-9-O-11-deoxo-11-deoxy-9,11-N-nitriloethano-6-O-methylerythromycin A 11,12-cyclic carbamate (1) Using 2.0 g of tricyclic carbamate described in a literature (The Journal of Antibiotics, 2001, Vol. 54, No. 8, p. 664-678), a reaction was carried out in a similar manner described in Example 7 (1) to give 1.4 g of a 3'-N-demethyl compound.

(2) Using 300 mg of the compound obtained in the above (1), a reaction was carried out in a similar manner described in Example 13 to give 280 mg of the titled compound.

MS (ESI) m/z=874.6 [M+H]+

13C NMR (126 MHz, CHLOROFORM-d) δ ppm 9.15, 10.47, 10.99, 12.62, 16.08, 18.62, 19.73, 20.17, 21.55, 21.60, 21.93, 29.32, 34.84, 36.65, 36.86, 39.85, 45.61, 49.51, 58.10, 59.80, 63.63, 65.74, 68.79, 70.74, 72.57, 75.41, 77.83, 77.98, 79.23, 80.26, 82.01, 95.86, 102.94, 127.38, 128.54, 128.96, 138.85, 176.76

EXAMPLE 69

11-amino-3'-N-demethyl-3'-N-(2-(1,3-dioxo-1,3-dihydroisoindol-2-yl)-ethyl)-9-O-deoxo-11-deoxy-9,11-N-nitriloethano-6-O-methylerythromycin A 11,12-cyclic carbamate Using 400 mg of the compound obtained in Example 68 (1), a reaction was carried out in a similar manner described in Example 7 (2) to give 424 mg of the titled compound.

MS (ESI) m/z=957.6 [M+H]+

1H NMR (600 MHz, CHLOROFORM-d) δ ppm 0.83 (t, J=7.57 Hz, 3H) 1.29 (d, J=5.96 Hz, 3H) 1.36-1.41 (m, 6H) 1.82-1.91 (m, 2H) 2.31 (s, 3H) 2.32-2.37 (m, 1H) 2.37-2.41 (m, 1H) 2.49-2.60 (m, 2H) 2.64-2.75 (m, 3H) 2.79-2.88 (m, 2H) 2.96-3.04 (m, 2H) 3.06 (s, 3H) 3.15-3.20 (m, 2H) 3.30 (s, 3H) 3.43-3.50 (m, 1H) 3.59-3.62 (m, 1H) 3.64-3.67 (m, 1H) 3.95-4.04 (m, 2H) 4.41 (d, J=7.34 Hz, 1H) 4.88-4.91 (m, 1H) 4.95-4.98 (m, 1H) 7.68-7.72 (m, 2H) 7.80-7.85 (m, 2H)

EXAMPLE 70

11-amino-3'-N-demethyl-3'-N-(2-aminoethyl)-9-O-deoxo-11-deoxy-9,11-N-nitriloethano-6-O-methyl-erythromycin A 11,12-cyclic carbamate Using 350 mg of the compound obtained in Example 69, a reaction was carried out in a similar manner described in Example 8 to give 383 mg of the titled compound.

MS (ESI) m/z=827.6 [M+H]+

1H NMR (600 MHz, CHLOROFORM-d) δ ppm 0.83 (t, J=7.34 Hz, 3H) 1.00-1.09 (m, 6H) 1.27-1.32 (m, 3H) 1.37-1.43 (m, 6H) 1.64-1.70 (m, 1H) 2.28 (s, 3H) 2.33-2.42 (m, 2H) 2.45-2.51 (m, 1H) 2.58-2.64 (m, 1H) 2.81-2.87 (m, 1H) 2.96-3.03 (m, 2H) 3.07 (s, 3H) 3.21-3.25 (m, 1H) 3.32 (s, 3H) 3.43-3.49 (m, 1H) 3.61-3.64 (m, 1H) 3.65-3.67 (m, 1H) 3.72-3.83 (m, 3H) 3.95-4.04 (m, 2H) 4.40-4.43 (m, 1H) 4.89-4.91 (m, 1H) 4.95-4.99 (m, 1H)

EXAMPLE 71

11-amino-3'-N-demethyl-3'-N-(2-dimethylaminoethyl)-9-O-deoxo-11-deoxy-9,11-N-nitriloethano-6-O-methylerythromycin A 11,12-cyclic carbamate Using 383 mg of the compound obtained in Example 70, a reaction was carried out in a similar manner described in Example 9 to give 254 mg of the titled compound.

MS (ESI) m/z=855.6 [M+H]+

13C NMR (126 MHz, CHLOROFORM-d) δ ppm 9.05, 10.49, 11.00, 12.60, 16.06, 18.74, 19.77, 20.14, 21.60, 21.94, 30.55, 34.88, 36.65, 37.71, 38.21, 40.11, 42.59, 43.41, 45.60, 45.66, 49.59, 49.68, 50.04, 50.98, 58.19, 59.82, 64.81, 65.73, 68.86, 71.21, 72.76, 75.41, 77.94, 78.07, 79.36, 79.98, 82.01, 96.00, 103.22, 156.43, 176.92

EXAMPLE 72

11-amino-3'-N-demethyl-3'-N-(2-benzyloxycarbonylaminoethyl)-9-O-deoxo-11-deoxy-9,11-N-nitriloethano-6-O-methylerythromycin A 11,12-cyclic carbamate 300 mg of the compound obtained in Example 68 (1) was suspended in 2 ml of acetone, 163 mg of N-benzyloxycarbonyl-2-iodoethylamine described in a literature (Organic & Biomolecular Chemistry, 2004, Vol. 2, No. 18, p. 2593-2603), and 48 mg of sodium bicarbonate were added in this order, and the mixture was stirred under reflux for 72 hours. Water was added to the reaction solution, and the mixture was extracted with chloroform. The organic layer was dried over anhydrous magnesium sulfate, and filtered. The filtrate was evaporated under reduced pressure, and the resulting residue was purified by silica gel column chromatography (acietone:hexane:triethylamine=10:10:0.2) to give 170 mg of the titled compound.

MS (ESI) m/z=961.7 [M+H]+

13C NMR (126 MHz, CHLOROFORM-d) δ ppm 9.40, 10.48, 11.00, 12.65, 16.07, 18.71, 19.75, 20.09, 21.48, 21.60, 21.94, 34.86, 36.66, 37.20, 38.18, 39.86, 42.58, 43.34, 45.62, 49.57, 49.68, 50.03, 52.53, 59.82, 64.96, 65.79, 66.74, 68.78, 71.42, 72.78, 75.48, 77.90, 78.00, 79.24, 80.32, 81.98, 96.02, 103.00, 128.14, 128.20, 128.58, 136.72, 156.40, 156.64, 176.75

EXAMPLE 73

11-amino-2'-O-(3-oxobut-1-enyl)-9-O-deoxo-11-deoxy-9,11-N-nitriloethano-6-O-methylerythromycin A 11,12-cyclic carbamate Using 1.0 g of tricyclic carbamate described in a literature (The Journal of Antibiotics, 2001, Vol. 54, No. 8, p. 664-678), a reaction was carried out in a similar manner described in Example 1 to give 290 mg of the titled compound.

MS (ESI) m/z=866.7 [M+H]$^+$

13C NMR (126 MHz, CHLOROFORM-d) δ ppm 8.86, 10.49, 11.03, 12.85, 15.98, 18.76, 19.68, 20.18, 21.37, 21.62, 21.95, 27.87, 31.55, 34.85, 36.71, 39.92, 40.85, 45.69, 49.59, 49.93, 59.88, 63.33, 65.91, 68.43, 72.86, 75.61, 77.56, 77.89, 79.16, 79.93, 82.01, 83.85, 95.77, 100.66, 108.21, 164.65

EXAMPLE 74

11-amino-4"-O-acetyl-3'-dedimethylamino-11,2'-dideoxy-2'-dimethylamino-3'-(4-methylpiperidin-1-yl)-6-O-methylerythromycin A 11,12-cyclic carbamate (1) Using 1.0 g of 2',4"-O-acetyl-cyclic carbamate obtained by the method described in a literature (Journal of Medicinal Chemistry, 2003, Vol. 46, No. 13, p. 2706), a reaction was carried out in a similar manner described in Example 14 (1) to give 1.1 g of a 2'-OH compound.

(2) 500 mg of the compound obtained in the above (1) was dissolved in 1 ml of chloroform, and 260 μl of triethylamine was added. a solution of 100 μl of methanesulfonyl chloride in 1 ml of chloroform was added under ice cooling, the mixture was stirred for 4 hours being raised to room temperature. A saturated aqueous sodium bicarbonate solution was added to the reaction solution, and the mixture was extracted with chloroform. The organic layer was dried over anhydrous magnesium sulfate, and filtered. The filtrate was evaporated under reduced pressure, and the resulting residue was purified by silica gel column chromatography (acetone:hexane:triethylamine=3:10:0.2 to 6:10:0.2) to give 196 mg of a 2'-OMs compound.

(3) 177 mg of the compound obtained in the above (2) was dissolved in 2 ml of N,N-dimethylformamide, and 286 μl of 1-methylpiperazine was added. The mixture was stirred at 60° C. for 3 hours, and stirred at 75° C. for 2 hours. A saturated aqueous sodium bicarbonate solution was added to the reaction solution, and the mixture was extracted with ethyl acetate. The organic layer was washed with a saturated aqueous sodium bicarbonate solution, dried over anhydrous magnesium sulfate, and filtered. The filtrate was evaporated under reduced pressure, and the resulting residue was purified by silica gel column chromatography (chloroform:methanol:ammonia water solution=20:1:0.1) to give 180 mg of the titled compound.

MS (ESI) m/z=897.6 [M+H]$^+$

13C NMR (126 MHz, CHLOROFORM-d) δ ppm 8.69, 10.53, 13.43, 13.74, 16.05, 18.18, 18.36, 20.49, 21.00, 21.30, 22.01, 22.03, 35.25, 37.56, 40.28, 40.78, 44.29, 45.02, 45.87, 45.97, 49.81, 50.16, 55.25, 57.78, 59.48, 59.65, 63.30, 67.39, 72.60, 75.76, 78.59, 78.76, 78.87, 80.54, 83.94, 96.80, 101.61, 158.38, 170.65, 177.10, 218.09

EXAMPLE 75

3-O-(3-methoxybenzoyl)-5-O-(2'-O-(3-oxobut-1-enyl)desosaminyl)-6-O-methylerythronolide A 11,12-cyclic carbonate (1) Using 3.0 g of 2'-O-acetyl-3-OH cyclic carbonate obtained by the method described in a literature (Journal of Medicinal Chemistry, 2003, Vol. 46, No. 13, p. 2706), and using 2.08 g of 3-methoxy benzoic acid instead of 2-pyridyl acetate hydrochloride and 30 ml of methylene chloride instead of chloroform, a reaction was carried out in a similar manner described in Example 15 (1) to give 2.47 g of a 3-O-(3-methoxyphenyl)acetyl compound.

(2) 2.47 g of the compound obtained in the above (1) was suspended in 50 ml of methanol, 500 mg of sodium bicarbonate was added, and the mixture was stirred at room temperature for 15 hours. The reaction solution was evaporated under reduced pressure, and the resulting residue was crystallized from ether and hexane to give 1.64 g of a 2'-OH compound.

(3) Using 500 mg of the compound obtained in the above (2), a reaction was carried out in a similar manner described in Example 1 to give 274 mg of the titled compound.

MS (ESI) m/z=840.4 [M+Na]$^+$

13C NMR (126 MHz, CHLOROFORM-d) δ ppm 9.07, 10.19, 12.97, 13.24, 15.26, 18.41, 19.46, 20.69, 22.08, 27.94, 31.74, 36.32, 37.61, 38.77, 40.73, 43.12, 45.11, 50.11, 55.54, 62.95, 68.85, 75.73, 77.96, 78.12, 79.88, 80.85, 83.04, 84.90, 99.87, 108.40, 114.43, 120.12, 122.27, 129.90, 130.96, 154.06, 159.94, 164.26, 165.52, 174.07, 197.34, 211.94

EXAMPLE 76

11-amino-11-deoxy-5-O-(2'-O-benzyloxycarbonyl-3'-N-demethyl-3'-N-benzyldesosaminyl)-6-O-methylerythronolide A 11,12-cyclic carbamate (1) Using 5 g of the compound obtained in Example 14 (1) and using 20 ml of 1,4-dioxane instead of chloroform, a reaction was carried out in a similar manner described in Example 54 to give 4.23 g of a 2'-benzyloxycarbonyl compound.

(2) Using 600 mg of the compound obtained in the above (1), a reaction was carried out in a similar manner described in Example 7 (1) to give 330 mg of a 3'-N-demethyl compound.

(3) Using 330 mg of the compound obtained in the above (2), a reaction was carried out in a similar manner described in Example 13 to give 288 mg of the titled compound.

MS (ESI) m/z=825.3 [M+H]$^+$

13C NMR (126 MHz, CHLOROFORM-d) δ ppm 7.46, 10.34, 13.44, 14.00, 15.38, 18.33, 19.29, 21.13, 22.21, 32.12, 35.74, 36.62, 37.34, 38.95, 44.30, 45.43, 49.65, 58.34, 58.85, 62.65, 69.03, 69.51, 75.76, 75.85, 77.97, 78.17, 82.19, 83.97, 100.01, 100.06, 126.92, 128.25, 128.44, 128.54, 128.61, 139.72, 154.76, 158.56, 175.21

EXAMPLE 77

3'-N-demethyl-2'-O-(3-phenylpropyl)-6-O-methylerythromycin A 145 mg of the compound synthesized in Example 24 was dissolved in 1.5 ml of tetrahydrofuran and 0.75 ml of water, 45 mg of N-bromosuccinimide was added, and the mixture was stirred at room temperature for 0.5 hours. The reaction solution was poured into a saturated aqueous sodium bicarbonate solution, and extracted with chloroform. The combined organic layer was dried over anhydrous magnesium sulfate, and then concentrated. The resulting residue was purified by silica gel column chromatography (acetone:hexane:triethylamine=30:50:1) to give 54 mg of the titled compound.

MS (ESI) m/z=852.5 [M+H]$^+$

13C NMR (126 MHz, CHLOROFORM-d) δ ppm 8.42, 10.66, 12.31, 15.92, 16.15, 17.96, 18.78, 19.93, 21.09, 21.34, 21.53, 31.41, 32.45, 34.89, 37.41, 39.19, 39.59, 44.98, 45.35, 49.49, 50.46, 60.12, 65.85, 68.12, 69.10, 72.65, 76.66, 77.90, 78.43, 79.82, 95.80, 102.07, 125.91, 128.29, 128.40, 141.76, 176.06, 220.86

EXAMPLE 78

2'-O-(4-nitrobenzyl)-6-O-methylerythromycin A

Using 2.00 g of the compound obtained in Example 24 (1) and using 4-nitrobenzyl bromide instead of 1-bromo-3-phenylpropane, a reaction was carried out in a similar manner described in Example 24 (2) and (3) to give 0.62 g of the titled compound.

MS (ESI) m/z=883.5 [M+H]$^+$

1H NMR (600 MHz, CHLOROFORM-d) δ ppm 0.82 (t, J=7.34 Hz, 3H) 0.91 (d, J=7.79 Hz, 3H) 1.08-1.15 (m, 6H) 1.15-1.18 (m, 6H) 1.20 (d, J=5.96 Hz, 3H) 1.22-1.32 (m, 1H) 1.25 (s, 3H) 1.29 (d, J=6.42 Hz, 3H) 1.39 (s, 3H) 1.41-1.50 (m, 1H) 1.53-1.65 (m, 2H) 1.66-1.95 (m, 4H) 2.16 (d, J=10.09 Hz, 1H) 2.27 (s, 6H) 2.33 (d, J=15.13 Hz, 1H) 2.57-2.70 (m, 2H) 2.72-2.80 (m, 1H) 2.95-3.05 (m, 2H) 3.02 (s, 3H) 3.09 (d, J=8.25 Hz, 1H) 3.17 (s, 1H) 3.33 (s, 3H) 3.44-3.51 (m, 1H) 3.67 (d, J=7.34 Hz, 1H) 3.75 (s, 1H) 3.78 (d, J=7.79 Hz, 1H) 3.94 (s, 1H) 3.95-4.00 (m, 1H) 4.51 (d, J=7.34 Hz, 1H) 4.86 (d, J=12.84 Hz, 1H) 4.90 (d, J=4.59 Hz, 1H) 4.97 (d, J=12.84 Hz, 1H) 5.02 (dd, J=11.23, 2.06 Hz, 1H) 7.53 (d, J=8.71 Hz, 2H) 8.18 (d, J=8.71 Hz, 2H)

EXAMPLE 79

2'-O-(4-pyridylmethyl)-6-O-methylerythromycin A

Using 1.00 g of the compound obtained in Example 24 (1) and using 4-pyridylmethylbromide hydrobromide instead of 1-bromo-3-phenylpropane, a reaction was carried out in a similar manner described in Example 24 (2) and (3) to give 0.15 g of the titled compound.

MS (ESI) m/z=839.5 [M+H]$^+$

1H NMR (600 MHz, CHLOROFORM-d) δ ppm 0.77 (t, J=7.34 Hz, 3H) 0.87 (d, J=7.79 Hz, 3H) 1.04-1.09 (m, 6H) 1.10-1.14 (m, 6H) 1.15 (d, J=5.96 Hz, 3H) 1.17-1.25 (m, 1H) 1.21 (s, 3H) 1.25 (d, J=5.96 Hz, 3H) 1.35 (s, 3H) 1.36-1.44 (m, 1H) 1.48-1.60 (m, 2H) 1.62-1.90 (m, 4H) 2.12-2.20 (m, 1H) 2.24 (s, 6H) 2.29 (d, J=15.13 Hz, 1H) 2.52-2.66 (m, 2H) 2.68-2.77 (m, 1H) 2.97 (s, 2H) 2.97 (s, 3H) 3.05 (dd, J=10.09, 7.34 Hz, 1H) 3.10-3.19 (m, 1H) 3.29 (s, 3H) 3.39-3.48 (m, 1H) 3.62 (d, J=7.79 Hz, 1H) 3.70 (s, 1H) 3.73 (d, J=8.71 Hz, 1H) 3.85-3.98 (m, 2H) 4.46 (d, J=7.34 Hz, 1H) 4.72 (d, J=13.30 Hz, 1H) 4.82-4.89 (m, 2H) 4.97 (dd, J=11.00, 2.29 Hz, 1H) 7.24 (d, J=4.58 Hz, 2H) 8.50 (s, 2H)

EXAMPLE 80

2'-O-(4-aminobenzyl)-6-O-methylerythromycin A 787 mg of the compound obtained in Example 78 was dissolved in 80 ml of methanol, 80 mg of 5% palladium-carbon was added, and the mixture was stirred at room temperature for 6 hours in a hydrogen atmosphere at 1 atm. The reaction solution was filtered, the filtrate was evaporated under reduced pressure, and the resulting residue was purified by silica gel column chromatography (chloroform:methanol:ammonia water solution=30:1:0.1 to 20:1:0.1). The resulting residue was recrystallized from ethyl acetate to give 293 mg of the titled compound.

MS (ESI) m/z=853.8 [M+H]$^+$

1H NMR (600 MHz, CHLOROFORM-d) δ ppm 0.80-0.86 (m, 3H) 1.03-1.08 (m, 3H) 1.10-1.32 (m, 22H) 1.38-1.42 (m, 3H) 1.43-1.50 (m, 1H) 1.53-1.58 (m, 1H) 1.61-1.71 (m, 2H) 1.78-1.96 (m, 3H) 2.14-2.19 (m, 1H) 2.22 (s, 6H) 2.30-2.36 (m, 1H) 2.57-2.66 (m, 2H) 2.78-2.85 (m, 1H) 2.96-3.05 (m, 2H) 3.03 (s, 3H) 3.06-3.11 (m, 1H) 3.30 (s, 3H) 3.40-3.49 (m, 1H) 3.61-3.69 (m, 3H) 3.78-3.82 (m, 1H) 3.93-4.00 (m, 2H) 4.42-4.45 (m, 1H) 4.56-4.60 (m, 1H) 4.76-4.80 (m, 1H) 4.88-4.92 (m, 1H) 5.00-5.05 (m, 1H) 6.61-6.65 (m, 2H) 7.13-7.18 (m, 2H)

EXAMPLE 81

2'-O-(4-dimethylaminobenzyl)-6-O-methylerythromycin A

Using 77 mg of the compound obtained in Example 80, a reaction was carried out in a similar manner described in Example 9 to give 40 mg of the titled compound.

MS (ESI) m/z=881.6 [M+H]$^+$

1H NMR (600 MHz, CHLOROFORM-d) δ ppm 0.83 (t, J=7.34 Hz, 3H) 1.08 (d, J=7.34 Hz, 3H) 1.12 (d, J=6.88 Hz, 3H) 1.13-1.16 (m, 6H) 1.16-1.19 (m, 6H) 1.20-1.25 (m, 1H) 1.22 (s, 3H) 1.29 (d, J=6.42 Hz, 3H) 1.38-1.42 (m, 3H) 1.42-1.50 (m, 1H) 1.55 (dd, J=15.13, 5.04 Hz, 1H) 1.63-1.73 (m, 2H) 1.80-1.95 (m, 3H) 2.17 (d, J=10.09 Hz, 1H) 2.23 (s, 6H) 2.33 (d, J=15.13 Hz, 1H) 2.57-2.66 (m, 2H) 2.78-2.85 (m, 1H) 2.92 (s, 6H) 2.96-3.02 (m, 2H) 3.03 (s, 3H) 3.10 (d, J=10.09, 7.34 Hz, 1H) 3.17-3.21 (m, 1H) 3.30 (s, 3H) 3.41-3.50 (m, 1H) 3.68 (d, J=7.79 Hz, 1H) 3.77 (d, J=1.38 Hz, 1H) 3.81 (d, J=8.71 Hz, 1H) 3.94-4.00 (m, 2H) 4.44 (d, J=7.34 Hz, 1H) 4.59 (d, J=11.00 Hz, 1H) 4.81 (d, J=11.00 Hz, 1H) 4.90 (d, J=4.59 Hz, 1H) 5.03 (dd, J=11.00, 2.29 Hz, 1H) 6.68 (d, J=8.71 Hz, 2H) 7.24 (d, J=8.71 Hz, 2H)

EXAMPLE 82

3'-N-demethyl-6,2'-di-O-methylerythromycin A

Using 1.57 g of the compound obtained in Example 31, a reaction was carried out in a similar manner described in Example 77 to give 0.34 g of the titled compound.

MS (ESI) m/z=748.7 [M+H]$^+$

1H NMR (600 MHz, CHLOROFORM-d) δ ppm 0.84 (t, J=7.34 Hz, 3H) 1.04 (d, J=7.34 Hz, 3H) 1.14 (s, 10H) 1.17-1.22 (m, 6H) 1.24 (s, 3H) 1.29 (d, J=6.42 Hz, 3H) 1.39 (s, 3H) 1.41-1.51 (m, 1H) 1.52-1.72 (m, 3H) 1.73-1.82 (m, 2H) 1.82-1.96 (m, 2H) 2.15 (d, J=10.09 Hz, 1H) 2.34 (d, J=15.13 Hz, 1H) 2.38 (s, 3H) 2.40-2.47 (m, 1H) 2.58-2.64 (m, 1H) 2.70 (dd, J=9.63, 7.79 Hz, 1H) 2.79-2.87 (m, 1H) 2.94-3.05 (m, 2H) 3.02 (s, 3H) 3.20 (s, 1H) 3.30 (s, 3H) 3.49-3.58 (m, 1H) 3.54 (s, 3H) 3.66 (d, J=7.79 Hz, 1H) 3.77 (d, J=1.38 Hz, 1H) 3.80 (d, J=8.25 Hz, 1H) 3.93-4.02 (m, 1H) 3.98 (s, 1H) 4.43 (d, J=7.79 Hz, 1H) 4.91 (d, J=5.04 Hz, 1H) 5.04 (dd, J=11.00, 2.29 Hz, 1H)

EXAMPLE 83

2'-O-methyl-9-deoxo-9a-aza-9a-methyl-9a-homo-erythromycin A

Using 1.18 g of 9-deoxo-9a-aza-9a-methyl-9a-homoerythromycin A and using methyl iodide instead of 1-bromo-3-phenylpropane, a reaction was carried out in a similar manner described in Example 24 to give 70 mg of the titled compound.

MS (ESI) m/z=763.6 [M+H]$^+$

1H NMR (600 MHz, CHLOROFORM-d) δ ppm 0.88 (t, J=7.45 Hz, 3H) 0.90 (d, J=6.12 Hz, 3H) 1.02 (d, J=7.64 Hz, 3H) 1.06-1.10 (m, 6H) 1.16-1.20 (m, 6H) 1.23 (s, 1H) 1.23 (s, 3H) 1.26-1.35 (m, 1H) 1.30 (s, 3H) 1.31 (d, J=6.50 Hz, 3H) 1.38-1.50 (m, 1H) 1.57 (dd, J=15.10, 5.16 Hz, 1H) 1.66-1.74 (m, 2H) 1.83-2.14 (m, 5H) 2.26-2.40 (m, 1H) 2.31 (s, 3H) 2.36 (s, 6H) 2.51-2.64 (m, 2H) 2.64-2.76 (m, 2H) 2.90 (dd, J=10.13, 7.45 Hz, 1H) 2.94-3.05 (m, 1H) 3.01 (t, J=9.75 Hz, 1H) 3.32 (s, 3H) 3.44-3.51 (m, 1H) 3.53 (s, 3H) 3.65 (d, J=7.65 Hz, 1H) 3.68 (s, 1H) 4.00-4.11 (m, 1H) 4.31-4.35 (m, 1H) 4.39 (d, J=7.26 Hz, 1H) 4.70 (dd, J=9.94, 2.68 Hz, 1H) 5.07 (s, 1H) 5.17 (d, J=4.97 Hz, 1H) 9.22-9.66 (m, 1H)

EXAMPLE 84

5-O-(2'-O-methyl)desosaminyl-6-O-methylerythronolide A 0.40 g of the compound obtained in Example 31 was dissolved in 5 ml of methanol, 5 ml of 1.5N hydrochloric acid was added, and the mixture was stirred at room temperature for 60 hours.

A saturated aqueous sodium bicarbonate solution was added to the reaction solution to be adjusted to be basic, and then the mixture was extracted with chloroform. The organic layer was washed with saturated brine, dried over anhydrous magnesium sulfate, and filtered. The filtrate was evaporated under reduced pressure, and the resulting residue was purified by silica gel column chromatography (chloroform:methanol:ammonia water solution=20:1:0.1) to give 0.32 g of the titled compound.

MS (ESI) m/z=604.5 [M+H]$^+$

1H NMR (600 MHz, CHLOROFORM-d) δ ppm 0.83 (t, J=7.40 Hz, 3H) 1.06 (d, J=7.68 Hz, 3H) 1.09-1.14 (m, 6H) 1.17 (s, 3H) 1.19 (d, J=6.31 Hz, 3H) 1.20-1.28 (m, 1H) 1.25 (d, J=6.58 Hz, 3H) 1.30 (s, 3H) 1.42-1.54 (m, 2H) 1.59-1.70 (m, 1H) 1.86-2.04 (m, 3H) 2.08-2.16 (m 1H) 2.32 (s, 6H) 2.52-2.70 (m, 3H) 2.91 (dd, J=10.15, 7.40 Hz, 1H) 2.95 (s, 3H) 2.98-3.04 (m, 1H) 3.25 (s, 1H) 3.39-3.52 (m, 2H) 3.56 (s, 3H) 3.75 (d, J=2.47 Hz, 1H) 3.85 (d, J=1.65 Hz, 1H) 3.93 (s, 1H) 4.47 (d, J=7.68 Hz, 1H) 5.17 (dd, J=10.97, 2.47 Hz, 1H)

EXAMPLE 85

3'-N-demethyl-3'-N-(4-dimethylaminobenzyl)-6,2'-di-O-methylerythromycin A

Using 0.25 g of the compound obtained in Example 82 and using 4-dimethylaminobenzaldehyde instead of phthalimideacetaldehyde, a reaction was carried out in a similar manner described in Example 7 (2) to give 0.12 g of the titled compound.

MS (ESI) m/z=881.8 [M+H]$^+$

1H NMR (600 MHz, CHLOROFORM-d) δ ppm 0.84 (t, J=7.34 Hz, 3H) 1.07 (d, J=7.79 Hz, 3H) 1.10-1.14 (m, 6H) 1.15 (s, 3H) 1.18-1.21 (m, 9H) 1.28 (d, J=6.42 Hz, 3H) 1.30-1.37 (m, 1H) 1.39 (s, 3H) 1.43-1.50 (m, 1H) 1.54 (dd, J=15.13, 5.04 Hz, 1H) 1.60-1.69 (m, 1H) 1.70-1.96 (m, 4H) 2.11 (d, J=10.55 Hz, 1H) 2.24 (s, 3H) 2.33 (d, J=15.13 Hz, 1H) 2.56-2.65 (m, 1H) 2.66-2.74 (m, 1H) 2.80-2.88 (m, 1H) 2.91 (s, 6H) 2.93-3.01 (m, 3H) 3.02 (s, 3H) 3.20 (s, 1H) 3.23 (s, 3H) 3.38-3.45 (m, 1H) 3.50 (d, J=13.30 Hz, 1H) 3.58 (s, 3H) 3.64 (d, J=7.34 Hz, 1H) 3.71 (d, J=12.84 Hz, 1H) 3.77 (s, 1H) 3.79 (s, 1H) 3.92-4.00 (m, 1H) 3.97 (s, 1H) 4.38 (d, J=7.34 Hz, 1H) 4.90 (d, J=5.04 Hz, 1H) 5.04 (dd, J=11.00, 2.29 Hz, 1H) 6.69 (d, J=8.71 Hz, 2H) 7.20 (d, J=8.71 Hz, 2H)

EXAMPLE 86

3-O-(4-methoxyphenyl)acetyl-5-O-(2'-O-methyldesosaminyl)-6-O-methylerythronolide A Using 96 mg of the compound obtained in Example 84 and using 4-methoxyphenylacetic acid instead of 2-pyridyl acetate hydrochloride, a reaction was carried out in a similar manner described in Example 15 (1) to give 0.12 g of the titled compound.

MS (ESI) m/z=752.6 [M+H]$^+$

1H NMR (600 MHz, CHLOROFORM-d) δ ppm 0.80 (t, J=7.34 Hz, 3H) 0.87 (d, J=6.88 Hz, 3H) 1.08 (d, J=5.96 Hz, 3H) 1.09-1.13 (m, 9H) 1.14 (s, 3H) 1.15-1.21 (m, 1H) 1.21-1.29 (m, 1H) 1.25 (s, 3H) 1.39-1.84 (m, 3H) 1.86-1.96 (m, 1H) 2.13-2.21 (m, 1H) 2.37 (s, 6H) 2.45-2.60 (m, 2H) 2.77-2.88 (m, 2H) 2.89-2.97 (m, 1H) 2.99 (q, J=6.57 Hz, 1H) 3.03 (s, 3H) 3.23 (s, 1H) 3.55 (s, 3H) 3.56-3.66 (m, 2H) 3.78 (s, 3H) 3.79-3.82 (m, 2H) 3.90 (d, J=7.34 Hz, 1H) 3.94 (s, 1H) 5.03 (d, J=11.00 Hz, 1H) 5.14 (dd, J=11.00, 1.83 Hz, 1H) 6.84 (d, J=8.71 Hz, 2H) 7.24 (d, J=8.25 Hz, 2H)

EXAMPLE 87

4''-O-acetyl-6,2'-di-O-methylerythromycin A 1.00 g of the compound obtained in Example 31 was suspended in 13 ml of chloroform, 0.44 ml of acetic anhydride and 81 mg of 4-dimethylaminopyridine were added in this order, and the mixture was stirred at room temperature for 61 hours. A saturated aqueous sodium bicarbonate solution was added to the reaction solution, and the mixture was extracted with chloroform. The organic layer was washed with a saturated aqueous ammonium chloride solution, subsequently saturated brine, dried over anhydrous magnesium sulfate, and filtered. The filtrate was evaporated under reduced pressure, and the resulting residue was purified by silica gel column chromatography (chloroform:methanol:ammonia water solution=20:1:0.1), to give 0.92 g of the titled compound.

MS (ESI) m/z=804.7 [M+H]$^+$

1H NMR (600 MHz, CHLOROFORM-d) δ ppm 0.84 (t, J=7.34 Hz, 3H) 1.05-1.17 (m, 21H) 1.20 (d, J=7.34 Hz, 3H) 1.22-1.27 (m, 1H) 1.37 (s, 3H) 1.42-1.71 (m, 4H) 1.75-1.84 (m, 1H) 1.85-1.95 (m, 2H) 2.09 (s, 3H) 2.37 (s, 6H) 2.37-2.41 (m, 1H) 2.55-2.70 (m, 2H) 2.83-2.91 (m, 2H) 2.96-3.02 (m, 1H) 3.02 (s, 3H) 3.19 (s, 1H) 3.29 (s, 3H) 3.54 (s, 3H) 3.64 (d, J=7.34 Hz, 1H) 3.67-3.73 (m, 1H) 3.77 (s, 1H) 3.80 (d, J=8.25 Hz, 1H) 3.97 (s, 1H) 4.27-4.35 (m, 1H) 4.52 (d, J=7.34 Hz, 1H) 4.65 (d, J=10.09 Hz, 1H) 4.97 (d, J=5.04 Hz, 1H) 5.05 (dd, J=11.00, 2.29 Hz, 1H)

EXAMPLE 88

9-deoxo-9-(E)-hydroxyimino-6,2'-di-O-methylerythromycin A (compound E) and 9-deoxo-9-(Z) hydroxyimino-6,2'-di-O-methylerythromycin A (compound F)

1.00 g of the compound obtained in Example 31 was suspended in 13 ml of methanol, 0.46 g of hydroxylamine hydrochloride and 0.54 g of imidazole were added in this order, and the mixture was stirred under reflux for 15 hours. Water was added to the reaction solution, and the mixture was extracted with chloroform. The organic layer was washed with saturated brine, dried over anhydrous magnesium sulfate, and filtered. The filtrate was evaporated under reduced pressure, and the resulting residue was purified by silica gel column chromatography (chloroform:methanol:ammonia water solution=20:1:0.1), to give 0.85 g of a compound E and 0.11 g of a compound F.

9-deoxo-9-(E)-hydroxyimino-6,2'-di-O-methylerythromycin A (compound E)

MS (ESI) m/z=777.6 [M+H]$^+$

1H NMR (600 MHz, CHLOROFORM-d) δ ppm 0.84 (t, J=7.45 Hz, 3H) 0.99 (d, J=7.26 Hz, 3H) 1.04 (d, J=7.64 Hz, 3H) 1.11-1.26 (m, 17H) 1.29 (d, J=6.12 Hz, 3H) 1.44-1.73 (m, 4H) 1.47 (s, 3H) 1.84-1.98 (m, 2H) 2.19 (d, J=10.32 Hz, 1H) 2.31-2.35 (m, 1H) 2.36 (s, 6H) 2.52-2.61 (m, 2H) 2.82-2.92 (m, 2H) 3.00 (t, J=9.75 Hz, 1H) 3.10 (s, 3H) 3.23 (s, 1H) 3.31 (s, 3H) 3.40-3.49 (m, 1H) 3.53 (s, 3H) 3.65 (d, J=7.64 Hz, 1H) 3.68-3.77 (m, 2H) 3.78 (d, J=9.17 Hz, 1H) 3.95-4.04 (m, 1H) 4.36 (s, 1H) 4.41 (d, J=7.26 Hz, 1H) 4.92 (d, J=4.59 Hz, 1H) 5.10 (dd, J=11.09, 2.29 Hz, 1H) 7.10 (br. s., 1H)

9-deoxo-9-(Z)-hydroxyimino-6,2'-di-O-methylerythromycin A (compound F)

MS (ESI) m/z=777.7 [M+H]$^+$

1H NMR (600 MHz, CHLOROFORM-d) δ ppm 0.85 (t, J=7.34 Hz, 3H) 1.04 (d, J=7.79 Hz, 3H) 1.06 (d, J=6.88 Hz, 3H) 1.16 (s, 3H) 1.18-1.22 (m, 12H) 1.23 (s, 3H) 1.29 (d, J=5.96 Hz, 3H) 1.29 (d, J=5.96 Hz, 3H) 1.38 (s, 3H) 1.43-1.73 (m, 5H) 1.85-1.99 (m, 2H) 2.14-2.22 (m, 1H) 2.29-2.34 (m, 1H) 2.35 (s, 6H) 2.51-2.60 (m, 1H) 2.73-2.90 (m, 3H) 2.97-3.03 (m, 1H) 3.11 (s, 3H) 3.17-3.27 (m, 1H) 3.38-3.47 (m, 1H) 3.53 (s, 3H) 3.61 (d, J=7.79 Hz, 1H) 3.81 (d, J=9.17 Hz, 1H) 3.94-4.01 (m, 1H) 4.39 (d, J=7.34 Hz, 1H) 4.91 (d, J=4.58 Hz, 1H) 5.04 (dd, J=11.00, 2.29 Hz, 1H)

EXAMPLE 89

11-amino-3'-dedimethylamino-11,2'-dideoxy-2'-dimethylamino-3'-(4-methylpiperazin-1-yl)-6-O-methylerythromycin A 11,12-cyclic carbamate 120 mg of the compound obtained in Example 74 was dissolved in 2 ml of methanol, 40 μl of 1,8-diazabicyclo[5.4.0]undecan-7-ene was added, and the mixture was stirred under reflux for 7 hours. The reaction solution was evaporated under reduced pressure, and the resulting residue was purified by silica gel column chromatography (chloroform:methanol:ammonia water solution=10:1:0.1) to give 109 mg of the titled compound.

MS (ESI) m/z=855.6 [M+H]$^+$

1H NMR (600 MHz, CHLOROFORM-d) δ ppm 0.82-0.88 (m, 3H) 0.92-0.98 (m, 3H) 1.06-1.30 (m, 18H) 1.36-1.43 (m, 6H) 1.47-1.81 (m, 7H) 2.27 (s, 3H) 2.30-2.36 (m, 2H) 2.36-2.59 (m, 9H) 2.49 (s, 6H) 2.61-2.76 (m, 3H) 2.83-2.89 (m, 1H) 2.92 (s, 3H) 2.97-3.03 (m, 1H) 3.30 (s, 3H) 3.52-3.56 (m, 1H) 3.65-3.67 (m, 1H) 3.70-3.77 (m, 1H) 3.80-3.84 (m, 1H) 3.99-4.06 (m, 1H) 4.86-4.89 (m, 1H) 4.93-4.96 (m, 1H) 5.06-5.11 (m, 1H) 5.76 (s, 1H)

EXAMPLE 90

3'-N-demethyl-3'-N-(4-pyridylmethyl)-6-O-methylerythromycin A

Using 200 mg of the compound obtained in Example 32 (1) and isonicotinaldehyde instead of benzaldehyde, a reaction was carried out in a similar manner described in Example 13 to give 80 mg of the titled compound.

MS (ESI) m/z=825.5 [M+H]$^+$

1H NMR (600 MHz, CHLOROFORM-d) δ ppm 0.80-0.85 (m, 3H) 1.01-1.35 (m, 25H) 1.36-1.41 (m, 3H) 1.42-1.51 (m, 1H) 1.52-1.58 (m, 1H) 1.65-1.70 (m, 1H) 1.71-1.77 (m, 1H) 1.78-1.85 (m, 1H) 1.86-1.95 (m, 2H) 2.06-2.10 (m, 1H) 2.25 (s, 3H) 2.30-2.35 (m, 1H) 2.49-2.63 (m, 2H) 2.83-2.90 (m, 1H) 2.95-3.04 (m, 2H) 3.02 (s, 3H) 3.17 (s, 1H) 3.18 (s, 3H) 3.27 (s, 1H) 3.28-3.33 (m, 1H) 3.43-3.51 (m, 2H) 3.62-3.65 (m, 1H) 3.72-3.79 (m, 2H) 3.75 (s, 1H) 3.91-3.98 (m, 1H) 3.96 (s, 1H) 4.40-4.44 (m, 1H) 4.89-4.92 (m, 1H) 5.02-5.06 (m, 1H) 7.22-7.25 (m, 2H) 8.52-8.56 (m, 2H)

EXAMPLE 91

3'-N-demethyl-3'-N-(4-dimethylaminobenzyl)-6-O-methylerythromycin A (compound G) and 3'-N-didemethyl-3'-N-bis(4-dimethylaminobenzyl)-6-O-methylerythromycin A (compound H)

(1) 20 g of 6-O-methylerythromycin A was dissolved in 50 ml of tetrahydrofuran, 25 ml of water was added, subsequently 7.1 g of N-bromosuccinimide was added, and the mixture was stirred for 2 hours. A saturated aqueous sodium bicarbonate solution was added to the reaction solution, and the mixture was extracted with ethyl acetate. The organic layer was dried over anhydrous magnesium sulfate, and filtered. The filtrate was evaporated under reduced pressure, and the resulting residue was purified by silica gel column chromatography (chloroform:methanol:ammonia water solution=20:1:0.1). 4.1 g of the resulting residue was crystallized from ethyl acetate to give 2.7 g of a white crystal. It was turned out that this crystal was a mixture of the compound obtained in Example 32 (1) and the compound obtained in Example 43 (1), and its ratio was 4:1 by NMR analysis.

(2) 1 g of the compound obtained in the above (1) was dissolved in chloroform, 264 mg of 4-dimethylamino benzaldehyde and 375 mg of sodium triacetoxyborohydride were added in this order, and the mixture was stirred under reflux for 3 hours. After being down to room temperature, 375 mg of sodium triacetoxyborohydride was added, the mixture was stirred for 1 hour, and stirred under reflux 3 hours. Further, the said operation was repeated two times, the reaction solution was washed with a saturated aqueous sodium bicarbonate solution, dried over anhydrous magnesium sulfate, and filtered. The filtrate was evaporated under reduced pressure, and the resulting residue was purified by silica gel column chromatography (acetone:hexane:triethylamine=15:85:0.3 to 10:40:0.2). The resulting residue was recrystallized from 2-propanol, and then purified with silica gel column chromatography (acetone:hexane:triethylamine=10:50:0.2 to 10:20:0.2) to give 85 mg of a compound G and 4 mg of a compound H.

3'-N-demethyl-3'-N-(4-dimethylaminobenzyl)-6-O-methylerythromycin A (compound G)

MS (ESI) m/z=867.7 [M+H]$^+$

1H NMR (600 MHz, CHLOROFORM-d) δ ppm 0.80-0.86 (m, 3H) 1.00-1.31 (m, 24H) 1.37-1.41 (m, 3H) 1.42-1.56 (m, 2H) 1.67-1.73 (m, 2H) 1.79-1.95 (m, 3H) 2.04-2.08 (m, 1H) 2.20 (s, 3H) 2.29-2.33 (m, 1H) 2.46-2.61 (m, 2H) 2.83-2.90 (m, 1H) 2.91-2.93 (m, 6H) 2.95-3.03 (m, 2H) 3.01 (s, 3H) 3.10 (s, 3H) 3.16-3.19 (m, 1H) 3.24-3.32 (m, 2H) 3.40-3.47 (m, 1H) 3.58-3.68 (m, 2H) 3.71-3.77 (m, 2H) 3.90-3.99 (m, 2H) 4.37-4.41 (m, 1H) 4.88-4.92 (m, 1H) 5.01-5.06 (m, 1H) 6.65-6.68 (m, 2H) 7.10-7.13 (m, 2H)

3'-N-didemethyl-3'-N-bis(4-dimethylaminobenzyl)-6-O-methylerythromycin A (compound H)

MS (ESI) m/z=986.8 [M+H]$^+$
1H NMR (600 MHz, CHLOROFORM-d) δ ppm 0.78-0.86 (m, 3H) 0.97-1.04 (m, 3H) 1.06-1.31 (m, 22H) 1.34-1.41 (m, 3H) 1.40-1.60 (m, 3H) 1.66-1.71 (m, 1H) 1.76-1.94 (m, 3H) 1.95-2.01 (m, 1H) 2.21-2.27 (m, 1H) 2.51-2.61 (m, 2H) 2.77 (s, 3H) 2.80-3.04 (m, 3H) 2.91 (s, 12H) 3.00 (s, 3H) 3.07-3.19 (m, 2H) 3.31-3.43 (m, 2H) 3.52-3.57 (m, 1H) 3.60-3.70 (m, 2H) 3.73-3.80 (m, 2H) 3.83-3.90 (m, 1H) 3.96 (s, 1H) 4.29-4.34 (m, 1H) 4.85-4.90 (m, 1H) 5.01-5.06 (m, 1H) 6.62-6.68 (m, 4H) 7.08-7.13 (m, 4H)

EXAMPLE 92

3'-N-demethyl-3'-N-(4-hydroxybenzyl)-6-O-methyl-erythromycin A

Using 1 g of the compound obtained in Example 32 and using 4-hydroxybenzaldehyde instead of benzaldehyde, a reaction was carried out in a similar manner described in Example 13 to give 409 mg of the titled compound.
MS (ESI) m/z=840.5 [M+H]$^+$
1H NMR (600 MHz, CHLOROFORM-d) δ ppm 0.79-0.86 (m, 3H) 0.97-1.31 (m, 25H) 1.36-1.40 (m, 3H) 1.41-1.58 (m, 2H) 1.65-1.73 (m, 2H) 1.76-1.95 (m, 3H) 2.04-2.11 (m, 3H) 2.20 (s, 3H) 2.28-2.35 (m, 1H) 2.44-2.60 (m, 2H) 2.83-2.90 (m, 1H) 2.94-3.03 (m, 2H) 3.01 (s, 3H) 3.14 (s, 3H) 3.18 (s, 1H) 3.23-3.29 (m, 1H) 3.30-3.35 (m, 1H) 3.40-3.47 (m, 1H) 3.58-3.63 (m, 1H) 3.64-3.69 (m, 1H) 3.71-3.77 (m, 2H) 3.89-3.98 (m, 1H) 3.96 (s, 1H) 4.36-4.41 (m, 1H) 4.88-4.92 (m, 1H) 5.01-5.07 (m, 1H) 6.71-6.78 (m, 2H) 7.08-7.14 (m, 2H)

EXAMPLE 93

4"-O-acetyl-11-amino-3'-N-demethyl-11,2'-dideoxy-2'-dimethylamino-3'-N-benzyl-6-O-methylerythromycin A 11,12-cyclic carbamate Using 600 mg of the compound obtained in Example 74 (2) and using N-methylbenzylamine instead of 1-methylpiperazine, a reaction was carried out in a similar manner described in Example 74 (3) to give 414 mg of the titled compound.
MS (ESI) m/z=918.7 [M+H]$^+$
1H NMR (600 MHz, CHLOROFORM-d) δ ppm 0.79-0.86 (m, 3H) 0.96-1.41 (m, 27H) 1.43-1.63 (m, 3H) 1.64-1.69 (m, 1H) 1.72-1.90 (m, 4H) 1.98 (s, 3H) 2.11 (s, 3H) 2.30-2.35 (m, 1H) 2.49 (s, 6H) 2.49-2.56 (m, 1H) 2.69-2.76 (m, 1H) 2.80-2.88 (m, 3H) 2.91 (s, 3H) 3.11 (s, 3H) 3.44-3.49 (m, 1H) 3.54-3.65 (m, 3H) 3.77-3.81 (m, 1H) 3.89-3.97 (m, 1H) 4.34-4.43 (m, 1H) 4.59-4.63 (m, 1H) 4.86-4.90 (m, 1H) 4.97-5.00 (m, 1H) 5.04-5.08 (m, 1H) 5.75 (s, 1H) 7.15-7.36 (m, 5H)

EXAMPLE 94

11-amino-3'-N-demethyl-11,2'-dideoxy-2'-dimethy-lamino-3'-N-benzyl-6-O-methylerythromycin A 11,12-cyclic carbamate Using 120 mg of the compound obtained in Example 93, a reaction was carried out in a similar manner described in Example 89 to give 109 mg of the titled compound.
MS (ESI) m/z=876.7 [M+H]$^+$
1H NMR (500 MHz, CHLOROFORM-d) δ ppm 0.81-0.90 (m, 3H) 0.97-1.44 (m, 27H) 1.46-1.97 (m, 8H) 2.12-2.16 (m, 3H) 2.22-2.32 (m, 2H) 2.51 (s, 3H) 2.53-2.64 (m, 1H) 2.73-2.92 (m, 4H) 2.94 (s, 3H) 2.96-3.03 (m, 1H) 3.16 (s, 3H) 3.54-3.65 (m, 3H) 3.66-3.70 (m, 1H) 3.79-3.92 (m, 2H) 4.03-4.12 (m, 1H) 4.85-4.91 (m, 1H) 4.98-5.04 (m, 1H) 5.06-5.12 (m, 1H) 5.78 (s, 1H) 7.19-7.35 (m, 5H)

EXAMPLE 95

4"-O-acetyl-11-amino-3'-dedimethylamino-11,2'-dideoxy-2'-dimethylamino-3'-(4-morpholino)-6-O-methylerythromycin A 11,12-cyclic carbamate Using 500 mg of the compound obtained in Example 74 (2) and using morpholine instead of 1-methylpiperazine, a reaction was carried out in a similar manner described in Example 74 (3) to give 220 mg of the titled compound.
MS (ESI) m/z=884.8 [M+H]$^+$
1H NMR (600 MHz, CHLOROFORM-d) δ ppm 0.82-0.88 (m, 3H) 0.95-1.00 (m, 3H) 1.05-1.22 (m, 18H) 1.36-1.43 (m, 6H) 1.47-1.82 (m, 7H) 1.84-1.93 (m, 1H) 2.05 (s, 3H) 2.35-2.41 (m, 1H) 2.44-2.60 (m, 5H) 2.49 (s, 6H) 2.64-2.75 (m, 3H) 2.83-2.89 (m, 1H) 2.92 (s, 3H) 3.27 (s, 3H) 3.50-3.55 (m, 1H) 3.65 (s, 1H) 3.69-3.84 (m, 6H) 4.33-4.41 (m, 1H) 4.62-4.67 (m, 1H) 4.88-4.92 (m, 1H) 4.95-4.99 (m, 1H) 5.06-5.11 (m, 1H) 5.77 (s, 1H)

EXAMPLE 96

11-amino-3'-dedimethylamino-11,2'-dideoxy-2'-dimethylamino-3'-(4-morpholino)-6-O-methylerythromycin A 11,12-cyclic carbamate Using 140 mg of the compound obtained in Example 95, a reaction was carried out in a similar manner described in Example 89 to give 105 mg of the titled compound.
MS (ESI) m/z=842.8 [M+H]$^+$
1H NMR (600 MHz, CHLOROFORM-d) δ ppm 0.82-0.90 (m, 3H) 0.91-0.98 (m, 3H) 1.07-1.44 (m, 24H) 1.47-1.82 (m, 7H) 1.84-1.93 (m, 1H) 2.30-2.36 (m, 2H) 2.42-2.60 (m, 6H) 2.49 (s, 6H) 2.63-2.67 (m, 1H) 2.68-2.75 (m, 1H) 2.83-2.89 (m, 1H) 2.93 (s, 3H) 2.98-3.04 (m, 1H) 3.29 (s, 3H) 3.52-3.56 (m, 1H) 3.66 (s, 1H) 3.67-3.77 (m, 5H) 3.81-3.85 (m, 1H) 3.96-4.05 (m, 1H) 4.86-4.90 (m, 1H) 4.95-4.98 (m, 1H) 5.06-5.11 (m, 1H) 5.74-5.78 (m, 1H)

EXAMPLE 97

11-amino-3'-dedimethylamino-11,2'-dideoxy-2'-dimethylamino-3'-(4-benzylpiperazin-1-yl)-6-O-methyl-erythromycin A 11,12-cyclic carbamate (1) Using 600 mg of the compound obtained in Example 74 (2) and 1-benzylpiperazine instead of 1-methylpiperazine, a reaction was carried out in a similar manner described in Example 74 (3) to give 576 mg of the titled compound.

(2) Using 120 mg of the compound obtained in the above (1), a reaction was carried out in a similar manner described in Example 89 to give 101 mg of the titled compound.

MS (ESI) m/z=931.8 [M+H]$^+$

1H NMR (600 MHz, CHLOROFORM-d) δ ppm 0.82-0.88 (m, 3H) 0.92-0.98 (m, 3H) 1.07-1.44 (m, 24H) 1.47-1.82 (m, 7H) 1.84-1.93 (m, 1H) 2.28-2.36 (m, 2H) 2.40-2.59 (m, 9H) 2.48 (s, 6H) 2.61-2.75 (m, 3H) 2.83-2.89 (m, 1H) 2.92 (s, 3H) 2.97-3.03 (m, 1H) 3.27 (s, 3H) 3.41-3.56 (m, 3H) 3.66 (s, 1H) 3.69-3.77 (m, 1H) 3.79-3.84 (m, 1H) 3.98-4.05 (m, 1H) 4.84-4.90 (m, 1H) 4.91-4.95 (m, 1H) 5.06-5.10 (m, 1H) 5.76 (s, 1H) 7.20-7.32 (m, 5H)

EXAMPLE 98

4"-O-acetyl-11-amino-3'-dedimethylamino-11,2'-dideoxy-2'-dimethylamino-3'-(1-piperidino)-6-O-methylerythromycin A 11,12-cyclic carbamate Using 400 mg of the compound obtained in Example 74 (2) and piperidine instead of 1-methylpiperazine, a reaction was carried out in a similar manner described in Example 74 (3) to give 335 mg of the titled compound.

MS (ESI) m/z=882.7 [M+H]$^+$

1H NMR (600 MHz, CHLOROFORM-d) δ ppm 0.82-0.88 (m, 3H) 0.97-1.03 (m, 3H) 1.06-1.22 (m, 18H) 1.35-1.82 (m, 19H) 1.84-1.92 (m, 1H) 2.07 (s, 3H) 2.33-2.59 (m, 6H) 2.48 (s, 6H) 2.70-2.80 (m, 3H) 2.84-2.89 (m, 1H) 2.92 (s, 3H) 3.27 (s, 3H) 3.52-3.57 (m, 1H) 3.65-3.67 (m, 1H) 3.73-3.83 (m, 2H) 4.37-4.44 (m, 1H) 4.61-4.65 (m, 1H) 4.87-4.92 (m, 1H) 4.95-4.98 (m, 1H) 5.07-5.10 (m, 1H) 5.78 (s, 1H)

EXAMPLE 99

11-amino-3'-dedimethylamino-11,2'-dideoxy-2'-dimethylamino-3'-(1-piperidino)-6-O-methylerythromycin A 11,12-cyclic carbamate Using 235 mg of the compound obtained in Example 98, a reaction was carried out in a similar manner described in Example 89 to give 108 mg of the titled compound.

MS (ESI) m/z=840.7 [M+H]$^+$

1H NMR (600 MHz, CHLOROFORM-d) δ ppm 0.81-0.88 (m, 3H) 0.94-1.00 (m, 3H) 1.09-1.29 (m, 18H) 1.36-1.81 (m, 19H) 1.83-1.92 (m, 1H) 2.27-2.37 (m, 2H) 2.36-2.50 (m, 4H) 2.48 (s, 6H) 2.51-2.59 (m, 1H) 2.61-2.77 (m, 3H) 2.83-2.89 (m, 1H) 2.92 (s, 3H) 2.95-3.02 (m, 1H) 3.28 (s, 3H) 3.52-3.56 (m, 1H) 3.66 (s, 1H) 3.67-3.75 (m, 1H) 3.80-3.84 (m, 1H) 3.99-4.08 (m, 1H) 4.85-4.90 (m, 1H) 4.94-4.97 (m, 1H) 5.06-5.11 (m, 1H) 5.77 (s, 1H)

EXAMPLE 100

4"-O-acetyl-3'-dedimethylamino-2'-deoxy-2'-dimethylamino-3'-(1-piperidino)-6-O-methylerythromycin A (1) 50 g of 6-O-methylerythromycin A was suspended in chloroform, 3.3 g of 4-dimethylaminopyridine and 22 ml of acetic anhydride were added in this order, and the mixture was stirred at room temperature for 3 hours. The reaction solution was washed with a saturated aqueous sodium bicarbonate solution, dried over anhydrous magnesium sulfate, and filtered. The filtrate was evaporated under reduced pressure, and the resulting residue was suspended in 500 ml of methanol, and the mixture was stirred at 60° C. for 15 hours. The reaction solution was evaporated under reduced pressure, and the resulting residue was dissolved in ethyl acetate. The resultant was washed with a saturated aqueous sodium bicarbonate solution, dried over anhydrous magnesium sulfate, and filtered to give 65 g of a 6-O-methylerythromycin A 4"-O-acetyl compound.

(2) Using 65 g of the compound obtained in the above (1), a reaction was carried out in a similar manner described in Example 74 (2). That is, 65 g of the compound obtained in the above (1) was dissolved in 350 ml of chloroform, and 28 ml of triethylamine was added. A solution of 10 ml of methanesulfonyl chloride in 150 ml of chloroform was added dropwise under ice cooling, and the mixture was stirred for 1 hour. Thereafter, the reaction solution was stirred for 1 hour being raised to room temperature. A saturated aqueous sodium bicarbonate solution was added to the reaction solution, and the mixture was extracted with chloroform. The organic layer was dried over anhydrous magnesium sulfate, and filtered. The filtrate was evaporated under reduced pressure, and the resulting residue was purified by silica gel column chromatography [(acetone:hexane:triethylamine=10:10:0.2):hexane=1:2 to 1:1], to give 36 g of a 2'-OMs compound.

(3) 36 g of the compound obtained in the above (2) was dissolved in 150 ml of N,N-dimethylformamide, 54 ml of piperidine was added, the mixture was stirred at 60° C. for 3 hours, and at 75° C. for 2 hours. A saturated aqueous sodium bicarbonate solution was added to the reaction solution, and the mixture was extracted with ethyl acetate. The organic layer was washed with a saturated aqueous sodium bicarbonate solution, dried over anhydrous magnesium sulfate, and filtered. The filtrate was evaporated under reduced pressure, and the resulting residue was purified by silica gel column chromatography [(chloroform:methanol:ammonia water solution=10:1:0.1):chloroform=3:7], to give 30 g of the titled compound.

MS (ESI) m/z=857.8 [M+H]$^+$

1H NMR (600 MHz, CHLOROFORM-d) δ ppm 0.81-0.87 (m, 3H) 0.97-1.03 (m, 3H) 1.05-1.21 (m, 24H) 1.37-1.86 (m, 13H) 1.87-1.95 (m, 1H) 2.07 (s, 3H) 2.34-2.39 (m, 1H) 2.40-2.52 (m, 4H) 2.50 (s, 6H) 2.56-2.63 (m, 1H) 2.73-2.83 (m, 3H) 2.96-3.03 (m, 1H) 3.02 (s, 3H) 3.27 (s, 3H) 3.56-3.60 (m, 1H) 3.73-3.83 (m, 3H) 3.96 (s, 1H) 4.38-4.45 (m, 1H) 4.61-4.64 (m, 1H) 4.89-4.92 (m, 1H) 4.96-4.98 (m, 1H) 5.01-5.06 (m, 1H)

EXAMPLE 101

3'-dedimethylamino-2'-deoxy-2'-dimethylamino-3'-(1-piperidino)-6-O-methylerythromycin A Using 5.0 g of the compound obtained in Example 100, a reaction was carried out in a similar manner described in Example 89 to give 2.5 g of the titled compound.

MS (ESI) m/z=815.7 [M+H]$^+$

1H NMR (600 MHz, CHLOROFORM-d) δ ppm 0.79-0.86 (m, 3H) 0.94-1.00 (m, 3H) 1.06-1.30 (m, 24H) 1.36-1.84 (m, 13H) 1.86-1.95 (m, 1H) 2.28-2.35 (m, 2H) 2.36-2.52 (m, 4H) 2.48 (s, 6H) 2.54-2.71 (m, 3H) 2.73-2.82 (m, 1H) 2.94-3.03 (m, 2H) 3.01 (s, 3H) 3.28 (s, 3H) 3.55-3.60 (m, 1H) 3.68-3.76 (m, 2H) 3.78-3.82 (m, 1H) 3.95 (s, 1H) 4.02-4.09 (m, 1H) 4.85-4.89 (m, 1H) 4.94-4.97 (m, 1H) 5.00-5.05 (m, 1H)

EXAMPLE 102

3'-N-demethyl-3'-N-(2-(1,3-dioxo-1,3-dihydroindol-2-yl)-ethyl)-6,2'-di-O-methylerythromycin A Using 500 mg of the compound obtained in Example 82, a reaction was carried out in a similar manner described in Example 7 (2) to give 412 mg of the titled compound.

MS (ESI) m/z=921.9 [M+H]+
1H NMR (600 MHz, CHLOROFORM-d) δ ppm 0.78-0.88 (m, 3H) 0.97-1.02 (m, 3H) 1.06-1.29 (m, 22H) 1.32-1.38 (m, 3H) 1.40-1.64 (m, 4H) 1.72-1.95 (m, 3H) 2.23-2.28 (m, 1H) 2.30-2.36 (m, 1H) 2.42 (s, 3H) 2.52-2.63 (m, 2H) 2.75-2.86 (m, 3H) 2.86-2.94 (m, 1H) 2.94-3.02 (m, 2H) 3.00 (s, 3H) 3.30 (s, 3H) 3.35-3.43 (m, 1H) 3.40 (s, 3H) 3.58-3.62 (m, 1H) 3.68-3.79 (m, 2H) 3.81-3.88 (m, 1H) 3.91-3.98 (m, 2H) 4.32-4.36 (m, 1H) 4.88-4.92 (m, 1H) 5.01-5.06 (m, 1H) 7.67-7.72 (m, 2H) 7.78-7.85 (m, 2H)

EXAMPLE 103

3'-N-demethyl-3'-N-(2-aminoethyl)-6,2'-di-O-methylerythromycin A

Using 322 mg of the compound obtained in Example 102 and using ethanol instead of methanol, a reaction was carried out in a similar manner described in Example 8 to give 227 mg of the titled compound.

MS (ESI) m/z=791.7 [M+H]+
1H NMR (600 MHz, CHLOROFORM-d) δ ppm 0.78-0.85 (m, 3H) 0.99-1.31 (m, 25H) 1.33-1.39 (m, 3H) 1.40-1.50 (m, 1H) 1.51-1.94 (m, 6H) 2.30 (s, 3H) 2.29-2.35 (m, 1H) 2.50-2.65 (m, 4H) 2.66-2.78 (m, 2H) 2.78-2.88 (m, 2H) 2.93-3.02 (m, 2H) 3.00 (s, 3H) 3.29 (s, 3H) 3.37-3.44 (m, 1H) 3.51 (s, 3H) 3.60-3.64 (m, 1H) 3.73-3.79 (m, 2H) 3.91-3.99 (m, 1H) 4.33-4.38 (m, 1H) 4.86-4.91 (m, 1H) 4.99-5.05 (m, 1H)

EXAMPLE 104

3'-N-demethyl-3'-N-(2-dimethylaminoethyl)-6,2'-di-O-methylerythromycin A 161 mg of the compound obtained in Example 103 was dissolved in chloroform, 21 μl of a 37% aqueous formaldehyde solution and 56 mg of sodium triacetoxyborohydride were added in this order, and the mixture was stirred at room temperature for 14 hours. A saturated aqueous sodium bicarbonate solution was added to the reaction solution, and the mixture was extracted with chloroform. The organic layer was washed with saturated brine, dried over anhydrous magnesium sulfate, and filtered. The filtrate was evaporated under reduced pressure. Using the resulting residue, the said operation was conducted again. The resulting residue was purified by silica gel column chromatography (chloroform:methanol:ammonia water solution=20:1:0.1). The resulting residue was recrystallized from 2-propanol to give 37 mg of the titled compound.

MS (ESI) m/z=819.7 [M+H]+
1H NMR (600 MHz, CHLOROFORM-d) δ ppm 0.80-0.86 (m, 3H) 1.00-1.31 (m, 25H) 1.36-1.40 (m, 3H) 1.41-1.95 (m, 7H) 2.13-2.18 (m, 1H) 2.25 (s, 6H) 2.31-2.47 (m, 3H) 2.35 (s, 3H) 2.53-2.63 (m, 3H) 2.66-2.73 (m, 1H) 2.81-2.89 (m, 2H) 2.95-3.03 (m, 2H) 3.02 (s, 3H) 3.30 (s, 3H) 3.38-3.45 (m, 1H) 3.51 (s, 3H) 3.62-3.65 (m, 1H) 3.75-3.80 (m, 2H) 3.93-3.99 (m, 2H) 4.36-4.39 (m, 1H) 4.89-4.92 (m, 1H) 5.01-5.05 (m, 1H)

EXAMPLE 105

2'-O-ethyl-6-O-methylerythromycin A

Using 650 mg of the compound obtained in Example 24 (1) and using ethyl iodide instead of 1-bromo-3-phenylpropane, a reaction was carried out in a similar manner described in Example 24 (2) and (3) to give 160 mg of the titled compound.

MS (ESI) m/z=776.6 [M+H]+
13C NMR (126 MHz, CHLOROFORM-d) δ ppm 8.46, 10.66, 12.30, 15.70, 15.93, 16.13, 17.97, 18.82, 19.97, 21.08, 21.43, 21.53, 33.24, 34.89, 37.43, 39.29, 39.69, 41.32, 45.01, 45.35, 49.48, 50.49, 64.17, 65.84, 67.40, 68.02, 69.09, 72.67, 74.25, 76.63, 77.94, 78.50, 79.83, 79.92, 95.83, 102.93, 176.15, 220.90

EXAMPLE 106

3'-N-demethyl-3'-N-(2,2-dimethoxyethyl)-6,2'-di-O-methylerythromycin A (compound J) and 3'-N-demethyl-3'-N-(1-methylethyl)-6,2'-di-O-methylerythromycin A (compound K)

500 mg of the compound obtained in Example 82 was dissolved in methanol, 2.7 ml of isopropyl iodide and 1.16 ml of diisopropylethylamine were added, and the mixture was stirred at 50° C. for 19 hours. After the reaction, water was added to the reaction solution, and the mixture was extracted with ethyl acetate. The organic layer was washed with saturated brine, dried over anhydrous magnesium sulfate, and filtered. The solvent was evaporated under reduced pressure, and the resulting residue (590 mg) was purified by silica gel column chromatography (hexane:acetone:triethylamine=50:15:1) to give 330 mg of 3'-N-demethyl-3'-(2,2-dimethoxyethyl)-6,2'-di-O-methylerythromycin A (compound J) and 30 mg of 3'-N-demethyl-3'-(1-methylethyl)-6,2'-di-O-methylerythromycin A (compound K).

3'-N-demethyl-3'-N-(2,2-dimethoxyethyl)-6,2'-di-O-methylerythromycin A (compound J)

MS (ESI) m/z=836.7 [M+H]+
13C NMR (126 MHz, CHLOROFORM-d) δ ppm 8.36, 10.65, 12.31, 15.95, 16.11, 17.99, 18.82, 19.89, 21.07, 21.40, 21.51, 34.56, 34.88, 37.39, 39.16, 39.28, 39.60, 45.04, 45.28, 49.47, 50.53, 53.48, 53.98, 56.67, 60.02, 64.85, 65.71, 68.09, 69.09, 72.67, 74.25, 77.95, 78.00, 78.48, 80.19, 81.73, 95.83, 103.09, 104.25, 176.06, 220.90

3'-N-demethyl-3'-N-(1-methylethyl)-6,2'-di-O-methylerythromycin A (compound K)

MS (ESI) m/z=790.7 [M+H]+
13C NMR (126 MHz, CHLOROFORM-d) δ ppm 8.43, 10.65, 12.31, 15.95, 16.09, 18.00, 18.84, 19.86, 20.84, 21.07, 21.26, 21.46, 21.52, 31.70, 34.88, 35.52, 37.37, 39.29, 39.57, 45.08, 45.23, 49.46, 50.55, 52.10, 60.52, 61.44, 65.62, 68.17, 69.09, 72.44, 74.27, 78.05, 78.10, 78.51, 80.38, 81.60, 95.92, 103.20, 176.09, 220.97.

EXAMPLE 107

4"-O-acetyl-2'-O-ethyl-6-O-methylerythromycin A 61 mg of the compound obtained in Example 105 was dissolved in 2 ml of acetone, 10 mg of 4-dimethylaminopyridine and 30 μl of acetic anhydride were added, and the mixture was stirred at room temperature overnight. After concentrating the reaction solution, a 2N aqueous sodium hydroxide solution and water were added to the reaction solution, and the mixture was extracted with ethyl acetate. The organic layer was washed with a saturated aqueous ammonium chloride solution, subsequently saturated brine, and dried over anhydrous magnesium sulfate. The filtrate was evaporated under reduced pressure, and the resulting residue was purified by silica gel column chromatography (hexane:acetone:triethylamine=50:15:1) to give 41 mg of the titled compound.

MS (ESI) m/z=818.7 [M+H]$^+$
13C NMR (126 MHz, CHLOROFORM-d) δ ppm 8.42, 10.63, 12.35, 15.75, 15.92, 16.15, 18.00, 18.43, 19.87, 20.94, 21.11, 21.70, 34.28, 35.20, 37.39, 39.19, 41.45, 45.12, 49.54, 50.55, 63.11, 63.82, 67.17, 67.28, 69.12, 72.60, 74.26, 76.60, 77.55, 78.39, 78.69, 79.84, 80.17, 95.72, 102.59, 170.60, 175.97, 220.90.

EXAMPLE 108

2'-O-(3-benzyloxypropyl)-6-O-methylerythromycin A

Using 10.00 g of the compound obtained in Example 24 (1) and using 3-benzyloxypropyl bromide instead of 1-bromo-3-phenylpropane, a reaction was carried out in a similar manner described in Example 24 (2) and (3) to give 0.62 g of the titled compound.

MS (ESI) m/z=896.7 [M+H]$^+$
1H NMR (600 MHz, CHLOROFORM-d) δ ppm 0.84 (t, J=7.34 Hz, 3H) 1.03 (d, J=7.79 Hz, 3H) 1.08-1.14 (m, 9H) 1.15-1.22 (m, 7H) 1.23 (s, 3H) 1.28 (d, J=5.96 Hz, 3H) 1.37 (s, 3H) 1.43-1.50 (m, 1H) 1.57-1.68 (m, 3H) 1.72-1.95 (m, 5H) 2.16 (d, J=10.55 Hz, 1H) 2.32 (s, 6H) 2.32-2.35 (m, 1H) 2.50-2.63 (m, 2H) 2.78-2.86 (m, 1H) 2.89-2.95 (m, 1H) 2.94-3.01 (m, 2H) 3.01 (s, 3H) 3.19 (s, 1H) 3.30 (s, 3H) 3.39-3.47 (m, 1H) 3.53-3.60 (m, 2H) 3.64 (d, J=7.34 Hz, 1H) 3.66-3.73 (m, 1H) 3.76 (s, 1H) 3.79 (d, J=7.79 Hz, 1H) 3.85-3.90 (m, 1H) 3.92-3.99 (m, 1H) 3.96 (s, 1H) 4.38 (d, J=7.34 Hz, 1H) 4.49 (d, J=1.83 Hz, 2H) 4.91 (d, J=4.13 Hz, 1H) 5.03 (dd, J=11.00, 2.29 Hz, 1H) 7.26-7.30 (m, 1H) 7.30-7.36 (m, 4H)

EXAMPLE 109

2'-O-(3-hydroxypropyl)-6-O-methylerythromycin A (compound L) and 3'-N-demethyl-2'-O-(3-hydroxypropyl)-6-O-methylerythromycin A (compound M)

0.40 g of the compound obtained in Example 108 was dissolved in a mixed solution of 4 ml of methanol and 4 ml of ethyl acetate, 200 mg of 20% palladium hydroxide-carbon was added, and the mixture was stirred at room temperature for 18 hours in a hydrogen atmosphere having 1 atm pressure. After filtering the reaction solution, the filtrate was evaporated under reduced pressure, and the resulting residue was purified by silica gel column chromatography (chlorofrom:methanol:ammonia water solution=30:1:0.1 to 10:1:0.1) to give 0.13 g of a compound L and 0.12 g of a compound M.

2'-O-(3-hydroxypropyl)-6-O-methylerythromycin A (compound L)

MS (ESI) m/z=806.6 [M+H]$^+$
1H NMR (600 MHz, CHLOROFORM-d) δ ppm 0.84 (t, J=7.57 Hz, 3H) 1.03 (d, J=7.79 Hz, 3H) 1.10-1.22 (m, 16H) 1.24 (s, 3H) 1.28 (d, J=5.96 Hz, 3H) 1.38 (s, 3H) 1.43-1.51 (m, 1H) 1.54-1.96 (m, 8H) 2.14 (d, J=10.09 Hz, 1H) 2.28 (s, 6H) 2.34 (d, J=14.21 Hz, 1H) 2.46-2.53 (m, 1H) 2.56-2.64 (m, 1H) 2.79-2.89 (m, 2H) 2.96-3.02 (m, 2H) 3.02 (s, 3H) 3.19 (s, 1H) 3.31 (s, 3H) 3.39-3.56 (m, 2H) 3.60-3.67 (m, 2H) 3.75-3.84 (m, 3H) 3.92-3.99 (m, 1H) 3.96 (s, 1H) 4.04-4.11 (m, 1H) 4.43 (d, J=7.34 Hz, 1H) 4.91 (d, J=4.59 Hz, 1H) 5.04 (dd, J=11.00, 2.29 Hz, 1H) 5.80 (br. s., 1H)

3'-N-demethyl-2'-O-(3-hydroxypropyl)-6-O-methylerythromycin A (compound M)

MS (ESI) m/z=792.5 [M+H]$^+$
1H NMR (600 MHz, CHLOROFORM-d) δ ppm 0.84 (t, J=7.57 Hz, 3H) 1.03 (d, J=7.34 Hz, 3H) 1.04-1.08 (m, 1H) 1.10-1.14 (m, 6H) 1.15 (s, 3H) 1.17-1.21 (m, 6H) 1.24 (s, 3H) 1.28 (d, J=5.96 Hz, 3H) 1.38 (s, 3H) 1.42-1.51 (m, 1H) 1.54-1.62 (m, 2H) 1.70-1.81 (m, 3H) 1.83-1.97 (m, 2H) 2.00-2.06 (m, 1H) 2.15 (d, J=10.09 Hz, 1H) 2.34 (d, J=15.13 Hz, 1H) 2.42 (s, 3H) 2.43-2.48 (m, 1H) 2.55-2.64 (m, 2H) 2.71-2.77 (m, 1H) 2.79-2.88 (m, 1H) 2.96-3.03 (m, 2H) 3.02 (s, 3H) 3.20 (s, 1H) 3.31 (s, 3H) 3.46-3.52 (m, 1H) 3.57-3.63 (m, 1H) 3.64-3.72 (m, 2H) 3.75-3.86 (m, 3H) 3.92-3.99 (m, 1H) 3.96 (s, 1H) 4.04-4.11 (m, 1H) 4.44 (d, J=7.79 Hz, 1H) 4.91 (d, J=4.13 Hz, 1H) 5.04 (dd, J=11.00, 2.29 Hz, 1H)

EXAMPLE 110

4"-O-acetyl-2'-O-(3-benzyloxypropyl)-6-O-methylerythromycin A

Using 0.25 g of the compound obtained in Example 108, a reaction was carried out in a similar manner described in Example 87 to give 0.20 g of the titled compound.

MS (ESI) m/z=938.6 [M+H]$^+$
1H NMR (600 MHz, CHLOROFORM-d) δ ppm 0.84 (t, J=7.34 Hz, 3H) 1.05 (d, J=7.79 Hz, 3H) 1.08-1.15 (m, 18H) 1.20 (d, J=7.34 Hz, 3H) 1.22-1.27 (m, 1H) 1.35 (s, 3H) 1.43-1.51 (m, 1H) 1.53-1.66 (m, 3H) 1.72-1.80 (m, 1H) 1.82-1.96 (m, 4H) 2.07-2.09 (m, 3H) 2.34 (s, 6H) 2.38 (d, J=15.13 Hz, 1H) 2.53-2.66 (m, 2H) 2.82-2.88 (m, 1H) 2.90-2.94 (m, 1H) 2.97 (m, 1H) 3.01 (s, 3H) 3.19 (s, 1H) 3.29 (s, 3H) 3.53-3.59 (m, 2H) 3.63 (d, J=7.34 Hz, 1H) 3.65-3.73 (m, 2H) 3.74-3.77 (m, 1H) 3.79 (d, J=9.17 Hz, 1H) 3.85-3.90 (m, 1H) 3.96 (s, 1H) 4.27-4.34 (m, 1H) 4.48-4.50 (m, 3H) 4.64 (d, J=10.09 Hz, 1H) 4.96 (d, J=5.04 Hz, 1H) 5.05 (dd, J=10.78, 2.06 Hz, 1H) 7.26-7.30 (m, 1H) 7.31-7.35 (m, 4H)

EXAMPLE 111

4"-O-acetyl-2'-O-(3-hydroxypropyl)-6-O-methylerythromycin A (compound N) and 4"-O-acetyl-3'-N-demethyl-2'-O-(3-hydroxypropyl)-6-O-methylerythromycin A (compound O)

Using 0.20 g of the compound obtained in Example 110, a reaction was carried out in a similar manner described in Example 109 to give 72 mg of a compound N and 82 mg of a compound O.

4"-O-acetyl-2'-O-(3-hydroxypropyl)-6-O-methylerythromycin A (compound N)

MS (ESI) m/z=848.5 [M+H]$^+$
1H NMR (600 MHz, CHLOROFORM-d) δ ppm 0.84 (t, J=7.34 Hz, 3H) 1.05 (d, J=7.79 Hz, 3H) 1.10-1.15 (m, 15H) 1.16 (d, J=5.96 Hz, 3H) 1.20 (d, J=7.34 Hz, 3H) 1.24-1.33 (m, 1H) 1.36 (s, 3H) 1.38-1.51 (m, 1H) 1.56-1.73 (m, 5H) 1.74-1.82 (m, 1H) 1.85-1.96 (m, 2H) 2.09 (s, 3H) 2.29 (s, 6H) 2.39 (d, J=15.13 Hz, 1H) 2.54-2.62 (m, 2H) 2.83-2.91 (m, 2H) 2.97-3.01 (m, 1H) 3.02 (s, 3H) 3.19 (s, 1H) 3.29 (s, 3H) 3.50-3.56 (m, 1H) 3.59-3.65 (m, 2H) 3.65-3.72 (m, 1H) 3.75-3.84 (m, 3H) 3.96 (s, 1H) 4.04-4.08 (m, 1H) 4.27-4.33 (m, 1H) 4.54 (d, J=7.34 Hz, 1H) 4.65 (d, J=10.09 Hz, 1H) 4.96 (d, J=5.04 Hz, 1H) 5.05 (dd, J=11.00, 2.29 Hz, 1H)

4"-O-acetyl-3'-N-demethyl-2'-O-(3-hydroxypropyl)-
6-O-methylerythromycin A (compound O)

MS (ESI) m/z=834.4 [M+H]$^+$
1H NMR (600 MHz, CHLOROFORM-d) δ ppm 0.84 (t, J=7.34 Hz, 3H) 0.98-1.04 (m, 1H) 1.05 (d, J=7.34 Hz, 3H) 1.08-1.16 (m, 18H) 1.20 (d, J=7.34 Hz, 3H) 1.21-1.25 (m, 1H) 1.36 (s, 3H) 1.42-1.51 (m, 1H) 1.54-1.64 (m, 2H) 1.68-1.81 (m, 3H) 1.85-1.95 (m, 2H) 1.98-2.04 (m, 1H) 2.09 (s, 3H) 2.38 (d, J=15.13 Hz, 1H) 2.42 (s, 3H) 2.49-2.62 (m, 2H) 2.67-2.73 (m, 1H) 2.83-2.91 (m, 1H) 2.96-3.01 (m, 1H) 3.02 (s, 3H) 3.19 (s, 1H) 3.28 (s, 3H) 3.56-3.85 (m, 7H) 3.96 (s, 1H) 4.03-4.08 (m, 1H) 4.27-4.34 (m, 1H) 4.55 (d, J=7.79 Hz, 1H) 4.65 (d, J=10.09 Hz, 1H) 4.96 (d, J=4.59 Hz, 1H) 5.05 (dd, J=11.00, 1.83 Hz, 1H)

EXAMPLE 112

4"-O-acetyl-2'-O-(3-acetyloxypropyl)-6-O-methyl-erythromycin A

Using 0.49 g of the compound L obtained in Example 109, a reaction was carried out in a similar manner described in Example 87 to give 0.45 g of the titled compound.

MS (ESI) m/z=890.5 [M+H]$^+$
1H NMR (600 MHz, CHLOROFORM-d) δ ppm 0.84 (t, J=7.34 Hz, 3H) 1.04 (d, J=7.79 Hz, 3H) 1.10-1.15 (m, 18H) 1.20 (d, J=7.34 Hz, 3H) 1.21-1.27 (m, 1H) 1.36 (s, 3H) 1.42-1.51 (m, 1H) 1.55-1.70 (m, 3H) 1.74-1.80 (m, 1H) 1.83-1.95 (m, 4H) 2.04 (s, 3H) 2.08 (s, 3H) 2.36 (s, 6H) 2.38 (d, 1H) 2.54-2.71 (m, 2H) 2.82-2.94 (m, 2H) 2.97-3.01 (m, 1H) 3.01 (s, 3H) 3.19 (br. s., 1H) 3.30 (s, 3H) 3.61-3.73 (m, 3H) 3.77 (d, J=1.38 Hz, 1H) 3.80 (d, J=8.25 Hz, 1H) 3.84-3.90 (m, 1H) 3.96 (br. s., 1H) 4.11-4.19 (m, 2H) 4.26-4.34 (m, 1H) 4.51 (d, J=7.34 Hz, 1H) 4.64 (d, J=10.09 Hz, 1H) 4.97 (d, J=4.58 Hz, 1H) 5.05 (dd, J=11.00, 2.29 Hz, 1H)

EXAMPLE 113

2'-O-(3-(1,3-dioxo-1,3-dihydroisoindol-2-yl)propyl)-6-O-methylerythromycin A 0.70 g of the compound L obtained in Example 109 was dissolved in 17 ml of tetrahydrofuran, then 0.28 g of phthalimide, 0.55 g of triphenylphosphine and 0.95 ml of diethyldiazocarboxylic ester in 2.2M tetrahydrofuran solution were added, and the mixture was stirred at room temperature for 16 hours. After concentrating the reaction solution, the resulting residue was purified by silica gel column chromatography (chlorofrom:methanol:ammonia water solution=50:1:0.1 to 10:1:0.1) to give 0.45 g of the titled compound.

MS (ESI) m/z=935.7 [M+H]$^+$
1H NMR (600 MHz, CHLOROFORM-d) δ ppm 0.84 (t, J=7.34 Hz, 3H) 1.04 (d, J=7.34 Hz, 3H) 1.10 (d, J=4.59 Hz, 3H) 1.12 (d, J=4.59 Hz, 3H) 1.14 (s, 3H) 1.16-1.23 (m, 7H) 1.25 (s, 3H) 1.28 (d, J=6.42 Hz, 3H) 1.37 (s, 3H) 1.42-1.51 (m, 1H) 1.57-1.69 (m, 3H) 1.75-1.81 (m, 1H) 1.82-1.98 (m, 4H) 2.18 (d, J=10.09 Hz, 1H) 2.31 (s, 6H) 2.35 (d, J=15.13 Hz, 1H) 2.50-2.62 (m, 2H) 2.80-2.88 (m, 1H) 2.88-2.94 (m, 1H) 2.96-3.00 (m, 3H) 3.01 (s, 3H) 3.19 (s, 1H) 3.36 (s, 3H) 3.40-3.46 (m, 1H) 3.64 (d, J=7.34 Hz, 1H) 3.68-3.88 (m, 5H) 3.92-4.06 (m, 1H) 3.96 (s, 1H) 4.42 (d, J=7.34 Hz, 1H) 4.92 (d, J=4.59 Hz, 1H) 5.04 (dd, J=11.00, 2.29 Hz, 1H) 7.71 (dd, J=5.27, 2.98 Hz, 2H) 7.83 (dd, J=5.50, 3.21 Hz, 2H)

EXAMPLE 114

2'-O-(3-aminopropyl)-6-O-methylerythromycin A 0.62 g of the compound obtained in Example 113 was dissolved in 132 ml of methanol, 1 ml of hydrazine was added, and the mixture was stirred under reflux for 2 hours. The reaction solution was evaporated under reduced pressure, and the resulting residue was purified by silica gel column chromatography (chloroform:methanol:ammonia water solution: 5:1:0.1) to give 0.46 g of the titled compound.

MS (ESI) m/z=805.5 [M+H]$^+$
1H NMR (600 MHz, CHLOROFORM-d) δ ppm 0.84 (t, J=7.34 Hz, 3H) 1.02 (d, J=7.34 Hz, 3H) 1.10-1.16 (m, 9H) 1.17-1.21 (m, 7H) 1.24 (s, 3H) 1.28 (d, J=6.42 Hz, 3H) 1.38 (s, 3H) 1.42-1.96 (m, 9H) 2.31 (s, 6H) 2.34 (d, J=14.67 Hz, 1H) 2.47-2.54 (m, 1H) 2.55-2.63 (m, 1H) 2.78-2.90 (m, 3H) 2.94-3.01 (m, 3H) 3.02 (s, 3H) 3.19 (s, 1H) 3.32 (s, 3H) 3.40-3.47 (m, 1H) 3.52-3.59 (m, 1H) 3.65 (d, J=7.34 Hz, 1H) 3.76 (d, J=1.38 Hz, 1H) 3.78 (d, J=7.79 Hz, 1H) 3.92-4.03 (m, 3H) 4.40 (d, J=7.34 Hz, 1H) 4.90 (d, J=4.59 Hz, 1H) 5.04 (dd, J=11.00, 2.29 Hz, 1H)

EXAMPLE 115

2'-O-(3-dimethylaminopropyl)-6-O-methylerythromycin A

Using 0.12 g of the compound obtained in Example 114, a reaction was carried out in a similar manner described in Example 9 to give 75 mg of the titled compound.

MS (ESI) m/z=833.5 [M+H]$^+$
1H NMR (600 MHz, CHLOROFORM-d) δ ppm 0.84 (t, J=7.57 Hz, 3H) 1.04 (d, J=7.34 Hz, 3H) 1.11-1.14 (m, 6H) 1.14 (s, 3H) 1.16-1.19 (m, 6H) 1.20-1.22 (m, 1H) 1.23 (s, 3H) 1.28 (d, J=5.96 Hz, 3H) 1.38 (s, 3H) 1.42-1.51 (m, 1H) 1.53-1.59 (m, 1H) 1.59-1.68 (m, 2H) 1.69-1.95 (m, 4H) 2.18-2.21 (m, 1H) 2.22 (s, 6H) 2.33 (s, 6H) 2.34-2.37 (m, 3H) 2.50-2.64 (m, 2H) 2.78-2.87 (m, 1H) 2.88-2.94 (m, 1H) 2.95-3.01 (m, 2H) 3.01 (s, 3H) 3.18 (s, 1H) 3.31 (s, 3H) 3.38-3.48 (m, 1H) 3.56-3.67 (m, 2H) 3.74-3.83 (m, 3H) 3.95 (s, 1H) 3.95-4.01 (m, 1H) 4.37 (d, J=7.34 Hz, 1H) 4.90 (d, J=4.59 Hz, 1H) 5.03 (dd, J=11.00, 2.29 Hz, 1H)

EXAMPLE 116

4"-O-acetyl-2'-O-(3-dimethylaminopropyl)-6-O-methylerythromycin A

Using 0.10 g of the compound obtained in Example 115, a reaction was carried out in a similar manner described in Example 87 to give 69 mg of the titled compound.

MS (ESI) m/z=875.5 [M+H]$^+$
1H NMR (600 MHz, CHLOROFORM-d) δ ppm 0.84 (t, J=7.34 Hz, 3H) 1.06 (d, J=7.34 Hz, 3H) 1.09-1.15 (m, 18H) 1.20 (d, J=7.34 Hz, 3H) 1.22-1.28 (m, 1H) 1.35 (s, 3H) 1.42-1.52 (m, 1H) 1.56-1.66 (m, 3H) 1.69-1.81 (m, 3H) 1.83-1.96 (m, 2H) 2.08 (s, 3H) 2.22 (s, 6H) 2.31-2.35 (m, 2H) 2.36 (s, 6H) 2.38 (d, J=15.13 Hz, 1H) 2.53-2.68 (m, 2H) 2.82-2.94 (m, 2H) 2.95-3.00 (m, 1H) 3.01 (s, 3H) 3.18 (s, 1H) 3.30 (s, 3H) 3.55-3.62 (m, 1H) 3.63 (d, J=7.34 Hz, 1H) 3.65-3.71 (m, 1H) 3.77 (d, J=1.38 Hz, 1H) 3.78-3.86 (m, 2H) 3.95 (s, 1H)

4.27-4.35 (m, 1H) 4.49 (d, J=7.34 Hz, 1H) 4.64 (d, J=9.63 Hz, 1H) 4.96 (d, J=5.04 Hz, 1H) 5.05 (dd, J=11.00, 2.29 Hz, 1H)

EXAMPLE 117

2'-O-(3-methanesulfonylamidepropyl)-6-O-methylerythromycin A 0.12 g of the compound obtained in Example 114 was dissolved in 2 ml of diethylether to which 2 ml of a saturated aqueous sodium bicarbonate solution and 18 µl of methanesulfonyl chloride were added, and the mixture was vigorously stirred at room temperature for 2 hours. Another 3 ml of a saturated sodium bicarbonate was added to the reaction solution, and the mixture was extracted with ethyl acetate. The combined organic layer was dried over anhydrous magnesium sulfate, and concentrated. The resulting residue was purified by silica gel column chromatography (chloroform:methanol:ammonia water solution: 30:1:0.1) to give 70 mg of the titled compound.

MS (ESI) m/z=883.5 [M+H]+

1H NMR (600 MHz, CHLOROFORM-d) δ ppm 0.84 (t, J=7.57 Hz, 3H) 1.00 (d, J=7.34 Hz, 3H) 1.11-1.15 (m, 9H) 1.16-1.23 (m, 7H) 1.24 (s, 3H) 1.28 (d, J=6.42 Hz, 3H) 1.38 (s, 3H) 1.42-1.51 (m, 1H) 1.55-1.62 (m, 2H) 1.65-1.80 (m, 4H) 1.83-1.96 (m, 2H) 2.13 (d, J=10.09 Hz, 1H) 2.31 (s, 6H) 2.32-2.35 (m, 1H) 2.43-2.49 (m, 1H) 2.56-2.64 (m, 1H) 2.80-2.87 (m, 2H) 2.88 (s, 3H) 2.96-3.05 (m, 2H) 3.02 (s, 3H) 3.19 (s, 1H) 3.20-3.25 (m, 2H) 3.30 (s, 3H) 3.39-3.45 (m, 1H) 3.48 (s, 1H) 3.49-3.53 (m, 1H) 3.64 (d, J=7.34 Hz, 1H) 3.77 (s, 1H) 3.78 (d, J=9.17 Hz, 1H) 3.92-3.98 (m, 1H) 3.95 (s, 1H) 3.99-4.04 (m, 1H) 4.42 (d, J=7.34 Hz, 1H) 4.91 (d, J=4.13 Hz, 1H) 5.05 (dd, J=11.00, 2.29 Hz, 1H)

EXAMPLE 118

4"-O-acetyl-3'-N-demethyl-2'-O-(3-(4-morpholino)propyl)-6-methylerythromycin A (1) 0.38 g of the compound O obtained in Example 111 was dissolved in 2 ml of diethylether, then 2 ml of a saturated aqueous sodium bicarbonate solution and 18 µl of benzyl chloroformate were added, and the mixture was vigorously stirred at room temperature for 2 hours. Another 3 ml of a saturated aqueous sodium bicarbonate solution was added to the reaction solution, and the mixture was extracted with ethyl acetate. The combined organic layer was dried over anhydrous magnesium sulfate, and concentrated.

The resulting residue was purified by silica gel column chromatography (chloroform:methanol:ammonia water solution=30:1:0.1) to give 0.38 g of a 3'-benzyloxycarbonyl compound.

(2) 0.38 g of the compound obtained in the above (1) was dissolved in 4 ml of tetrahydrofuran, then 137 µl of triethylamine and 78 µl of methanesulfonyl chloride were added, and the mixture was stirred at room temperature for 6 hours. A saturated aqueous sodium bicarbonate solution was added to the reaction solution, and the mixture was extracted with ethyl acetate. The combined organic layer was dried over anhydrous magnesium sulfate, and concentrated to give 0.32 g of a mesyloxy compound.

(3) To acetone were added 0.18 g of the compound obtained in the above (2) and 46 mg of lithium bromide, and the mixture was stirred under reflux for 16 hours. After concentrating the reaction solution, the residue was poured into water, and extracted with chloroform. The combined organic layer was dried over anhydrous magnesium sulfate, and then concentrated. The resulting residue was purified by silica gel column chromatography (hexane:acetone:triethylamine=100:10:0.2 to 10:10:0.2) to give 73 mg of a bromo compound.

(4) 0.28 g of the compound obtained in the above (2) was dissolved in 10 ml of ethanol, then morpholine was added, and the mixture was stirred under reflux for 6 hours. After concentrating the reaction solution, the residue was poured into water, and extracted with chloroform. The combined organic layer was dried over anhydrous magnesium sulfate, and then concentrated. The resulting residue was purified by silica gel column chromatography (chloroform:methanol:ammonia water solution=50:1:0.1) to give 0.23 g of a morpholino compound.

(5) 0.23 g of the compound obtained in the above (4) was dissolved in 20 ml of tetrahydrofuran, then 0.23 g of 5% palladium-carbon was added, and the mixture was stirred at room temperature for 72 hours in a hydrogen atmosphere having 1 atm pressure. The reaction solution was filtered, the filtrate was concentrated, and the resulting residue was purified by silica gel column chromatography (chloroform:methanol:ammonia water solution=50:1:0.1 to 10:1:0.1) to give 0.18 g of the titled compound.

MS (ESI) m/z=903.5 [M+H]+

1H NMR (600 MHz, CHLOROFORM-d) δ ppm 0.84 (t, J=7.34 Hz, 3H) 1.03 (d, J=7.34 Hz, 3H) 1.08-1.16 (m, 19H) 1.20 (d, J=7.34 Hz, 3H) 1.37 (s, 3H) 1.41-1.51 (m, 1H) 1.55-1.65 (m, 2H) 1.71-1.79 (m, 3H) 1.83-1.97 (m, 3H) 2.09 (s, 3H) 2.30-2.37 (m, 2H) 2.38 (s, 3H) 2.39-2.64 (m, 7H) 2.74-2.80 (m, 1H) 2.81-2.89 (m, 1H) 2.96-3.00 (m, 1H) 3.02 (s, 3H) 3.19 (s, 1H) 3.28 (s, 3H) 3.48-3.54 (m, 1H) 3.64 (d, J=6.88 Hz, 1H) 3.71 (t, J=4.81 Hz, 4H) 3.74-3.78 (m, 1H) 3.77 (s, 1H) 3.80 (d, J=10.09 Hz, 1H) 3.86-3.93 (m, 1H) 3.97 (s, 1H) 4.27-4.35 (m, 1H) 4.54 (d, J=7.79 Hz, 1H) 4.65 (d, J=9.63 Hz, 1H) 4.96 (d, J=5.04 Hz, 1H) 5.05 (dd, J=11.00, 2.29 Hz, 1H)

EXAMPLE 119

4"-O-acetyl-2'-O-(3-(4-morpholino)propyl)-6-O-methylerythromycin A

Using 0.15 g of the compound obtained in Example 118, a reaction was carried out in a similar manner described in Example 9 to give 0.14 g of the titled compound.

MS (ESI) m/z=917.5[M+H]+

1H NMR (600 MHz, CHLOROFORM-d) δ ppm 0.84 (t, J=7.34 Hz, 3H) 1.04 (d, J=7.79 Hz, 3H) 1.08-1.15 (m, 18H) 1.20 (d, J=7.34 Hz, 3H) 1.22-1.27 (m, 1H) 1.35 (s, 3H) 1.41-1.52 (m, 1H) 1.56-1.68 (m, 3H) 1.70-1.96 (m, 4H) 2.08 (s, 3H) 2.35 (s, 6H) 2.36-2.46 (m, 8H) 2.53-2.67 (m, 2H) 2.80-2.92 (m, 2H) 2.95-3.01 (m, 1H) 3.01 (s, 3H) 3.18 (s, 1H) 3.30 (s, 3H) 3.55-3.74 (m, 7H) 3.74-3.85 (m, 3H) 3.95 (s, 1H) 4.25-4.34 (m, 1H) 4.49 (d, J=7.34 Hz, 1H) 4.64 (d, J=9.63 Hz, 1H) 4.96 (d, J=5.04 Hz, 1H) 5.05 (dd, J=11.23, 2.06 Hz, 1H)

EXAMPLE 120

2'-O-(3-(4-morpholino) propyl-6-O-methylerythromycin A 107 mg of the compound obtained in Example 119 was added to a mixed solvent of 5 ml of methanol and 5 ml of water, to which 0.16 g of potassium carbonate was added, the mixture was stirred at room temperature for 48 hours, and stirred under reflux for 2 hours. The reaction solution was poured into a saturated aqueous ammonium chloride solution, and extracted with chloroform. The combined organic layer was dried over anhydrous magnesium sulfate, and concentrated.

The resulting residue was purified by silica gel column chromatography (chloroform:methanol:ammonia water solution=30:1:0.1) to give 28 mg of the titled compound.

MS (ESI) m/z=875.4 [M+H]$^+$

1H NMR (600 MHz, CHLOROFORM-d) δ ppm 0.83 (t, J=7.34 Hz, 3H) 1.02 (d, J=7.34 Hz, 3H) 1.11 (d, J=2.75 Hz, 3H) 1.12 (d, J=2.75 Hz, 3H) 1.14 (s, 3H) 1.15-1.24 (m, 10H) 1.27 (d, J=6.42 Hz, 3H) 1.37 (s, 3H) 1.40-1.97 (m, 9H) 2.32 (s, 6H) 2.33-2.46 (m, 7H) 2.49-2.55 (m, 1H) 2.55-2.63 (m, 1H) 2.77-2.86 (m, 1H) 2.87-2.92 (m, 1H) 2.94-3.03 (m, 2H) 3.01 (s, 3H) 3.18 (s, 1H) 3.30 (s, 3H) 3.38-3.46 (m, 1H) 3.57-3.62 (m, 1H) 3.64 (d, J=7.79 Hz, 1H) 3.69-3.72 (m, 4H) 3.74-3.85 (m, 3H) 3.94 (s, 1H) 3.95-4.00 (m, 1H) 4.36 (d, J=6.88 Hz, 1H) 4.89 (d, J=4.58 Hz, 1H) 5.03 (dd, J=11.00, 2.29 Hz, 1H)

EXAMPLE 121

4"-O-acetyl-3'-N-demethyl-2'-O-(3-(4-hydroxypiperidin-1-yl)propyl)-6-O-methylerythromycin A Using 0.30 g of the compound O obtained in Example 111 and using 4-hydroxypiperidine instead of morpholine, a reaction was carried out in a similar manner described in Example 118 (1), (0.2), (4) and (5) to give 0.16 g of the titled compound.

MS (ESI) m/z=917.5 [M+H]$^+$

1H NMR (600 MHz, CHLOROFORM-d) δ ppm 0.84 (t, J=7.34 Hz, 3H) 1.02 (d, J=7.79 Hz, 3H) 1.06-1.17 (m, 19H) 1.20 (d, J=7.34 Hz, 3H) 1.36 (s, 3H) 1.42-1.51 (m, 1H) 1.54-1.65 (m, 5H) 1.68-1.80 (m, 3H) 1.82-1.97 (m, 4H) 2.02-2.17 (m, 2H) 2.08 (s, 3H) 2.27-2.37 (m, 2H) 2.38 (s, 6H) 2.41-2.48 (m, 1H) 2.50-2.64 (m, 2H) 2.68-2.81 (m, 3H) 2.81-2.89 (m, 1H) 2.95-3.00 (m, 1H) 3.01 (s, 3H) 3.20 (s, 1H) 3.28 (s, 3H) 3.45-3.52 (m, 1H) 3.64 (d, J=6.88 Hz, 1H) 3.66-3.75 (m, 1H) 3.76 (s, 1H) 3.79 (d, J=9.17 Hz, 1H) 3.86-3.93 (m, 1H) 3.97 (s, 1H) 4.27-4.35 (m, 1H) 4.53 (d, J=7.79 Hz, 1H) 4.64 (d, J=9.63 Hz, 1H) 4.96 (d, J=5.04 Hz, 1H) 5.05 (dd, J=11.00, 2.29 Hz, 1H)

EXAMPLE 122

4"-O-acetyl-2'-O-(3-(4-hydropiperidin-1-yl)propyl)-6-O-methylerythromycin A

Using 0.13 g of the compound obtained in Example 121, a reaction was carried out in a similar manner described in Example 9 to give 0.12 g of the titled compound.

MS (ESI) m/z=931.5 [M+H]$^+$

1H NMR (600 MHz, CHLOROFORM-d) δ ppm 0.84 (t, J=7.34 Hz, 3H) 1.05 (d, J=7.79 Hz, 3H) 1.10 (s, 3H) 1.11-1.14 (m, 15H) 1.15 (s, 3H) 1.20 (d, J=7.34 Hz, 3H) 1.21-1.26 (m, 1H) 1.35 (s, 3H) 1.42-1.51 (m, 1H) 1.53-1.69 (m, 4H) 1.70-1.81 (m, 3H) 1.83-1.96 (m, 4H) 2.08 (s, 3H) 2.10-2.15 (m, 2H) 2.35 (s, 6H) 2.36-2.41 (m, 2H) 2.55-2.66 (m, 2H) 2.71-2.80 (m, 2H) 2.81-2.92 (m, 2H) 2.96-3.00 (m, 1H) 3.01 (s, 3H) 3.19 (s, 1H) 3.30 (s, 3H) 3.54-3.61 (m, 1H) 3.61-3.64 (m, 1H) 3.65-3.73 (m, 2H) 3.75-3.85 (m, 3H) 3.96 (s, 1H) 4.27-4.33 (m, 1H) 4.49 (d, J=7.34 Hz, 1H) 4.64 (d, J=9.63 Hz, 1H) 4.96 (4, J=5.04 Hz, 1H) 5.05 (dd, J=11.00, 2.29 Hz, 1H)

EXAMPLE 123

2'-O-(3-(4-hydroxypiperidin-1-yl)propyl)-6-O-methylerythromycin A

Using 107 mg of the compound obtained in Example 122, a reaction was carried out in a similar manner described in Example 120 to give 44 mg of the titled compound.

MS (ESI) m/z=889.5 [M+H]$^+$

1H NMR (600 MHz, CHLOROFORM-d) δ ppm 0.83 (t, J=7.34 Hz, 3H) 1.02 (d, J=7.79 Hz, 3H) 1.09-1.13 (m, 6H) 1.14 (s, 3H) 1.15-1.20 (m, 6H) 1.19-1.24 (m, 1H) 1.22 (s, 3H) 1.26 (d, J=5.96 Hz, 3H) 1.36 (s, 3H) 1.42-1.50 (m, 1H) 1.51-1.67 (m, 4H) 1.69-1.95 (m, 7H) 2.07-2.17 (m, 3H) 2.31 (s, 6H) 2.33-2.45 (m, 3H) 2.48-2.55 (m, 1H) 2.55-2.62 (m, 1H) 2.71-2.77 (m, 2H) 2.77-2.85 (m, 1H) 2.86-2.92 (m, 1H) 2.95-2.99 (m, 2H) 3.00 (s, 3H) 3.19 (s, 1H) 3.30 (s, 3H) 3.38-3.44 (m, 1H) 3.44-3.47 (m, 1H) 3.57 (m, 1H) 3.63 (d, J=8.25 Hz, 1H) 3.65-3.72 (m, 2H) 3.75-3.83 (m, 3H) 3.93-3.99 (m, 2H) 4.36 (d, J=7.34 Hz, 1H) 4.89 (d, J=4.59 Hz, 1H) 5.02 (dd, J=11.00, 2.29 Hz, 1H)

EXAMPLE 124

4"-O-acetyl-2'-O-(3-(4-(2-dimethylaminoethyl)piperidin1-yl)propyl)-6-O-methylerythromycin A Using 0.27 g of the compound O obtained in Example 111, using 4-hydroxypiperidine instead of morpholine, a reaction was carried out in a similar manner described in Example 118 (1), (2), (4) and (5) and Example 9 to give 46 mg of the titled compound.

MS (ESI) m/z=987.8 [M+H]$^+$

1H NMR (600 MHz, CHLOROFORM-d) δ ppm 0.83 (t, J=7.34 Hz, 3H) 1.03 (d, J=7.79 Hz, 3H) 1.08-1.13 (m, 15H) 1.14 (s, 3H) 1.19 (d, J=7.34 Hz, 3H) 1.21-1.30 (m, 1H) 1.34 (s, 3H) 1.38-1.51 (m, 1H) 1.54-1.68 (m, 3H) 1.70-1.80 (m, 3H) 1.80-1.95 (m, 2H) 2.07 (s, 3H) 2.21-2.26 (m, 7H) 2.34 (s, 6H) 2.35-2.68 (m, 16H) 2.81-2.91 (m, 2H) 2.95-3.00 (m, 1H) 3.00 (s, 3H) 3.20 (br. s., 1H) 3.29 (s, 3H) 3.55-3.72 (m, 3H) 3.73-3.83 (m, 3H) 3.95 (s, 1H) 4.26-4.34 (m, 1H) 4.48 (d, J=−7.34 Hz, 1H) 4.63 (d, J=9.63 Hz, 1H) 4.95 (d, J=5.04 Hz, 1H) 5.04 (dd, J=11.00, 2.29 Hz, 1H)

EXAMPLE 125

2'-O-(3-(4-(2-dimethylaminoethyl)piperidin-1-yl)propyl)-6-O-methylerythromycin A Using 16 mg of the compound obtained in Example 124, a reaction was carried out in a similar manner described in Example 120 to give 7 mg of the titled compound.

MS (ESI) m/z=945.7 [M+H]$^+$

1H NMR (499 MHz, CHLOROFORM-d) δ ppm 0.84 (t, J=7.40 Hz, 3H) 1.02 (d, J=7.40 Hz, 3H) 1.12 (d, J=2.19 Hz, 3H) 1.13 (d, J=2.47 Hz, 3H) 1.15 (s, 3H) 1.16-1.25 (m, 10H) 1.28 (d, J=6.31 Hz, 3H) 1.37 (s, 3H) 1.41-1.96 (m, 9H) 2.29 (s, 6H) 2.33 (s, 6H) 2.34-2.66 (m, 17H) 2.78-2.86 (m, 1H) 2.87-2.92 (m, 1H) 2.95-3.01 (m, 2H) 3.01 (s, 3H) 3.19 (br. s., 1H) 3.30 (s, 3H) 3.38-3.47 (m, 1H) 3.56-3.66 (m, 2H) 3.74-3.83 (m, 3H) 3.92-4.01 (m, 2H) 4.37 (d, J=7.40 Hz, 1H) 4.90 (d, J=4.66 Hz, 1H) 5.03 (dd, J=10.97, 2.47 Hz, 1H)

EXAMPLE 126

2'-O-(2-benzyloxyethyl)-6-O-methylerythromycin A

Using 6.06 g of the compound obtained in Example 24 (1) and using 2-benzyloxyethyl bromide instead of 1-bromo-3- phenylpropane, a reaction was carried out in a similar manner described in Example 24 (2) and (3) to give 98 mg of the titled compound.

MS (ESI) m/z=882.6 [M+H]+
1H NMR (600 MHz, CHLOROFORM-d) δ ppm 0.85 (t, J=7.34 Hz, 3H) 1.02 (d, J=7.79 Hz, 3H) 1.09-1.14 (m, 9H) 1.16-1.21 (m, 6H) 1.20-1.26 (m, 1H) 1.23 (s, 3H) 1.28 (d, J=6.42 Hz, 3H) 1.38 (s, 3H) 1.43-1.51 (m, 1H) 1.52-1.71 (m, 3H) 1.73-1.88 (m, 2H) 1.88-1.96 (m, 1H) 2.18 (d, J=10.55 Hz, 1H) 2.29-2.33 (m, 1H) 2.35 (s, 6H) 2.58 (s, 2H) 2.75-2.85 (m, 1H) 2.93-3.00 (m, 3H) 3.02 (s, 3H) 3.19 (s, 1H) 3.31 (s, 3H) 3.41-3.50 (m, 1H) 3.59-3.69 (m, 2H) 3.73-3.80 (m, 1H) 3.76 (s, 1H) 3.80 (d, J=8.25 Hz, 1H) 3.82-3.87 (m, 1H) 3.93-4.02 (m, 2H) 3.95 (s, 1H) 4.41 (d, J=7.34 Hz, 1H) 4.55 (m, 2H) 4.90 (d, J=4.59 Hz, 1H) 5.03 (dd, J=11.00, 2.29 Hz, 1H) 7.26-7.30 (m, 1H) 7.30-7.35 (m, 4H)

EXAMPLE 127

2'-O-(2-hydroxyethyl)-6-O-methylerythromycin A (compound P) and 3'-N-demethyl-2'-O-(2-hydroxyethyl)-6-O-methylerythromycin A (compound Q)

Using 90 mg of the compound obtained in Example 126, a reaction was carried out in a similar manner described in Example 109 to give 51 mg of a compound P and 15 mg of a compound Q.

2'-O-(2-hydroxyethyl)-6-O-methylerythromycin A (compound P)

MS (ESI) m/z=792.4 [M+H]+
1H NMR (600 MHz, CHLOROFORM-d) δ ppm 0.84 (t, J=7.57 Hz, 3H) 1.05 (d, J=7.79 Hz, 3H) 1.10-1.15 (m, 9H) 1.19 (d, J=7.34 Hz, 3H) 1.21 (d, J=6.42 Hz, 3H) 1.22-1.27 (m, 1H) 1.24 (s, 3H) 1.28 (d, J=6.42 Hz, 3H) 1.37 (s, 3H) 1.41-1.52 (m, 1H) 1.53-1.62 (m, 2H) 1.69-1.81 (m, 2H) 1.83-1.96 (m, 2H) 2.16 (d, J=10.09 Hz, 1H) 2.30 (s, 6H) 2.33 (d, J=15.13 Hz, 1H) 2.51-2.63 (m, 2H) 2.80-2.92 (m, 2H) 2.95-3.04 (m, 2H) 3.02 (s, 3H) 3.18 (s, 1H) 3.31 (s, 3H) 3.41-3.48 (m, 1H) 3.49-3.55 (m, 1H) 3.58-3.64 (m, 2H) 3.66 (d, J=7.34 Hz, 1H) 3.76 (s, 1H) 3.79 (d, J=8.71 Hz, 1H) 3.92-4.02 (m, 2H) 3.95 (s, 1H) 4.41 (d, J=7.34 Hz, 1H) 4.91 (d, J=4.59 Hz, 1H) 5.04 (dd, J=11.00, 2.29 Hz, 1H)

3'-N-demethyl-2'-O-(2-hydroxyethyl)-6-O-methylerythromycin A (compound Q)

MS (ESI) m/z=778.4 [M+H]+
1H NMR (600 MHz, CHLOROFORM-d) δ ppm 0.84 (t, J=7.34 Hz, 3H) 1.04 (d, J=7.79 Hz, 3H) 1.06-1.09 (m, 1H) 1.10-1.13 (m, 6H) 1.14 (s, 3H) 1.16-1.20 (m, 6H) 1.24 (s, 3H) 1.28 (d, J=6.42 Hz, 3H) 1.37 (s, 3H) 1.40-1.52 (m, 1H) 1.54-1.60 (m, 2H) 1.73-1.81 (m, 1H) 1.82-1.95 (m, 2H) 2.00-2.04 (m, 1H) 2.16 (d, J=11.00 Hz, 1H) 2.33 (d, J=15.13 Hz, 1H) 2.40-2.46 (m, 1H) 2.48 (s, 3H) 2.54-2.64 (m, 1H) 2.71 (br. s., 1H) 2.78-2.87 (m, 1H) 2.89-2.95 (m, 1H) 2.95-3.01 (m, 3H) 3.01 (s, 3H) 3.19 (s, 1H) 3.31 (s, 3H) 3.42-3.55 (m, 1H) 3.59-3.68 (m, 3H) 3.69-3.74 (m, 1H) 3.76 (d, J=1.38 Hz, 1H) 3.79 (d, J=9.17 Hz, 1H) 3.89-3.99 (m, 3H) 4.41 (d, J=7.34 Hz, 1H) 4.91 (d, J=4.58 Hz, 1H) 5.04 (dd, J=11.00, 2.29 Hz, 1H)

EXAMPLE 128

2'-O-(4-hydroxybutyl)-6-O-methylerythromycin A (compound R) and 3'-N-demethyl-2'-O-(4-hydroxybutyl)-6-O-methylerythromycin A (compound S)

(1) Using 10.00 g of the compound obtained in Example 24 (1) and using 4-benzyloxybutyl bromide instead of 1-bromo-3-phenylpropane, a reaction was carried out in a similar manner described in Example 24 (2) and (3) to give 0.81 g of a benzyloxy compound.

(2) Successively using 0.50 g of the compound obtained in the above (1), a reaction was carried out in a similar manner described in Example 109 to give 83 mg of a compound R and 87 mg of a compound S.

2'-O-(4-hydroxybutyl)-6-O-methylerythromycin A (compound R)

MS (ESI) m/z=820.5 [M+H]+
1H NMR (600 MHz, CHLOROFORM-d) δ ppm 0.84 (t, J=7.34 Hz, 3H) 1.05 (d, J=7.79 Hz, 3H) 1.11-1.15 (m, 9H) 1.16-1.20 (m, 6H) 1.20-1.23 (m, 1H) 1.24 (s, 3H) 1.28 (d, J=6.42 Hz, 3H) 1.37 (s, 3H) 1.41-1.51 (m, 1H) 1.53-1.72 (m, 8H) 1.74-1.81 (m, 1H) 1.82-1.97 (m, 2H) 2.19 (d, J=10.09 Hz, 1H) 2.27 (s, 6H) 2.33 (d, J=14.67 Hz, 1H) 2.47-2.53 (m, 1H) 2.56-2.64 (m, 1H) 2.78-2.91 (m, 2H) 2.96-3.01 (m, 2H) 3.02 (s, 3H) 3.19 (s, 1H) 3.32 (s, 3H) 3.39-3.49 (m, 1H) 3.60-3.72 (m, 4H) 3.77 (d, J=0.92 Hz, 1H) 3.79 (d, J=8.71 Hz, 1H) 3.87-3.93 (m, 1H) 3.93-3.99 (m, 1H) 3.95 (s, 1H) 4.42 (d, J=7.34 Hz, 1H) 4.91 (d, J=4.59 Hz, 1H) 5.04 (dd, J=11.00, 2.29 Hz, 1H)

3'-N-demethyl-2'-O-(4-hydroxybutyl)-6-O-methylerythromycin A (compound S)

MS (ESI) m/z=806.4 [M+H]+
1H NMR (600 MHz, CHLOROFORM-d) δ ppm 0.84 (t, J=7.34 Hz, 3H) 1.02 (d, J=7.34 Hz, 3H) 1.04-1.10 (m, 1H) 1.10-1.13 (m, 6H) 1.15 (s, 3H) 1.17-1.20 (m, 6H) 1.20-1.26 (m, 2H) 1.24 (s, 3H) 1.28 (d, J=6.42 Hz, 3H) 1.38 (s, 3H) 1.42-1.51 (m, 1H) 1.53-1.97 (m, 8H) 2.18 (d, J=10.09 Hz, 1H) 2.33 (d, J=15.13 Hz, 1H) 2.37 (s, 3H) 2.41-2.50 (m, 1H) 2.56-2.66 (m, 1H) 2.77-2.86 (m, 2H) 2.93-3.02 (m, 2H) 3.02 (s, 3H) 3.20 (s, 1H) 3.31 (s, 3H) 3.49-3.57 (m, 2H) 3.62-3.68 (m, 2H) 3.71 (q, J=7.03 Hz, 2H) 3.76 (s, 1H) 3.80 (d, J=8.71 Hz, 1H) 3.88-4.01 (m, 2H) 3.96 (s, 1H) 4.44 (d, J=7.79 Hz, 1H) 4.91 (d, J=4.58 Hz, 1H) 5.04 (dd, J=11.00, 2.29 Hz, 1H)

EXAMPLE 129

3'-N-demethyl-3'-N-(3-benzyloxypropyl)-6,2'-di-O-methylerythromycin A 0.40 g of the compound obtained in Example 82 was dissolved in 6 ml of ethanol to which 1 ml of 3-benzyloxypropyl bromide and 1 ml of diisopropylethylamine were added, and the mixture was stirred under reflux for 12 hours. After concentrating the reaction solution, the resulting residue was purified by silica gel column chromatography (chloroform:methanol:ammonia water solution=50:1:0.1 to 30:1:0.1) to give 0.31 g of the titled compound.

MS (ESI) m/z=896.7 [M+H]+
1H NMR (600 MHz, CHLOROFORM-d) δ ppm 0.84 (t, J=7.57 Hz, 3H) 1.05 (d, J=7.79 Hz, 3H) 1.11-1.14 (m, 6H) 1.14 (s, 3H) 1.15-1.20 (m, 6H) 1.20-1.26 (m, 1H) 1.23 (s, 3H) 1.28 (d, J=5.96 Hz, 3H) 1.38 (s, 3H) 1.42-1.51 (m, 1H) 1.52-1.68 (m, 3H) 1.72-1.96 (m, 5H) 2.13 (d, J=10.55 Hz, 1H) 2.32 (s, 3H) 2.34 (d, J=15.13 Hz, 1H) 2.49-2.71 (m, 4H) 2.80-2.89 (m, 1H) 2.95-3.02 (m, 2H) 3.02 (s, 3H) 3.19 (s, 1H) 3.29 (s, 3H) 3.37-3.43 (m, 1H) 3.50 (s, 3H) 3.53 (td, J=6.42, 1.38 Hz, 2H) 3.64 (d, J=7.34 Hz, 1H) 3.74-3.82 (m, 2H) 3.93-4.00 (m, 1H) 3.97 (s, 1H) 4.37 (d, J=7.34 Hz, 1H) 4.49

(d, J=1.83 Hz, 2H) 4.91 (d, J=4.58 Hz, 1H) 5.04 (dd, J=11.00, 2.29 Hz, 1H) 7.26-7.30 (m, 1H) 7.31-7.36 (m, 4H)

EXAMPLE 130

3'-N-demethyl-3'-N-(3-dimethylaminopropyl)-6,2'-di-O-methylerythromycin A

Using 1.00 g of the compound obtained in Example 82 and using 3-dimethylaminopropyl bromide hydrobromide instead of 3-benzyloxypropyl bromide, a reaction was carried out in a similar manner described in Example 129 to give 0.14 g of the titled compound.

MS (ESI) m/z=833.6 [M+H]$^+$

1H NMR (600 MHz, CHLOROFORM-d) δ ppm 0.84 (t, J=7.34 Hz, 3H) 1.05 (d, J=7.79 Hz, 3H) 1.11-1.16 (m, 6H) 1.15-1.21 (m, 6H) 1.21-1.26 (m, 1H) 1.23 (s, 3H) 1.28 (d, J=6.42 Hz, 3H) 1.38 (s, 3H) 1.42-1.71 (m, 6H) 1.75-2.00 (m, 4H) 2.17-2.30 (m, 6H) 2.32 (s, 6H) 2.34 (d, J=15.13 Hz, 2H) 2.43-2.49 (m, 1H) 2.55-2.65 (m, 3H) 2.80-2.90 (m, 2H) 2.96-3.02 (m, 2H) 3.02 (s, 3H) 3.19 (s, 1H) 3.30 (s, 3H) 3.38-3.44 (m, 1H) 3.52 (s, 3H) 3.64 (d, J=7.34 Hz, 1H) 3.76-3.80 (m, 2H) 3.93-4.00 (m, 1H) 3.97 (s, 1H) 4.37 (d, J=7.34 Hz, 1H) 4.90 (d, J=5.04 Hz, 1H) 5.04 (dd, J=11.00, 2.29 Hz, 1H)

EXAMPLE 131

3'-N-demethyl-3'-N-(3-(4-morpholino)propyl)-6,2'-di-O-methylerythromycin A (1) Using 1.02 g of the compound obtained in Example 82 and using 3-chloropropyl bromide instead of 3-benzyloxypropyl bromide, a reaction was carried out in a similar manner described in Example 129 to give 0.10 g of a chloro compound.

(2) Successively using 92 mg of the compound obtained in the above (1), a reaction was carried out in a similar manner described in Example 118 (4) to give 77 mg of the titled compound.

MS (ESI) m/z=875.7 [M+H]$^+$

1H NMR (600 MHz, CHLOROFORM-d) δ ppm 0.84 (t, J=7.57 Hz, 3H) 1.05 (d, J=7.34 Hz, 3H) 1.11-1.14 (m, 6H) 1.14 (s, 3H) 1.16-1.20 (m, 6H) 1.23 (s, 3H) 1.24-1.26 (m, 1H) 1.28 (d, J=6.42 Hz, 3H) 1.39 (s, 3H) 1.43-1.50 (m, 1H) 1.52-1.70 (m, 4H) 1.74-1.96 (m, 4H) 2.32 (s, 3H) 2.32-2.52 (m, 6H) 2.55-2.64 (m, 3H) 2.80-2.90 (m, 3H) 2.96-3.02 (m, 2H) 3.02 (s, 3H) 3.18 (s, 1H) 3.30 (s, 3H) 3.39-3.46 (m, 1H) 3.51 (s, 3H) 3.64 (d, J=7.34 Hz, 1H) 3.66-3.69 (m, 1H) 3.71 (t, J=4.59 Hz, 4H) 3.77 (d, J=1.38 Hz, 1H) 3.79 (d, J=9.17 Hz, 1H) 3.94-4.00 (m, 1H) 3.96 (s, 1H) 4.37 (d, J=6.88 Hz, 1H) 4.91 (d, J=4.58 Hz, 1H) 5.04 (dd, J=11.00, 2.29 Hz, 1H)

EXAMPLE 132

3'-N-demethyl-3'-N-(3-hydroxypropyl)-6,2'-di-O-methylerythromycin A

Using 1.00 g of the compound obtained in Example 129, a reaction was carried out in a similar manner described in Example 109 to give 0.68 g of the titled compound.

MS (ESI) m/z=806.6 [M+H]$^+$

1H NMR (600 MHz, CHLOROFORM-d) δ ppm 0.84 (t, J=7.34 Hz, 3H) 1.05 (d, J=7.34 Hz, 3H) 1.10-1.16 (m, 9H) 1.17-1.21 (m, 6H) 1.24 (s, 3H) 1.26-1.32 (m, 1H) 1.28 (d, J=5.96 Hz, 3H) 1.38 (s, 3H) 1.42-1.95 (m, 9H) 2.20 (d, J=10.09 Hz, 1H) 2.33 (s, 3H) 2.33-2.36 (m, 1H) 2.56-2.69 (m, 2H) 2.73-2.90 (m, 4H) 2.96-3.02 (m, 2H) 3.02 (s, 3H) 3.19 (s, 1H) 3.32 (s, 3H) 3.42-3.48 (m, 1H) 3.51 (s, 3H) 3.66 (d, J=7.79 Hz, 1H) 3.77 (s, 1H) 3.79 (d, J=8.71 Hz, 1H) 3.82 (t, J=5.04 Hz, 2H) 3.96 (s, 1H) 3.96-4.00 (m, 1H) 4.39 (d, J=7.34 Hz, 1H) 4.91 (d, J=4.58 Hz, 1H) 5.03 (dd, J=11.00, 2.29 Hz, 1H) 5.47 (br. s., 1H)

EXAMPLE 133

3-N-demethyl-3'-N-(3-(1,3-dioxo-1,3-dihydroisoindol-2-yl-propyl)-6,2'-di-O-methylerythromycin A Using 0.75 g of the compound obtained in Example 132, a reaction was carried out in a similar manner described in Example 113 to give 0.35 g of the titled compound.

MS (ESI) m/z=935.6 [M+H]$^+$

1H NMR (600 MHz, CHLOROFORM-d) δ ppm 0.84 (t, J=7.34 Hz, 3H) 1.04 (d, J=7.79 Hz, 3H) 1.09-1.32 (m, 19H) 1.38 (s, 3H) 1.41-2.04 (m, 9H) 2.13-2.17 (m, 1H) 2.26-2.43 (m, 6H) 2.52-2.76 (m, 3H) 2.78-2.91 (m, 2H) 2.96-3.01 (m, 2H) 3.02 (s, 3H) 3.18 (s, 1H) 3.29 (s, 3H) 3.30-3.31 (m, 1H) 3.41-3.53 (m, 1H) 3.49 (s, 3H) 3.61-3.66 (m, 2H) 3.68-3.81 (m, 4H) 3.95 (s, 1H) 3.96-4.01 (m, 1H) 4.39 (d, J=6.88 Hz, 1H) 4.91 (d, J=4.58 Hz, 1H) 5.04 (dd, J=11.00, 2.29 Hz, 1H) 7.70 (dd, J=5.27, 2.98 Hz, 2H) 7.83 (dd, J=5.27, 2.98 Hz, 2H)

EXAMPLE 134

3'-N-demethyl-3'-N-(3-aminopropyl)-6,2'-di-O-methylerythromycin A

Using 0.30 g of the compound obtained in Example 133, a reaction was carried out in a similar manner described in Example 114 to give 0.35 g of the titled compound.

MS (ESI) m/z=805.5 [M+H]$^+$

1H NMR (600 MHz, CHLOROFORM-d) δ ppm 0.84 (t, J=7.34 Hz, 3H) 1.04 (d, J=7.34 Hz, 3H) 1.10-1.14 (m, 6H) 1.14 (s, 3H) 1.24 (s, 8H) 1.24 (s, 3H) 1.28 (d, J=5.96 Hz, 3H) 1.38 (s, 3H) 1.43-1.96 (m, 8H) 2.32 (s, 3H) 2.34 (d, J=15.13 Hz, 1H) 2.54-2.63 (m, 3H) 2.65-2.73 (m, 1H) 2.80-2.94 (m, 3H) 2.96-3.02 (m, 2H) 3.02 (s, 3H) 3.31 (s, 3H) 3.40-3.47 (m, 1H) 3.54 (s, 3H) 3.65 (d, J=7.79 Hz, 1H) 3.77 (d, J=1.83 Hz, 1H) 3.78 (d, J=8.71 Hz, 1H) 3.93-4.00 (m, 2H) 4.37 (d, J=6.88 Hz, 1H) 4.90 (d, J=4.59 Hz, 1H) 5.04 (dd, J=11.00, 2.29 Hz, 1H)

EXAMPLE 135

4"-O-acetyl-3'-N-demethyl-3'-N-(3-dimethylaminopropyl)-6,2'-di-O-methylerythromycin A Using 45 mg of the compound obtained in Example 130, a reaction was carried out in a similar manner described in Example 87 to give 40 mg of the titled compound.

MS (ESI) m/z=874.6 [M+H]$^+$

1H NMR (600 MHz, CHLOROFORM-d) δ ppm 0.84 (t, J=7.57 Hz, 3H) 1.07 (d, J=7.79 Hz, 3H) 1.10 (s, 3H) 1.10-1.15 (m, 15H) 1.20 (d, J=7.34 Hz, 3H) 1.22-1.29 (m, 1H) 1.36 (s, 3H) 1.43-1.52 (m, 1H) 1.55-1.71 (m, 5H) 1.75-1.83 (m, 1H) 1.85-1.95 (m, 2H) 2.09 (s, 3H) 2.21 (s, 6H) 2.25-2.33 (m, 2H) 2.34 (s, 3H) 2.38 (d, J=15.13 Hz, 1H) 2.45-2.52 (m, 1H) 2.53-2.63 (m, 2H) 2.65-2.72 (m, 1H) 2.84-2.91 (m, 2H) 2.97-3.01 (m, 1H) 3.02 (s, 3H) 3.19 (s, 1H) 3.28 (s, 3H) 3.51 (s, 3H) 3.63 (d, J=7.34 Hz, 1H) 3.65-3.74 (m, 1H) 3.75-3.81 (m, 2H) 3.97 (s, 1H) 4.27-4.35 (m, 1H) 4.49 (d, J=7.34 Hz, 1H) 4.64 (d, J=9.63 Hz, 1H) 4.96 (d, J=5.04 Hz, 1H) 5.05 (dd, J=11.00, 2.29 Hz, 1H)

EXAMPLE 136

4"-O-acetyl-3'-N-demethyl-3'-N-(3-acetoxypropyl)-6,2'-di-O-methylerythromycin A Using 0.77 g of the compound obtained in Example 132, a reaction was carried out in a similar manner described in Example 87 to give 0.79 g of the titled compound.

MS (ESI) m/z=890.5 [M+H]$^+$

1H NMR (600 MHz, CHLOROFORM-d) δ ppm 0.84 (t, J=7.34 Hz, 2H) 1.07 (d, J=7.79 Hz, 3H) 1.10 (s, 3H) 1.11-1.16 (m, 15H) 1.20 (d, J=7.34 Hz, 3H) 1.22-1.28 (m, 1H) 1.37 (s, 3H) 1.43-1.51 (m, 1H) 1.58-1.67 (m, 3H) 1.75-1.83 (m, 3H) 1.85-1.95 (m, 2H) 2.04 (s, 3H) 2.09 (s, 3H) 2.34 (s, 3H) 2.39 (d, J=15.13 Hz, 1H) 2.55-2.70 (m, 4H) 2.83-2.91 (m, 2H) 2.97-3.01 (m, 1H) 3.02 (s, 3H) 3.18 (s, 1H) 3.29 (s, 3H) 3.50 (s, 3H) 3.63 (d, J=6.88 Hz, 1H) 3.66-3.75 (m, 2H) 3.75-3.78 (m, 1H) 3.80 (d, J=8.71 Hz, 1H) 3.96 (s, 1H) 4.13 (t, J=6.65 Hz, 2H) 4.27-4.35 (m, 1H) 4.49 (d, J=7.34 Hz, 1H) 4.65 (d, J=9.63 Hz, 1H) 4.97 (d, J=5.04 Hz, 1H) 5.05 (dd, J=11.00, 2.29 Hz, 1H)

EXAMPLE 137

4"-O-acetyl-3'-N-demethyl-3'-N-(3-hydroxypropyl)-6,2'-di-O-methylerythromycin A To a mixed solvent of 64 ml of methanol and 8 ml of water was added 0.66 g of the compound obtained in Example 136, to which 0.15 g of potassium carbonate was added, and the mixture was stirred at room temperature for 2 hours. The reaction solution was poured into water, and extracted with ethyl acetate. The combined organic layer was dried over anhydrous magnesium sulfate, and then concentrated. The resulting residue was purified by silica gel column chromatography (chloroform:methanol:ammonia water solution=30:1:0.1) to 0.46 g of the titled compound.

MS (ESI) m/z=848.5 [M+H]$^+$

1H NMR (600 MHz, CHLOROFORM-d) δ ppm 0.84 (t, J=7.34 Hz, 3H) 1.07 (d, J=7.34 Hz, 3H) 1.10-1.17 (m, 18H) 1.20 (d, J=7.34 Hz, 3H) 1.22-1.33 (m, 1H) 1.36 (s, 3H) 1.41-1.75 (m, 6H) 1.76-1.82 (m, 1H) 1.84-1.96 (m, 2H) 2.09 (s, 3H) 2.35 (s, 3H) 2.39 (d, J=15.13 Hz, 1H) 2.54-2.63 (m, 1H) 2.71-2.77 (m, 1H) 2.79-2.91 (m, 4H) 2.96-3.01 (m, 1H) 3.02 (s, 3H) 3.18 (s, 1H) 3.30 (s, 3H) 3.51 (s, 3H) 3.65 (d, J=7.34 Hz, 1H) 3.68-3.84 (m, 5H) 3.96 (s, 1H) 4.27-4.34 (m, 1H) 4.52 (d, J=7.34 Hz, 1H) 4.65 (d, J=10.09) Hz, 1H) 4.97 (d, J=5.04 Hz, 1H) 5.05 (dd, J=11.00, 2.29 Hz, 1H) 5.51 (br. s., 1H)

EXAMPLE 138

3'-N-dedimethyl-6,2'-di-O-methylerythromycin A

After dissolving 0.31 g of sodium in 50 ml of methanol, 1.00 g of the compound obtained in Example 82 and 0.85 g of iodine were added, and the mixture was stirred at room temperature for 6 hours. A saturated aqueous sodium thiosulfate solution was added to the reaction solution, subsequently a saturated aqueous ammonium chloride solution was added, and the mixture was extracted with ethyl acetate. The combined organic layer was dried over anhydrous magnesium sulfate, and then concentrated. The resulting residue was purified by silica gel column chromatography (hexane:acetone:triethylamine=50:10:0.2 to 10:10:0.2) to 0.20 g of the titled compound.

MS (ESI) m/z=734.5 [M+H]$^+$

1H NMR (499 MHz, CHLOROFORM-d) δ ppm 0.84 (t, J=7.40 Hz, 3H) 1.05 (d, J=7.68 Hz, 3H) 1.10-1.14 (m, 6H) 1.14 (s, 3H) 1.16-1.21 (m, 6H) 1.21-1.25 (m, 1H) 1.23 (s, 3H) 1.28 (d, J=6.31 Hz, 3H) 1.39 (s, 3H) 1.43-1.64 (m, 4H) 1.73-1.96 (m, 3H) 2.14 (br. s., 2H) 2.33 (d, J=14.81 Hz, 1H) 2.50-2.64 (m, 2H) 2.68-2.77 (m, 1H) 2.81-2.89 (m, 1H) 2.95-3.02 (m, 2H) 3.03 (s, 3H) 3.30 (s, 3H) 3.50-3.57 (m, 1H) 3.58 (s, 3H) 3.65 (d, J=7.40 Hz, 1H) 3.77 (d, J=1.65 Hz, 1H) 3.79 (d, J=8.23 Hz, 1H) 3.93-4.00 (m, 1H) 4.40 (d, J=7.68 Hz, 1H) 4.91 (d, J=4.39 Hz, 1H) 5.04 (dd, J=10.97, 2.47 Hz, 1H)

EXAMPLE 139

3'-N-dedimethylamino-3-(4-morpholino)-6,2'-di-O-methylerythromycin A

To 10 ml of dimethylsulfoxide were added 0.20 g of the compound obtained in Example 138, 26 μl of di(2-bromoethyl)ether and 59 μl of triethylamine, and the mixture was stirred in an oil bath at 90° C. for 4 hours. The reaction solution was poured into water, and extracted with diethyl ether. The combined organic layer was washed with saturated brine, dried over anhydrous magnesium sulfate, and then concentrated. The resulting residue was purified by silica gel column chromatography (hexane:acetone:triethylamine=50:10:0.2 to 10:10:0.2) to give 0.16 g of the titled compound.

MS (ESI) m/z=804.5 [M+H]$^+$

1H NMR (600 MHz, CHLOROFORM-d) δ ppm 0.84 (t, J=7.34 Hz, 3H) 1.05 (d, J=7.34 Hz, 3H) 1.11-1.13 (m, 6H) 1.14 (s, 3H) 1.17-1.20 (m, 6H) 1.23 (s, 3H) 1.24-1.27 (m, 1H) 1.28 (d, J=5.96 Hz, 3H) 1.38 (s, 3H) 1.41-1.50 (m, 1H) 1.52-1.65 (m, 2H) 1.68-1.96 (m, 4H) 2.13 (d, J=10.55 Hz, 1H) 2.33 (d, J=15.13 Hz, 1H) 2.50-2.70 (m, 6H) 2.80-2.91 (m, 2H) 2.96-3.02 (m, 2H) 3.02 (s, 3H) 3.18 (s, 1H) 3.30 (s, 3H) 3.39-3.46 (m, 1H) 3.54 (s, 3H) 3.64 (d, J=7.34 Hz, 1H) 3.65-3.75 (m, 4H) 3.76 (s, 1H) 3.78 (d, J=8.71 Hz, 1H) 3.91-3.99 (m, 1H) 3.96 (s, 1H) 4.39 (d, J=7.34 Hz, 1H) 4.90 (d, J=4.59 Hz, 1H) 5.04 (dd, J=11.00, 2.29 Hz, 1H)

EXAMPLE 140

4"-O-acetyl-3'-N-dedimethylamino-3-(4-morpholino)-6,2'-di-O-methylerythromycin A Using 67 mg of the compound obtained in Example 139, a reaction was carried out in a similar manner described in Example 87 to give 63 mg of the titled compound.

MS (ESI) m/z=846.4 [M+H]$^+$

1H NMR (600 MHz, CHLOROFORM-d) δ ppm 0.83 (t, J=7.57 Hz, 3H) 1.07 (d, J=7.34 Hz, 3H) 1.09 (s, 3H) 1.10-1.17 (m, 15H) 1.19 (d, J=7.34 Hz, 3H) 1.23-1.32 (m, 1H) 1.35 (s, 3H) 1.42-1.52 (m, 1H) 1.57-1.63 (m, 1H) 1.65-1.74 (m, 2H) 1.75-1.82 (m, 1H) 1.85-1.97 (m, 2H) 2.08 (s, 3H) 2.38 (d, J=15.13 Hz, 1H) 2.53-2.73 (m, 6H) 2.84-2.91 (m, 2H) 2.96-3.01 (m, 1H) 3.02 (s, 3H) 3.18 (s, 1H) 3.28 (s, 3H) 3.54 (s, 3H) 3.63 (d, J=6.88 Hz, 1H) 3.65-3.74 (m, 5H) 3.76 (s, 1H) 3.78 (d, J=8.25 Hz, 1H) 3.96 (s, 1H) 4.26-4.33 (m, 1H) 4.51 (d, J=7.34 Hz, 1H) 4.64 (d, J=10.09 Hz, 1H) 4.96 (d, J=5.04 Hz, 1H) 5.05 (dd, J=11.00, 2.29 Hz, 1H)

EXAMPLE 141

9-deoxo-9-(S)-hydroxy-6,2'-di-O-methylerythromycin A 0.50 g of the compound obtained in Example 31 was dissolved in 5 ml of tetrahydrofuran to which 3.1 ml of a 1M lithium triethylborohydride-tetrahydrofuran solution was added dropwise in a dry ice-acetone bath, and the mixture was stirred for 4 hours. A saturated aqueous ammonium chloride solution was added to the reaction solution, and the mixture was extracted with ethyl acetate. The combined organic layer was dried over anhydrous magnesium sulfate, and then concentrated. 10 ml of ethylene glycol and 3 ml of pyridine were added to the residue, and the solvent was evaporated under reduced pressure. The resulting residue was pour into water, and extracted with chloroform. The combined organic layer was dried with anhydrous magnesium sulfate, and then concentrated to give 0.30 g of the titled compound.

MS (ESI) m/z=764.4 [M+H]$^+$

1H NMR (600 MHz, CHLOROFORM-d) δ ppm 0.84 (t, J=7.34 Hz, 3H) 0.92 (d, J=7.34 Hz, 3H) 1.08-1.11 (m, 6H) 1.12 (s, 3H) 1.19 (d, J=5.96 Hz, 3H) 1.22 (d, J=6.88 Hz, 3H) 1.23-1.24 (m, 1H) 1.24 (s, 3H) 1.29 (d, J=6.42 Hz, 3H) 1.38 (s, 3H) 1.38-1.40 (m, 1H) 1.44-1.52 (m, 1H) 1.54-1.73 (m, 3H) 1.86 (q, J=7.34 Hz, 1H) 1.90-1.99 (m, 2H) 2.11-2.21 (m, 1H) 2.18 (d, J=10.09 Hz, 1H) 2.32-2.39 (m, 7H) 2.51-2.59 (m, 1H) 2.81-2.89 (m, 1H) 2.91-2.98 (m, 1H) 2.97-3.04 (m, 2H) 3.27-3.30 (m, 1H) 3.31 (s, 3H) 3.36 (s, 3H) 3.42-3.49 (m, 1H) 3.52 (s, 3H) 3.55 (s, 1H) 3.76 (d, J=9.17 Hz, 1H) 3.81 (d, J=6.88 Hz, 1H) 3.93-4.06 (m, 1H) 4.31 (s, 1H) 4.44 (d, J=7.34 Hz, 1H) 4.95 (d, J=4.13 Hz, 1H) 5.18 (dd, J=11.00, 2.29 Hz, 1H) 5.63 (d, J=10.09 Hz, 1H)

EXAMPLE 142

9-deoxo-9-(S)-amino-6,2'-di-O-methylerythromycin A (compound T) and 9-deoxo-9-(R)-amino-6,2'-di-O-methylerythromycin A (compound U)

(1) 0.50 g of the compound obtained in Example 31 was dissolved in 7 ml of ethanol, 0.32 ml of hydrazine monohydrate was added, and the mixture was stirred under reflux for 60 hours. The reaction solution was poured into water, and extracted with chloroform. The organic layer was washed with saturated brine, dried over anhydrous magnesium sulfate, and then concentrated to give 0.38 g of a hydrazone compound.

(2) 0.38 g of the compound obtained in the above (1) was dissolved in 6 ml of methanol-water (2:1), and 200 μl of 3N hydrochloric acid was added in a salt-ice bath. 2 ml of an aqueous solution of 0.17 g of sodium nitrite was slowly added. Another 500 μl of 3N hydrochloric acid was added to be adjusted to pH4, and the mixture was stirred for 15 minutes. 0.38 g of potassium carbonate, 1 ml of methanol and 19 mg of sodium borohydride were added in this order, and the mixture was still stirred for another 30 minutes. The reaction solution was adjusted to pH2 by 3N hydrochloric acid, and the solution was stirred for another 30 minutes. The reaction solution was poured into saturated aqueous sodium bicarbonate solution, and extracted with chloroform. The organic layer was washed with saturated brine, dried over anhydrous magnesium sulfate, and concentrated. The resulting residue was purified by silica gel column chromatography (chloroform:methanol:ammonia water solution=30:1:0.1 to 10:1:0.1) to give 38 mg of a compound T and 62 mg of a compound U.

9-deoxo-9-(S))-amino-6,2'-di-O-methylerythromycin A (compound T)

MS (ESI) m/z=763.4 [M+H]$^+$

1H NMR (600 MHz, CHLOROFORM-d) δ ppm 0.81 (t, J=7.34 Hz, 3H) 1.00 (d, J=6.88 Hz, 3H) 1.06-1.10 (m, 7H) 1.12 (d, J=7.34 Hz, 3H) 1.17-1.20 (m, 6H) 1.22 (s, 3H) 1.23-1.26 (m, 1H) 1.30 (d, J=5.96 Hz, 3H) 1.44 (s, 3H) 1.45-1.49 (m, 1H) 1.55 (dd, J=15.13, 4.59 Hz, 1H) 1.64-1.70 (m, 1H) 1.76 (dd, J=14.67, 4.59 Hz, 1H) 1.79-1.85 (m, 1H) 1.87-2.05 (m, 3H) 2.34 (s, 6H) 2.34-2.39 (m, 3H) 2.51-2.61 (m, 2H) 2.81-2.92 (m, 2H) 2.98 (d, J=9.17 Hz, 1H) 3.29 (s, 3H) 3.31 (s, 3H) 3.39-3.45 (m, 1H) 3.51 (s, 3H) 3.67 (s, 1H) 3.70 (d, J=8.71 Hz, 1H) 3.82 (d, J=9.63 Hz, 1H) 3.95-4.03 (m, 1H) 4.35 (d, J=7.34 Hz, 1H) 4.91 (d, J=4.58 Hz, 1H) 5.08 (dd, J=11.23, 2.52 Hz, 1H)

9-deoxo-9-(R)-amino-6,2'-di-O-methylerythromycin A (compound U)

MS (ESI) m/z=763.5 [M+H]$^+$

1H NMR (600 MHz, CHLOROFORM-d) δ ppm 0.85 (t, J=7.34 Hz, 3H) 0.93 (d, J=6.42 Hz, 3H) 1.04 (d, J=6.88 Hz, 3H) 1.09-1.13 (m, 6H) 1.14-1.17 (m, 1H) 1.19 (d, J=6.42 Hz, 3H) 1.20 (d, J=6.88 Hz, 3H) 1.23 (s, 3H) 1.24-1.25 (m, 1H) 1.30 (d, J=5.96 Hz, 3H) 1.41 (s, 3H) 1.47-1.58 (m, 3H) 1.62-1.70 (m, 2H) 1.83-2.04 (m, 3H) 2.34 (s, 6H) 2.34-2.38 (m, 2H) 2.53-2.60 (m, 1H) 2.82-2.87 (m, 1H) 2.89-2.95 (m, 1H) 2.98 (d, J=9.17 Hz, 1H) 3.29 (s, 6H) 3.37-3.45 (m, 1H) 3.49 (d, J=1.38 Hz, 1H) 3.51 (s, 3H) 3.69 (d, J=8.25 Hz, 1H) 3.83 (d, J=9.63 Hz, 1H) 3.96-4.04 (m, 1H) 4.35 (d, J=7.34 Hz, 1H) 4.75 (dd, J=10.55, 1.83 Hz, 1H) 4.92 (d, J=4.58 Hz, 1H)

EXAMPLE 143

9-deoxo-9-(S)-dimethylamino-6,2'-di-β-methylerythromycin A

Using 26 mg of the compound T obtained in Example 142, a reaction was carried out in a similar manner described in Example 9 to give 21 mg of the titled compound.

MS (ESI) m/z=791.5 [M+H]$^+$

1H NMR (600 MHz, CHLOROFORM-d) δ ppm 0.84 (t, J=7.34 Hz, 3H) 1.01 (d, J=6.88 Hz, 3H) 1.03 (d, J=6.88 Hz, 3H) 1.05 (s, 3H) 1.06-1.11 (m, 1H) 1.12 (d, J=7.34 Hz, 3H) 1.15-1.26 (m, 10H) 1.29 (d, J=6.42 Hz, 3H) 1.38 (s, 3H) 1.44-1.58 (m, 2H) 1.64-1.75 (m, 1H) 1.84-2.04 (m, 4H) 2.24 (d, J=10.09 Hz, 1H) 2.29-2.40 (m, 15H) 2.56-2.63 (m, 1H) 2.82-2.88 (m, 2H) 2.98 (t, J=9.86 Hz, 1H) 3.28 (s, 3H) 3.31 (s, 3H) 3.39-3.45 (m, 1H) 3.52 (s, 3H) 3.53-3.57 (m, 1H) 3.66 (d, J=8.71 Hz, 1H) 3.94-4.03 (m, 2H) 4.37 (d, J=7.34 Hz, 1H) 4.87 (d, J=4.13 Hz, 1H) 4.96 (dd, J=11.00, 2.29 Hz, 1H)

EXAMPLE 144

9-deoxo-9-(S)-acetamide-6,2'-di-O-methylerythromycin A

Using 25 mg of the compound T obtained in Example 142 and using acetic anhydride instead of methanesulfonyl chloride, a reaction was carried out in a similar manner described in Example 117 to give 21 mg of the titled compound.

MS (ESI) m/z=805.5 [M+H]$^+$

1H NMR (600 MHz, CHLOROFORM-d) δ ppm 0.87 (t, J=7.34 Hz, 3H) 0.97 (d, J=6.42 Hz, 3H) 1.04 (d, J=6.88 Hz, 3H) 1.08 (s, 3H) 1.15 (d, J=7.34 Hz, 3H) 1.19 (d, J=5.96 Hz, 3H) 1.20 (d, J=6.88 Hz, 3H) 1.23 (s, 3H) 1.24-1.26 (m, 1H) 1.30 (d, J=5.96 Hz, 3H) 1.43 (s, 3H) 1.49-1.58 (m, 2H) 1.65-1.71 (m, 1H) 1.72-1.77 (m, 1H) 1.79-1.96 (m, 4H) 1.98 (s, 3H) 2.06-2.13 (m, 1H) 2.22-2.28 (m, 1H) 2.34 (s, 6H) 2.35-2.39 (m, 1H) 2.52 (br. s., 1H) 2.56-2.63 (m, 1H) 2.82-3.01 (m, 3H) 3.28 (s, 3H) 3.33 (s, 3H) 3.36-3.46 (m, 2H) 3.49 (s, 3H) 3.64-3.73 (m, 3H) 3.91 (d, J=9.63 Hz, 1H) 3.95-4.00

EXAMPLE 145

9-deoxo-9-(S)-methanesulfonylamide-6,2'-di-O-methylerythromycin A

Using 25 mg of the compound T obtained in Example 142, a reaction was carried out in a similar manner described in Example 117 to give 3 mg of the titled compound.

MS (ESI) m/z=841.4 [M+H]$^+$
1H NMR (600 MHz, CHLOROFORM-d) δ ppm 0.85 (t, J=7.34 Hz, 3H) 1.01 (d, J=6.88 Hz, 3H) 1.09 (d, J=7.34 Hz, 3H) 1.12 (s, 3H) 1.17-1.26 (m, 13H) 1.29 (d, J=5.96 Hz, 3H) 1.35-1.40 (m, 1H) 1.41 (s, 3H) 1.47-1.72 (m, 4H) 1.85-1.98 (m, 2H) 2.00-2.08 (m, 1H) 2.17-2.23 (m, 1H) 2.34-2.36 (m, 6H) 2.36-2.38 (m, 1H) 2.52-2.60 (m, 1H) 2.62 (s, 1H) 2.81-2.89 (m, 1H) 2.89-3.13 (m, 3H) 2.97 (s, 3H) 3.30 (s, 3H) 3.39 (s, 3H) 3.40-3.45 (m, 2H) 3.51 (s, 3H) 3.68 (s, 1H) 3.77 (d, J=7.79 Hz, 1H) 3.80 (d, J=10.09 Hz, 1H) 3.96-4.02 (m, 1H) 4.40 (d, J=7.34 Hz, 1H) 4.85-4.99 (m, 2H) 6.90 (d, J=9.17 Hz, 1H)

EXAMPLE 146

4"-O-acetyl-9-deoxo-9-(S)-hydroxy-6,2'-di-O-methylerythromycin A

Using 0.43 g of the compound obtained in Example 141, a reaction was carried out in a similar manner described in Example 87 to give 0.25 g of the titled compound.

MS (ESI) m/z=806.5 [M+H]$^+$
1H NMR (600 MHz, CHLOROFORM-d) δ ppm 0.83 (t, J=7.34 Hz, 3H) 0.91 (d, J=7.34 Hz, 3H) 1.07-1.17 (m, 18H) 1.22 (d, J=6.42 Hz, 3H) 1.23-1.27 (m, 1H) 1.35 (s, 3H) 1.36-1.41 (m, 1H) 1.42-1.53 (m, 1H) 1.55-1.69 (m, 3H) 1.81-1.88 (m, 1H) 1.90-2.01 (m, 2H) 2.08 (s, 3H) 2.11-2.16 (m, 1H) 2.37 (s, 6H) 2.40 (d, J=15.13 Hz, 1H) 2.63-2.69 (m, 1H) 2.80-2.88 (m, 1H) 2.93-2.99 (m, 1H) 3.02 (s, 1H) 3.25-3.32 (m, 1H) 3.29 (s, 3H) 3.34 (s, 3H) 3.51 (s, 3H) 3.54 (s, 1H) 3.67-3.72 (m, 1H) 3.75 (d, J=10.55 Hz, 1H) 3.79 (d, J=6.42 Hz, 1H) 4.30-4.39 (m, 2H) 4.55 (d, J=7.34 Hz, 1H) 4.64 (d, J=9.63 Hz, 1H) 5.02 (d, J=5.04 Hz, 1H) 5.19 (dd, J=11.46, 2.29 Hz, 1H) 5.70 (d, J=10.09 Hz, 1H)

EXAMPLE 147

4"-O-acetyl-9-deoxo-9-(S)-(3-dimethylaminopropionyloxy)-6,2'-di-O-methylerythromycin A (compound V) and 4"-O-acetyl-9-deoxo-9-(S)-(3-dimethylaminopropionyloxy)-11-O-(3-dimethylaminopropionyl)-6,2'-di-O-methylerythromycin A (compound W)

0.43 g of the compound obtained in Example 146 was dissolved in a mixed solvent of 16 ml of toluene and 16 ml of chloroform to which 0.51 ml of 3-chloropropionyl chloride and 0.75 ml of triethylamine were added, and the mixture was stirred at room temperature for 6 hours. The reaction solution was poured into a saturated aqueous sodium bicarbonate solution, and extracted with chloroform. The combined organic layer was dried over anhydrous magnesium sulfate, and then concentrated. The resulting residue was dissolved in 10 ml of acetonitrile to which 2.4 ml of diisopropylethylamine and 2.2 ml of a 50% aqueous dimethylamine solution were added, and the mixture was stirred in sealed tube in an oil bath at 90° C. for 16 hours. The reaction solution was poured into water, and extracted with chloroform. The combined organic layer was dried over anhydrous magnesium sulfate, and then concentrated. The resulting residue was purified by silica gel column chromatography (chloroform:methanol:ammonia water solution=30:1:0.1 to 10:1:0.1) to give 0.18 g of a compound V and 31 mg of a compound W.

4"-O-acetyl-9-deoxo-9-(S)-(3-dimethylaminopropionyloxy)-6,2'-di-O-methylerythromycin A (compound V)

MS (ESI) m/z=905.5 [M+H]$^+$
1H NMR (600 MHz, CHLOROFORM-d) δ ppm 0.85 (t, J=7.34 Hz, 3H) 0.99 (d, J=6.88 Hz, 3H) 1.04-1.16 (m, 13H) 1.18 (d, J=7.34 Hz, 3H) 1.21-1.25 (m, 6H) 1.26-1.32 (m, 1H) 1.34 (s, 3H) 1.41-1.50 (m, 1H) 1.58-1.67 (m, 2H) 1.77-1.85 (m, 1H) 1.89-1.97 (m, 2H) 2.09 (s, 3H) 2.11-2.21 (m, 2H) 2.22 (s, 6H) 2.36 (s, 6H) 2.41-2.51 (m, 3H) 2.64-2.81 (m, 2H) 2.95-3.01 (m, 1H) 3.27 (s, 3H) 3.30 (s, 3H) 3.52 (s, 3H) 3.59 (s, 1H) 3.67-3.74 (m, 3H) 3.75 (d, J=6.88 Hz, 1H) 3.79-3.82 (m, 1H) 4.32-4.41 (m, 1H) 4.56 (d, J=7.34 Hz, 1H) 4.65 (d, J=10.09 Hz, 1H) 4.76-4.81 (m, 1H) 4.99 (dd, J=10.09, 3.21 Hz, 1H) 5.07 (d, J=4.59 Hz, 1H)

4"-O-acetyl-9-deoxo-9-(S)-(3-dimethylaminopropionyloxy)-11-O-(3-dimethylaminopropionyl)-6,2'-di-O-methylerythromycin A (compound W)

MS (ESI) m/z=1004.7 [M+H]$^+$
1H NMR (600 MHz, CHLOROFORM-d) δ ppm 0.82 (t, J=7.57 Hz, 3H) 0.94 (d, J=6.42 Hz, 3H) 1.03-1.21 (m, 22H) 1.21-1.33 (m, 1H) 1.35 (s, 3H) 1.49-1.66 (m, 3H) 1.74-1.88 (m, 2H) 1.96-2.02 (m, 1H) 2.08 (s, 3H) 2.19 (d, J=7.79 Hz, 6H) 2.24-2.26 (m, 6H) 2.29-2.43 (m, 4H) 2.35 (s, 6H) 2.44-2.68 (m, 4H) 2.72-2.79 (m, 1H) 2.88-3.04 (m, 5H) 3.24 (s, 3H) 3.27-3.31 (m, 3H) 3.52 (s, 3H) 3.60-3.69 (m, 1H) 3.71 (d, J=7.79 Hz, 1H) 4.02 (d, J=6.42 Hz, 1H) 4.29-4.40 (m, 1H) 4.50 (d, J=7.34 Hz, 1H) 4.60-4.70 (m, 3H) 5.00 (d, J=5.04 Hz, 1H) 5.22 (s, 1H)

EXAMPLE 148

4"-O-acetyl-11-amino-11-deoxy-6,2'-di-O-methylerythromycin A 11,12-cyclic carbamate (1) To 7 ml of chloroform were added 0.75 g of the compound obtained in Example 87 and 0.76 ml of pyridine, subsequently was added 0.83 g of triphosgene by portions at room temperature in a nitrogen atmosphere, and then the mixture was stirred for 4 hours. The reaction solution was poured into a saturated aqueous sodium bicarbonate solution, and extracted with chloroform. The organic layer was dried over anhydrous magnesium sulfate, and concentrated. The resulting residue was purified by silica gel column chromatography (hexane:acetone:triethylamine=60:10:0.2 to 10:10:0.2) to give 0.43 g of a carbonate compound.

(2) To 7 ml of N,N-dimethylformamide were added 0.43 g of the compound obtained in the above (1) and 0.13 ml of 1,1,3,3-tetramethylguanidine, and the mixture was stirred in an oil bath at 100° C. for 8 hours. The reaction solution was poured into a 10% aqueous sodium hydroxide solution under ice cooling, and extracted with ethyl acetate. The combined organic layer was washed with saturated brine, dried over anhydrous magnesium sulfate, and concentrated. The resulting residue was purified by silica gel column chromatography (chloroform:methanol:ammonia water solution=30:1:0.1) to give 0.45 g of a deoxy compound.

(3) To 15 ml of N,N-dimethylformamide and 24 ml of tetrahydrofuran were added 0.45 g of the compound obtained in the above (2) and 0.28 g of 1,1'-carbonyldiimidazole, to which 36 mg of 60% sodium hydride was added, and the mixture was still stirred at room temperature for 20 hours. The reaction solution was poured into a saturated aqueous ammonium chloride solution, and extracted with ethyl acetate. The combined organic layer was dried over anhydrous magnesium sulfate, and then concentrated. The resulting residue was purified by silica gel column chromatography (chloroform:methanol:ammonia water solution=20:1:0.1) to give 0.40 g of a imidazoxy compound.

(4) To 18 ml of acetonitrile was added 0.21 g of the compound obtained in the above (3) and 12 ml of ammonia water solution, and the mixture was stirred for 48 hours. After concentrating the reaction solution, the residue was poured into a saturated aqueous ammonium chloride solution, and extracted with ethyl acetate. The combined organic layer was dried over anhydrous magnesium sulfate, and then concentrated. The resulting residue was added to 3 ml of N,N-dimethylformamide and 4 ml of tetrahydrofuran, to which 11 mg of 60% sodium hydride was added under ice cooling, and the mixture was still stirred for 1 hour. The reaction solution was poured into a saturated aqueous ammonium chloride solution, and extracted with ethyl acetate. The combined organic layer was dried over anhydrous magnesium sulfate, and concentrated. The resulting residue was purified by silica gel column chromatography (chloroform:methanol:ammonia water solution=10:1:0.1) to give 77 mg of the titled compound.

MS (ESI) m/z=829.5 [M+H]$^+$

1H NMR (600 MHz, CHLOROFORM-d) δ ppm 0.85 (t, J=7.34 Hz, 3H) 1.07 (d, J=7.34 Hz, 3H) 1.09-1.17 (m, 15H) 1.21 (d, J=7.34 Hz, 3H) 1.23-1.27 (m, 1H) 1.35 (s, 3H) 1.42 (s, 3H) 1.47-1.94 (m, 7H) 2.09 (s, 3H) 2.37 (s, 6H) 2.37-2.41 (m, 1H) 2.51-2.59 (m, 1H) 2.62-2.69 (m, 1H) 2.77-2.90 (m, 3H) 2.93 (s, 3H) 3.29 (s, 3H) 3.54 (s, 3H) 3.60 (d, J=7.34 Hz, 1H) 3.63-3.68 (m, 1H) 3.69 (s, 1H) 3.82 (d, J=7.34 Hz, 1H) 4.26-4.34 (m, 1H) 4.50 (d, J=7.34 Hz, 1H) 4.65 (d, J=9.63 Hz, 1H) 4.94 (d, J=5.04 Hz, 1H) 5.09 (dd, J=10.55, 2.75 Hz, 1H) 5.78 (s, 1H)

EXAMPLE 149

4''-O-acetyl-11-(4-(4-(pyridin-3-yl)-1H-imidazol-1-yl)butylamino)-11-deoxy-6,2'-di-O-methylerythromycin A 11,12-cyclic carbamate To 1 ml of tetrahydrofuran were added 0.21 g of the compound obtained in Example 148 (3) and 0.27 g of 4-(4-(pyridin-3-yl)-1H-imidazol-1-yl)butylamine described in a literature (Bioorganic Medicinal Chemistry Letters, 1999, Vol. 21, No. 9, p. 3075-3080), and the mixture was stirred for 24 hours. The reaction solution was poured into a saturated aqueous ammonium chloride solution, and extracted with ethyl acetate. The combined organic layer was dried over anhydrous magnesium sulfate, and concentrated. The resulting residue was added to 3 ml of N,N-dimethylformamide and 4 ml of tetrahydrofuran to which 11 mg of 60% sodium hydride was added under ice cooling, and the mixture was stirred for 1 hour. The reaction solution was poured into a saturated aqueous ammonium chloride solution, and extracted with ethyl acetate. The combined organic layer was dried over anhydrous magnesium sulfate, and concentrated. The resulting residue was purified by silica gel column chromatography (chloroform:methanol:ammonia water solution=10:1:0.1) to give 80 mg of the titled compound.

MS (ESI) m/z=1028.6 [M+H]$^+$

1H NMR (600 MHz, CHLOROFORM-d) δ ppm 0.80 (t, J=7.34 Hz, 3H) 1.01 (d, J=6.88 Hz, 3H) 1.06-1.17 (m, 12H) 1.23 (d, J=7.34 Hz, 3H) 1.24-1.27 (m, 1H) 1.35 (s, 3H) 1.42 (s, 3H) 1.49-1.56 (m, 1H) 1.57-1.76 (m, 6H) 1.85-1.94 (m, 4H) 2.09 (s, 3H) 2.37 (s, 6H) 2.37-2.41 (m, 1H) 2.54-2.70 (m, 2H) 2.82-2.88 (m, 1H) 2.89-2.96 (m, 1H) 2.98 (s, 3H) 3.07-3.12 (m, 1H) 3.29 (s, 3H) 3.54 (s, 3H) 3.60-3.70 (m, 4H) 3.73 (d, J=9.17 Hz, 1H) 3.76-3.82 (m, 1H) 4.03 (t, J=7.57 Hz, 2H) 4.26-4.33 (m, 1H) 4.51 (d, J=7.34 Hz, 1H) 4.64 (d, J=9.63 Hz, 1H) 4.91-4.96 (m, 2H) 7.25-7.29 (m, 4H) 7.34 (d, J=1.38 Hz, 1H) 7.55 (d, J=1.38 Hz, 1H) 8.07 (td, J=7.91, 2.06, 1.95 Hz, 1H) 8.44 (dd, J=4.59, 1.38 Hz, 1H) 8.94 (d, J=1.83 Hz, 1H)

EXAMPLE 150

11-amino-11-deoxy-6,2'-di-O-methylerythromycin A 11,12-cyclic carbamate

Using 77 mg of the compound obtained in Example 148, a reaction was carried out in a similar manner described in Example 89 to give 44 mg of the titled compound.

MS (ESI) m/z=787.3 [M+H]$^+$

1H NMR (600 MHz, CHLOROFORM-d) δ ppm 0.86 (t, J=7.57 Hz, 3H) 1.04 (d, J=7.34 Hz, 3H) 1.12 (d, J=7.34 Hz, 3H) 1.14 (d, J=6.88 Hz, 3H) 1.18 (d, J=5.96 Hz, 3H) 1.20 (d, J=7.34 Hz, 3H) 1.21-1.22 (m, 1H) 1.23 (s, 3H) 1.28 (d, J=6.42 Hz, 3H) 1.37 (s, 3H) 1.42 (s, 3H) 1.48-1.60 (m, 2H) 1.62-1.70 (m, 2H) 1.72-1.93 (m, 3H) 2.15 (d, J=10.09 Hz, 1H) 2.31-2.34 (m, 1H) 2.34 (s, 6H) 2.51-2.60 (m, 2H) 2.73-2.81 (m, 1H) 2.82-2.89 (m, 2H) 2.93 (s, 3H) 3.00 (t, J=9.86 Hz, 1H) 3.30 (s, 3H) 3.38-3.45 (m, 1H) 3.53 (s, 3H) 3.61 (d, J=7.79 Hz, 1H) 3.68 (s, 1H) 3.81 (d, J=7.34 Hz, 1H) 3.91-3.98 (m, 1H) 4.38 (d, J=7.34 Hz, 1H) 4.89 (d, J=4.59 Hz, 1H) 5.08 (dd, J=10.55, 2.29 Hz, 1H) 5.77 (s, 1H)

EXAMPLE 151

11-(4-(4-(pyridin-3-yl)-1H-imidazol-1-yl)butylamino)-11-deoxy-6,2'-di-O-methylerythromycin A 11,12-cyclic carbamate Using 85 mg of the compound obtained in Example 149, a reaction was carried out in a similar manner described in Example 89 to give 57 mg of the titled compound.

MS (ESI) m/z=986.7 [M+H]$^+$

1H NMR (600 MHz, CHLOROFORM-d) δ ppm 0.80 (t, J=7.57 Hz, 3H) 1.00 (d, J=6.88 Hz, 3H) 1.06 (d, J=7.34 Hz, 3H) 1.14 (d, J=6.88 Hz, 3H) 1.19 (d, J=5.96 Hz, 3H) 1.21 (d, J=7.34 Hz, 3H) 1.23-1.25 (m, 1H) 1.24 (s, 3H) 1.27 (d, J=5.96 Hz, 3H) 1.37 (s, 3H) 1.42 (s, 3H) 1.47-1.59 (m, 2H) 1.63-1.76 (m, 4H) 1.81-1.96 (m, 5H) 2.17 (d, J=9.63 Hz, 1H) 2.34 (d, J=15.59 Hz, 1H) 2.36 (s, 6H) 2.52-2.66 (m, 2H) 2.83-2.92 (m, 2H) 2.98 (s, 3H) 2.98-3.01 (m, 1H) 3.06-3.12 (m, 1H) 3.30 (s, 3H) 3.39-3.47 (m, 1H) 3.54 (s, 3H) 3.62 (s, 1H) 3.63 (d, J=7.34 Hz, 1H) 3.64-3.69 (m, 1H) 3.72 (d, J=9.17 Hz, 1H) 3.74-3.80 (m, 1H) 3.92-3.97 (m, 1H) 3.99-4.05 (m, 2H) 4.39 (d, J=7.34 Hz, 1H) 4.87 (d, J=4.58 Hz, 1H) 4.92 (dd, J=11.00, 2.29 Hz, 1H) 7.25-7.28 (m, 1H) 7.34 (d, J=1.38 Hz, 1H) 7.55 (d, J=0.92 Hz, 1H) 8.06 (td, J=7.91, 2.06, 1.95 Hz, 1H) 8.43 (d, J=4.13 Hz, 1H) 8.94 (s, 1H)

EXAMPLE 152

9-deoxo-9a-aza-6,2'-di-O-methyl-9a-homoerythromycin A (1) 2.45 g of the compound E obtained in Example 88 was dissolved in a mixed solvent of 24 ml of pyridine and 8 ml of diethylether in which 1.50 g of p-toluenesulfonyl chloride was added under ice cooling, and the mixture was stirred for 4 hours. 20 ml of 10% aqueous sodium hydroxide solution was added, and the mixture was stirred for another 1 hour. The mixture was extracted with ethyl acetate and the combined organic layer was washed with saturated brine, dried over anhydrous magnesium sulfate, and concentrated. The resulting residue was purified by silica gel column chromatography (chloroform:methanol:ammonia water solution=50:1:0.1) to give 1.90 g of a yellowish red solid.

(2) To 25 ml of acetic acid were added 1.90 g of the compound obtained in the above (1) and 0.21 g of platinum oxide (IV), and the mixture was stirred at room temperature in a hydrogen atmosphere at 2.5 atm for 18 hours. The reaction solution was filtered, and then concentrated. The resulting residue was purified by silica gel column chromatography (chloroform:methanol:ammonia water solution=50:1:0.1 to 10:1:0.1) to give 0.71 g of the titled compound.

MS (ESI) m/z=763.4 [M+H]$^+$

1H NMR (600 MHz, CHLOROFORM-d) δ ppm 0.88 (t, J=7.57 Hz, 3H) 0.95 (d, J=6.88 Hz, 3H) 1.02-1.06 (m, 6H) 1.07 (s, 3H) 1.19 (d, J=6.42 Hz, 3H) 1.21-1.25 (m, 7H) 1.29 (d, J=6.42 Hz, 3H) 1.32 (s, 3H) 1.34-1.44 (m, 1H) 1.46-1.54 (m, 1H) 1.57 (dd, J=14.90, 4.81 Hz, 1H) 1.64-1.72 (m, 2H) 1.86-1.94 (m, 2H) 2.09-2.15 (m, 1H) 2.16 (d, J=10.09 Hz, 1H) 2.32 (d, J=14.21 Hz, 1H) 2.35 (s, 6H) 2.51-2.63 (m, 2H) 2.63-2.70 (m, 1H) 2.80-2.89 (m, 2H) 3.01 (m, 1H) 3.30 (s, 3H) 3.31 (s, 3H) 3.35-3.37 (m, 1H) 3.43-3.49 (m, 1H) 3.53 (s, 3H) 3.67-3.74 (m, 1H) 3.79 (d, J=6.88 Hz, 1H) 3.99-4.06 (m, 1H) 4.10 (d, J=8.71 Hz, 1H) 4.42 (d, J=7.34 Hz, 1H) 4.85 (dd, J=10.55, 1.83 Hz, 1H) 4.93 (d, J=4.13 Hz, 1H)

EXAMPLE 153

9-deoxo-9a-aza-9a-methyl-6,2'-di-O-methyl-9a-homoerythromycin A 70 mg of the compound obtained in Example 152 was added to 2 ml of chloroform, 68 μl of 37% aqueous formaldehyde solution and 36 μl of formic acid were added, and the mixture was stirred in an oil bath at 80° C. in a sealed tube for 2 hours. The reaction solution was poured into an aqueous sodium bicarbonate solution, and extracted with chloroform. The combined organic layer was dried over anhydrous magnesium sulfate, and then filtered. The resulting residue was purified by silica gel column chromatography (chloroform:methanol:ammonia water solution=30:1:0.1) to give 30 mg of the titled compound.

MS (ESI) m/z=777.6 [M+H]$^+$

1H NMR (600 MHz, CHLOROFORM-d) δ ppm 0.90 (t, J=7.34 Hz, 3H) 0.94 (d, J=6.88 Hz, 3H) 1.01-1.08 (m, 4H) 1.06 (d, J=7.34 Hz, 3H) 1.13 (s, 3H) 1.19 (d, J=5.96 Hz, 3H) 1.21-1.26 (m, 7H) 1.29 (d, J=6.42 Hz, 3H) 1.33 (s, 3H) 1.45-2.07 (m, 7H) 2.10-2.15 (m, 1H) 2.18 (d, J=10.09 Hz, 1H) 2.28-2.33 (m, 1H) 2.31 (s, 3H) 2.35 (s, 6H) 2.45-2.60 (m, 2H) 2.69-2.78 (m, 1H) 2.78-2.85 (m, 1H) 2.87-2.92 (m, 1H) 3.00 (t, J=9.63 Hz, 1H) 3.26 (s, 3H) 3.31 (s, 3H) 3.43-3.51 (m, 1H) 3.54 (s, 3H) 3.58 (s, 1H) 3.73 (d, J=6.88 Hz, 1H) 3.98-4.07 (m, 2H) 4.42 (d, J=7.34 Hz, 1H) 4.89 (dd, J=9.63, 2.29 Hz, 1H) 4.93 (d, J=4.58 Hz, 1H)

EXAMPLE 154

9-deoxo-9a-aza-9a-acetyl-6,2'-di-O-methyl-9a-homoerythromycin A

Using 100 mg of the compound obtained in Example 152 and using acetic anhydride instead of methanesulfonyl chloride, a reaction was carried out in a similar manner described in Example 117 to give 86 mg of the titled compound.

MS (ESI) m/z=805.5 [M+H]$^+$

1H NMR (600 MHz, CHLOROFORM-d) δ ppm 0.88 (t, J=7.57 Hz, 3H) 0.98-1.01 (m, 6H) 1.17-1.25 (m, 14H) 1.28 (d, J=6.42 Hz, 3H) 1.39 (s, 3H) 1.45 (s, 3H) 1.47-1.53 (m, 1H) 1.54-1.70 (m, 4H) 1.81-1.88 (m, 1H) 1.91 (s, 1H) 2.01 (s, 3H) 2.12-2.16 (m, 1H) 2.18 (d, J=10.09 Hz, 1H) 2.31 (d, J=15.59 Hz, 1H) 2.35 (s, 6H) 2.50-2.57 (m, 1H) 2.76-2.94 (m, 3H) 3.02 (t, J=9.40 Hz, 1H) 3.14-3.19 (m, 1H) 3.29 (s, 3H) 3.31 (s, 3H) 3.49 (s, 3H) 3.50-3.51 (m, 2H) 3.70 (d, J=6.42 Hz, 1H) 3.92-4.01 (m, 2H) 4.31 (d, T=6.42 Hz, 1H) 4.46 (d, J=7.34 Hz, 1H) 4.84-4.89 (m, 1H) 4.91 (d, J=4.13 Hz, 1H) 5.05 (d, J=9.63 Hz, 1H)

EXAMPLE 155

3-deoxy-3-oxo-5-O-(2'-O-methyldesosaminyl)-6-O-methylerythronolide A

After adding 40 mg of N-chlorosuccinimide to 2 ml of dichloromethane, 43 μl of dimethylsulfide was added in a dry ice-ethanol bath and then the temperature was raised up to −30° C. and the mixture was stirred for 30 minutes. Thereafter, a solution of 0.12 g of the compound obtained in Example 84 in dichloromethane was added, and the mixture was stirred for 1 hour. Another portion of 53 μl of diisopropylethylamine was added, and the mixture was still stirred for 30 minutes. After raised up to room temperature, the reaction solution was poured into a saturated aqueous sodium bicarbonate solution, and extracted with chloroform. The combined organic layer was washed with a saturated aqueous sodium thiosulfate solution and saturated brine in this order, dried over anhydrous magnesium sulfate, and concentrated. The resulting residue was purified by silica gel column chromatography (chloroform:methanol:ammonia water solution-30:1:0.1) to give 56 mg of the titled compound.

MS (ESI) m/z=602.4 [M+H]$^+$

1H NMR (600 MHz, CHLOROFORM-d) δ ppm 0.85 (t, J=7.34 Hz, 3H) 1.09-1.17 (m, 6H) 1.19-1.23 (m, 7H) 1.27-1.34 (m, 9H) 1.47-1.55 (m, 1H) 1.56-1.63 (m, 1H) 1.65-1.79 (m, 2H) 1.90-2.00 (m, 1H) 2.34 (s, 6H) 2.56-2.64 (m, 2H) 2.70 (s, 3H) 2.86-2.92 (m, 1H) 2.99-3.04 (m, 1H) 3.06-3.13 (m, 1H) 3.25 (s, 1H) 3.49-3.56 (m, 1H) 3.53 (s, 3H) 3.83 (q, J=6.88 Hz, 1H) 3.87 (s, 1H) 3.92 (d, J=1.38 Hz, 1H) 4.28 (d, J=7.34 Hz, 1H) 4.36 (d, J=5.96 Hz, 1H) 5.12 (dd, J=11.00, 2.29 Hz, 1H)

EXAMPLE 156

3-O-(4-pyridyl)acetyl-5-O-(2'-O-methyldesosaminyl)-6-O-methylerythronolide A

Using 77 mg of the compound obtained in Example 84 and using 4-pyridylacetate hydrochloride instead of 2-pyridylacetate hydrochloride, and dichloromethane instead of chloroform, a reaction was carried out in a similar manner described in Example 15 (1) to give 69 mg of the titled compound.

MS (ESI) m/z=723.6 [M+H]$^+$

1H NMR (600 MHz, CHLOROFORM-d) δ ppm 0.79 (t, J=7.34 Hz, 3H) 0.88 (d, J=6.88 Hz, 3H) 1.07 (d, J=5.96 Hz, 3H) 1.09-1.14 (m, 12H) 1.14-1.24 (m, 1H) 1.26 (s, 3H) 1.40-1.51 (m, 2H) 1.53-1.58 (m, 1H) 1.74-1.81 (m, 1H) 1.87-1.96 (m, 1H) 2.14-2.22 (m, 1H) 2.32 (s, 6H) 2.40-2.47 (m, 1H) 2.52-2.59 (m, 1H) 2.77-2.86 (m, 2H) 2.91-3.01 (m, 2H) 3.02 (s, 3H) 3.22 (s, 1H) 3.55 (s, 3H) 3.68 (m, 2H) 3.76 (d, J=3.67 Hz, 1H) 3.80 (s, 1H) 3.88 (d, J=6.88 Hz, 1H) 3.93 (s, 1H) 5.06

(d, J=11.00 Hz, 1H) 5.14 (d, J=13.30 Hz, 1H) 7.27 (d, J=5.04 Hz, 2H) 8.55 (d, J=4.58 Hz, 2H)

EXAMPLE 157

3-O-(3-benzyloxycarbamoylpropionyl)-5-O-(2'-O-methyldesosaminyl)-6-O-methylerythronolide A Using 77 mg of the compound obtained in Example 84 and using benzyloxycarbonyl-β-alanine instead of 2-pyridylacetate hydrochloride, and dichloromethane instead of chloroform, a reaction was carried out in a similar manner described in Example 15 (1) to give 69 mg of the titled compound.

MS (ESI) m/z=809.5 [M+H]$^+$

1H NMR (600 MHz, CHLOROFORM-d) δ ppm 0.82 (t, J=7.34 Hz, 3H) 1.02 (d, J=6.88 Hz, 3H) 1.08-1.13 (m, 12H) 1.15 (s, 3H) 1.17-1.24 (m, 1H) 1.27 (s, 3H) 1.43-1.53 (m, 2H) 1.59-1.64 (m, 1H) 1.76-1.83 (m, 1H) 1.89-1.97 (m, 1H) 2.14-2.21 (m, 1H) 2.32 (s, 6H) 2.41-2.70 (m, 4H) 2.79-2.86 (m, 2H) 2.97-3.02 (m, 1H) 3.03 (s, 3H) 3.19-3.25 (m, 2H) 3.40-3.52 (m, 2H) 3.52 (s, 3H) 3.68-3.73 (m, 1H) 3.81 (d, J=1.83 Hz, 1H) 3.92 (d, J=7.34 Hz, 1H) 3.95 (s, 1H) 5.00-5.12 (m, 3H) 5.16 (dd, J=11.00, 2.29 Hz, 1H) 5.34-5.40 (m, 1H) 7.28-7.37 (m, H)

EXAMPLE 158

3-O-(3-aminopropionyl)-5-O-(2'-O-methyldesosaminyl)-6-O-methylerythronolide A

Using 0.11 g of the compound obtained in Example 157, a reaction was carried out in a similar manner described in Example 118 (5) to give 71 mg of the titled compound.

MS (ESI) m/z=675.6 [M+H]$^+$

1H NMR (600 MHz, CHLOROFORM-d) δ ppm 0.81 (t, J=7.34 Hz, 3H) 1.06 (d, J=6.88 Hz, 3H) 1.08-1.12 (m, 9H) 1.14 (s, 3H) 1.15 (d, J=6.42 Hz, 3H) 1.16-1.24 (m, 1H) 1.26 (s, 3H) 1.41-1.52 (m, 2H) 1.65 (br. s., 2H) 1.62-1.67 (m, 1H) 1.75-1.83 (m, 1H) 1.85-1.97 (m, 1H) 2.14-2.22 (m, 1H) 2.32 (s, 6H) 2.46-2.59 (m, 3H) 2.60-2.70 (m, 1H) 2.80-2.88 (m, 2H) 2.90-3.03 (m, 3H) 3.04 (s, 3H) 3.23-3.30 (m, 1H) 3.52 (s, 3H) 3.74 (d, J=3.67 Hz, 1H) 3.81 (d, J=1.83 Hz, 1H) 3.97 (d, J=7.34 Hz, 1H) 5.08 (d, J=10.55 Hz, 1H) 5.15 (dd, J=11.23, 2.06 Hz, 1H)

EXAMPLE 159

3-O-(3-dimethylaminopropionyl)-5-O-(2'-O-methyl)-6-O-methylerythronolide A

Using 34 mg of the compound obtained in Example 158, a reaction was carried out in a similar manner described in Example 9 to give 25 mg of the titled compound.

MS (ESI) m/z=703.6 [M+H]$^+$

1H NMR (600 MHz, CHLOROFORM-d) δ ppm 0.82 (t, J=7.57 Hz, 3H) 1.07 (d, J=6.88 Hz, 3H) 1.09-1.13 (m, 9H) 1.15 (s, 3H) 1.17 (d, J=5.96 Hz, 3H) 1.19-1.25 (m, 1H) 1.27 (s, 3H) 1.42-1.52 (m, 2H) 1.62-1.66 (m, 1H) 1.77-1.83 (m, 1H) 1.89-1.96 (m, 1H) 2.14-2.20 (m, 1H) 2.22 (s, 6H) 2.33 (s, 6H) 2.46-2.66 (m, 2H) 2.82-2.87 (m, 2H) 2.97-3.03 (m, 1H) 3.04 (s, 3H) 3.17-3.31 (m, 2H) 3.53 (s, 3H) 3.76 (d, J=3.67 Hz, 1H) 3.82 (d, J=1.83 Hz, 1H) 3.93 (br. s., 1H) 3.96 (d, J=7.34 Hz, 1H) 5.07 (d, J=11.00 Hz, 1H) 5.16 (dd, J=11.46, 2.29 Hz, 1H)

EXAMPLE 160

4"-O-(3-dimethylaminopropionyl)-6,2'-di-O-methylerythromycin A

Using 0.10 g of the compound obtained in Example 31, a reaction was carried out in a similar manner described in Example 147 to give 66 mg of the titled compound.

MS (ESI) m/z=861.5 [M+H]$^+$

1H NMR (600 MHz, CHLOROFORM-d) δ ppm 0.83 (t, J=7.34 Hz, 3H) 1.07 (d, J=7.34 Hz, 3H) 1.18 (m, 22H) 1.36 (s, 3H) 1.42-1.51 (m, 1H) 1.57-2.03 (m, 7H) 2.22 (s, 6H) 2.37 (s, 6H) 2.37-2.40 (m, 1H) 2.43-2.69 (m, 6H) 2.83-2.91 (m, 2H) 2.97-3.01 (m, 1H) 3.01-3.02 (m, 3H) 3.28 (s, 3H) 3.54 (s, 3H) 3.63 (d, J=6.88 Hz, 1H) 3.67-3.73 (m, 1H) 3.77 (d, J=1.38 Hz, 1H) 3.79 (d, J=9.17 Hz, 1H) 3.96 (br. s., 1H) 4.27-4.35 (m, 1H) 4.53 (d, J=7.79 Hz, 1H) 4.66 (d, J=9.63 Hz, 1H) 4.96 (d, J=5.04 Hz, 1H) 5.05 (dd, J=11.00, 2.29 Hz, 1H)

EXAMPLE 161

4"-O-acetyl-3'-demethyl-3'-benzyloxycarbonyl-6-O-methylerythromycin A

Using 2.00 g of the compound obtained in Example 41 (1), a reaction was carried out in a similar manner described in Example 77 to give 0.90 g of a demethyl compound.

Subsequently, using 0.38 g of the obtained compound and using benzyloxycarbonyl chloride instead of methanesulfonyl chloride, and chloroform instead of diethylether, a reaction was carried out in a similar manner described in Example 117 to give 0.27 g of the titled compound.

1H NMR (600 MHz, CHLOROFORM-d) δ ppm 0.83 (t, J=7.57 Hz, 3H) 0.99-1.18 (m, 18H) 1.21 (d, J=6.88 Hz, 3H) 1.36 (s, 3H) 1.41-1.53 (m, 2H) 1.57-2.04 (m, 5H) 2.10 (s, 3H) 2.24 (m, 1H) 2.40 (d, J=14.67 Hz, 1H) 2.54-2.62 (m, 1H) 2.85-2.92 (m, 2H) 2.87 (s, 3H) 2.95-3.09 (m, 2H) 3.03 (s, 3H) 3.17 (s, 1H) 3.36 (s, 3H) 3.37-3.40 (m, 1H) 3.63-3.70 (m, 1H) 3.74 (s, 1H) 3.77 (d, J=9.63 Hz, 1H) 3.82-3.94 (m, 2H) 3.96 (s, 1H) 4.26-4.44 (m, 2H) 4.65 (d, J=9.63 Hz, 1H) 4.68 (d, J=6.88 Hz, 1H) 4.99 (d, J=5.04 Hz, 1H) 5.07 (dd, J=11.00, 2.29 Hz, 1H) 5.10 (d, 1H) 5.20 (d, 1H) 7.27-7.37 (m, 5H)

Reference Example 1

4-[3-(methylamino)propyl]pyridine (1) 3.0 g of 4-pyridinepropanol was dissolved in 90 ml of chloroform, 9.4 g of carbon tetrabromide and 7.5 g of triphenylphosphine was added under ice cooling, and the mixture was stirred for 2 hours. Ether was added to the reaction solution, and the mixture was extracted with 1N hydrochloric acid, and then the aqueous layer was washed with ether. The aqueous layer was adjusted to be basic with 6N sodium hydroxide, and extracted with ether. The organic layer was dried over anhydrous magnesium sulfate, and filtered. The filtrate was evaporated under reduced pressure to give 4.86 g of 4-(3-bromopropyl)pyridine.

(2) 4.86 g of the compound obtained in the above (1) was suspended in 22 ml of isopropanol, 22 ml of an aqueous methylamine solution was added, and the mixture was stirred at room temperature for 18 hours. The reaction solution was azeotropically evaporated with ethanol under reduced pressure. The resulting residue was purified by NH silica gel column chromatography [(chloroform:methanol:ammonia water solution=10:1:0.1):chloroform=1:1] to give 1.4 g of the titled compound.

MS (ESI) m/z=151.1 [M+H]$^+$

1H NMR (600 MHz, CHLOROFORM-d) δ ppm 1.78-1.84 (m, 2H) 2.42 (s, 3H) 2.58-2.62 (m, 2H) 2.63-2.67 (m, 2H) 7.09-7.12 (m, 2H) 8.46-8.49 (m, 2H)

EXAMPLE 162

4"-O-acetyl-3'-N-demethyl-2'-deoxy-2'-dimethylamino-3'-N-(3-(4-pyridyl)propyl)-6-O-methylerythromycin A (1) 100 g of 6-O-methylerythromycin A was azeotropically evaporated with toluene and dried under reduced pressure. The resulting residue was suspended in 400 ml of chloroform, in which 6.5 g of 4-dimethylaminopyridine was added. 44 ml of acetic anhydride was added under ice cooling, and the mixture was stirred for 15 hours being raised to room temperature. The reaction solution was washed with a saturated aqueous sodium bicarbonate solution, dried over anhydrous magnesium sulfate, and then filtered. The filtrate was evaporated under reduced pressure, the resulting residue was suspended in 500 ml of methanol, and stirred under reflux for 15 hours. The reaction solution was cooled to room temperature, and then the resulting solid was collected by filtration to give 91.7 g of a 6-O-methylerythromycin A 4"-O-acetyl compound.

(2) 2.0 g of the compound obtained in the above (1) was dissolved in 15 ml of chloroform, and 1.24 ml of triethylamine was added to which 10 ml of a solution of 588 μl of methanesulfonyl chloride dissolved in chloroform was added under ice cooling, and the mixture was stirred for 16 hours being raised to room temperature. A saturated aqueous sodium bicarbonate solution was added to the reaction solution, and the mixture was extracted with chloroform. The organic layer was dried over anhydrous magnesium sulfate, filtered, and the filtrate was evaporated under reduced pressure. The resulting residue was purified by [(acetone:hexane:triethylamine=10:10:0.2):hexane=1:2 to 1:1] to give 1.4 g of a 2'-OMs compound.

(3) 1.4 g of the compound obtained in the above (2) was dissolved in 16 ml of N,N-dimethylformamide, 1.4 g of the compound obtained in Reference Example (1) was added, and the mixture was stirred at 70° C. for 18 hours. Water was added to the reaction solution, and the mixture was extracted with ethyl acetate. The organic layer was washed with water, dried over anhydrous magnesium sulfate, and filtered. The filtrate was evaporated under reduced pressure and the resulting residue was purified by silica gel column chromatography [(chloroform:methanol:ammonia water solution=10:1:0.1):chloroform=1:9 to 3:7] to 354 mg of the titled compound.

MS (ESI) m/z=922.5 [M+H]$^+$

1H NMR (600 MHz, CHLOROFORM-d) δ ppm 0.80-0.87 (m, 3H) 0.96-1.02 (m, 3H) 1.05-1.21 (m, 21H) 1.39 (s, 3H) 1.41-1.95 (m, 10H) 2.05 (s, 3H) 2.24 (s, 3H) 2.34-2.39 (m, 1H) 2.42-2.65 (m, 6H) 2.49 (s, 6H) 2.75-2.85 (m, 2H) 2.95-3.04 (m, 1H) 3.02 (s, 3H) 3.22-3.25 (m, 3H) 3.57-3.61 (m, 1H) 3.72-3.81 (m, 2H) 3.97 (s, 1H) 3.97 (s, 1H) 4.35-4.43 (m, 1H) 4.61-4.65 (m, 1H) 4.88-4.95 (m, 2H) 5.02-5.07 (m, 1H) 7.05-7.12 (m, 2H) 8.45-8.51 (m, 2H)

EXAMPLE 163

3'-N-demethyl-2'-deoxy-2'-dimethylamino-3'-N-(3-(4-pyridyl)propyl)-6-O-methylerythromycin A Using 200 mg of the compound obtained in Example 162, a reaction was carried out in a similar manner described in Example 89 to give 146 mg of the titled compound.

MS (ESI) m/z=880.4 [M+H]$^+$

1H NMR (600 MHz, CHLOROFORM-d) δ ppm 0.80-0.88 (m, 3H) 0.91-1.00 (m, 3H) 1.06-1.21 (m, 18H) 1.25-1.31 (m, 3H) 1.42 (s, 3H) 1.43-1.84 (m, 9H) 1.86-1.96 (m, 1H) 2.24 (s, 3H) 2.27-2.33 (m, 2H) 2.43-2.63 (m, 6H) 2.47 (s, 6H) 2.67-2.73 (m, 1H) 2.74-2.82 (m, 1H) 2.94-3.03 (m, 2H) 3.01 (s, 3H) 3.22 (s, 3H) 3.52-3.58 (m, 1H) 3.71-3.85 (m, 3H) 3.95 (s, 1H) 3.98-4.05 (m, 1H) 4.80-4.89 (m, 1H) 4.92-4.95 (m, 1H) 5.01-5.05 (m, 1H) 7.07-7.12 (m, 2H) 8.46-8.51 (m, 2H)

EXAMPLE 164

4"-O-acetyl-3'-dedimethylamino-2'-deoxy-2'-dimethylamino-3'-(4-hydroxypiperidin-1-yl)-6-O-methylerythromycin A Using 3.2 g of the compound obtained in Example 162 (2), and 4-hydroxypiperidine instead of the compound obtained in Reference Example (1), a reaction was carried out in a similar manner described in Example 162 (3) to give 706 mg of the titled compound.

MS (ESI) m/z=873.6 [M+H]$^+$

1H NMR (600 MHz, CHLOROFORM-d) δ ppm 0.81-0.87 (m, 3H) 0.96-1.01 (m, 3H) 1.04-1.21 (m, 21H) 1.44 (s, 3H) 1.43-1.51 (m, 1H) 1.54-2.17 (m, 13H) 2.11 (s, 3H) 2.39-2.45 (m, 1H) 2.48 (s, 6H) 2.55-2.72 (m, 3H) 2.72-2.80 (m, 1H) 2.81-2.88 (m, 1H) 2.90-2.95 (m, 1H) 2.96-3.05 (m, 1H) 3.01 (s, 3H) 3.18 (s, 1H) 3.28 (s, 3H) 3.51-3.65 (m, 2H) 3.71-3.81 (m, 2H) 3.82-3.87 (m, 1H) 3.95 (s, 1H) 4.40-4.49 (m, 1H) 4.65-4.70 (m, 1H) 4.88-4.91 (m, 1H) 5.00-5.05 (m, 2H)

EXAMPLE 165

3'-dedimethylamino-2'-deoxy-2'-dimethylamino-3'-(4-hydropiperidin-1-yl)-6-O-methylerythromycin A Using 495 mg of the compound obtained in Example 164, a reaction was carried out in a similar manner described in Example 89 to give 352 mg of the titled compound.

MS (ESI) m/z=831.5 [M+H]$^+$

1H NMR (600 MHz, CHLOROFORM-d) δ ppm 0.79-0.85 (m, 3H) 0.93-1.00 (m, 3H) 1.06-1.29 (m, 21H) 1.41 (s, 3H) 1.40-1.94 (m, 10H) 2.07-2.23 (m, 2H) 2.15 (s, 3H) 2.29-2.36 (m, 2H) 2.47 (s, 6H) 2.50-2.62 (m, 1H) 2.63-2.71 (m, 2H) 2.73-2.86 (m, 2H) 2.93-3.03 (m, 2H) 3.00 (s, 3H) 3.17 (s, 1H) 3.28 (s, 3H) 3.54-3.58 (m, 1H) 3.62-3.76 (m, 3H) 3.78-3.81 (m, 1H) 3.94 (s, 1H) 4.03-4.09 (m, 1H) 4.85-4.88 (m, 1H) 4.95-4.97 (m, 1H) 4.99-5.04 (m, 1H)

EXAMPLE 166

4"-O-acetyl-3'-N-demethyl-2'-deoxy-2'-dimethylamino-3'-N-(2-dimethylaminoethyl)-6-O-methylerythromycin A Using 3.2 g of the compound obtained in Example 162 (2), and N,N,N'-trimethylenediamine instead of the compound obtained in Reference Example (1), a reaction was carried out in a similar manner described in Example 162 (3) to give 375 mg of the titled compound.

MS (ESI) m/z=874.6 [M+H]$^+$

1H NMR (600 MHz, CHLOROFORM-d) δ ppm 0.80-0.87 (m, 3H) 0.97-1.03 (m, 3H) 1.06-1.20 (m, 21H) 1.40 (s, 3H) 1.42-1.51 (m, 1H) 1.53-1.63 (m, 3H) 1.65-1.86 (m, 3H) 1.87-1.96 (m, 1H) 2.07 (s, 3H) 2.23 (s, 6H) 2.27 (s, 3H) 2.32-2.46 (m, 3H) 2.48-2.64 (m, 3H) 2.52 (s, 6H) 2.66-2.71 (m, 1H) 2.77-2.84 (m, 2H) 2.96-3.02 (m, 1H) 3.02 (s, 3H) 3.18 (s, 1H) 3.27 (s, 3H) 3.58-3.62 (m, 1H) 3.73-3.75 (m, 1H) 3.77-3.81 (m, 1H) 3.90-3.97 (m, 1H) 3.98 (s, 1H) 4.36-4.43 (m, 1H) 4.61-4.64 (m, 1H) 4.89-4.92 (m, 1H) 4.94-4.96 (m, 1H) 5.01-5.06 (m, 1H)

EXAMPLE 167

3'-N-demethyl-2'-deoxy-2'-dimethylamino-3'-N-(2-dimethylaminoethyl)-6-O-methylerythromycin A Using 265 mg of the compound obtained in Example 166, a reaction was carried out in a similar manner described in Example 89 to give 135 mg of the titled compound.

MS (ESI) m/z=832.6 [M+H]$^+$

1H NMR (600 MHz, CHLOROFORM-d) δ ppm 0.78-0.88 (m, 3H) 0.95-1.01 (m, 3H) 1.08-1.23 (m, 18H) 1.26-1.31 (m, 3H) 1.43 (s, 3H) 1.43-1.49 (m, 1H) 1.51-1.56 (m, 1H) 1.58-1.84 (m, 5H) 1.86-1.95 (m, 1H) 2.21 (s, 6H) 2.26 (s, 3H) 2.29-2.36 (m, 2H) 2.37-2.45 (m, 1H) 2.50 (s, 6H) 2.52-2.68 (m, 4H) 2.71-2.81 (m, 2H) 2.95-3.01 (m, 2H) 3.02 (s, 3H) 3.19 (s, 1H) 3.28 (s, 3H) 3.55-3.59 (m, 1H) 3.73-3.76 (m, 1H) 3.77-3.86 (m, 2H) 3.97 (s, 1H) 4.00-4.06 (m, 1H) 4.85-4.87 (m, 1H) 4.93-4.95 (m, 1H) 5.01-5.05 (m, 1H)

EXAMPLE 168

4"-O-acetyl-3'-dedimethylamino-2'-deoxy-2'-dimethylamino-3'-(4-(2-dimethylaminoethyl)piperazin-1-yl)-6-O-methylerythromycin A Using 3.2 g of the compound obtained in Example 162 (2), and 1-(2-dimethylaminoethyl)piperazine instead of the compound obtained in Reference Example (1), a reaction was carried out in a similar manner described in Example 162 (3) to give 1.05 g of the titled compound.

MS (ESI) m/z=929.7 [M+H]$^+$

1H NMR (600 MHz, CHLOROFORM-d) δ ppm 0.81-0.87 (m, 3H) 0.97-1.02 (m, 3H) 1.05-1.21 (m, 21H) 1.41 (s, 3H) 1.42-1.51 (m, 1H) 1.53-1.69 (m, 3H) 1.70-1.86 (m, 3H) 1.87-1.95 (m, 1H) 2.06 (s, 3H) 2.23 (s, 6H) 2.33-2.67 (m, 14H) 2.50 (s, 6H) 2.73-2.83 (m, 3H) 2.94-3.03 (m, 1H) 3.01 (s, 3H) 3.18 (s, 1H) 3.28 (s, 3H) 3.56-3.60 (m, 1H) 3.72-3.76 (m, 1H) 3.76-3.85 (m, 2H) 3.96 (s, 1H) 4.37-4.44 (m, 1H) 4.61-4.66 (m, 1H) 4.89-4.92 (m, 1H) 4.94-4.97 (m, 1H) 5.01-5.05 (m, 1H)

EXAMPLE 169

3'-dedimethylamino-2'-deoxy-2'-dimethylamino-3'-(4-(2-dimethylaminoethyl)piperazin-1-yl)-6-O-methylerythromycin A Using 830 mg of the compound obtained in Example 168, a reaction was carried out in a similar manner described in Example 89 to give 249 mg of the titled compound.

MS (ESI) m/z=887.7 [M+H]$^+$

1H NMR (600 MHz, CHLOROFORM-d) δ ppm 0.80-0.87 (m, 3H) 0.93-0.98 (m, 3H) 1.07-1.19 (m, 15H) 1.20-1.24 (m, 3H) 1.26-1.30 (m, 3H) 1.40-1.51 (m, 1H) 1.42 (s, 3H) 1.52-1.85 (m, 6H) 1.86-1.95 (m, 1H) 2.23 (s, 6H) 2.30-2.37 (m, 2H) 2.38-2.66 (m, 14H) 2.49 (s, 6H) 2.67-2.71 (m, 1H) 2.73-2.81 (m, 1H) 2.96-3.04 (m, 2H) 3.01 (s, 3H) 3.19 (s, 1H) 3.29 (s, 3H) 3.56-3.59 (m, 1H) 3.70-3.77 (m, 2H) 3.78-3.82 (m, 1H) 4.00-4.08 (m, 1H) 4.84-4.89 (m, 1H) 4.92-4.98 (m, 1H) 4.99-5.06 (m, 1H)

EXAMPLE 170

4"-O-acetyl-3'-N-demethyl-2'-deoxy-2'-dimethylamino-3'-N-benzyl-6-O-methylerythromycin A Using 4.84 g of the compound obtained in Example 162 (2), and N-methylbenzylamine instead of the compound obtained in Reference Example (1), a reaction was carried out in a similar manner described in Example 162 (3) to give 302 mg of the titled compound.

MS (ESI) m/z=893.6 [M+H]$^+$

1H NMR (600 MHz, CHLOROFORM-d) δ ppm 0.81-0.88 (m, 3H) 1.02-1.07 (m, 3H) 1.08-1.22 (m, 21H) 1.42 (s, 3H) 1.43-1.53 (m, 1H) 1.57-1.71 (m, 3H) 1.79-1.87 (m, 3H) 1.87-1.96 (m, 1H) 2.01 (s, 3H) 2.14 (s, 3H) 2.33-2.38 (m, 1H) 2.54 (s, 6H) 2.55-2.64 (m, 1H) 2.78-2.91 (m, 3H) 2.96-3.02 (m, 1H) 3.03 (s, 3H) 3.13 (s, 3H) 3.51 (d, J=13.30 Hz, 1H) 3.61 (d, J=13.30 Hz, 1H) 3.63-3.67 (m, 1H) 3.74-3.77 (m, 1H) 3.79-3.83 (m, 1H) 3.94-4.02 (m, 1H) 3.98 (s, 1H) 4.39-4.47 (m, 1H) 4.62-4.66 (m, 1H) 4.89-4.94 (m, 1H) 5.00-5.07 (m, 2H) 7.18-7.41 (m, 5H)

EXAMPLE 171

3'-N-demethyl-2'-deoxy-2'-dimethylamino-3'-N-benzyl-6-O-methylerythromycin A

Using 200 mg of the compound obtained in Example 170, a reaction was carried out in a similar manner described in Example 89 to give 147 mg of the titled compound.

MS (ESI) m/z=851.6 [M+H]$^+$

1H NMR (600 MHz, CHLOROFORM-d) δ ppm 0.80-0.88 (m, 3H) 1.00-1.07 (m, 3H) 1.08-1.22 (m, 18H) 1.27-1.31 (m, 3H) 1.43 (s, 3H) 1.42-1.51 (m, 1H) 1.52-1.68 (m, 3H) 1.75-1.95 (m, 4H) 2.11-2.16 (m, 3H) 2.24-2.31 (m, 2H) 2.52 (s, 6H) 2.56-2.64 (m, 1H) 2.78-2.91 (m, 3H) 2.96-3.02 (m, 2H) 3.03 (s, 3H) 3.14 (s, 3H) 3.53-3.62 (m, 2H) 3.64-3.70 (m, 1H) 3.74-3.78 (m, 1H) 3.78-3.83 (m, 1H) 3.84-3.92 (m, 1H) 3.97 (s, 1H) 4.06-4.13 (m, 1H) 4.84-4.93 (m, 1H) 4.98-5.10 (m, 2H) 7.20-7.34 (m, 5H)

EXAMPLE 172

4"-O-acetyl-3'-N-demethyl-2'-deoxy-2'-dimethylamino-3'-N-(2-hydroxyethyl)-6-O-methylerythromycin A Using 1.5 g of the compound obtained in Example 162 (2), and 2-(methylamino)ethanol instead of the compound obtained in Reference Example (1), a reaction was carried out in a similar manner described in Example 162 (3) to give 316 mg of the titled compound.

MS (ESI) m/z=847.6 [M+H]$^+$

1H NMR (600 MHz, CHLOROFORM-d) δ ppm 0.81-0.87 (m, 3H) 0.99-1.04 (m, 3H) 1.06-1.21 (m, 21H) 1.40 (s, 3H) 1.41-1.52 (m, 1H) 1.52-1.86 (m, 6H) 1.88-1.96 (m, 1H) 2.31 (s, 3H) 2.31-2.36 (m, 1H) 2.36-2.41 (m, 1H) 2.54 (s, 6H)

2.57-2.63 (m, 1H) 2.67-2.72 (m, 1H) 2.74-2.84 (m, 3H) 2.96-3.01 (m, 1H) 3.03 (s, 3H) 3.19 (s, 1H) 3.28 (s, 3H) 3.48-3.54 (m, 1H) 3.56-3.66 (m, 2H) 3.73-3.75 (m, 1H) 3.78-3.82 (m, 1H) 3.97 (s, 1H) 4.01-4.08 (m, 1H) 4.33-4.39 (m, 1H) 4.62-4.66 (m, 1H) 4.90-4.93 (m, 1H) 4.94-4.97 (m, 1H) 5.00-5.07 (m, 1H)

EXAMPLE 173

3'-N-demethyl-2'-deoxy-2'-dimethylamino-3'-N-(2-hydroxyethyl)-6-O-methylerythromycin A Using 200 mg of the compound obtained in Example 172, a reaction was carried out in a similar manner described in Example 89 to give 134 mg of the titled compound.

MS (ESI) m/z=805.6 [M+H]$^+$

1H NMR (600 MHz, CHLOROFORM-d) δ ppm 0.80-0.87 (m, 3H) 0.96-1.02 (m, 3H) 1.09-1.31 (m, 21H) 1.39-1.51 (m, 1H) 1.42 (s, 3H) 1.53-1.73 (m, 4H) 1.76-1.85 (m, 2H) 1.87-1.96 (m, 1H) 2.28-2.34 (m, 1H) 2.31 (s, 3H) 2.36-2.43 (m, 1H) 2.47-2.65 (m, 7H) 2.70-2.90 (m, 4H) 2.96-3.03 (m, 2H) 3.02 (s, 3H) 3.19 (s, 1H) 3.28 (s, 3H) 3.49-3.54 (m, 1H) 3.58-3.65 (m, 2H) 3.73-3.76 (m, 1H) 3.77-3.81 (m, 1H) 3.85-3.94 (m, 1H) 3.96 (s, 1H) 4.02-4.10 (m, 1H) 4.85-4.89 (m, 1H) 4.92-4.96 (m, 1H) 5.01-5.05 (m, 1H)

EXAMPLE 174

4"-O-acetyl-3'-N-demethyl-2'-deoxy-2'-dimethylamino-6-O-methylerythromycin A

Using 6.0 g of the compound obtained in Example 162 (2), and an aqueous methylamine solution instead of the compound obtained in Reference Example (1), a reaction was carried out in a similar manner described in Example 162 (3) to give 1.67 g of the titled compound.

MS (ESI) m/z=803.5 [M+H]$^+$

1H NMR (600 MHz, CHLOROFORM-d) δ ppm 0.80-0.87 (m, 3H) 0.95-1.01 (m, 3H) 1.07-1.22 (m, 21H) 1.42 (s, 3H) 1.42-1.50 (m, 1H) 1.53-1.71 (m, 4H) 1.76-1.95 (m, 3H) 2.05 (s, 3H) 2.36-2.43 (m, 1H) 2.42 (s, 3H) 2.48-2.64 (m, 2H) 2.52 (s, 6H) 2.79-2.87 (m, 1H) 2.89-2.95 (m, 1H) 2.95-3.01 (m, 1H) 3.02 (s, 3H) 3.18 (s, 1H) 3.31 (s, 3H) 3.52-3.56 (m, 1H) 3.72-3.79 (m, 2H) 3.82-3.91 (m, 1H) 3.98 (s, 1H) 4.26-4.34 (m, 1H) 4.62-4.67 (m, 1H) 4.79-4.83 (m, 1H) 4.91-4.95 (m, 1H) 5.01-5.06 (m, 1H)

EXAMPLE 175

3'-N-demethyl-2'-deoxy-2'-dimethylamino-6-O-methylerythromycin A

Using 200 mg of the compound obtained in Example 174, a reaction was carried out in a similar manner described in Example 89 to give 135 mg of the titled compound.

MS (ESI) m/z=761.5 [M+H]$^+$

1H NMR (600 MHz, CHLOROFORM-d) δ ppm 0.81-0.86 (m, 3H) 0.92-0.96 (m, 3H) 1.08-1.14 (m, 9H) 1.14-1.20 (m, 6H) 1.23 (s, 3H) 1.27-1.31 (m, 3H) 1.37-1.42 (m, 1H) 1.43-1.49 (m, 1H) 1.46 (s, 3H) 1.49-1.54 (m, 1H) 1.56-1.63 (m, 1H) 1.65-1.70 (m, 1H) 1.74-1.85 (m, 2H) 1.87-1.95 (m, 1H) 2.29-2.37 (m, 2H) 2.39 (s, 3H) 2.51 (s, 6H) 2.56-2.63 (m, 1H) 2.76-2.84 (m, 1H) 2.89-2.93 (m, 1H) 2.95-3.00 (m, 2H) 3.02 (s, 3H) 3.28 (s, 3H) 3.51-3.54 (m, 1H) 3.74-3.79 (m, 2H) 3.89-3.96 (m, 1H) 3.96 (s, 1H) 4.04-4.11 (m, 1H) 4.86-4.90 (m, 1H) 4.96-5.00 (m, 1H) 5.02-5.06 (m, 1H)

EXAMPLE 176

3'-N-dedimethylamino-2'-deoxy-2'-dimethylamino-3'-(4-carboxymethylpiperazin-1-yl)-6-O-methylerythromycin A (1) Using 1.5 g of the compound obtained in Example 162 (2), and 1-(ethoxycarbonylmethyl)piperazine instead of the compound obtained in Reference Example (1), a reaction was carried out in a similar manner described in Example 162 (3) to give 305 mg of a 3'-(1-(ethoxycarbonylmethyl)piperazine compound.

(2) 300 g of the compound obtained in the above (1) was dissolved in 1.2 ml of methanol, 0.6 ml of water and 0.16 ml of 2N aqueous sodium hydroxide solution were added, and the mixture was stirred at 40° C. for 10 hours. The reaction solution was evaporated under reduced pressure, and the resulting residue was purified by column chromatography (chloroform:methanol:ammonia water solution=10:1:0.1) to give 238 mg of the said residue. 136 mg of the resulting residue was dissolved in 2 ml of methanol, to which 65 μl of 1,8-diazabicyclo[5.4.0]undecan-7-en
was added, and the mixture was stirred under reflux for 7 hours. The reaction solution was evaporated under reduced pressure, and the resulting residue was purified by silica gel column chromatography (chloroform:methanol:ammonia water solution=10:1:0.1) to give 109 mg of the titled compound.

MS (ESI) m/z=874.7 [M+H]$^+$

1H NMR (600 MHz, CHLOROFORM-d) δ ppm 0.81-0.87 (m, 3H) 0.91-0.95 (m, 3H) 1.08-1.29 (m, 21H) 1.42-1.43 (m, 3H) 1.43-1.51 (m, 1H) 1.54-1.85 (m, 6H) 1.87-1.95 (m, 1H) 2.24-2.32 (m, 1H) 2.43-4.15 (m, 10H) 2.54 (s, 3H) 2.56-2.63 (m, 1H) 2.65-2.83 (m, 9H) 2.93-3.08 (m, 1H) 3.01 (s, 1H) 3.26 (s, 3H) 3.56-3.60 (m, 1H) 3.68-3.85 (m, 3H) 4.00-4.07 (m, 1H) 4.84-4.88 (m, 1H) 4.95-4.98 (m, 1H) 5.01-5.05 (m, 1H)

EXAMPLE 177

4"-O-acetyl-3'-dedimethylamino-2'-deoxy-2'-dimethylamino-3'-(4-morpholino)-6-O-methylerythromycin A Using 2.0 g of the compound obtained in Example 162 (2), and morpholine instead of the compound obtained in Reference Example (1), a reaction was carried out in a similar manner described in Example 162 (3) to give 1.26 g of the titled compound.

MS (ESI) m/z=859.5 [M+H]$^+$

1H NMR (600 MHz, CHLOROFORM-d) δ ppm 0.81-0.87 (m, 3H) 0.96-1.00 (m, 3H) 1.06-1.19 (m, 21H) 1.42 (s, 3H) 1.42-1.51 (m, 1H) 1.55-1.86 (m, 6H) 1.87-1.95 (m, 1H) 2.04 (s, 3H) 2.36-2.42 (m, 1H) 2.45-2.55 (m, 4H) 2.50 (s, 6H) 2.56-2.63 (m, 1H) 2.65-2.71 (m, 2H) 2.74-2.81 (m, 1H) 2.96-3.04 (m, 1H) 3.02 (s, 3H) 3.17-3.19 (m, 1H) 3.28 (s, 3H) 3.56-3.59 (m, 1H) 3.69-3.83 (m, 6H) 3.95 (s, 1H) 4.35-4.41 (m, 1H) 4.88-4.91 (m, 1H) 4.96-4.99 (m, 1H) 5.01-5.05 (m, 1H)

EXAMPLE 178

3'-dedimethylamino-2'-deoxy-2'-dimethylamino-3'-(4-morpholino)-6-O-methylerythromycin A Using 300 mg of the compound obtained in Example 177, a reaction was carried out in a similar manner described in Example 89 to give 202 mg of the titled compound.

MS (ESI) m/z=817.5 [M+H]+
1H NMR (600 MHz, CHLOROFORM-d) δ ppm 0.93-0.98 (m, 3H) 1.09-1.25 (m, 21H) 1.26-1.32 (m, 3H) 1.43 (s, 3H) 1.43-1.51 (m, 1H) 1.54-1.86 (m, 6H) 1.87-1.96 (m, 1H) 2.29-2.37 (m, 2H) 2.43-2.54 (m, 4H) 2.50 (s, 6H) 2.55-2.68 (m, 3H) 2.73-2.80 (m, 1H) 2.95-3.05 (m, 2H) 3.02 (s, 3H) 3.15-3.19 (m, 1H) 3.29 (s, 3H) 3.57-3.62 (m, 1H) 3.66-3.84 (m, 7H) 3.94 (s, 1H) 3.99-4.07 (m, 1H) 4.85-4.90 (m, 1H) 4.96-5.00 (m, 1H) 5.01-5.07 (m, 1H)

EXAMPLE 179

4"-O-acetyl-3'-N-demethyl-2'-deoxy-2'-dimethyl-amino-3'-N-carboxymethyl-6-methylerythromycin A 400 mg of the compound obtained in Example 174 was dissolved in 4 ml of chloroform, 120 µl of glyoxylic acid was added. After the mixture was stirred at room temperature for 1 hour, 137 mg of sodium triacetoxyborohydride was added, and the mixture was stirred at room temperature for 3 hours. A saturated aqueous sodium bicarbonate solution was added to the reaction solution, and the mixture was extracted with chloroform. The organic layer was dried over anhydrous magnesium sulfate, filtered, evaporated under reduced pressure, and the resulting residue was purified by silica gel chromatography [(chloroform:methanol:ammonia water solution=10:1:0.1):chloroform=4:1 to 1:0] to give 380 mg of the titled compound.

MS (ESI) m/z=861.6 [M+H]+
1H NMR (600 MHz, CHLOROFORM-d) δ ppm 0.80-0.87 (m, 3H) 0.96-1.02 (m, 3H) 1.07-1.24 (m, 21H) 1.38 (s, 3H) 1.41-1.55 (m, 3H) 1.59-1.66 (m, 1H) 1.78-1.97 (m, 4H) 2.06 (s, 3H) 2.34-2.39 (m, 1H) 2.41 (s, 3H) 2.57-2.65 (m, 1H) 2.75 (s, 6H) 2.77-2.84 (m, 1H) 2.86-3.00 (m, 3H) 3.03 (s, 3H) 3.26 (s, 3H) 3.26-3.36 (m, 2H) 3.57-3.61 (m, 1H) 3.69-3.71 (m, 1H) 3.78-3.83 (m, 1H) 4.22-4.37 (m, 2H) 4.64-4.69 (m, 1H) 4.92-4.96 (m, 1H) 4.99-5.07 (m, 2H)

EXAMPLE 180

3'-N-demethyl-2'-deoxy-2'-dimethylamino-3'-N-carboxymethyl-6-O-methylerythromycin A Using 200 mg of the compound obtained in Example 179, a reaction was carried out in a similar manner described in Example 89 to give 128 mg of the titled compound.

MS (ESI) m/z=819.6 [M+H]+
1H NMR (600 MHz, CHLOROFORM-d) δ ppm 0.81-0.86 (m, 3H) 0.95-1.00 (m, 3H) 1.09-1.30 (m, 21H) 1.40 (s, 3H) 1.42-1.95 (m, 8H) 2.25-2.30 (m, 1H) 2.43 (s, 3H) 2.58-2.65 (m, 1H) 2.74 (s, 6H) 2.76-2.81 (m, 1H) 2.87-3.00 (m, 2H) 3.03 (s, 3H) 3.03-3.06 (m, 1H) 3.08-3.19 (m, 1H) 3.24-3.48 (m, 2H) 3.28 (s, 3H) 3.62-3.67 (m, 1H) 3.70-3.73 (m, 1H) 3.76-3.80 (m, 1H) 3.97-4.04 (m, 1H) 4.05-4.12 (m, 1H) 4.85-4.89 (m, 1H) 4.98-5.01 (m, 1H) 5.02-5.07 (m, 1H)

EXAMPLE 181

4"-O-acetyl-3'-N-demethyl-2'-deoxy-2'-dimethy-lamino-3'-N-(4-(4-morpholino)benzyl)-6-O-methyl-erythromycin A Using 1.0 g of the compound obtained in Example 174, and 4-(4-formylphenyl)morpholine instead of glyoxylic acid, a reaction was carried out in a similar manner described in Example 179 to give 500 mg of the titled compound.

MS (ESI) m/z=978.6 [M+H]+
1H NMR (600 MHz, CHLOROFORM-d) δ ppm 0.81-0.88 (m, 3H) 1.02-1.07 (m, 3H) 1.08-1.16 (m, 18H) 1.16-1.22 (m, 3H) 1.41 (s, 3H) 1.42-1.51 (m, 1H) 1.54-1.72 (m, 3H) 1.77-1.87 (m, 3H) 1.87-1.97 (m, 1H) 2.02 (s, 3H) 2.12 (s, 3H) 2.33-2.39 (m, 1H) 2.54 (s, 6H) 2.55-2.64 (m, 1H) 2.78-2.91 (m, 3H) 2.96-3.02 (m, 1H) 3.03 (s, 3H) 3.10-3.14 (m, 4H) 3.16 (s, 3H) 3.43-3.48 (m, 1H) 3.51-3.55 (m, 1H) 3.62-3.66 (m, 1H) 3.73-3.77 (m, 1H) 3.79-3.83 (m, 1H) 3.83-3.88 (m, 4H) 3.93-4.02 (m, 1H) 3.97 (s, 1H) 4.41-4.47 (m, 1H) 4.91-4.94 (m, 1H) 5.00-5.06 (m, 2H) 6.82-6.86 (m, 2H) 7.22-7.28 (m, 2H)

EXAMPLE 182

3'-N-demethyl-2'-deoxy-2'-dimethylamino-3'-N-(4-(4-morpholino)benzyl)methyl-6-O-methylerythro-mycin A Using 200 mg of the compound obtained in Example 181, a reaction was carried out in a similar manner described in Example 89 to give 148 mg of the titled compound.

MS (ESI) m/z=936.7 [M+H]+
1H NMR (600 MHz, CHLOROFORM-d) δ ppm 0.79-0.88 (m, 3H) 0.98-1.34 (m, 24H) 1.43 (s, 3H) 1.43-1.87 (m, 7H) 1.88-1.98 (m, 1H) 2.12 (s, 3H) 2.22-2.33 (m, 2H) 2.48-2.90 (m, 4H) 2.52 (s, 6H) 2.93-3.02 (m, 2H) 3.03 (s, 3H) 3.09-3.16 (m, 4H) 3.13-3.24 (m, 2H) 3.17 (s, 3H) 3.62-3.67 (m, 1H) 3.73-3.92 (m, 7H) 3.96 (s, 1H) 4.04-4.13 (m, 1H) 4.85-4.91 (m, 1H) 4.98-5.07 (m, 2H) 6.81-6.87 (m, 2H) 7.18-7.22 (m, 2H)

EXAMPLE 183

4"-O-acetyl-3'-N-demethyl-2'-deoxy-2'-dimethy-lamino-3'-N-acetyl-6-O-methylerythromycin A 200 mg of the compound obtained in Example 174 was suspended in 2 ml of acetone, to which 47 µl of acetic anhydride was added, and the mixture was stirred at room temperature for 15 hours. The reaction solution was evaporated under reduced pressure, and the resulting residue was purified by silica gel column chromatography [(acetone:hexane:triethylamine=10:10:0.2):hexane=1:1 to 4:1] to give 78 mg of the titled compound.

MS (ESI) m/z=845.6 [M+H]+
1H NMR (499 MHz, CHLOROFORM-d, 55° C.) δ ppm 0.81-0.89 (m, 3H) 1.00-1.07 (m, 3H) 1.07-1.28 (m, 21H) 1.40 (s, 3H) 1.42-1.74 (m, 5H) 1.75-1.98 (m, 3H) 2.01-2.20 (m, 6H) 2.06 (s, 3H) 2.33-2.40 (m, 1H) 2.53 (br. s., 6H) 2.55-2.66 (m, 1H) 2.76-3.06 (m, 4H) 3.04 (s, 3H) 3.14 (s, 1H) 3.29 (s, 3H) 3.56-3.68 (m, 1H) 3.73-3.78 (m, 1H) 3.78-3.85 (m, 1H) 3.89 (s, 1H) 4.08-4.26 (m, 1H) 4.37-4.53 (m, 1H) 4.63-4.69 (m, 1H) 4.92-5.10 (m, 3H)

EXAMPLE 184

3'-N-demethyl-2'-deoxy-2'-dimethylamino-3'-N-acetyl-6-O-methylerythromycin A

Using 140 mg of the compound obtained in Example 175, a reaction was carried out in a similar manner described in Example 183 to give 138 mg of the titled compound.

MS (ESI) m/z=803.5 [M+H]+
1H NMR (499 MHz, CHLOROFORM-d, SSC) δ ppm 0.82-0.88 (m, 3H) 0.98-1.05 (m, 3H) 1.08-1.30 (m, 21H) 1.41 (s, 3H) 1.41-1.71 (m, 5H) 1.74-1.98 (m, 3H) 2.00-2.20 (m, 6H) 2.27-2.34 (m, 1H) 2.49 (br. s., 6H) 2.55-2.66 (m, 1H)

2.77-3.06 (m, 5H) 3.03 (s, 3H) 3.30 (s, 3H) 3.63-3.72 (m, 1H) 3.73-3.78 (m, 1H) 3.79-3.84 (m, 1H) 3.88-3.90 (m, 1H) 4.02-4.23 (m, 2H) 4.87-5.08 (m, 3H)

EXAMPLE 185

4"-O-acetyl-3'-N-demethyl-2'-deoxy-2'-dimethylamino-3'-N-methanesulfonyl-6-O-methylerythromycin A Using 400 mg of the compound obtained in Example 174, a reaction was carried out in a similar manner described in Example 162 (2) to give 321 mg of the titled compound.
MS (ESI) m/z=881.6 [M+H]$^+$
1H NMR (600 MHz, CHLOROFORM-d) δ ppm 0.81-0.87 (m, 3H) 0.97-1.04 (m, 3H) 1.06-1.25 (m, 21H) 1.38 (s, 3H) 1.41-1.50 (m, 2H) 1.55-1.96 (m, 5H) 1.97-2.05 (m, 1H) 2.05 (s, 3H) 2.35-2.39 (m, 1H) 2.56 (s, 6H) 2.58-2.62 (m, 1H) 2.77-2.83 (m, 1H) 2.82 (s, 3H) 2.86-2.91 (m, 1H) 2.93 (s, 3H) 2.95-3.01 (m, 1H) 3.02 (s, 3H) 3.19 (s, 1H) 3.27 (s, 3H) 3.52-3.56 (m, 1H) 3.71-3.75 (m, 1H) 3.78-3.83 (m, 1H) 3.97 (s, 1H) 4.14-4.21 (m, 1H) 4.23-4.30 (m, 1H) 4.34-4.42 (m, 1H) 4.63-4.68 (m, 1H) 4.88-4.91 (m, 1H) 4.92-4.96 (m, 1H) 5.01-5.06 (m, 1H)

EXAMPLE 186

3'-N-demethyl-2'-deoxy-2'-dimethylamino-3'-N-methanesulfonyl-6-O-methylerythromycin A Using 200 mg of the compound obtained in Example 185, a reaction was carried out in a similar manner described in Example 89 to give 132 mg of the titled compound.
MS (ESI) m/z=839.6 [M+H]$^+$
1H NMR (600 MHz, CHLOROFORM-d) δ ppm 0.81-0.87 (m, 3H) 0.98-1.06 (m, 6H) 1.09-1.29 (m, 18H) 1.39 (s, 3H) 1.41-1.50 (m, 1H) 1.51-1.87 (m, 5H) 1.88-1.96 (m, 1H) 2.28-2.33 (m, 1H) 2.55 (s, 6H) 2.57-2.64 (m, 1H) 2.75-2.83 (m, 2H) 2.81 (s, 3H) 2.88-2.92 (m, 2H) 2.91 (s, 3H) 2.94-3.02 (m, 1H) 3.02 (s, 3H) 3.19 (s, 1H) 3.29 (s, 3H) 3.56-3.63 (m, 1H) 3.70-3.76 (m, 1H) 3.77-3.84 (m, 1H) 3.95 (s, 1H) 4.01-4.10 (m, 2H) 4.25-4.35 (m, 1H) 4.82-4.93 (m, 2H) 5.00-5.07 (m, 1H)

EXAMPLE 187

4"-O-acetyl-3'-N-demethyl-2'-deoxy-2'-dimethylamino-3'-N-(4-pyridylmethylamino)-6-O-methylerythromycin A Using 1.0 g of the compound obtained in Example 174 and using 4-pyridinecarboxyaldehyde instead of glyoxylic acid, a reaction was carried out in a similar manner described in Example 179 to give 509 mg of the titled compound.
MS (ESI) m/z=894.6 [M+H]$^+$
1H NMR (600 MHz, CHLOROFORM-d) δ ppm 0.81-0.87 (m, 3H) 0.98-1.05 (m, 3H) 1.07-1.22 (m, 21H) 1.42 (s, 3H) 1.43-1.51 (m, 1H) 1.60-1.72 (m, 3H) 1.76-1.88 (m, 3H) 1.87-1.96 (m, 1H) 1.97 (s, 3H) 2.15 (s, 3H) 2.35-2.40 (m, 1H) 2.55 (s, 6H) 2.57-2.64 (m, 1H) 2.76-2.83 (m, 1H) 2.83-2.87 (m, 2H) 2.97-3.02 (m, 1H) 3.03 (s, 3H) 3.17 (s, 3H) 3.45 (d, J=14.21 Hz, 1H) 3.62-3.67 (m, 1H) 3.69 (d, J=14.21 Hz, 1H) 3.73-3.76 (m, 1H) 3.79-3.84 (m, 1H) 3.94-4.02 (m, 1H) 3.96 (s, 1H) 4.39-4.46 (m, 1H) 4.65-4.69 (m, 1H) 4.90-4.94 (m, 1H) 4.99-5.07 (m, 2H) 7.33-7.37 (m, 2H) 8.50-8.53 (m, 2H)

EXAMPLE 188

3'-N-demethyl-2'-deoxy-2'-dimethylamino-3'-N-(4-pyridylmethyl)-6-O-methylerythromycin A Using 300 mg of the compound obtained in Example 187, a reaction was carried out in a similar manner described in Example 89 to give 164 mg of the titled compound.
MS (ESI) m/z=852.5 [M+H]$^+$
1H NMR (600 MHz, CHLOROFORM-d) δ ppm 0.81-0.87 (m, 3H) 0.97-1.04 (m, 3H) 1.08-1.24 (m, 18H) 1.27-1.32 (m, 3H) 1.42 (s, 3H) 1.42-1.52 (m, 1H) 1.55-1.96 (m, 7H) 2.14 (s, 3H) 2.22-2.30 (m, 2H) 2.53 (s, 6H) 2.56-2.64 (m, 1H) 2.76-2.87 (m, 2H) 2.88-2.93 (m, 1H) 2.95-3.06 (m, 2H) 3.03 (s, 3H) 3.19 (s, 3H) 3.58 (s, 2H) 3.66-3.71 (m, 1H) 3.73-3.77 (m, 1H) 3.78-3.82 (m, 1H) 3.86-3.93 (m, 1H) 3.95 (s, 1H) 4.07-4.14 (m, 1H) 4.86-4.92 (m, 1H) 4.99-5.08 (m, 2H) 7.26-7.31 (m, 2H) 8.49-8.54 (m, 2H)

EXAMPLE 189

4"-O-acetyl-3'-N-demethyl-2'-deoxy-2'-dimethylamino-3'-N-(3-pyridylmethyl)-O-methylerythromycin A Using 1.0 g of the compound obtained in Example 174, and 3-pyridinecarboxyaldehyde instead of glyoxylic acid, a reaction was carried out in a similar manner described in Example 179 to give 882 mg of the titled compound.
MS (ESI) m/z=894.6 [M+H]$^+$
1H NMR (600 MHz, CHLOROFORM-d) δ ppm 0.82-0.87 (m, 3H) 1.01-1.06 (m, 3H) 1.09-1.21 (m, 21H) 1.41 (s, 3H) 1.42-1.51 (m, 1H) 1.58-1.70 (m, 3H) 1.73-1.87 (m, 3H) 1.87-1.95 (m, 1H) 2.00 (s, 3H) 2.14 (s, 3H) 2.32-2.39 (m, 1H) 2.54 (s, 6H) 2.54-2.65 (m, 1H) 2.77-2.92 (m, 3H) 2.95-3.02 (m, 1H) 3.03 (s, 3H) 3.13 (s, 3H) 3.18 (s, 1H) 3.48-3.54 (m, 1H) 3.60-3.67 (m, 2H) 3.73-3.76 (m, 1H) 3.78-3.83 (m, 1H) 3.97 (s, 1H) 3.93-4.04 (m, 1H) 4.38-4.46 (m, 1H) 4.62-4.68 (m, 1H) 4.89-4.95 (m, 1H) 4.98-5.08 (m, 2H) 7.18-7.27 (m, 1H) 7.73-7.79 (m, 1H) 8.45-8.57 (m, 2H)

EXAMPLE 190

3'-N-demethyl-2'-deoxy-2'-dimethylamino-3'-N-(3-pyridylmethyl)-6-O-methylerythromycin A Using 300 mg of the compound obtained in Example 189, a reaction was carried out in a similar manner described in Example 89 to give 249 mg of the titled compound.
MS (ESI) m/z=852.5 [M+H]$^+$
1H NMR (600 MHz, CHLOROFORM-d) δ ppm 0.81-0.87 (m, 3H) 1.00-1.06 (m, 3H) 1.09-1.23 (m, 18H) 1.26-1.31 (m, 3H) 1.42 (s, 3H) 1.41-1.50 (m, 1H) 1.52-1.96 (m, 7H) 2.15 (s, 3H) 2.25-2.30 (m, 1H) 2.52 (s, 6H) 2.56-2.64 (m, 1H) 2.77-2.85 (m, 2H) 2.87-2.91 (m, 1H) 2.96-3.06 (m, 2H) 3.03 (s, 3H) 3.14 (s, 3H) 3.18 (s, 1H) 3.55-3.62 (m, 2H) 3.64-3.68 (m, 1H) 3.74-3.77 (m, 1H) 3.79-3.83 (m, 1H) 3.85-3.92 (m, 1H) 3.96 (s, 1H) 4.07-4.15 (m, 1H) 4.86-4.90 (m, 1H) 4.98-5.07 (m, 2H) 7.20-7.26 (m, 1H) 7.61-7.66 (m, 1H) 8.46-8.51 (m, 1H) 8.54-8.59 (m, 1H)

EXAMPLE 191

4"-O-acetyl-3'-N-demethyl-2'-deoxy-2'-dimethylamino-3'-N-(2-pyridylmethyl)-6-O-methylerythromycin A Using 1.0 g of the compound obtained in Example 174, and 2-pyridinecarboxyaldehyde instead of glyoxylic acid, a reaction was carried out in a similar manner described in Example 179 to give 1.04 g of the titled compound.

MS (ESI) m/z=894.6 [M+H]$^+$

1H NMR (600 MHz, CHLOROFORM-d) δ ppm 0.79-0.87 (m, 3H) 1.00-1.06 (m, 3H) 1.07-1.21 (m, 21H) 1.39-1.50 (m, 1H) 1.42 (s, 3H) 1.55-1.72 (m, 3H) 1.78-1.96 (m, 4H) 1.99 (s, 3H) 2.24 (s, 3H) 2.32-2.40 (m, 1H) 2.54 (s, 6H) 2.54-2.64 (m, 1H) 2.76-2.85 (m, 1H) 2.87-3.03 (m, 4H) 3.03 (s, 3H) 3.18 (s, 3H) 3.67 (d, J=14.21 Hz, 1H) 3.73-3.76 (m, 1H) 3.79-3.83 (m, 1H) 3.86 (d, J=14.21 Hz, 1H) 3.97 (s, 1H) 3.95-4.05 (m, 1H) 4.39-4.47 (m, 1H) 4.63-4.68 (m, 1H) 4.90-4.94 (m, 1H) 4.99-5.07 (m, 2H) 7.11-7.17 (m, 1H) 7.56-7.65 (m, 2H) 8.48-8.52 (m, 1H)

EXAMPLE 192

3'-N-demethyl-2'-deoxy-2'-dimethylamino-3'-N-(2-pyridylmethyl)-6-O-methylerythromycin A Using 300 mg of the compound obtained in Example 191, a reaction was carried out in a similar manner described in Example 89 to give 199 mg of the titled compound.

MS (ESI) m/z=852.5 [M+H]$^+$

1H NMR (600 MHz, CHLOROFORM-d) δ ppm 0.80-0.88 (m, 3H) 0.97-1.03 (m, 3H) 1.07-1.25 (m, 18H) 1.27-1.32 (m, 3H) 1.41-1.50 (m, 1H) 1.44 (s, 3H) 1.52-1.59 (m, 1H) 1.60-1.72 (m, 2H) 1.73-1.86 (m, 3H) 1.86-1.96 (m, 1H) 2.24 (s, 3H) 2.27-2.31 (m, 1H) 2.52 (s, 6H) 2.56-2.96 (m, 4H) 2.96-3.06 (m, 2H) 3.03 (s, 3H) 3.15 (s, 3H) 3.62-3.66 (m, 1H) 3.68 (d, J=14.21 Hz, 1H) 3.74-3.77 (m, 1H) 3.77-3.81 (m, 1H) 3.84 (d, J=14.21 Hz, 1H) 3.88-3.95 (m, 1H) 3.96 (s, 1H) 4.07-4.14 (m, 1H) 4.85-4.90 (m, 1H) 4.99-5.06 (m, 2H) 7.12-7.16 (m, 1H) 7.41-7.45 (m, 1H) 7.60-7.65 (m, 1H) 8.51-8.55 (m, 1H)

EXAMPLE 193

4"-O-acetyl-3'-N-demethyl-2'-deoxy-2'-dimethyl-amino-3'-N-(2-phenethyl)-6-O-methylerythromycin A Using 500 mg of the compound obtained in Example 174, and 2-phenethyl bromide instead of 3-benzyloxypropyl bromide, a reaction was carried out in a similar manner described in Example 129 to give 99 mg of the titled compound.

MS (ESI) m/z=907.6 [M+H]$^+$

1H NMR (600 MHz, CHLOROFORM-d) δ ppm 0.80-0.88 (m, 3H) 0.98-1.21 (m, 24H) 1.41 (s, 3H) 1.42-1.52 (m, 1H) 1.54-1.87 (m, 6H) 1.87-1.95 (m, 1H) 1.94 (s, 3H) 2.33-2.38 (m, 1H) 2.37 (s, 3H) 2.52 (s, 6H) 2.55-2.64 (m, 1H) 2.64-2.90 (m, 7H) 2.96-3.03 (m, 1H) 3.03 (s, 3H) 3.18 (s, 1H) 3.23 (s, 3H) 3.57-3.63 (m, 1H) 3.72-3.81 (m, 2H) 3.89-3.98 (m, 1H) 3.97 (s, 1H) 4.35-4.42 (m, 1H) 4.59-4.63 (m, 1H) 4.88-4.92 (m, 1H) 4.98-5.07 (m, 2H) 7.13-7.21 (m, 3H) 7.23-7.30 (m, 2H)

EXAMPLE 194

3'-N-demethyl-2'-deoxy-2'-dimethylamino-3'-N-(2-phenethyl)-6-O-methylerythromycin A Using 64 mg of the compound obtained in Example 193, a reaction was carried out in a similar manner described in Example 89 to give 42 mg of the titled compound.

MS (ESI) m/z=865.6 [M+H]$^+$

1H NMR (600 MHz, CHLOROFORM-d) δ ppm 0.80-0.87 (m, 3H) 0.97-1.03 (m, 3H) 1.08-1.22 (m, 18H) 1.26-1.31 (m, 3H) 1.44 (s, 3H) 1.43-1.72 (m, 5H) 1.76-1.86 (m, 2H) 1.87-1.96 (m, 1H) 2.26-2.34 (m, 1H) 2.36 (s, 3H) 2.52 (s, 6H) 2.56-2.64 (m, 1H) 2.65-2.83 (m, 7H) 2.93-3.04 (m, 2H) 3.02 (s, 3H) 3.18 (s, 3H) 3.56-3.61 (m, 1H) 3.73-3.80 (m, 2H) 3.81-3.88 (m, 1H) 3.96 (s, 1H) 3.99-4.07 (m, 1H) 4.83-4.87 (m, 1H) 4.97-5.07 (m, 2H) 7.11-7.33 (m, 5H)

EXAMPLE 195

4"-O-acetyl-3'-dedimethylamino-2'-deoxy-2'-dimethylamino-3'-(4-carboxypiperazin-1-yl)-6-O-methylerythromycin A (1) Using 3.0 g of the compound obtained in Example 162 (2), and ethyl isonipecotate instead of the compound obtained in Reference Example (1), a reaction was carried out in a similar manner described in Example 162 (3) to give 2.58 g of a 3'-(4-ethoxycarbonylpiperazin-1-yl) compound.

(2) Using 11.0 g of the compound obtained in the above (1), a reaction was carried out in a similar manner described in Example 176 (2) to give 749 mg of the titled compound.

MS (ESI) m/z=859.5 [M+H]$^+$

1H NMR (600 MHz, CHLOROFORM-d) δ ppm 0.79-0.87 (m, 3H) 0.92-0.99 (m, 3H) 1.06-1.31 (m, 21H) 1.43 (s, 3H) 1.41-1.51 (m, 1H) 1.52-1.99 (m, 11H) 2.23-2.38 (m, 3H) 2.56-2.65 (m, 1H) 2.62 (s, 6H) 2.68-2.91 (m, 6H) 2.94-3.04 (m, 2H) 3.02 (s, 3H) 3.27 (s, 3H) 3.58-3.65 (m, 1H) 3.70-3.83 (m, 3H) 3.98-4.06 (m, 1H) 4.84-4.89 (m, 1H) 4.99-5.07 (m, 2H)

EXAMPLE 196

4"-O-acetyl-3'-dedimethylamino-2'-deoxy-2'-dimethylamino-3-((±)-3-hydroxypiperidin-1-yl)-6-O-methylerythromycin A Using 1.5 g of the compound obtained in Example 162 (2), and 3-hydroxypiperidine instead of the compound obtained in Reference Example (1), a reaction was carried out in a similar manner described in Example 162 (3) to give 630 mg of the titled compound.

MS (ESI) m/z=873.5 [M+H]$^+$

1H NMR (600 MHz, CHLOROFORM-d) δ ppm 0.81-0.87 (m, 3H) 0.97-1.04 (m, 3H) 1.06-1.21 (m, 21H) 1.31-1.96 (m, 15H) 2.09-2.14 (m, 3H) 2.34-2.67 (m, 12H) 2.75-2.85 (m, 3H) 2.95-3.05 (m, 4H) 3.16-3.19 (m, 1H) 3.26-3.32 (m, 3H) 3.53-3.59 (m, 1H) 3.71-3.88 (m, 4H) 3.94-3.96 (m, 1H) 4.30-4.41 (m, 1H) 4.62-4.67 (m, 1H) 4.88-4.92 (m, 1H) 4.94-4.97 (m, 1H) 5.01-5.06 (m, 1H)

EXAMPLE 197

3'-dedimethylamino-2'-deoxy-2'-dimethylamino-3'-((±)-3-hydroxypiperidin-1-yl)-6-O-methylerythromycin A Using 300 mg of the compound obtained in Example 196, a reaction was carried out in a similar manner described in Example 89 to give 222 mg of the titled compound.

MS (ESI) m/z=831.5 [M+H]$^+$

1H NMR (600 MHz, CHLOROFORM-d) δ ppm 0.80-0.88 (m, 3H) 0.93-1.02 (m, 3H) 1.05-1.34 (m, 21H) 1.37-1.97 (m, 15H) 2.27-2.44 (m, 1H) 2.39-2.68 (m, 11H) 2.69-2.90 (m, 3H) 2.92-3.05 (m, 2H) 3.00-3.03 (m, 3H) 3.15-3.20 (m, 1H) 3.24-3.32 (m, 3H) 3.55-3.64 (m, 1H) 3.65-3.84 (m, 3H) 3.99-4.14 (m, 1H) 4.83-4.90 (m, 1H) 4.91-4.98 (m, 1H) 5.00-5.06 (m, 1H)

EXAMPLE 198

4''-O-acetyl-3'-N-demethyl-2'-deoxy-2'-dimethylamino-3'-N-(3-hydroxypropyl)-6-O-methylerythromycin A Using 1.5 g of the compound obtained in Example 162 (2), and 3-(methylamino)-1-propanol instead of the compound obtained in Reference Example (1), a reaction was carried out in a similar manner described in Example 162 (3) to give 350 mg of the titled compound.

MS (ESI) m/z=861.5 [M+H]$^+$
1H NMR (600 MHz, CHLOROFORM-d) δ ppm 0.80-0.87 (m, 3H) 0.99-1.04 (m, 3H) 1.07-1.21 (m, 21H) 1.39 (s, 3H) 1.41-1.51 (m, 1H) 1.58-1.96 (m, 7H) 2.08 (s, 3H) 2.26 (s, 3H) 2.34-2.40 (m, 1H) 2.49-2.64 (m, 2H) 2.54 (s, 6H) 2.67-2.75 (m, 1H) 2.77-2.85 (m, 2H) 2.88-2.95 (m, 1H) 2.96-3.01 (m, 1H) 3.02 (s, 3H) 3.17-3.19 (m, 1H) 3.26 (s, 3H) 3.57-3.61 (m, 1H) 3.69-3.79 (m, 3H) 3.79-3.83 (m, 1H) 3.96 (s, 1H) 4.03-4.10 (m, 1H) 4.37-4.45 (m, 1H) 4.63-4.67 (m, 1H) 4.90-4.95 (m, 2H) 5.01-5.05 (m, 1H)

EXAMPLE 199

3'-N-demethyl-2'-deoxy-2'-dimethylamino-3'-N-(3-hydroxypropyl)-6-O-methylerythromycin A Using 250 mg of the compound obtained in Example 198, a reaction was carried out in a similar manner described in Example 89 to give 149 mg of the titled compound.

MS (ESI) m/z=819.5 [M+H]$^+$
1H NMR (600 MHz, CHLOROFORM-d) δ ppm 0.80-0.88 (m, 3H) 0.97-1.03 (m, 3H) 1.08-1.20 (m, 15H) 1.22 (s, 3H) 1.26-1.31 (m, 3H) 1.43 (s, 3H) 1.43-1.51 (m, 1H) 1.50-1.85 (m, 8H) 1.86-1.95 (m, 1H) 2.26 (s, 3H) 2.29-2.34 (m, 1H) 2.45-2.53 (m, 1H) 2.53 (s, 6H) 2.57-2.65 (m, 1H) 2.69-2.81 (m, 3H) 2.82-2.86 (m, 1H) 2.93-3.02 (m, 1H) 3.03 (s, 3H) 3.26 (s, 3H) 3.58-3.63 (m, 1H) 3.65-3.78 (m, 4H) 3.79-3.83 (m, 1H) 3.86-3.93 (m, 1H) 3.94 (s, 1H) 4.01-4.09 (m, 1H) 4.83-4.88 (m, 2H) 5.01-5.05 (m, 1H)

EXAMPLE 200

4''-O-acetyl-3'-dedimethylamino-2'-deoxy-2'-dimethylamino-3'-((S)-3-hydroxypyrrolidin-1-yl)-6-O-methylerythromycin A (compound X)

4''-O-acetyl-3'-dedimethylamino-2'-deoxy-2'-dimethylamino-3'-((R)-3-hydroxypyrrolidin-1-yl)-6-O-methylerythromycin A (compound Y)

Using 1.5 g of the compound obtained in Example 162 (2), and DL-3-pyrrolidinol instead of the compound obtained in Reference Example (1), a reaction was carried out in a similar manner described in Example 162 (3) to give 410 mg of a compound X and 447 mg of a compound Y.

4''-O-acetyl-3'-dedimethylamino-2'-deoxy-2'-dimethylamino-3'-((S)-3-hydroxypyrrolidin-1-yl)-6-O-methylerythromycin A (compound X)

MS (ESI) m/z=859.5 [M+H]$^+$
1H NMR (600 MHz, CHLOROFORM-d) δ ppm 0.81-0.87 (m, 3H) 0.96-1.01 (m, 3H) 1.05-1.21 (m, 21H) 1.45 (s, 3H) 1.43-1.51 (m, 1H) 1.55-1.62 (m, 2H) 1.66-1.96 (m, 6H) 2.05-2.11 (m, 1H) 2.13 (s, 3H) 2.16-2.25 (m, 2H) 2.38-2.44 (m, 1H) 2.47-2.51 (m, 1H) 2.54 (s, 6H) 2.57-2.66 (m, 1H) 2.68-2.72 (m, 1H) 2.74-2.82 (m, 1H) 2.89-2.94 (m, 1H) 2.96-3.04 (m, 1H) 3.02 (s, 3H) 3.18 (s, 1H) 3.23-3.34 (m, 1H) 3.28 (s, 3H) 3.53-3.57 (m, 1H) 3.59-3.64 (m, 1H) 3.73-3.76 (m, 1H) 3.79-3.82 (m, 1H) 3.85-3.92 (m, 1H) 3.96 (s, 1H) 4.13-4.20 (m, 1H) 4.27-4.36 (m, 1H) 4.61-4.64 (m, 1H) 4.87-4.90 (m, 1H) 5.02-5.06 (m, 1H) 5.10-5.12 (m, 1H)

4''-O-acetyl-3'-dedimethylamino-2'-deoxy-2'-dimethylamino-3'-((R)-3-hydroxypyrrolidin-1-yl)-6-O-methylerythromycin A (compound Y)

MS (ESI) m/z=859.5 [M+H]$^+$
1H NMR (600 MHz, CHLOROFORM-d) δ ppm 0.79-0.89 (m, 3H) 0.95-1.00 (m, 3H) 1.06-1.22 (m, 22H) 1.41-1.51 (m, 1H) 1.47 (s, 3H) 1.53-1.71 (m, 3H) 1.73-1.86 (m, 4H) 1.87-1.96 (m, 1H) 2.11 (s, 3H) 2.12-2.24 (m, 1H) 2.37-2.42 (m, 1H) 2.47-2.65 (m, 4H) 2.52 (s, 6H) 2.72-2.82 (m, 2H) 2.85-3.04 (m, 3H) 3.01 (s, 3H) 3.17 (s, 1H) 3.26 (s, 3H) 3.52-3.57 (m, 1H) 3.72-3.82 (m, 2H) 3.88-3.97 (m, 1H) 3.95 (s, 1H) 4.28-4.39 (m, 2H) 4.65-4.69 (m, 1H) 4.85-4.89 (m, 1H) 4.95-4.99 (m, 1H) 5.01-5.05 (m, 1H)

EXAMPLE 201

3'-dedimethylamino-2'-deoxy-2'-dimethylamino-3'-((S)-3-hydroxypyrrolidin-1-yl)-6-O-methylerythromycin A Using 225 mg of the compound X obtained in Example 200, a reaction was carried out in a similar manner described in Example 89 to give 112 mg of the titled compound.

MS (ESI) m/z=817.5 [M+H]$^+$
1H NMR (600 MHz, CHLOROFORM-d) δ ppm 0.81-0.87 (m, 3H) 0.94-0.99 (m, 3H) 1.08-1.19 (m, 18H) 1.22 (s, 3H) 1.28-1.32 (m, 3H) 1.41-1.50 (m, 1H) 1.47 (s, 3H) 1.51-1.85 (m, 6H) 1.86-1.96 (m, 1H) 2.10-2.28 (m, 3H) 2.32-2.38 (m, 1H) 2.46-2.55 (m, 1H) 2.52 (s, 6H) 2.57-2.67 (m, 2H) 2.72-2.79 (m, 1H) 2.84-2.89 (m, 1H) 2.96-3.03 (m, 2H) 3.02 (s, 3H) 3.19-3.24 (m, 1H) 3.28 (s, 3H) 3.55-3.59 (m, 1H) 3.74-3.77 (m, 1H) 3.77-3.81 (m, 1H) 3.84-3.91 (m, 1H) 3.95 (s, 1H) 4.02-4.09 (m, 1H) 4.21-4.26 (m, 1H) 4.83-4.87 (m, 1H) 5.01-5.06 (m, 1H) 5.07-5.10 (m, 1H)

EXAMPLE 202

3'-dedimethylamino-2'-deoxy-2'-dimethylamino-3'-((R)-3-hydroxypyrrolidin-1-yl)-6-O-methylerythromycin A Using 250 mg of the compound Y obtained in Example 200, a reaction was carried out in a similar manner described in Example 89 to give 135 mg of the titled compound.

MS (ESI) m/z=817.5 [M+H]$^+$
1H NMR (600 MHz, CHLOROFORM-d) δ ppm 0.79-0.87 (m, 3H) 1.06-1.19 (m, 15H) 1.22 (s, 3H) 1.27-1.34 (m, 3H) 1.39-1.85 (m, 8H) 1.47 (s, 3H) 1.86-1.96 (m, 1H) 2.10-2.18 (m, 1H) 2.22-2.33 (m, 2H) 2.46-2.66 (m, 4H) 2.52 (s, 6H) 2.72-2.80 (m, 2H) 2.82-2.95 (m, 2H) 2.95-3.06 (m, 2H) 3.01 (s, 3H) 3.18 (s, 1H) 3.28 (s, 3H) 3.55-3.59 (m, 1H) 3.72-3.80 (m, 2H) 3.89-4.07 (m, 2H) 3.94 (s, 1H) 4.32-4.38 (m, 1H) 4.82-4.87 (m, 1H) 4.97-5.06 (m, 2H)

EXAMPLE 203

3-O-acetyl-5-O—(3'-dedimethylamino-2'-deoxy-2'-dimethylamino-3'-(4-morpholino)desosaminyl)-6-O-methylerythronolide A (1) Using 9 g of 3-O-acetyl-5-O-desosaminyl-6-O-methylerythronolide A described in a literature (Journal of Medicinal Chemistry, 2001, Vol. 44, No. 24, p. 4027-4030), a reaction was carried out in a similar manner described in Example 162 (2) to give 4.53 g of a 2'-OMs compound.

(2) Using 4.5 g of the compound obtained in the above (1), and morpholine instead of the compound obtained in Reference Example (1), a reaction was carried out in a similar manner described in Example 162 (3) to give 2.47 g of the titled compound.

MS (ESI) m/z=701.5 [M+H]$^+$

1H NMR (600 MHz, CHLOROFORM-d) δ ppm 0.81-0.86 (m, 3H) 1.00-1.17 (m, 18H) 1.29 (s, 3H) 1.42-1.54 (m, 2H) 1.55-1.74 (m, 3H) 1.75-1.82 (m, 1H) 1.89-1.97 (m, 1H) 2.15-2.22 (m, 1H) 2.18 (s, 3H) 2.43-2.60 (m, 5H) 2.48 (s, 6H) 2.64-2.71 (m, 2H) 2.78-2.85 (m, 1H) 2.97-3.03 (m, 1H) 3.06 (s, 3H) 3.60-3.74 (m, 6H) 3.77-3.80 (m, 1H) 3.96 (s, 1H) 4.71-4.74 (m, 1H) 5.03-5.07 (m, 1H) 5.15-5.20 (m, 1H)

EXAMPLE 204

5-O-(3'-dedimethylamino-2'-deoxy-2'-dimethylamino-3'-(4-morpholino)desosaminyl)-6-O-methylerythronolide A Using 1.2 g of the compound obtained in Example 203, a reaction was carried out in a similar manner described in Example 89 to give 130 mg of the titled compound.

MS (ESI) m/z=659.5 [M+H]$^+$

1H NMR (600 MHz, CHLOROFORM-d) δ ppm 0.79-0.86 (m, 3H) 0.98-1.03 (m, 3H) 1.08-1.28 (m, 15H) 1.34 (s, 3H) 1.39-1.53 (m, 2H) 1.69-1.82 (m, 2H) 1.86-1.97 (m, 2H) 2.02-2.09 (m, 1H) 2.38-2.50 (m, 2H) 2.44 (s, 6H) 2.52-2.71 (m, 5H) 2.84-2.90 (m, 1H) 2.94-3.03 (m, 1H) 2.96 (s, 3H) 3.23-3.26 (m, 1H) 3.50-3.53 (m, 1H) 3.61-3.72 (m, 6H) 3.80-3.88 (m, 2H) 3.89 (s, 1H) 5.07-5.12 (m, 1H) 5.13-5.18 (m, 1H)

EXAMPLE 205

3-O-(4-pyridylacetyl)-5-O-(3'-dedimethylamino-2'-deoxy-2'-dimethylamino-3'-(4-morpholino)desosaminyl)-6-O-methylerythronolide A Using 120 mg of the compound obtained in Example 204, and 4-pyridylacetate hydrochloride instead of 2-pyridylacetate hydrochloride, a reaction was carried out in a similar manner described in Example 15 (1) to give 123 mg of the titled compound.

MS (ESI) m/z=778.5 [M+H]$^+$

1H NMR (600 MHz, CHLOROFORM-d) δ ppm 0.75-0.84 (m, 3H) 0.90-0.98 (m, 3H) 0.99-1.17 (m, 15H) 1.28 (s, 3H) 1.36-1.53 (m, 2H) 1.56-1.83 (m, 3H) 1.88-1.99 (m, 1H) 2.18-2.28 (m, 1H) 2.42-2.61 (m, 5H) 2.49 (s, 6H) 2.73-2.84 (m, 2H) 2.86-2.93 (m, 1H) 2.95-3.02 (m, 1H) 3.04 (s, 3H) 3.22 (s, 1H) 3.57-3.80 (m, 9H) 3.94 (s, 1H) 4.69-4.76 (m, 1H) 5.08-5.13 (m, 1H) 5.14-5.20 (m, 1H) 7.21-7.27 (m, 2H) 8.54-8.59 (m, 2H)

EXAMPLE 206

3-O-(3-benzyloxycarbamoylpropionyl)-5-O-(3'-dedimethylamino-2'-deoxy-2'-dimethylamino-3'-(4-morpholino)desosaminyl)-6-O-methylerythronolide A (1) Using 5.0 g of 2'-O-acetyl-5-O-desosaminyl-6-O-methylerythronolide A described in a literature (Journal of Medicinal Chemistry, 2001, Vol. 44, No. 24, p. 4027-4030), N-carbobenzoxy-β-alanine instead of 2-pyridyl acetate hydrochloride, and dichloromethane instead of chloroform, a reaction was carried out in a similar manner described in Example 15 (1) to give 4.87 g of 3-O-(3-benzyloxy carbamoyl propionyl)-5-O-densosaminyl-6-O-methylerythronolide A.

(2) Using 4.87 g of the compound obtained in the above (1), a reaction was carried out in a similar manner described in Example 162 (2) to give 3.49 g of a 2'-OMs compound.

(3) Using 3.49 g of the compound obtained in the above (2), and morpholine instead of the compound obtained in Reference Example (1), a reaction was carried out in a similar manner described in Example 162 (3) to give 2.47 g of the titled compound.

MS (ESI) m/z=864.4 [M+H]$^+$

1H NMR (600 MHz, CHLOROFORM-d) δ ppm 0.79-0.85 (m, 3H) 0.98-1.07 (m, 9H) 1.09-1.18 (m, 9H) 1.28 (s, 3H) 1.37-1.42 (m, 1H) 1.44-1.53 (m, 1H) 1.56-1.70 (m, 2H) 1.75-1.82 (m, 1H) 1.89-1.98 (m, 1H) 2.17-2.24 (m, 1H) 2.35-2.42 (m, 2H) 2.45 (s, 6H) 2.47-2.59 (m, 3H) 2.60-2.78 (m, 3H) 2.78-2.85 (m, 2H) 2.96-3.03 (m, 1H) 3.05 (s, 3H) 3.47-3.53 (m, 2H) 3.61-3.70 (m, 6H) 3.76-3.79 (m, 1H) 3.95 (s, 1H) 4.65-4.69 (m, 1H) 5.01-5.13 (m, 3H) 5.15-5.19 (m, 1H) 5.52-5.58 (m, 1H) 7.27-7.38 (m, 5H)

EXAMPLE 207

3-O-(3-dimethylaminopropionyl)-5-O-(3'-dedimethylamino-2'-deoxy-2'-dimethylamino-3'-(4-morpholino)desosaminyl)-6-O-methylerythronolide A (1) 800 mg of the compound obtained in Example 206 was dissolved in 10 ml of methanol, to which 800 mg of 5% palladium-carbon was added, and the mixture was stirred at room temperature for 8 hours in a hydrogen atmosphere having 1 atm pressure. The reaction solution was filtered through Celite, and the filtrate was evaporated under reduced pressure. The resulting residue was purified by silica gel column chromatography [(chloroform:methanol:ammonia water solution=10:1:0.1):chloroform=1:1 to 3:1] to give 425 mg of 3-O-(3-aminopropionyl)-5-O-desosaminyl-6-O-methylerythronolide A.

(2) Using 415 mg of the compound obtained in the above (1), and 37% aqueous formaldehyde solution instead of glyoxyl acid, a reaction was carried out in a similar manner described in Example 179 to give 276 mg of the titled compound.

MS (ESI) m/z=758.5 [M+H]$^+$

1H NMR (600 MHz, CHLOROFORM-d) δ ppm 0.80-0.85 (m, 3H) 1.02-1.17 (m, 18H) 1.28 (s, 3H) 1.39-1.53 (m, 2H) 1.59-1.74 (m, 2H) 1.75-1.83 (m, 1H) 1.89-1.97 (m, 1H) 2.15-2.24 (m, 1H) 2.22 (s, 6H) 2.43-2.64 (m, 9H) 2.47 (s, 6H) 2.70-2.74 (m, 1H) 2.75-2.85 (m, 2H) 2.98-3.03 (m, 1H) 3.06 (s, 3H) 3.61-3.73 (m, 7H) 3.76-3.79 (m, 1H) 3.95 (s, 1H) 4.73-4.76 (m, 1H) 5.07-5.11 (m, 1H) 5.13-5.20 (m, 1H)

EXAMPLE 208

3-deoxy-3-oxo-5-O-(3'-dedimethylamino-2'-deoxy-2'-dimethylamino-3-(4-morpholino)desosaminyl)-6-O-methylerythronolide A (1) Using 1.0 g of 3-O-deoxy-3-O-oxo-6-O-methylerythronolide A described in a literature (Journal of Medicinal Chemistry, 1998, Vol. 21, No. 41, p. 4080-4100), a reaction was carried out in a similar manner described in Example 162 (2) to give 333 mg of a 2'-OMs compound.

(2) Using 323 mg of the compound obtained in the above (1), and morpholine instead of the compound obtained in Reference Example (1), a reaction was carried out in a similar manner described in Example 162 (3) to give 71 mg of the titled compound.

MS (ESI) m/z=657.5 [M+H]$^+$

1H NMR (600 MHz, CHLOROFORM-d) δ ppm 0.80-0.89 (m, 3H) 1.08-1.23 (m, 15H) 1.28-1.39 (m, 6H) 1.41-1.56 (m, 1H) 1.58-1.78 (m, 4H) 1.91-1.99 (m, 1H) 2.38-2.52 (m, 5H) 2.43 (s, 6H) 2.55-2.64 (m, 2H) 2.70 (s, 3H) 2.96-3.09 (m, 2H) 3.24 (s, 1H) 3.59-3.70 (m, 4H) 3.77-3.85 (m, 2H) 3.87 (s, 1H) 3.88-3.91 (m, 1H) 4.23-4.27 (m, 1H) 4.91-4.95 (m, 1H) 5.09-5.14 (m, 1H)

EXAMPLE 209

4''-O-acetyl-3'-dedimethylamino-2'-deoxy-2'-dimethylamino-3'-(4-morpholino)-6-O-methylerythromycin B (1) 2.0 g of 6-O-methylerythromycin B described in a literature (The Journal of Antibiotics, 1990, Vol. 43, No. 5, p. 544-549) was suspended in 20 ml of chloroform, to which 167 mg of 4-dimethylaminopyridine and 900 μl of acetic anhydride were added in this order, and the mixture was stirred at room temperature for 16 hours. The reaction solution was washed with a saturated aqueous sodium bicarbonate solution, dried over anhydrous magnesium sulfate, and then filtered. The filtrate was evaporated under reduced pressure, the resulting residue was suspended in 80 ml of methanol, and the mixture was stirred under reflux for 15 hours. The reaction solution was evaporated under reduced pressure, and the resulting residue was purified by [(acetone:hexane:triethylamine=10:10:0.2)] to give 1.7 g of 4''-O-acetyl-6-O-methylerythromycin B.

(2) 1.6 g of the compound obtained in the above (1) was dissolved in 10 ml of chloroform, and 866 μl of triethylamine was added to which 10 ml of a solution of 320 μl of methanesulfonyl chloride dissolved in chloroform was added under ice cooling, and the mixture was stirred for 16 hours being raised to room temperature. A saturated aqueous sodium bicarbonate solution was added to the reaction solution, and the mixture was extracted with chloroform. The organic layer was dried over anhydrous magnesium sulfate, filtered, and the filtrate was evaporated under reduced pressure. The resulting residue was purified by [(acetone:hexane:triethylamine=10:10:0.2):hexane=3:7 to 2:3] to give 1.4 g of a 2'-OMs compound.

(3) 660 mg of the compound obtained in the above (2) was dissolved in 8 ml of N,N-dimethylformamide, to which 878 μl of morpholine was added, and the mixture was stirred at 70° C. for 18 hours. Water was added to the reaction solution, and the mixture was extracted with ethyl acetate. The organic layer was washed with water, dried over anhydrous magnesium sulfate, and filtered. The filtrate was evaporated under reduced pressure, the resulting residue was purified by silica gel column chromatography [(acetone:hexane:triethylamine=10:10:0.2):hexane=3:7 to 2:3] to give 420 mg of the titled compound.

MS (ESI) m/z=843.6 [M+H]$^+$

1H NMR (600 MHz, CHLOROFORM-d) δ ppm 0.81-0.91 (m, 6H) 0.94-1.15 (m, 18H) 1.15-1.20 (m, 3H) 1.42 (s, 3H) 1.43-1.50 (m, 1H) 1.57-1.77 (m, 6H) 1.84-1.95 (m, 2H) 2.05 (s, 3H) 2.36-2.41 (m, 1H) 2.46-2.57 (m, 4H) 2.51 (s, 6H) 2.59-2.71 (m, 3H) 2.80-2.92 (m, 2H) 3.08 (s, 3H) 3.14-3.17 (m, 1H) 3.28 (s, 3H) 3.60-3.65 (m, 1H) 3.67-3.85 (m, 7H) 4.36-4.44 (m, 1H) 4.62-4.66 (m, 1H) 4.88-4.92 (m, 1H) 4.98-5.00 (m, 1H) 5.35-5.40 (m, 1H)

EXAMPLE 210

3'-dedimethylamino-2'-deoxy-2'-dimethylamino-3'-(4-morpholino)-6-O-methylerythromycin B 200 mg of the compound obtained in Example 209 was dissolved in 2 ml of methanol, to which 71 μl of 1,8-diazabicyclo[5.4.0]undecan-7-ene was added, and the mixture was stirred under reflux for 7 hours. The reaction solution was evaporated under reduced pressure, and the resulting residue was purified by silica gel column chromatography [(acetone:hexane:triethylamine=10:10:0.2):hexane=1:4 to 3:7] to give 170 mg of the titled compound.

MS (ESI) m/z=801.6 [M+H]$^+$

1H NMR (600 MHz, CHLOROFORM-d) δ ppm 0.81-0.90 (m, 6H) 0.95-1.00 (m, 6H) 1.07-1.11 (m, 3H) 1.12-1.20 (m, 6H) 1.22-1.26 (m, 3H) 1.27-1.31 (m, 3H) 1.43 (s, 3H) 1.43-1.50 (m, 1H) 1.56-1.74 (m, 6H) 1.83-1.94 (m, 2H) 2.30-2.34 (m, 1H) 2.35-2.38 (m, 1H) 2.46-2.51 (m, 4H) 2.51 (s, 6H) 2.56-2.69 (m, 3H) 2.79-2.86 (m, 1H) 2.87-2.92 (m, 1H) 2.99-3.03 (m, 1H) 3.07-3.10 (m, 3H) 3.13-3.15 (m, 1H) 3.30 (s, 3H) 3.63-3.66 (m, 1H) 3.67-3.80 (m, 6H) 3.81-3.85 (m, 1H) 4.01-4.08 (m, 1H) 4.87-4.90 (m, 1H) 4.98-5.01 (m, 1H) 5.35-5.40 (m, 1H)

EXAMPLE 211

3,11-dideoxy-5-O-(3'-dedimethylamino-2'-deoxy-2'-dimethylamino-3'-(4-morpholino)desosaminyl)-11-{4-[4-(pyridin-3-yl)-1H-imidazol-1-yl]butyl}-amino-3-oxo-6-O-methylerythronolide A 11,12-cyclic carbamate (1) 1.0 g of 3,11-O-dideoxy-5-desosaminyl-11-{4-[4-(pyridin-3-yl)-1H-imidazol-1-yl]butyl}amino-3-O-oxo-6-O-methylerythronolide A 11,12-cyclic carbamate described in a literature (Bioorganic Medicinal Chemistry Letters, 1999, Vol. 21, No. 9, p. 3075-3080) was dissolved in 8 ml of chloroform, to which 514 μl of triethylamine was added. Under ice cooling, 4 ml of a solution of 190 μl of methanesulfonyl chloride dissolved in chloroform was added thereto, and the mixture was stirred for 1 hour. Thereafter, the ice bath was removed, and the mixture was stirred for 4 hours being raised to room temperature. A saturated aqueous sodium bicarbonate solution was added to the reaction solution, the mixture was extracted with chloroform. The organic layer was dried over anhydrous magnesium sulfate, filtered, and then the filtrate was evaporated under reduced pressure. The resulting residue was purified by silica gel column chromatography [(chloroform:methanol:ammonia water solution=10:1:0.1):chloroform=1:4 to 1:2] to give 680 mg of a 2'-OMs compound.

(2) 672 mg of the compound obtained in the above (1) was dissolved in 8 ml of N,N-dimethylformamide, to which 856 μl of morpholine was added. The mixture was stirred at 70° C. for 12 hours, and at 85° C. for 13 hours. Water was added to the reaction solution, and the mixture was extracted with ethyl acetate. The organic layer was washed with water, dried over anhydrous magnesium sulfate, filtered, and the filtrate was evaporated under reduced pressure. The resulting residue was purified by silica gel column chromatography [(chloroform:methanol:ammonia water solution=10:1:0.1):chloroform=1:4 to 1:2] to give 365 mg of the titled compound.

MS (ESI) m/z=881.3 [M+H]$^+$

1H NMR (600 MHz, CHLOROFORM-d) δ ppm 0.80-0.85 (m, 3H) 0.96-1.02 (m, 3H) 1.11-1.20 (m, 9H) 1.32-1.40 (m, 6H) 1.47 (s, 3H) 1.51-1.76 (m, 6H) 1.82-1.99 (m, 4H) 2.38-2.52 (m, 5H) 2.43 (s, 6H) 2.54-2.63 (m, 2H) 2.61 (s, 3H) 2.97-3.04 (m, 1H) 3.09-3.16 (m, 1H) 3.56 (s, 1H) 3.59-3.86 (m, 8H) 3.96-4.03 (m, 2H) 4.11-4.16 (m, 1H) 4.89-4.94 (m, 2H) 7.26-7.30 (m, 1H) 7.31-7.35 (m, 1H) 7.52-7.54 (m, 1H) 8.05-8.10 (m, 1H) 8.42-8.46 (m, 1H) 8.94-8.97 (m, 1H)

EXAMPLE 212

6,11,4"-O-triacetyl-3'-dedimethylamino-2'-deoxy-2'-dimethylamino-3'-(4-morpholino)-9-deoxo-9a-aza-9a-methyl-9a-homoerythromycin A 1.21 g of 2'-O-methanesulfonyl-6,11,4"-O-triacetyl-9-deoxo-9a-aza-9a-methyl-9a-homoerythromycin A described in a patent document (WO 2003070174) was dissolved in 16 ml of N,N-dimethylformamide, to which 220 µl of morpholine was added, and the mixture was stirred at 70° C. for 15 hours. Ethyl acetate was added to the reaction solution followed by separation. The organic layer was washed with water and saturated brine in this order, dried over anhydrous magnesium sulfate, and filtered. Thereafter, the filtrate was evaporated under reduced pressure, and the resulting residue was purified by silica gel column chromatography [(acetone:hexane:triethylamine=10:10:0.2):hexane=1:4 to 3:7] to give 490 mg of the titled compound.

MS (ESI) m/z=944.6 [M+H]$^+$

1H NMR (600 MHz, CHLOROFORM-d) δ ppm 0.83-1.20 (m, 21H) 1.37 (s, 3H) 1.38-1.43 (m, 3H) 1.56-1.73 (m, 6H) 1.61 (s, 3H) 1.84 (s, 3H) 1.87-2.01 (m, 2H) 2.05 (s, 3H) 2.14 (s, 3H) 2.19 (s, 1H) 2.19 (s, 3H) 2.34-2.58 (m, 9H) 2.45 (s, 6H) 2.76-2.84 (m, 1H) 2.87-2.94 (m, 1H) 3.24-3.25 (m, 3H) 3.26-3.32 (m, 1H) 3.64-3.85 (m, 5H) 4.47-4.53 (m, 1H) 4.56-4.62 (m, 1H) 4.67-4.70 (m, 1H) 4.86-4.89 (m, 1H) 4.98-5.00 (m, 1H) 5.42-5.45 (m, 1H) 5.76-5.80 (m, 1H)

EXAMPLE 213

3'-dedimethylamino-2'-deoxy-2'-dimethylamino-3'-(4-morpholino)-9-deoxo-9a-aza-9a-methyl-9a-homoerythromycin A 200 mg of the compound obtained in Example 212 was dissolved in 3 ml of methanol, to which 124 µl of 1,8-diazabicyclo[5.4.0]undecan-7-ene was added, and the mixture was stirred under reflux for 18 hours. The reaction solution was evaporated under reduced pressure, and the resulting residue was purified by silica gel column chromatography [(chloroform:methanol:ammonia water solution: 10:1:0.1):chloroform=1:4 to 7:3] to give 56 mg of the titled compound.

MS (ESI) m/z=818.5 [M+H]$^+$

1H NMR (600 MHz, CHLOROFORM-d) δ ppm 0.84-0.91 (m, 6H) 0.92-0.98 (m, 3H) 1.02-1.12 (m, 6H) 1.13-1.18 (m, 3H) 1.19-1.24 (m, 6H) 1.26-1.40 (m, 7H) 1.42-1.75 (m, 4H) 1.78-2.11 (m, 5H) 2.26-2.35 (m, 1H) 2.32 (s, 3H) 2.45-2.81 (m, 8H) 2.52 (s, 6H) 2.97-3.05 (m, 1H) 3.33 (s, 3H) 3.60-3.83 (m, 7H) 4.00-4.14 (m, 2H) 4.42-4.46 (m, 1 fi) 4.65-4.71 (m, 1H) 4.96-5.00 (m, 1H) 5.00-5.06 (m, 1H)

EXAMPLE 214

4"-O-acetyl-3'-N-demethyl-3'-N-(2-dimethylaminoethyl)-6-methylerythromycin A

Using 5.0 g of the compound obtained in Example 162 (1), a reaction was carried out in a similar manner described in Example 7, Example 8 and Example 9 to give 986 mg of the titled compound.

MS (ESI) m/z=847.4 [M+H]$^+$

1H NMR (600 MHz, CHLOROFORM-d) δ ppm 0.77-0.87 (m, 3H) 1.06-1.23 (m, 24H) 1.20-1.30 (m, 1H) 1.37 (s, 3H) 1.42-1.51 (m, 1H) 1.58-1.73 (m, 3H) 1.80-1.97 (m, 3H) 2.10 (s, 3H) 2.22 (s, 6H) 2.30 (s, 3H) 2.30-2.37 (m, 1H) 2.37-2.51 (m, 3H) 2.51-2.60 (m, 2H) 2.63-2.71 (m, 1H) 2.85-2.94 (m, 1H) 2.96-3.02 (m, 1H) 3.03 (s, 3H) 3.12-3.19 (m, 2H) 3.31 (s, 3H) 3.61-3.66 (m, 1H) 3.67-3.79 (m, 3H) 3.97 (s, 1H) 4.30-4.38 (m, 1H) 4.51-4.55 (m, 1H) 4.63-4.68 (m, 1H) 4.95-4.99 (m, 1H) 5.03-5.08 (m, 1H)

EXAMPLE 215

4'-O-acetyl-3'-dedimethylamino-2'-deoxy-2'-(2-dimethylaminoethyl)-3'-(4-morpholino)-6-O-methyl-erythromycin A (1) Using 1.0 g of the compound obtained in Example 214, a reaction was carried out in a similar manner described in Example 162 (2) to give 1.12 g of a 2'-OMs compound.

(2) Using 1.12 g of the compound obtained in the above (1), and morpholine instead of the compound obtained in Reference Example (1), a reaction was carried out in a similar manner described in Example 162 (3) to give 514 mg of the titled compound.

MS (ESI) m/z=916.5 [M+H]$^+$

1H NMR (600 MHz, CHLOROFORM-d) δ ppm 0.79-0.87 (m, 3H) 0.95-1.01 (m, 3H) 1.05-1.22 (m, 21H) 1.40 (s, 3H) 1.42-1.52 (m, 1H) 1.55-1.85 (m, 6H) 1.87-1.96 (m, 1H) 2.04 (s, 3H) 2.19-2.41 (m, 4H) 2.24 (s, 6H) 2.47-2.63 (m, 2H) 2.52 (s, 6H) 2.65-2.69 (m, 1H) 2.74-2.81 (m, 2H) 2.82-2.90 (m, 1H) 3.02 (s, 2H) 3.02 (s, 3H) 3.28 (s, 3H) 3.58-3.61 (m, 1H) 3.67-3.85 (m, 7H) 3.93 (s, 1H) 4.35-4.41 (m, 1H) 4.88-4.91 (m, 1H) 4.94-4.96 (m, 1H) 5.01-5.06 (m, 1H)

EXAMPLE 216

3'-dedimethylamino-2'-deoxy-2'-(2-dimethylaminoethyl)-3'-(4-morpholino)-6-O-methylerythromycin A Using 414 mg of the compound obtained in Example 215, a reaction was carried out in a similar manner described in Example 89 to give 214 mg of the titled compound.

MS (ESI) m/z=874.4 [M+H]$^+$

1H NMR (600 MHz, CHLOROFORM-d) δ ppm 0.80-0.88 (m, 3H) 0.94-0.97 (m, 3H) 1.09-1.31 (m, 21H) 1.42 (s, 3H) 1.42-1.51 (m, 1H) 1.54-1.59 (m, 1H) 1.60-1.84 (m, 5H) 1.87-1.97 (m, 1H) 2.23 (s, 6H) 2.29-2.39 (m, 3H) 2.44-2.64 (m, 6H) 2.53 (s, 3H) 2.72-2.87 (m, 3H) 2.92-3.04 (m, 3H) 3.02 (s, 3H) 3.17 (s, 1H) 3.29 (s, 3H) 3.59-3.64 (m, 1H) 3.65-3.83 (m, 7H) 3.91 (s, 1H) 3.98-4.06 (m, 1H) 4.85-4.89 (m, 1H) 4.94-4.96 (m, 1H) 5.01-5.06 (m, 1H)

The structural formula of each compound of Examples is shown in the following tables.

TABLE 1-1
| Ex. No. | Structural Formula |
|---|---|
| 1 | 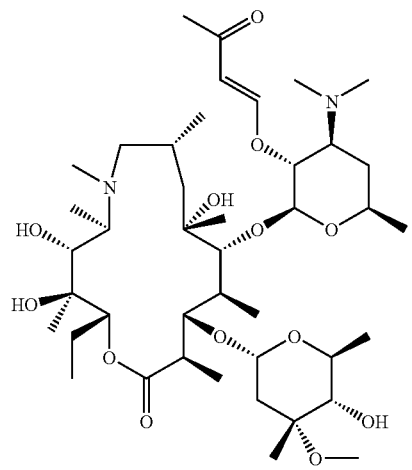 |
| 2 | 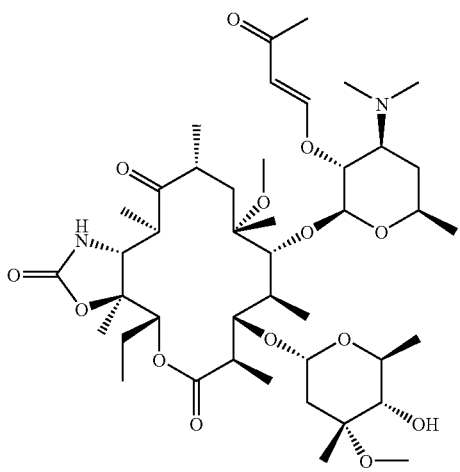 |
| 3 | 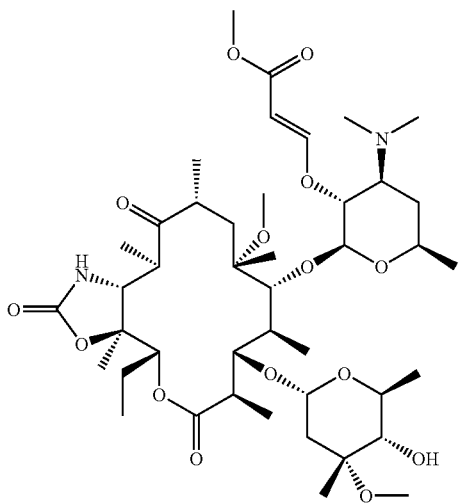 |

TABLE 1-1-continued
| Ex. No. | Structural Formula |
|---|---|
| 4 | 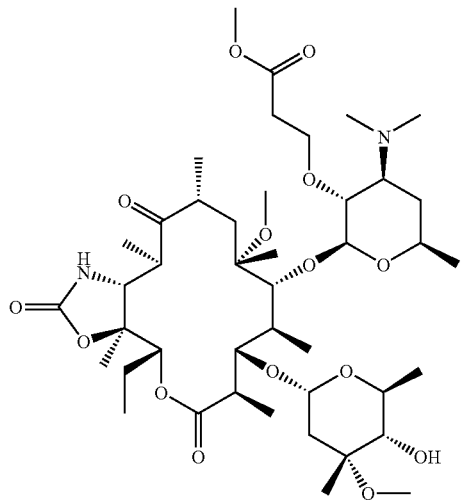 |
| 5 | 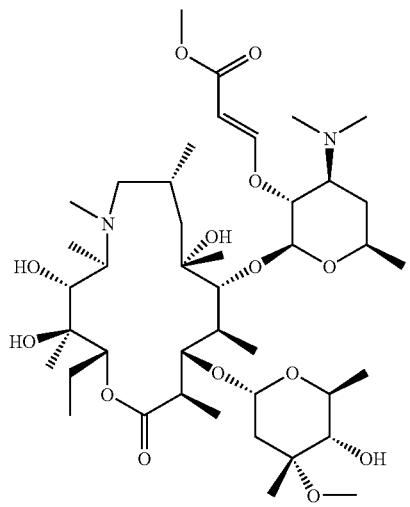 |
| 6 | 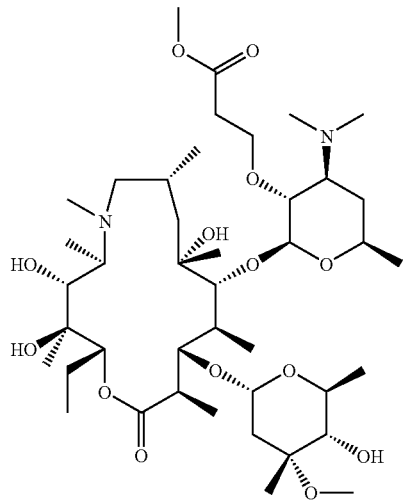 |

TABLE 1-1-continued
| Ex. No. | Structural Formula |
|---|---|
| 7 | 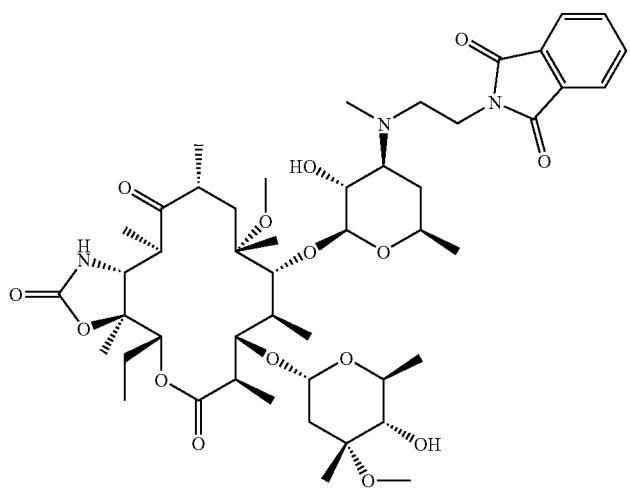 |
| 8 | 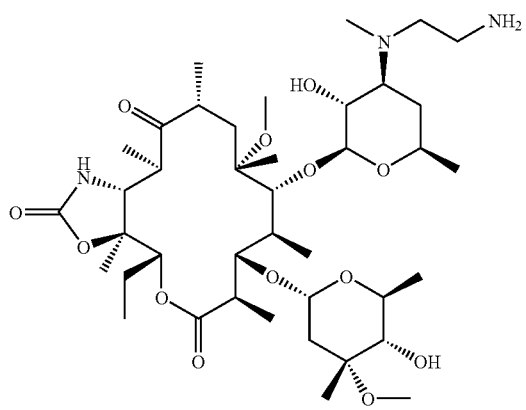 |
| 9 | 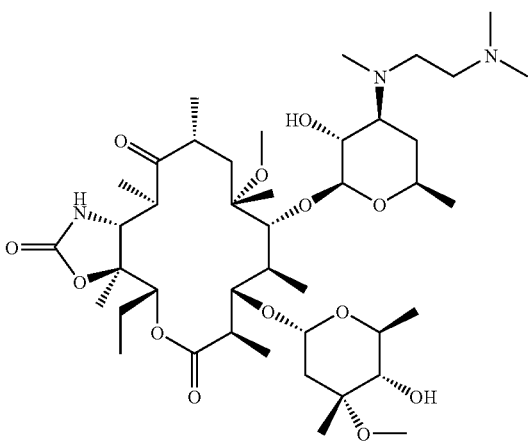 |

TABLE 1-1-continued

| Ex. No. | Structural Formula |
|---|---|
| 10 | (structure) |

TABLE 1-2

| Ex. No. | Structural Formula |
|---|---|
| 11 | (structure) |
| 12 | (structure) |

TABLE 1-2-continued

| Ex. No. | Structural Formula |
|---|---|
| 13 | (structure) |
| 14 | (structure) |

TABLE 1-2-continued
| Ex. No. | Structural Formula |
|---|---|
| 15 | 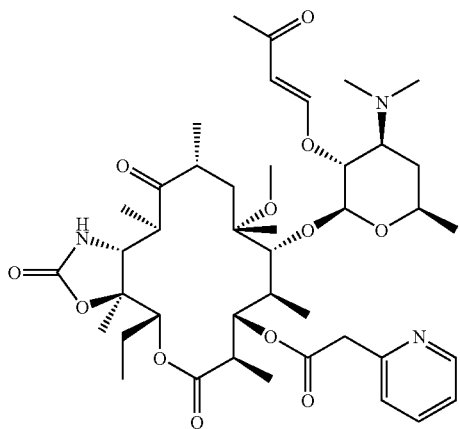 |
| 16 | 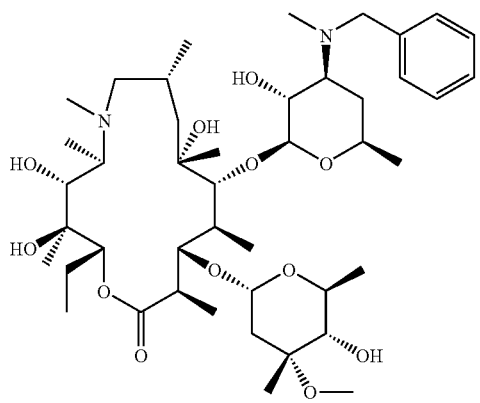 |
| 17 | 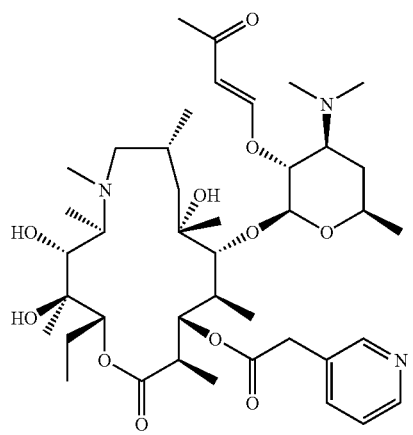 |
| 18 | 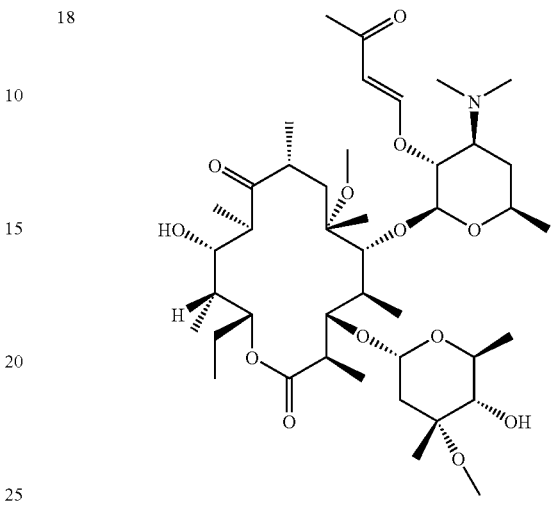 |
| 19 | 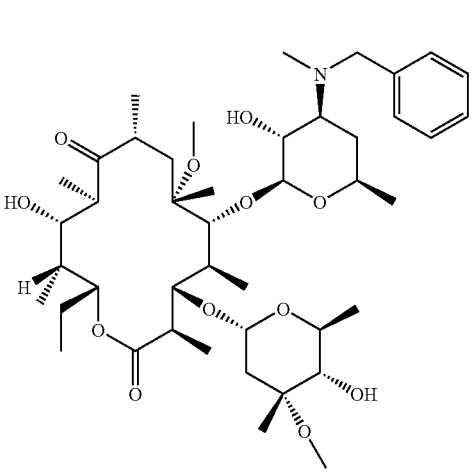 |
| 20 | 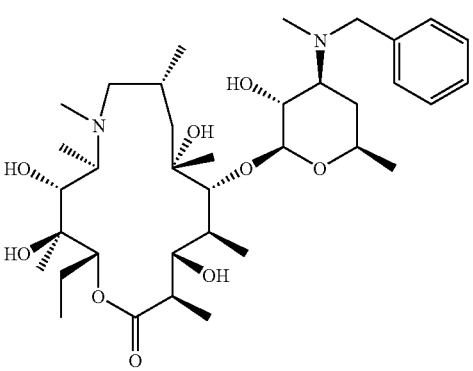 |

TABLE 1-3

| Ex. No. | Structural Formula |
|---|---|
| 21 | |
| 22 | |
| 23 | |
| 24 | |

TABLE 1-3-continued
| Ex. No. | Structural Formula |
|---|---|
| 25 | 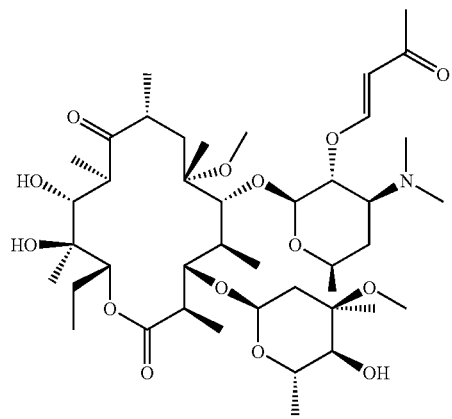 |
| 26 | 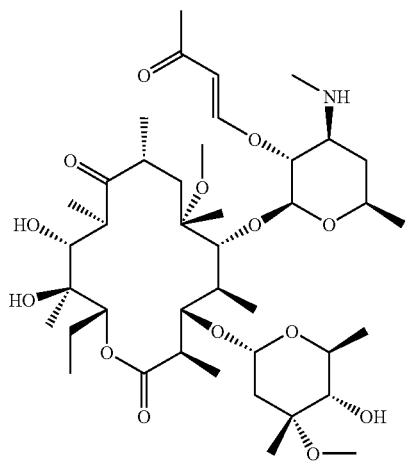 |
| 27 | 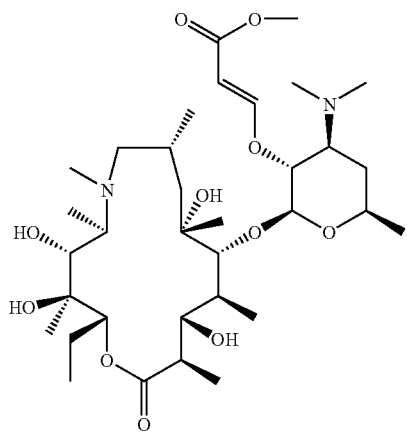 |

TABLE 1-3-continued
| Ex. No. | Structural Formula |
|---|---|
| 28 | 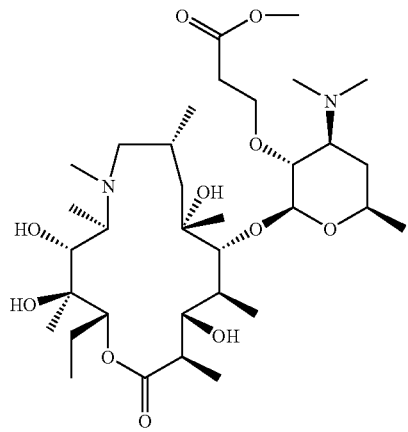 |
| 29 | 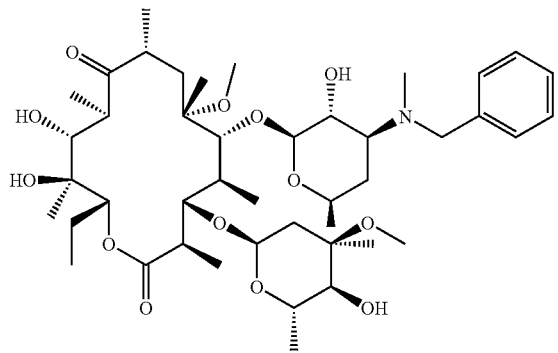 |
| 30 Compound A | 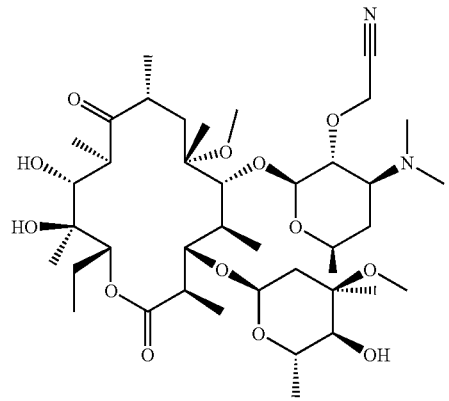 |

TABLE 1-4
| Ex. No. | Structural Formula |
| --- | --- |
| 30 Compound B | 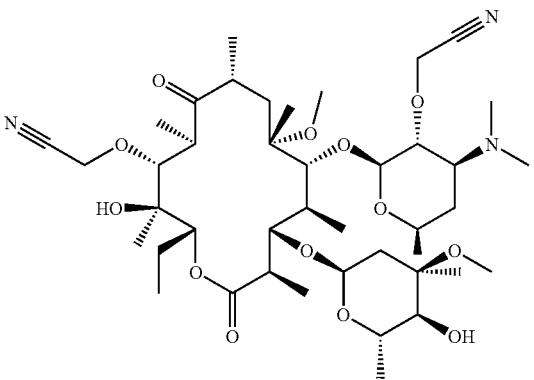 |
| 31 | 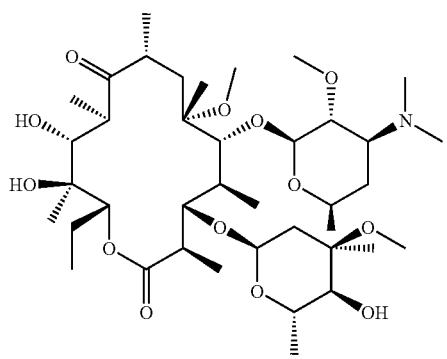 |
| 32 | 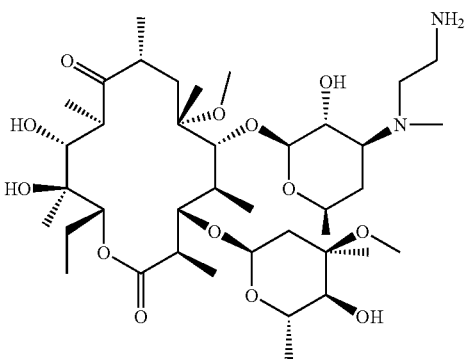 |
| 33 | 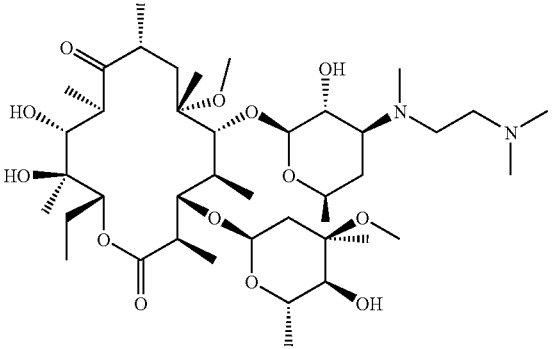 |

TABLE 1-4-continued
| Ex. No. | Structural Formula |
|---|---|
| 34 | 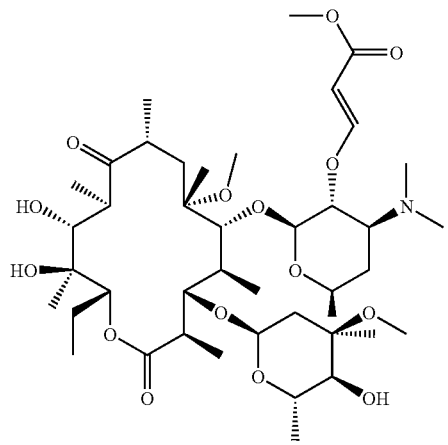 |
| 35 | 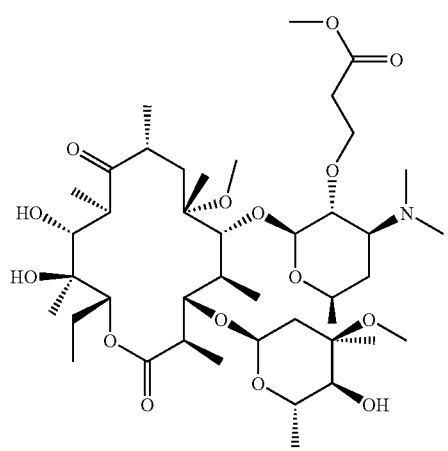 |
| 36 | 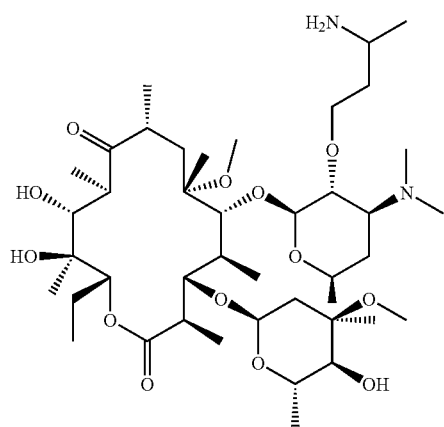 |

TABLE 1-4-continued
| Ex. No. | Structural Formula |
|---|---|
| 37 | 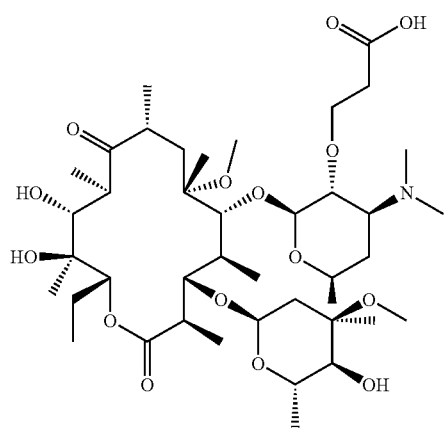 |
| 38 | 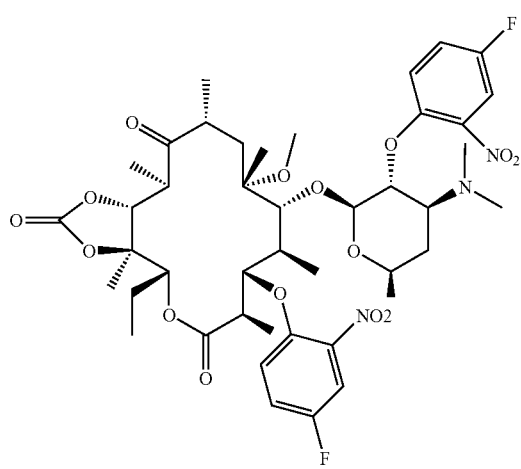 |
| 39 | 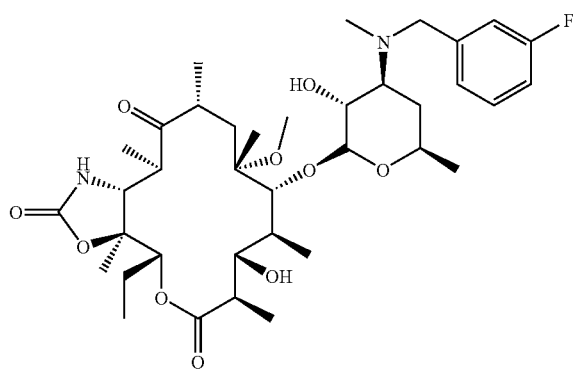 |

TABLE 1-5
| Ex. No. | Structural Formula |
|---|---|
| 40 | 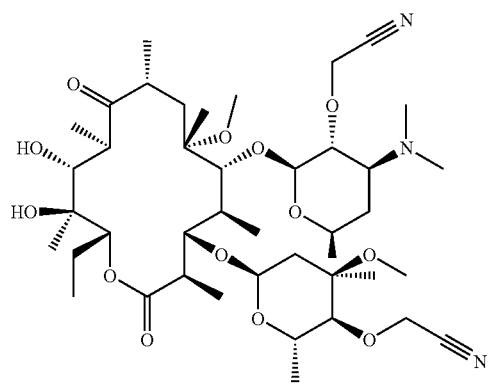 |
| 41 | 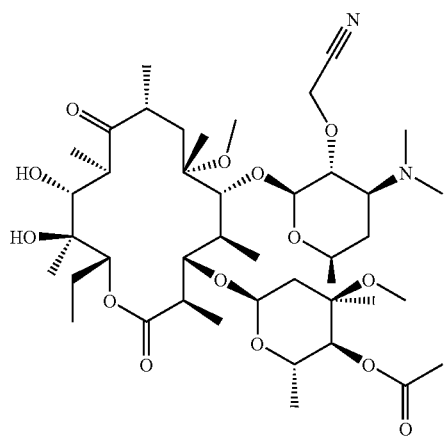 |
| 42 | 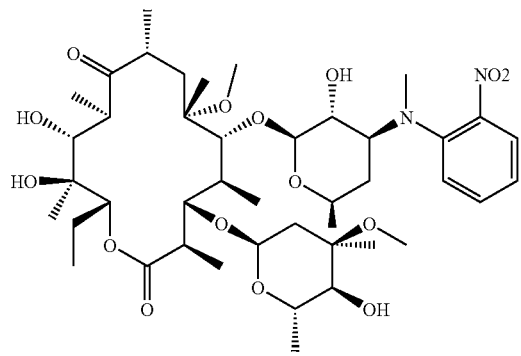 |
| 43 | 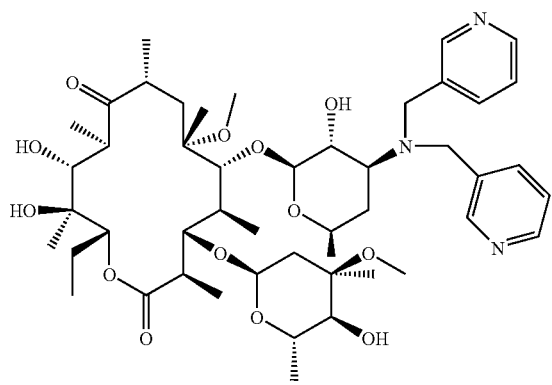 |

TABLE 1-5-continued
| Ex. No. | Structural Formula |
|---|---|
| 44 | 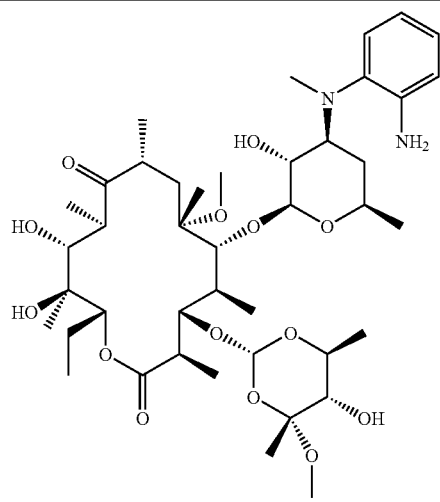 |
| 45 | 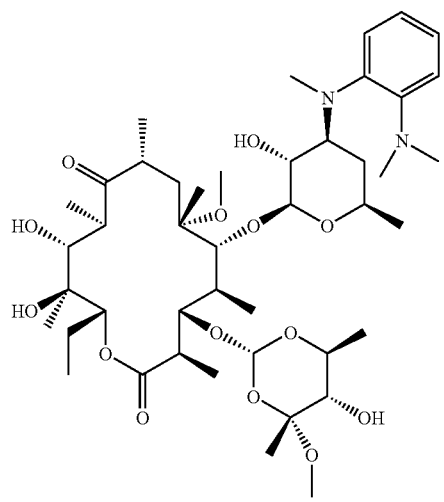 |
| 46 | 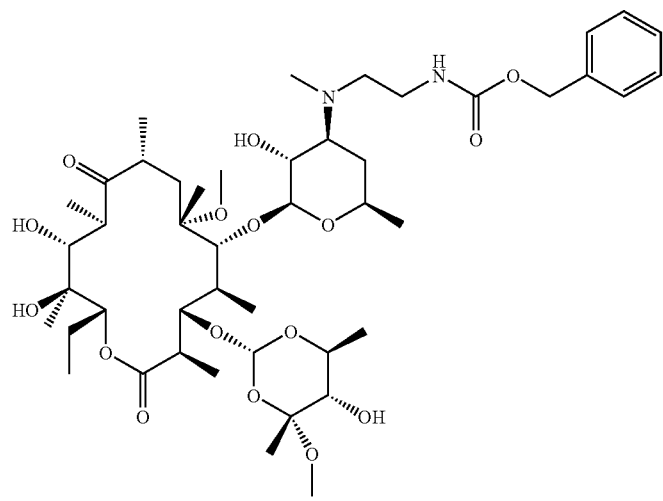 |

TABLE 1-5-continued

| Ex. No. | Structural Formula |
|---|---|
| 47 | |
| 48 | |
| 49 | |

TABLE 1-6

| Ex. No. | Structural Formula |
|---|---|
| 50 | |
| 51 Compound C | |
| 51 Compound D | |
| 52 | |
| 53 | |
| 54 | |
| 55 | |
| 56 | |

TABLE 1-6-continued

| Ex. No. | Structural Formula |
|---|---|
| 57 | |
| 58 | |

TABLE 1-7

| Ex. No. | Structural Formula |
|---|---|
| 59 | |
| 60 | |

TABLE 1-7-continued
| Ex. No. | Structural Formula |
|---|---|
| 61 | 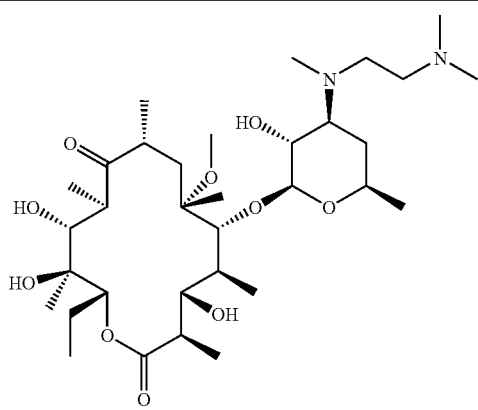 |
| 62 | 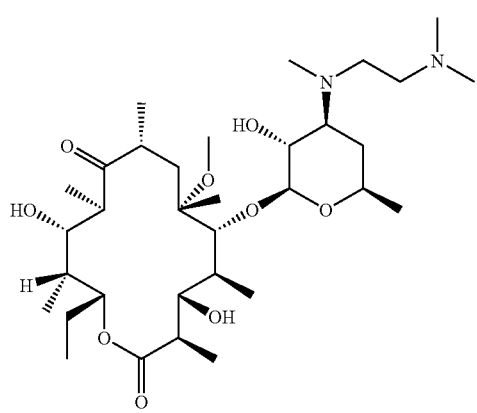 |
| 63 | 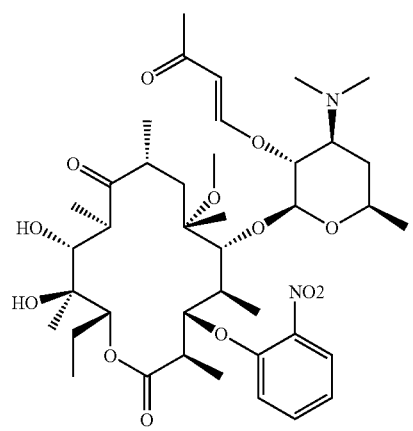 |

TABLE 1-7-continued
| Ex. No. | Structural Formula |
|---|---|
| 64 | 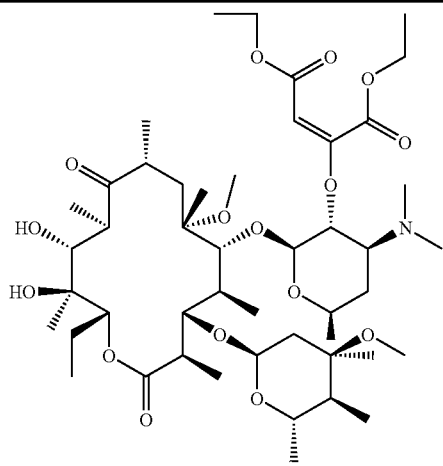 |
| 65 | 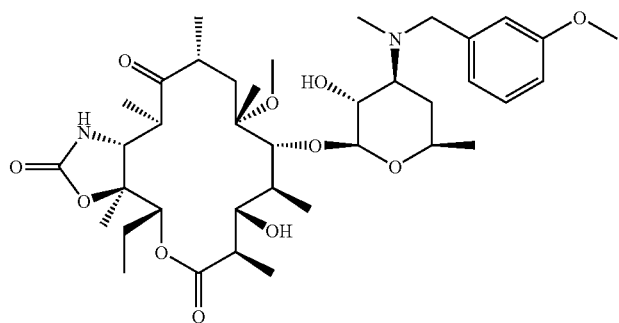 |
| 66 | 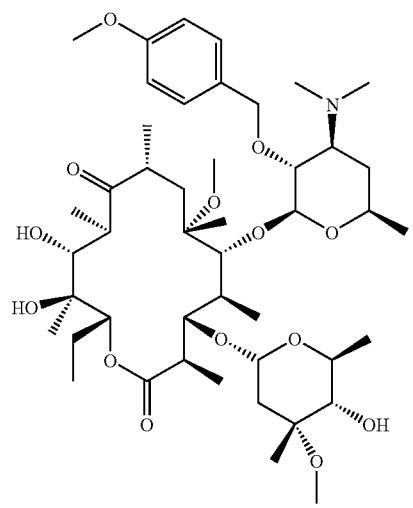 |

TABLE 1-7-continued
| Ex. No. | Structural Formula |
| --- | --- |
| 67 | 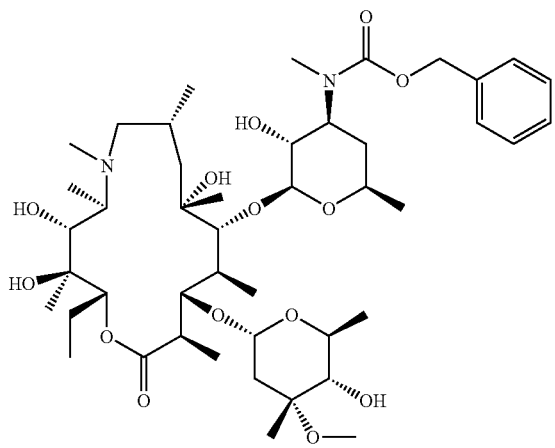 |
| 68 | 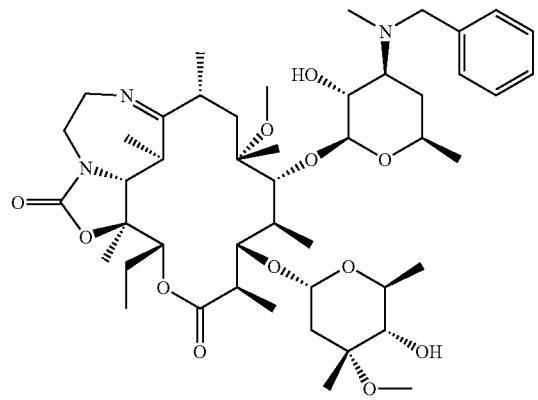 |
TABLE 1-8
| Ex. No. | Structural Formula |
| --- | --- |
| 69 | 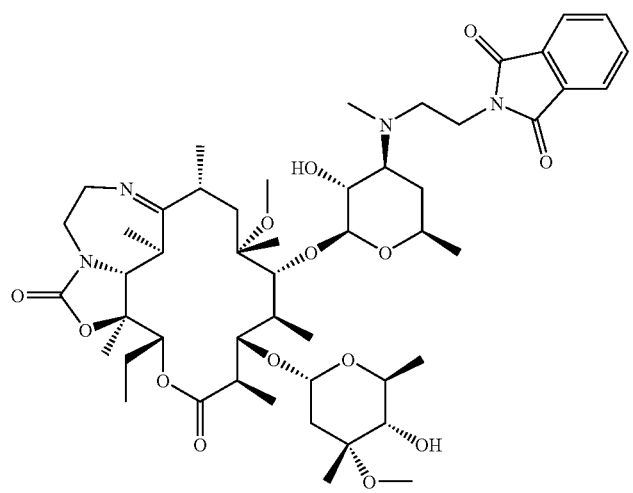 |

TABLE 1-8-continued
| Ex. No. | Structural Formula |
|---|---|
| 70 | 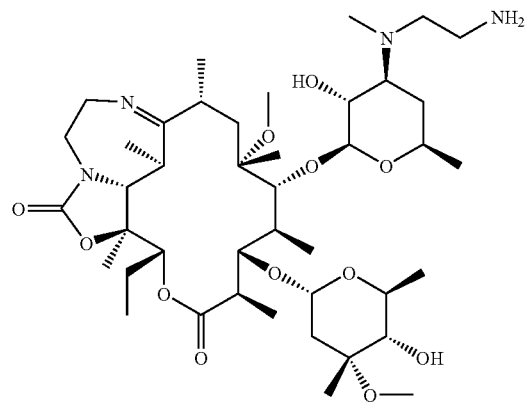 |
| 71 | 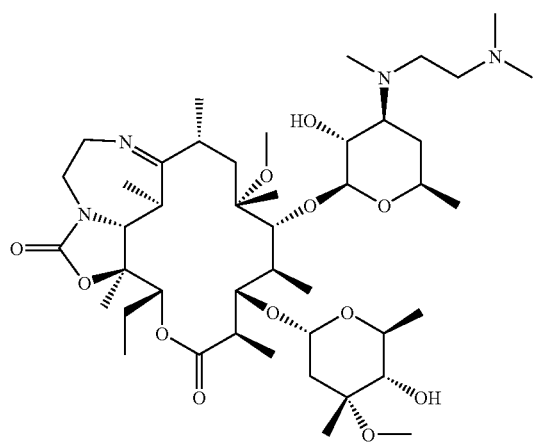 |
| 72 | 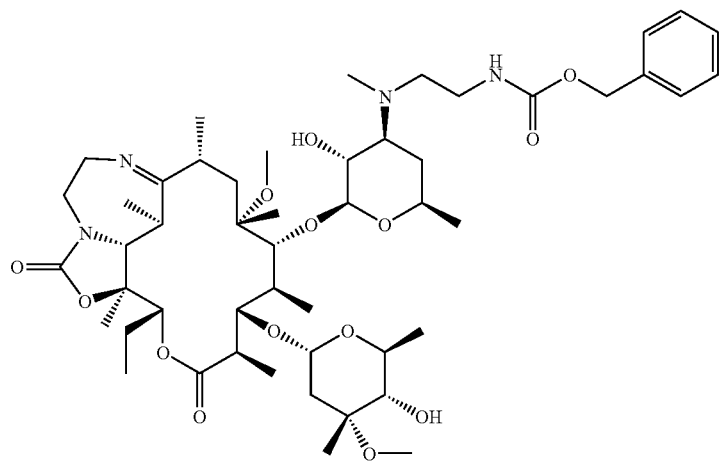 |

TABLE 1-8-continued
| Ex. No. | Structural Formula |
|---|---|
| 73 | 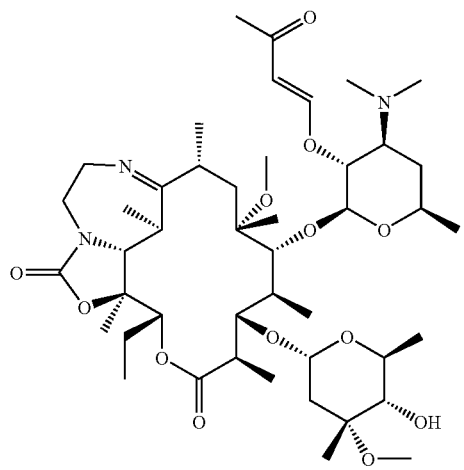 |
| 74 | 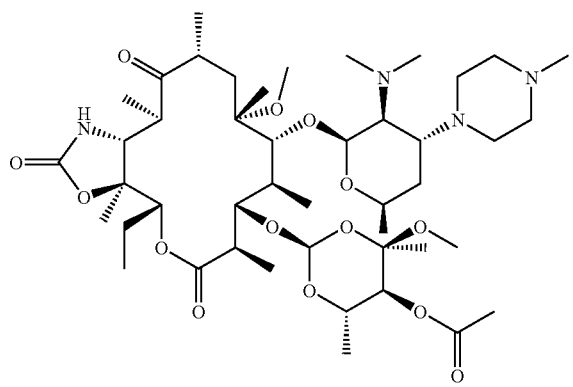 |
| 75 | 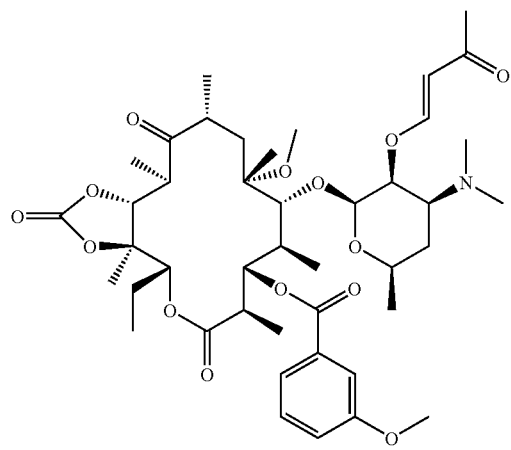 |

TABLE 1-8-continued

| Ex. No. | Structural Formula |
|---|---|
| 76 | |
| 77 | |
| 78 | |

TABLE 1-9
| Ex. No. | Structural Formula |
|---|---|
| 79 | 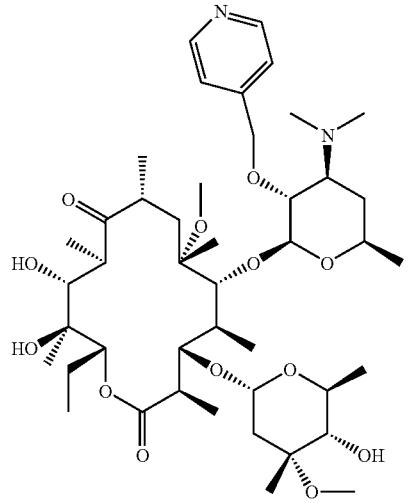 |
| 80 | 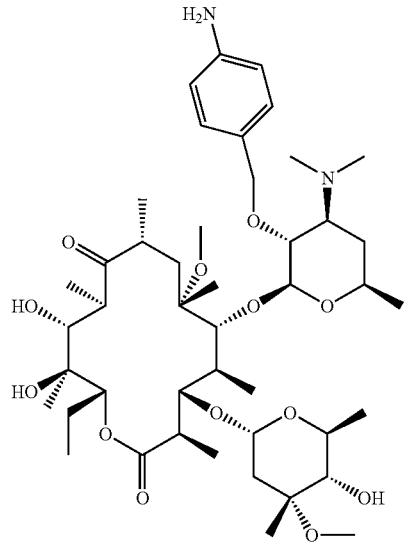 |
| 81 | 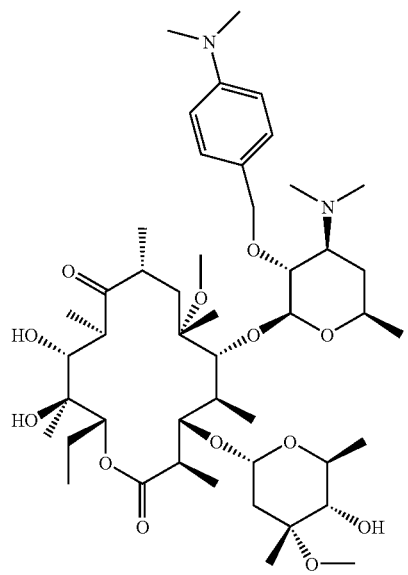 |

TABLE 1-9-continued
| Ex. No. | Structural Formula |
|---|---|
| 82 | 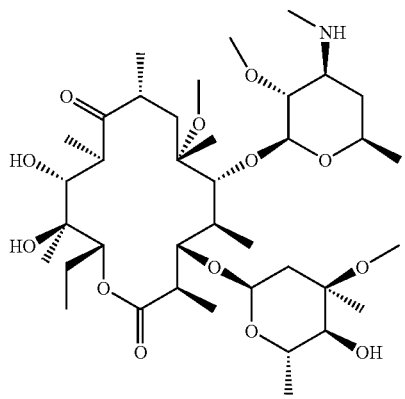 |
| 83 | 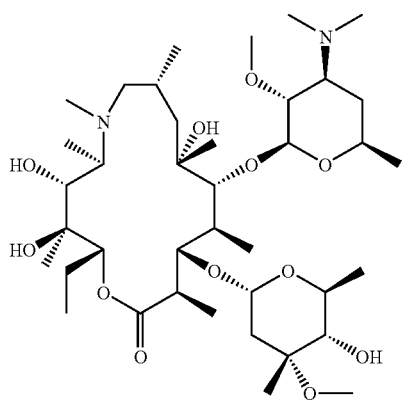 |
| 84 | 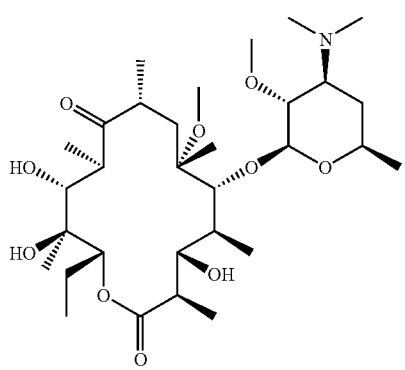 |
| 85 | 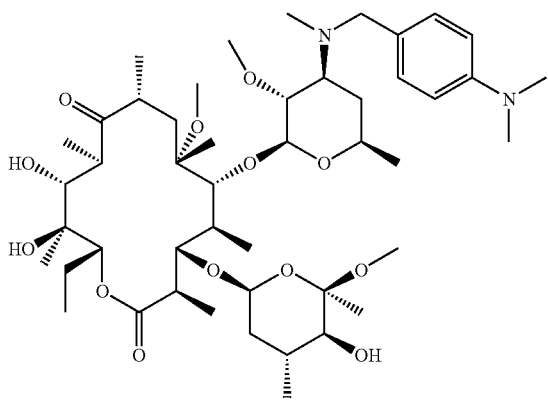 |

TABLE 1-9-continued

| Ex. No. | Structural Formula |
|---|---|
| 86 | |
| 87 | |
| 88 Compound E | |

TABLE 1-10
| Ex. No. | Structural Formula |
|---|---|
| 88 Compound F | 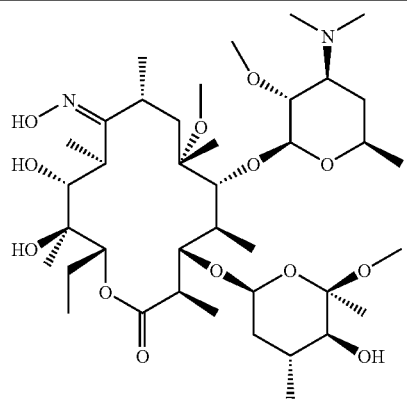 |
| 89 | 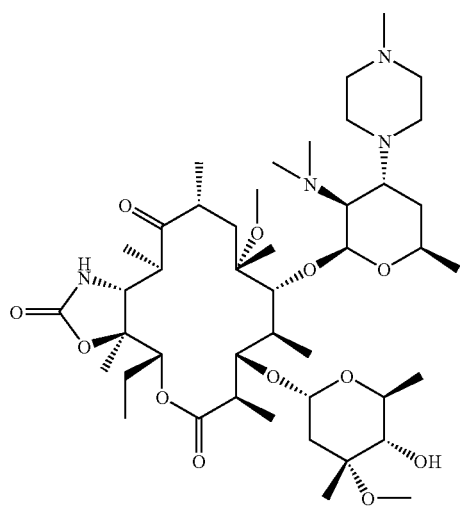 |
| 90 | 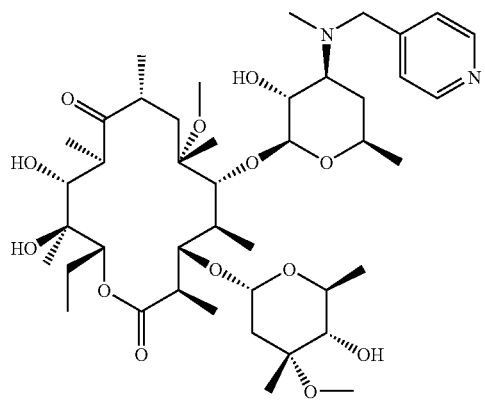 |

TABLE 1-10-continued
| Ex. No. | Structural Formula |
|---|---|
| 91 Compound G | 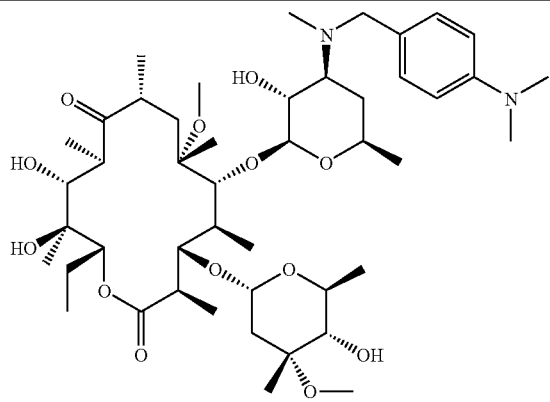 |
| 91 Compound H | 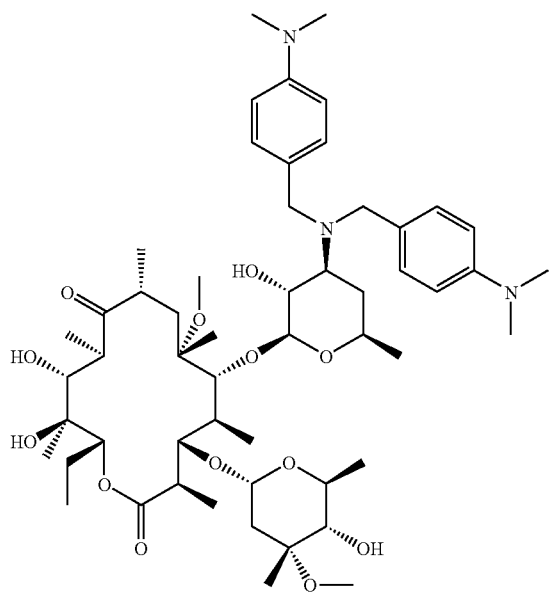 |
| 92 | 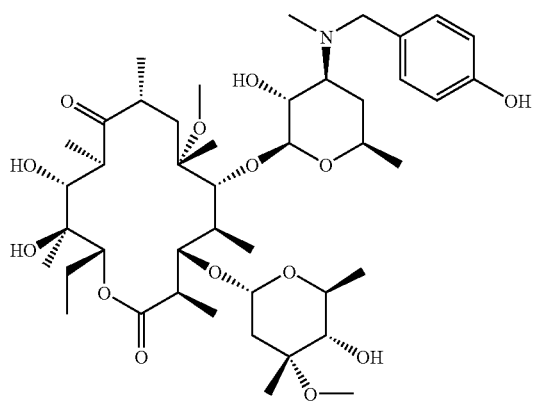 |

TABLE 1-10-continued
| Ex. No. | Structural Formula |
|---|---|
| 93 | 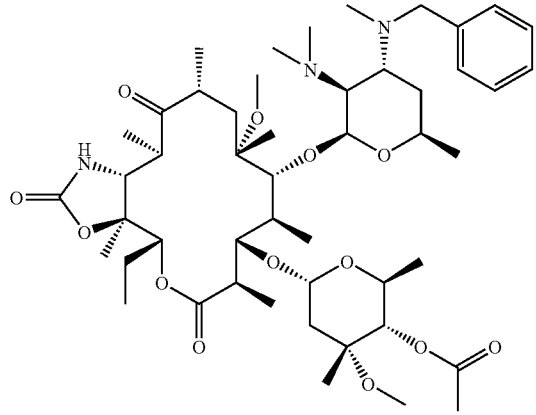 |
| 94 | 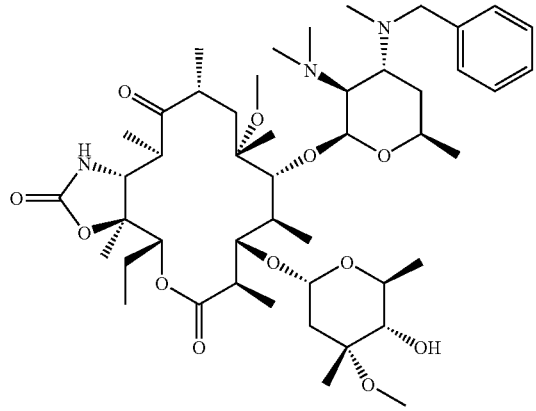 |
| 95 | 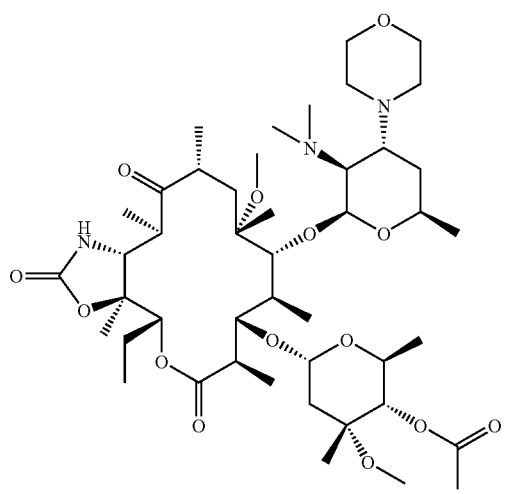 |

TABLE 1-10-continued
| Ex. No. | Structural Formula |
|---|---|
| 96 | 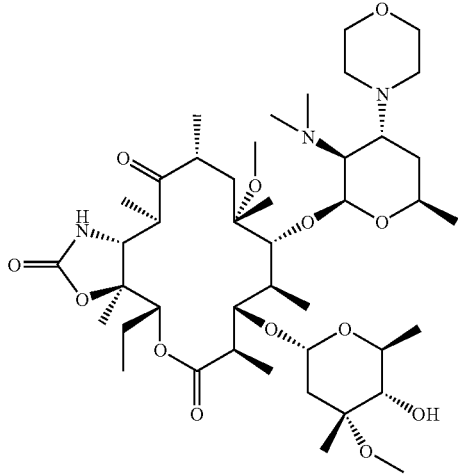 |
TABLE 1-11
| Ex. No. | Structural Formula |
|---|---|
| 97 | 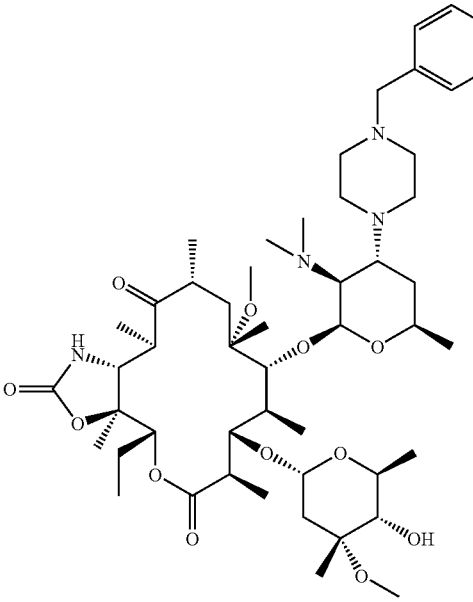 |
TABLE 1-11-continued
| Ex. No. | Structural Formula |
|---|---|
| 98 | 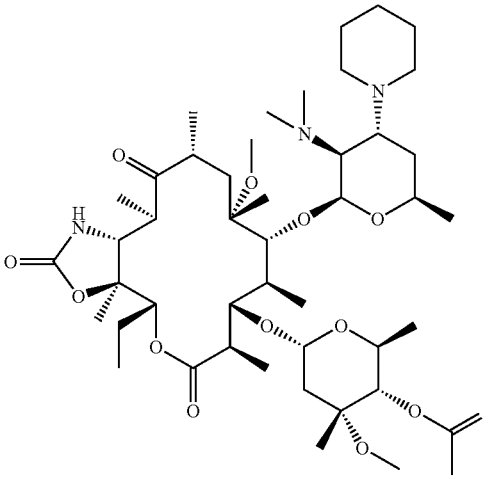 |

TABLE 1-11-continued

| Ex. No. | Structural Formula |
|---------|-------------------|
| 99 | |
| 100 | |
| 101 | |
| 102 | |
| 103 | |
| 104 | |
| 105 | |

TABLE 1-12
| Ex. No. | Structural Formula |
|---|---|
| 106 Compound J | |
| 106 Compound K | |
| 107 | |
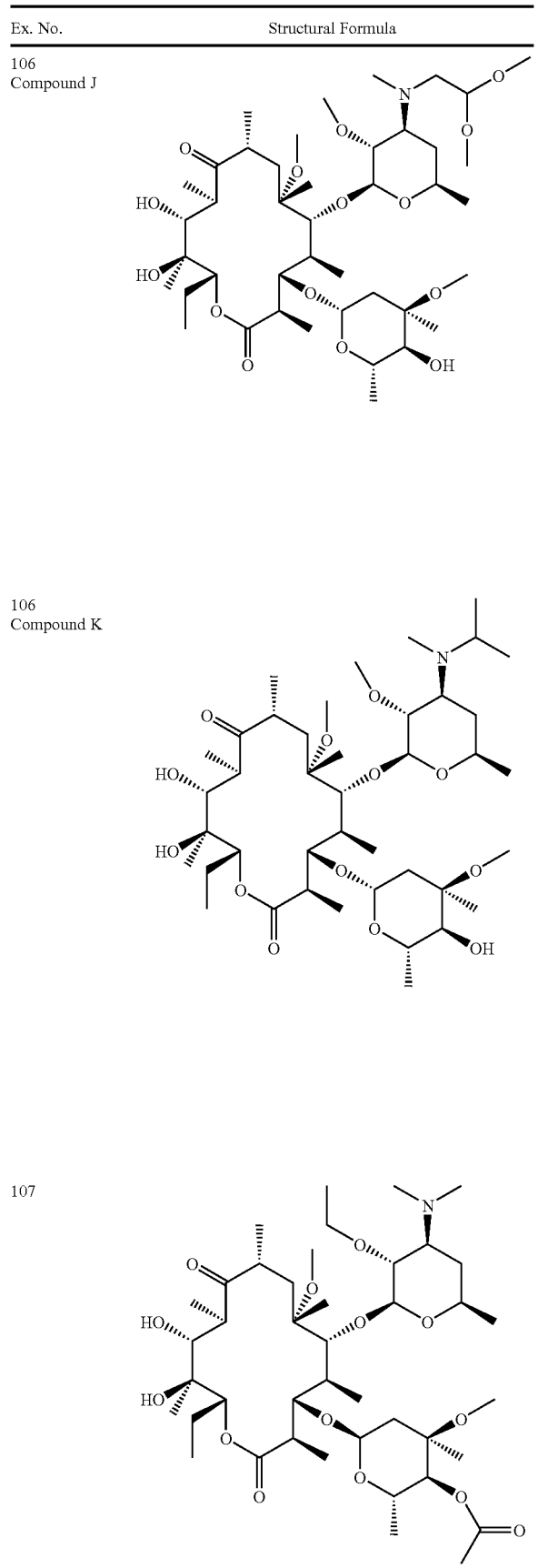
TABLE 1-12-continued
| Ex. No. | Structural Formula |
|---|---|
| 108 | |
| 109 Compound L | |
| 109 Compound M | |
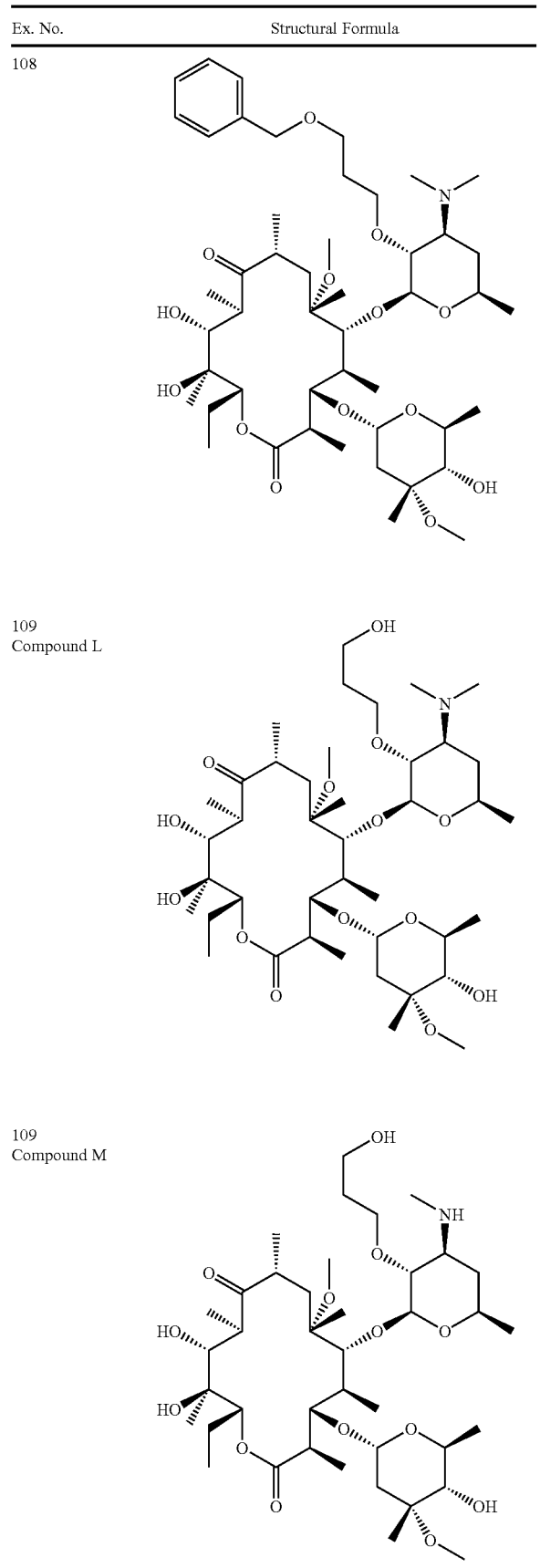

TABLE 1-12-continued

| Ex. No. | Structural Formula |
| --- | --- |
| 110 | |
| 111 Compound N | |
| 111 Compound O | |
| 112 | |

TABLE 1-13

| Ex. No. | Structural Formula |
| --- | --- |
| 113 | |
| 114 | |

TABLE 1-13-continued

| Ex. No. | Structural Formula |
|---|---|
| 115 | (structure) |
| 116 | (structure) |
| 117 | (structure) |
| 118 | (structure) |
| 119 | (structure) |
| 120 | (structure) |

TABLE 1-13-continued
| Ex. No. | Structural Formula |
|---|---|
| 121 | 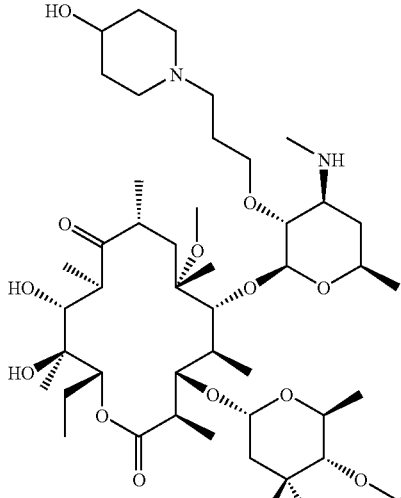 |
| 122 | |
TABLE 1-13-continued
| Ex. No. | Structural Formula |
|---|---|
| 122 | |
TABLE 1-14
| Ex. No. | Structural Formula |
|---|---|
| 123 | 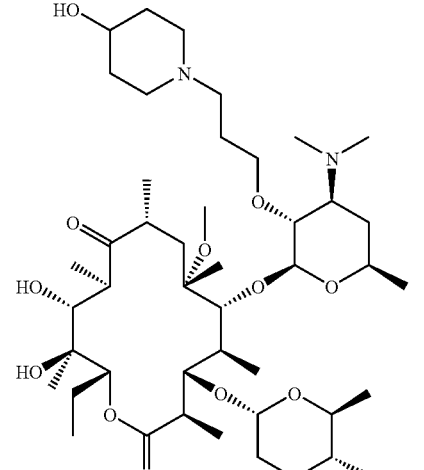 |

TABLE 1-14-continued
| Ex. No. | Structural Formula |
| --- | --- |
| 124 | 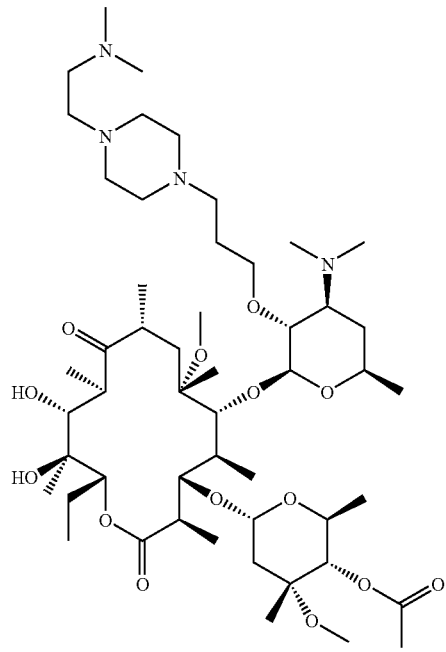 |
| 125 | 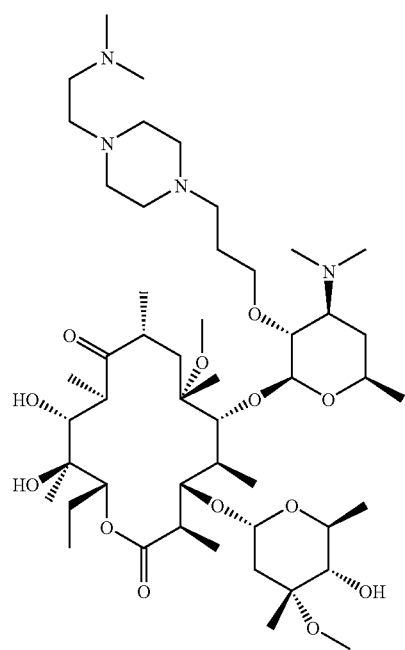 |

TABLE 1-14-continued
| Ex. No. | Structural Formula |
|---|---|
| 126 | 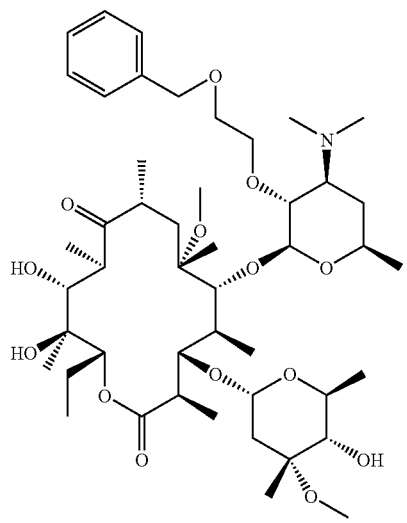 |
| 127<br>Compound P | 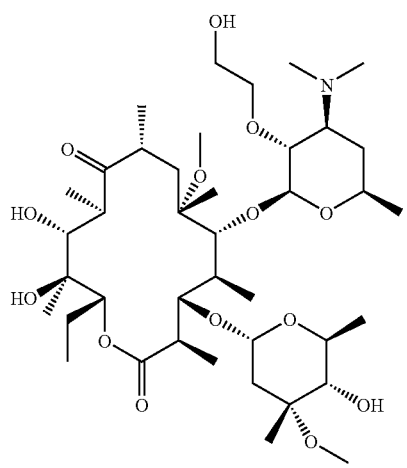 |
| 127<br>Compound Q | 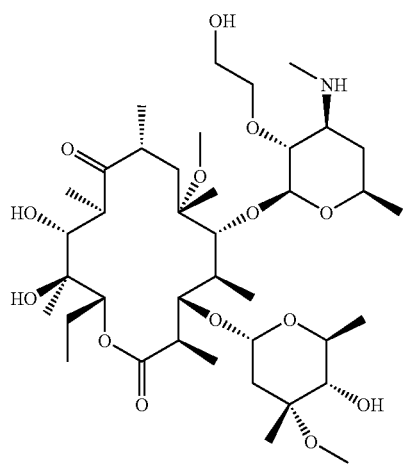 |

TABLE 1-14-continued
| Ex. No. | Structural Formula |
|---|---|
| 128 Compound R | 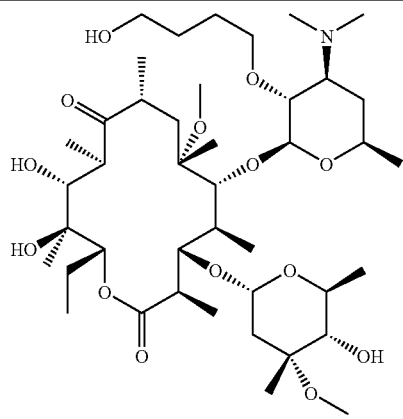 |
| 128 Compound S | 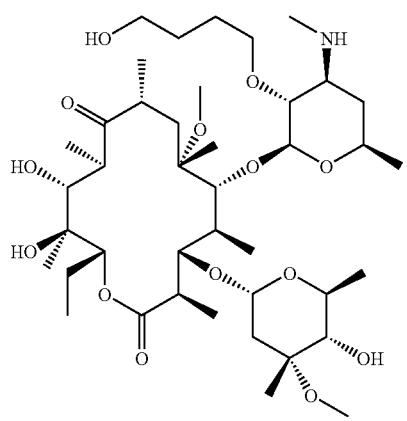 |
| 129 | 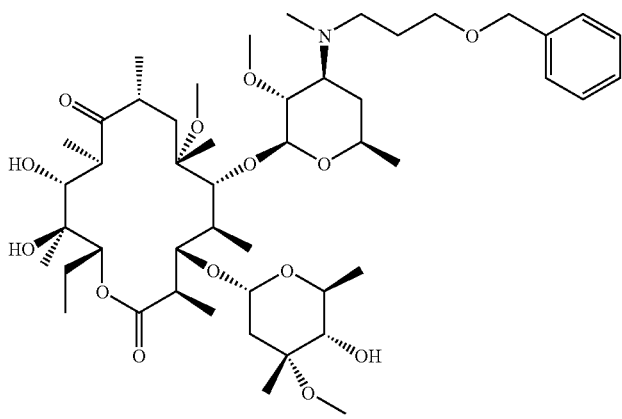 |

TABLE 1-14-continued
| Ex. No. | Structural Formula |
|---|---|
| 130 | 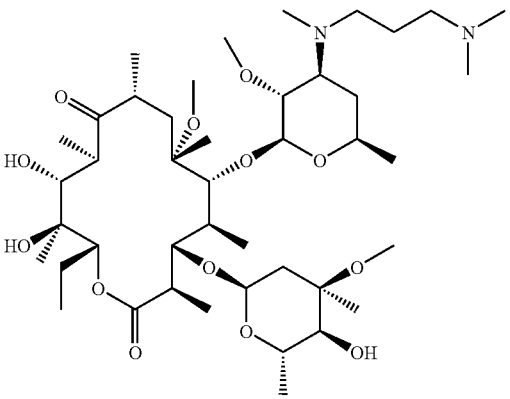 |
TABLE 1-15
| Ex. No. | Structural Formula |
|---|---|
| 131 | 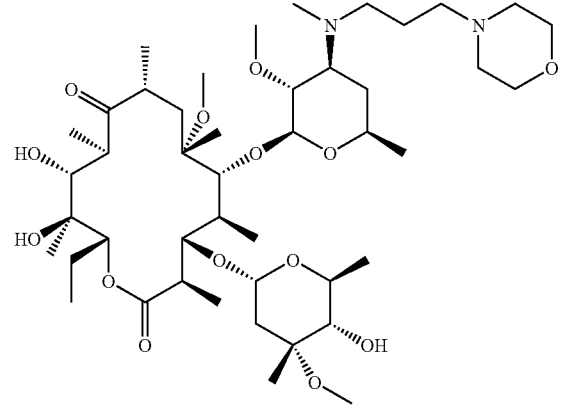 |
| 132 | 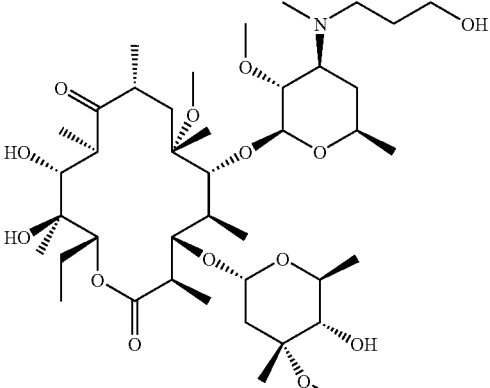 |

TABLE 1-15-continued
| Ex. No. | Structural Formula |
|---|---|
| 133 | 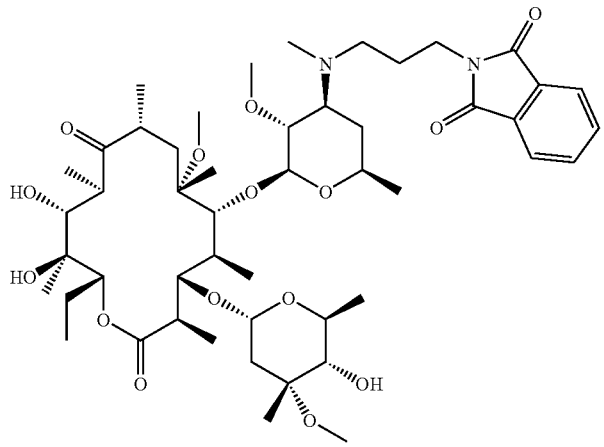 |
| 134 | 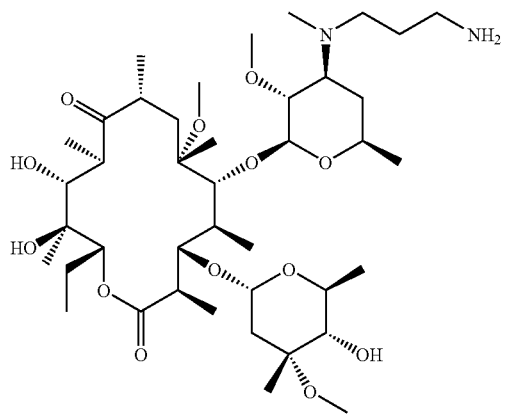 |
| 135 | 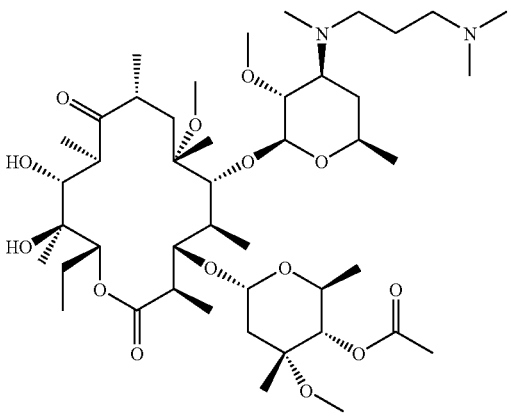 |

TABLE 1-15-continued
| Ex. No. | Structural Formula |
|---|---|
| 136 | 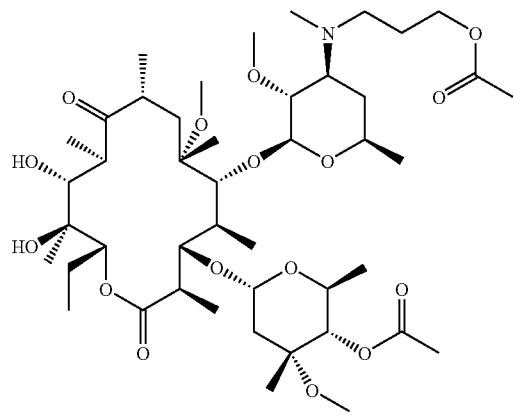 |
| 137 | 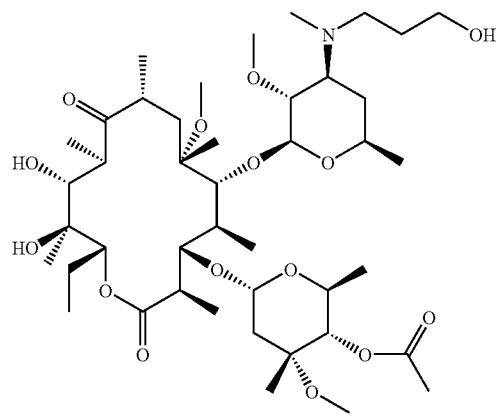 |
| 138 | 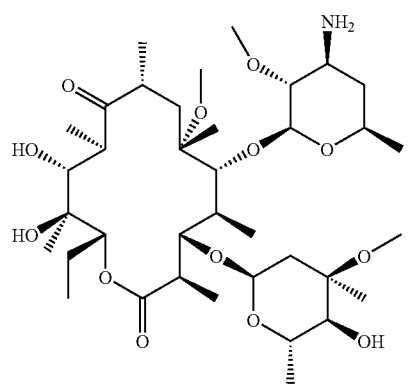 |

TABLE 1-15-continued
| Ex. No. | Structural Formula |
|---|---|
| 139 | 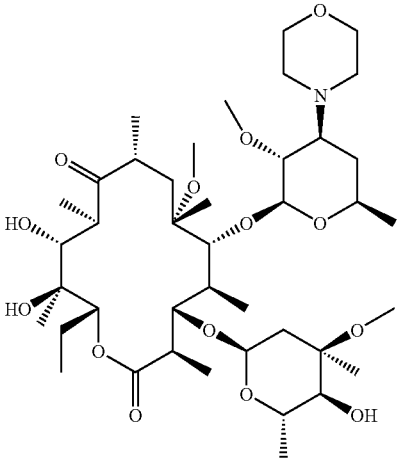 |
| 140 | 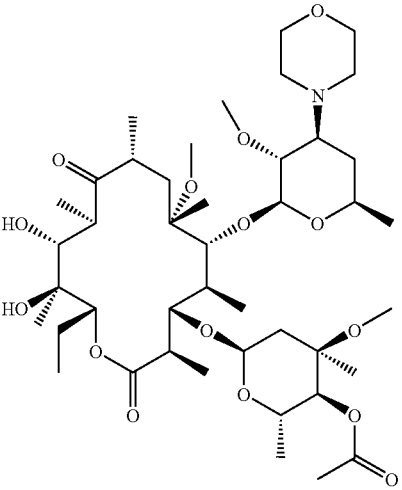 |
TABLE 1-16
| Ex. No. | Structural Formula |
|---|---|
| 141 | 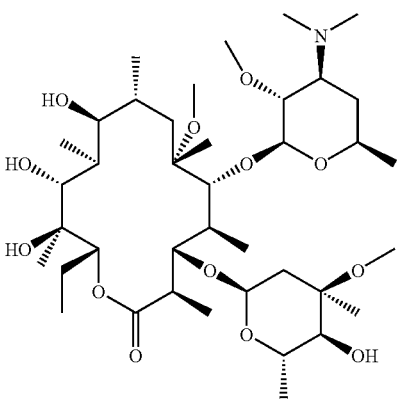 |

TABLE 1-16-continued
| Ex. No. | Structural Formula |
| --- | --- |
| 142 Compound T | 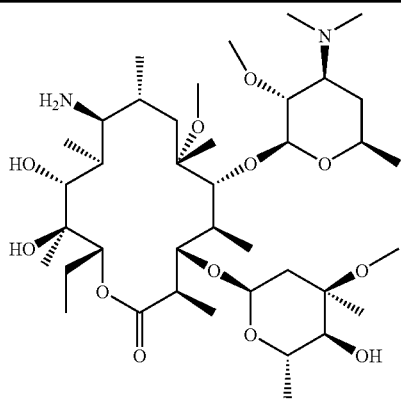 |
| 142 Compound U | 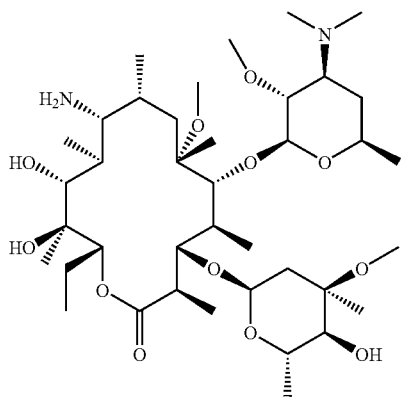 |
| 143 | 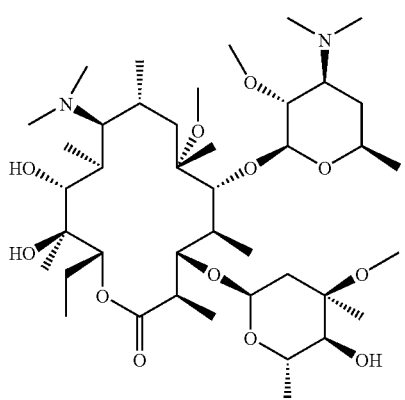 |
| 144 | 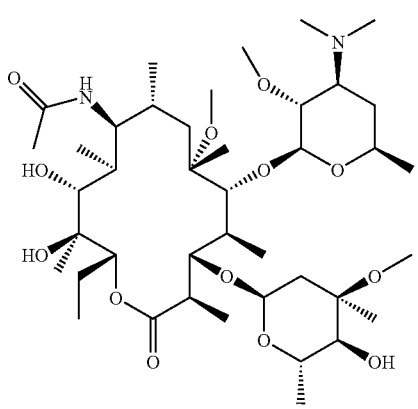 |

TABLE 1-16-continued
| Ex. No. | Structural Formula |
|---|---|
| 145 | 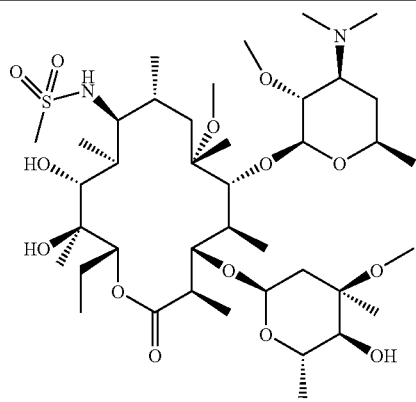 |
| 146 | 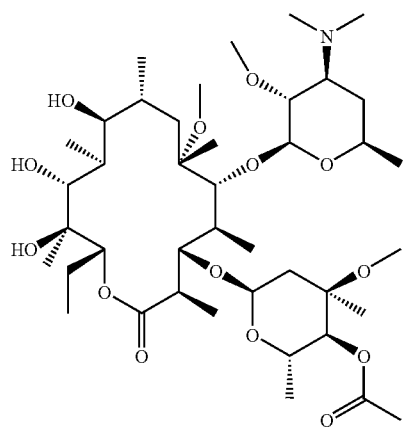 |
| 147 Compound V | 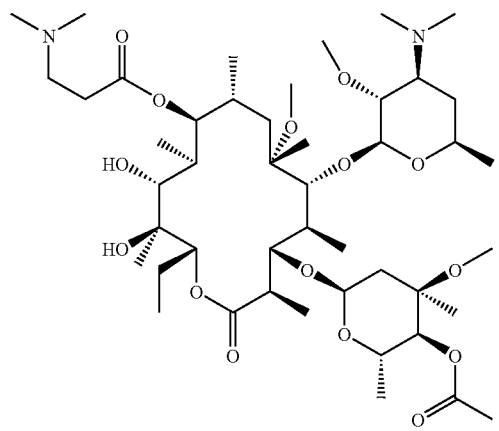 |

TABLE 1-16-continued
| Ex. No. | Structural Formula |
|---|---|
| 147 Compound W | 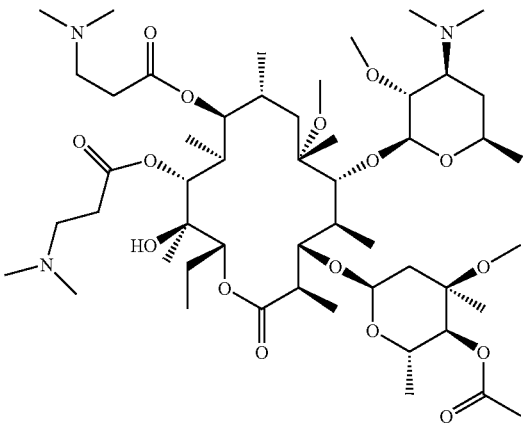 |
| 148 | 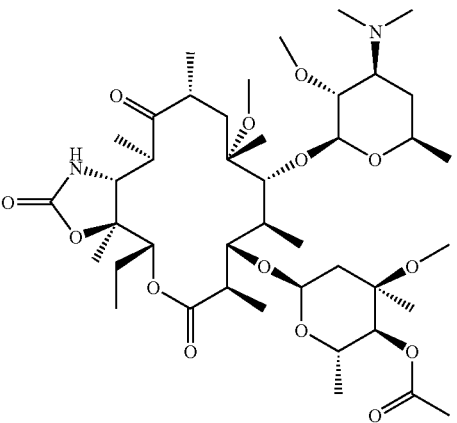 |
TABLE 1-17
| Ex. No. | Structural Formula |
|---|---|
| 149 | 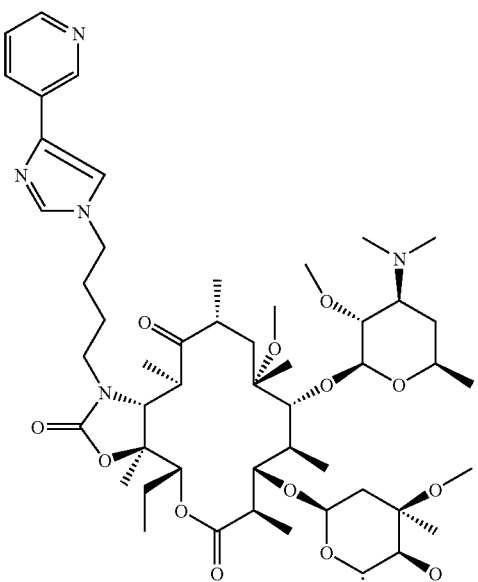 |
TABLE 1-17-continued
| Ex. No. | Structural Formula |
|---|---|
| 150 | 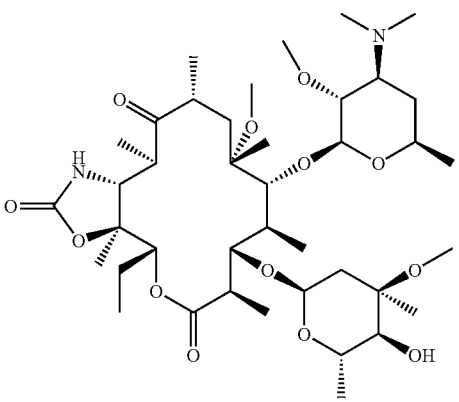 |

| Ex. No. | Structural Formula |
|---------|-------------------|
| 151 | 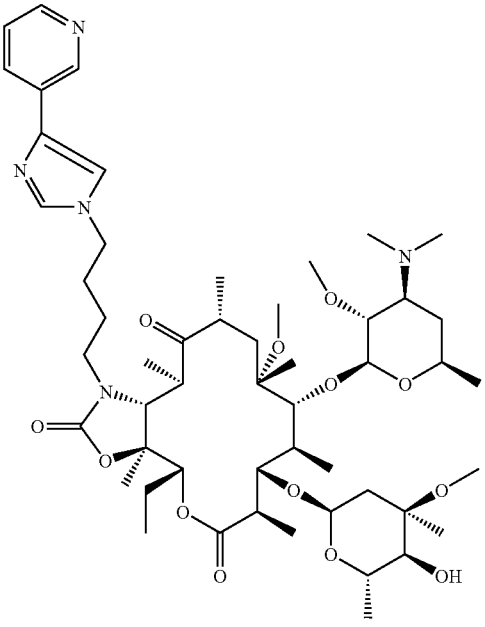 |
| 152 | 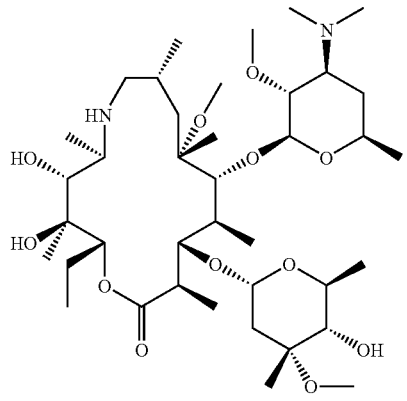 |
| 153 | 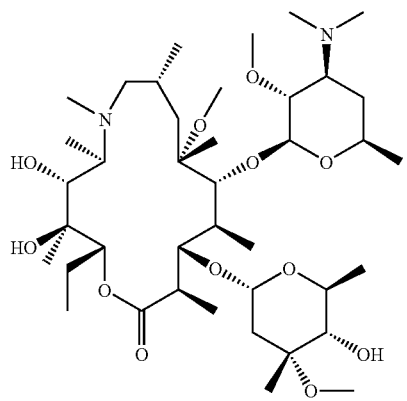 |
| Ex. No. | Structural Formula |
|---------|-------------------|
| 154 | 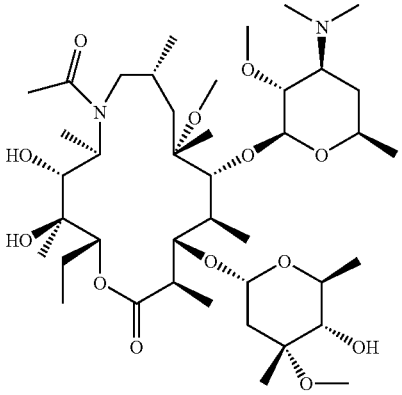 |
| 155 | 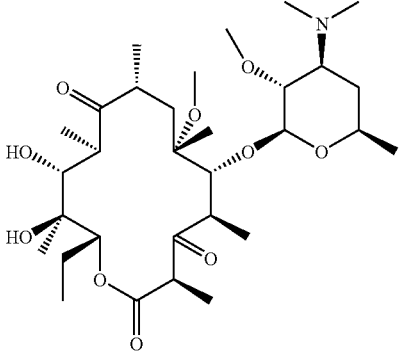 |
| 156 | 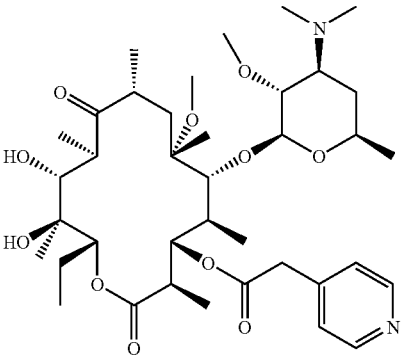 |
| 157 | 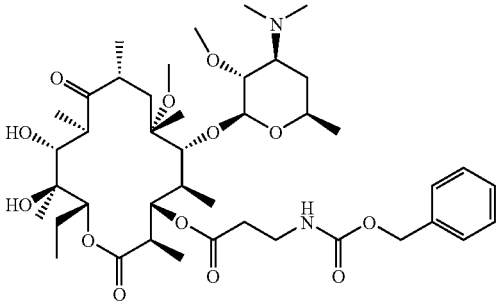 |

TABLE 1-17-continued
| Ex. No. | Structural Formula |
|---|---|
| 158 | 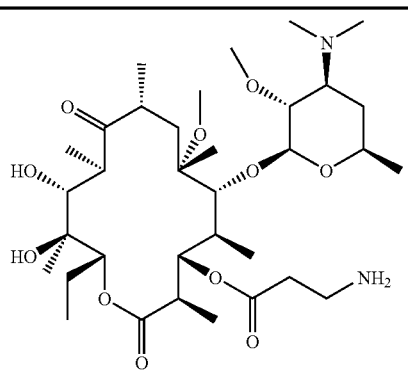 |
TABLE 1-18
| Ex. No. | Structural Formula |
|---|---|
| 159 | 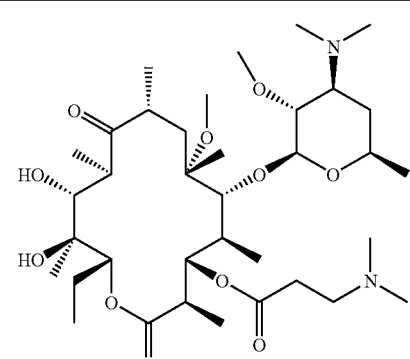 |
| 160 | 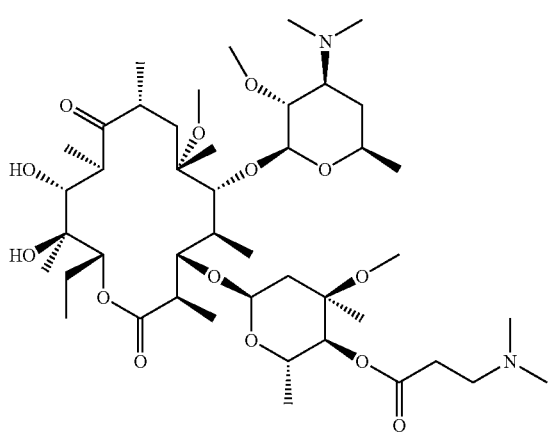 |

TABLE 1-18-continued
| Ex. No. | Structural Formula |
|---|---|
| 161 | 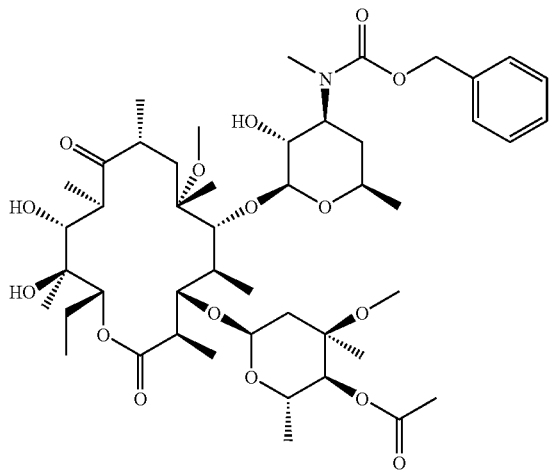 |
| 162 | 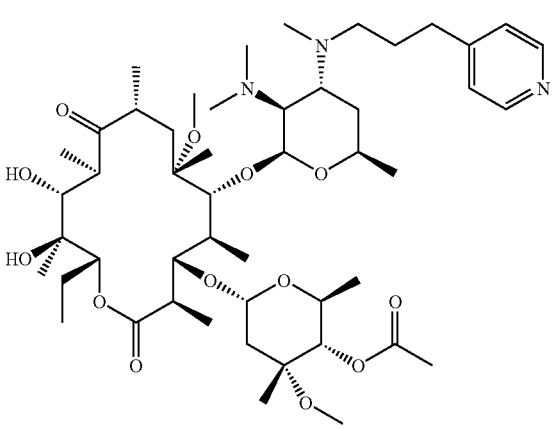 |
| 163 | 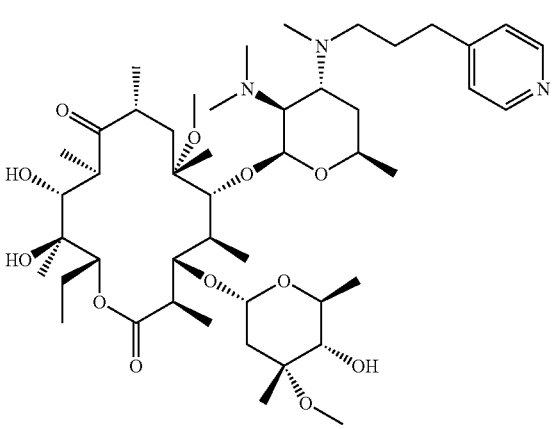 |

TABLE 1-18-continued
| Ex. No. | Structural Formula |
|---|---|
| 164 | 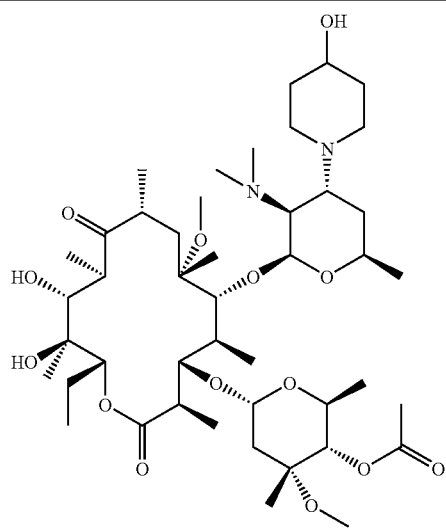 |
| 165 | 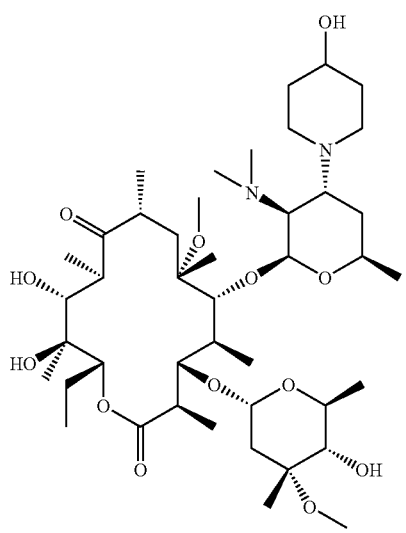 |
| 166 | 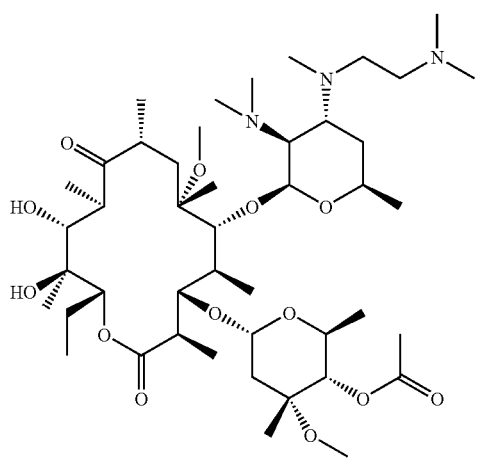 |

TABLE 1-18-continued
| Ex. No. | Structural Formula |
|---|---|
| 167 | 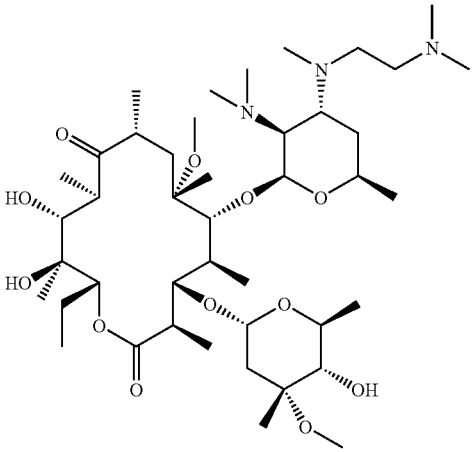 |
| 168 | 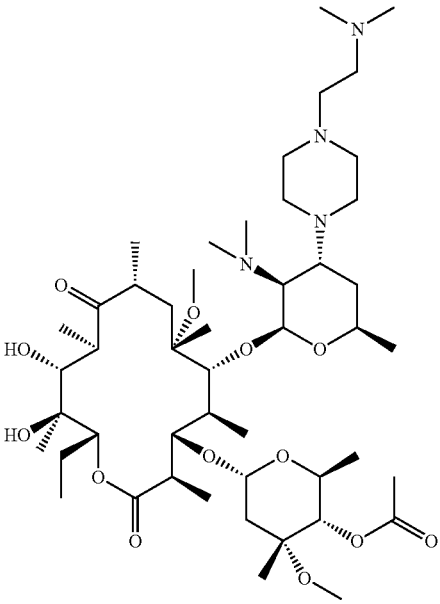 |

TABLE 1-19

| Ex. No. | Structural Formula |
|---|---|
| 169 | |
| 170 | |
| 171 | |

TABLE 1-19-continued

| Ex. No. | Structural Formula |
|---|---|
| 172 | |
| 173 | |
| 174 | |

TABLE 1-19-continued
| Ex. No. | Structural Formula |
|---|---|
| 175 | 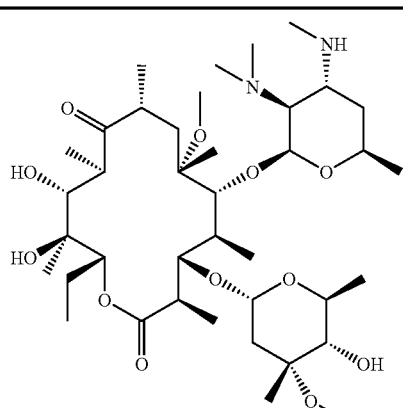 |
| 176 | 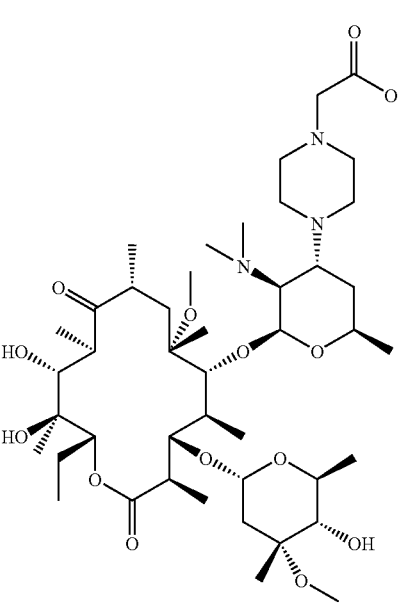 |
| 177 | 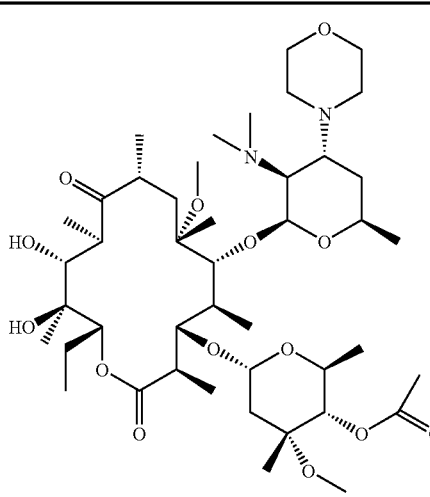 |
| 178 | 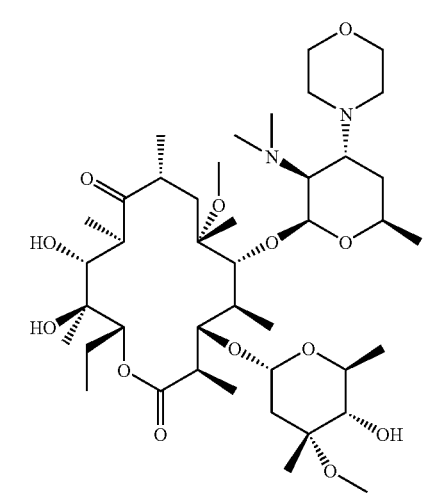 |
TABLE 1-20
| Ex. No. | Structural Formula |
|---|---|
| 179 | 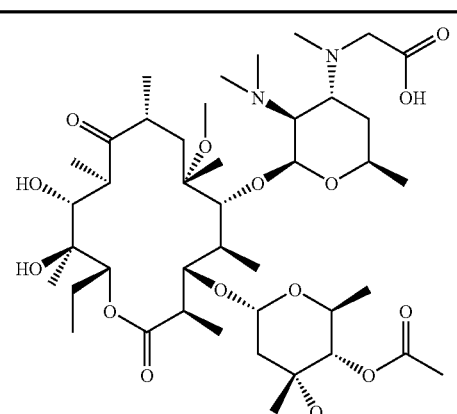 |

TABLE 1-20-continued
| Ex. No. | Structural Formula |
|---|---|
| 180 | 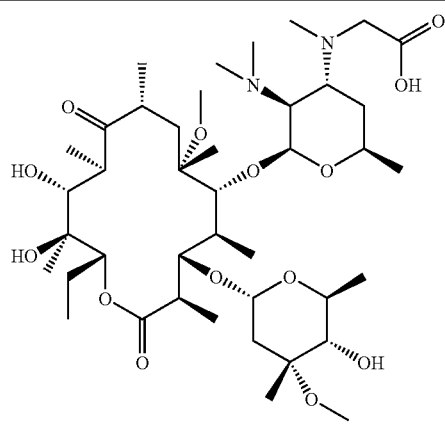 |
| 181 | 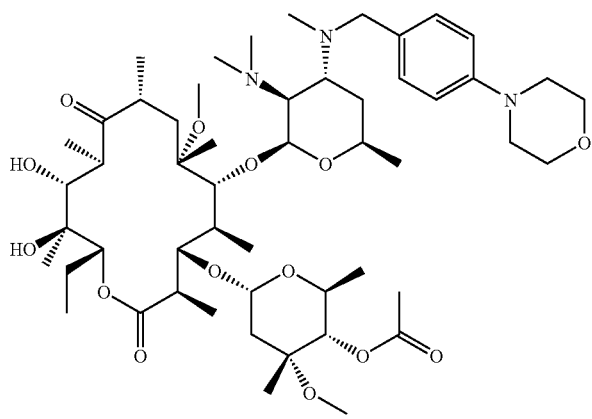 |
| 182 | 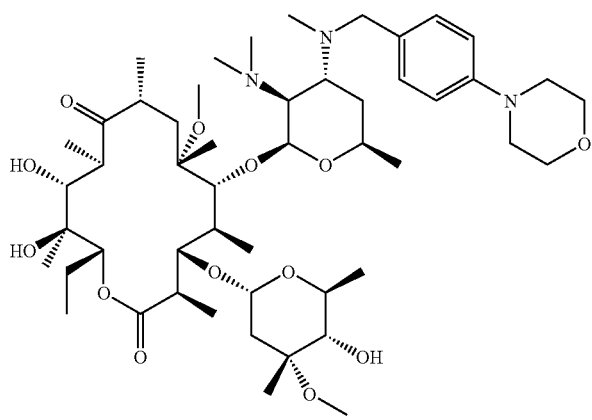 |

TABLE 1-20-continued
| Ex. No. | Structural Formula |
|---|---|
| 183 | 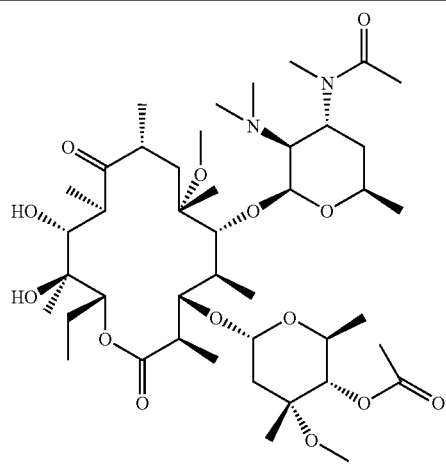 |
| 184 | 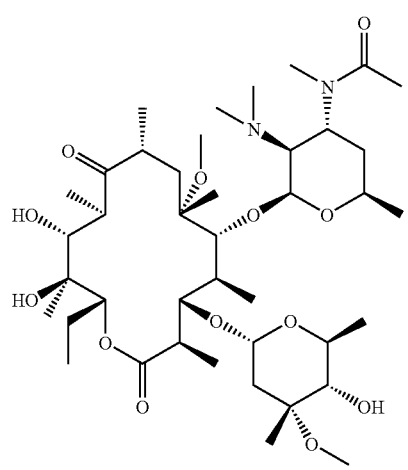 |
| 185 | 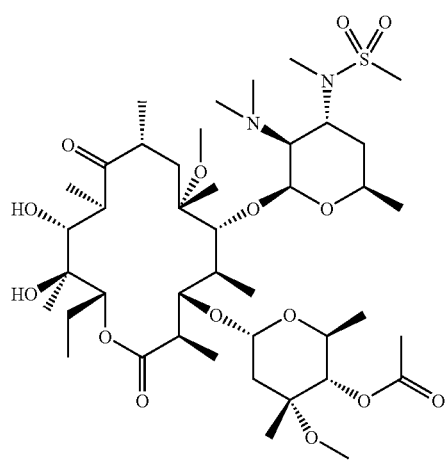 |

TABLE 1-20-continued
| Ex. No. | Structural Formula |
|---|---|
| 186 | 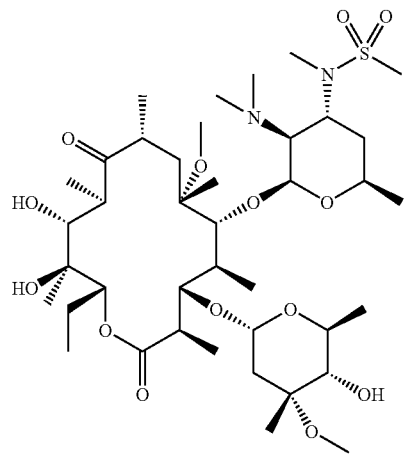 |
| 187 | 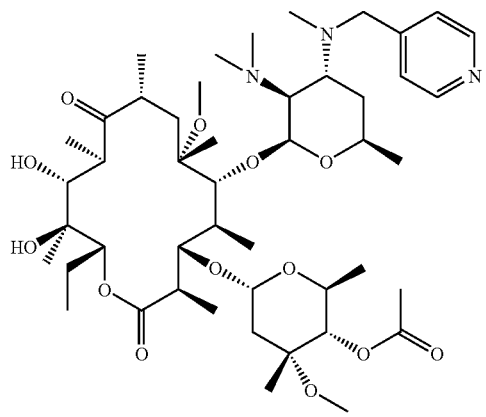 |
| 188 | 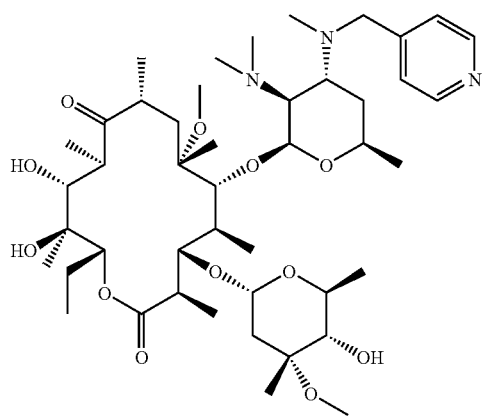 |

TABLE 1-21
| Ex. No. | Structural Formula |
|---|---|
| 189 | 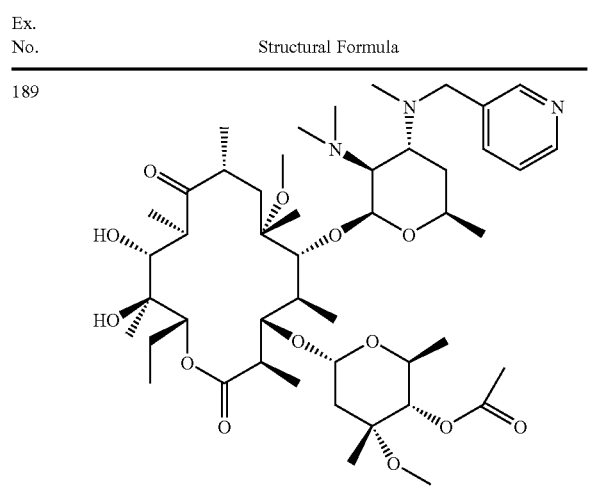 |
| 190 | 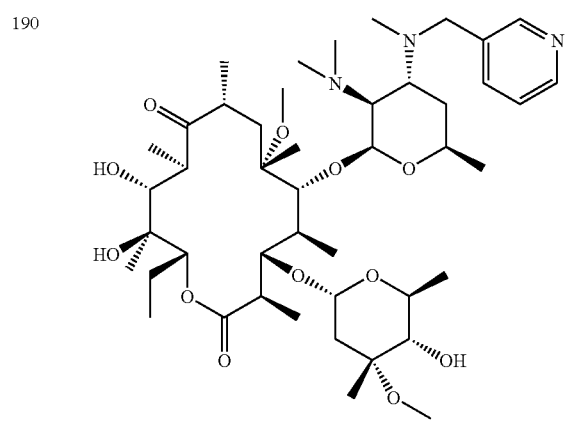 |
| 191 | 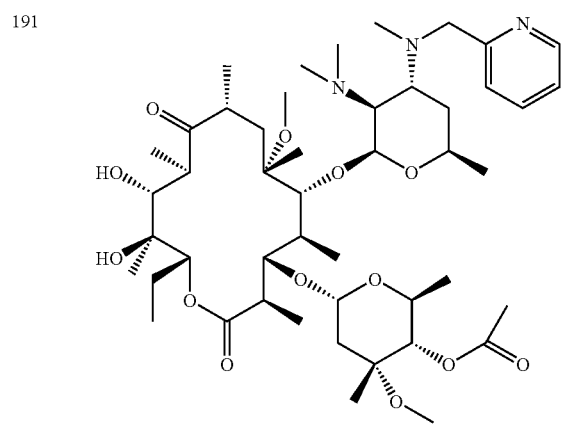 |
TABLE 1-21-continued
| Ex. No. | Structural Formula |
|---|---|
| 192 | 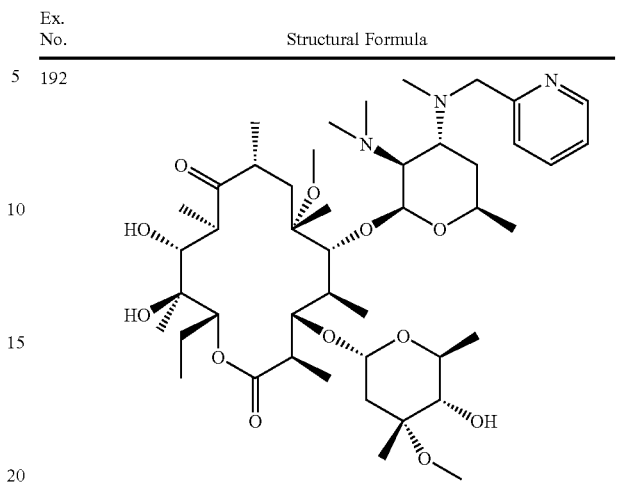 |
| 193 | 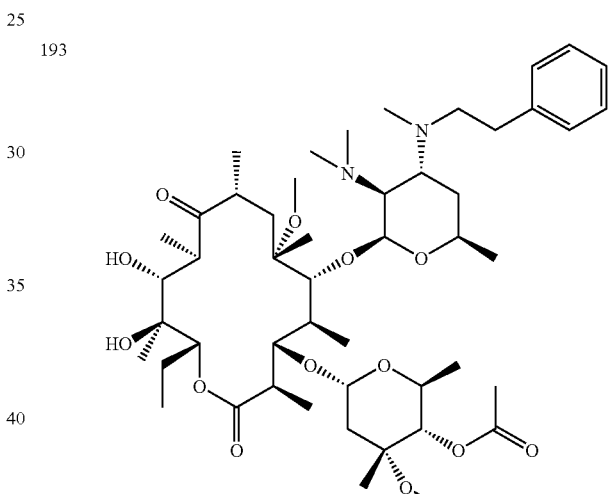 |
| 194 | 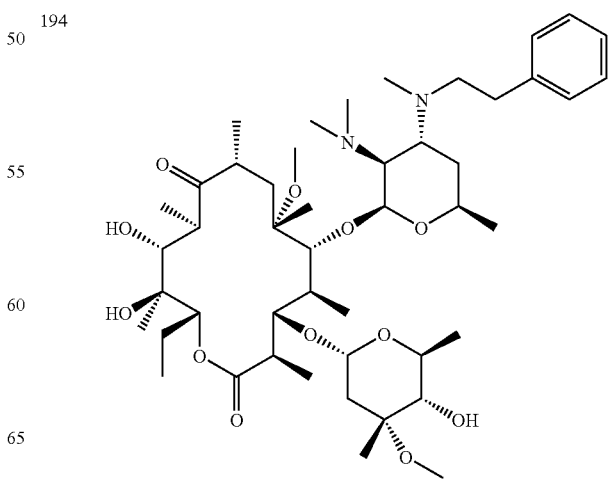 |

TABLE 1-21-continued

| Ex. No. | Structural Formula |
|---|---|
| 195 | (structure) |
| 196 | (structure) |
| 197 | (structure) |
| 198 | (structure) |

TABLE 1-22

| Ex. No. | Structural Formula |
|---|---|
| 199 | (structure) |

TABLE 1-22-continued
| Ex. No. | Structural Formula |
|---|---|
| 200 Compound X | 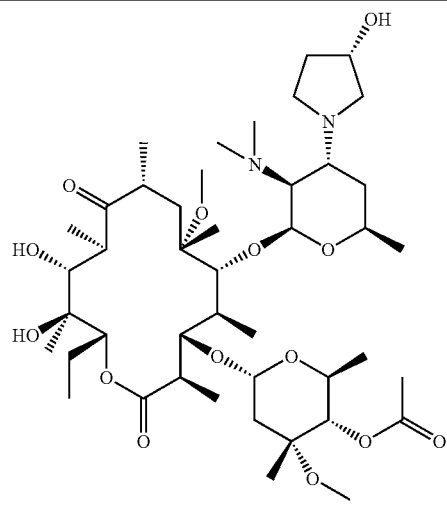 |
| 200 Compound Y | 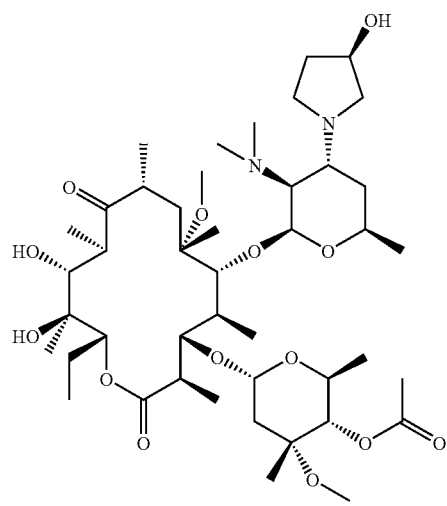 |
| 201 | 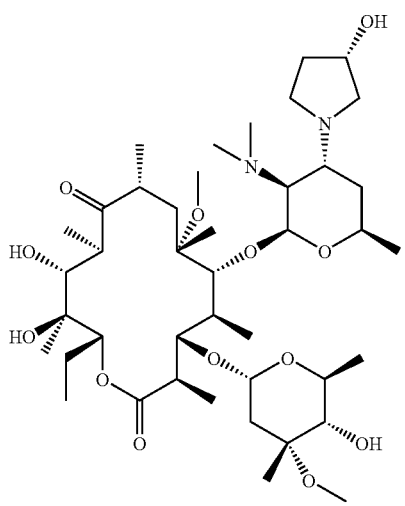 |

TABLE 1-22-continued
| Ex. No. | Structural Formula |
|---|---|
| 202 | 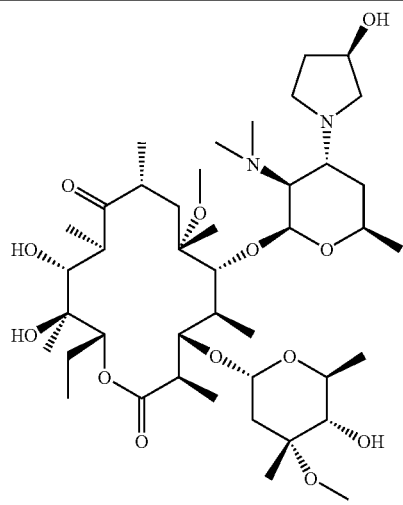 |
| 203 | 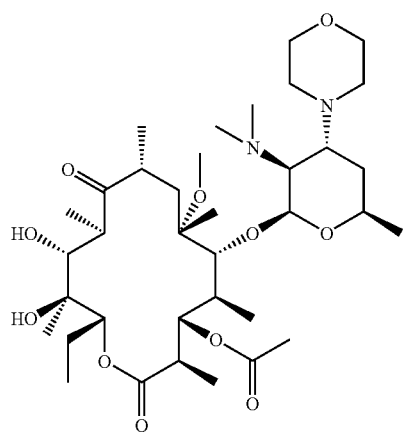 |
| 204 | 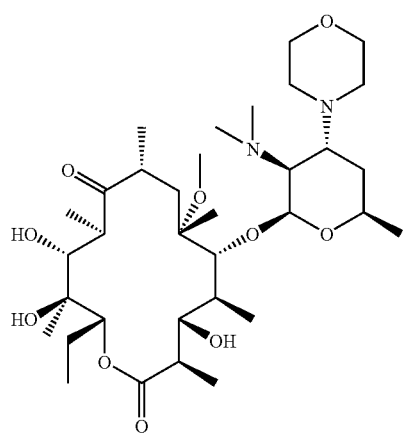 |

TABLE 1-22-continued
| Ex. No. | Structural Formula |
| --- | --- |
| 205 | 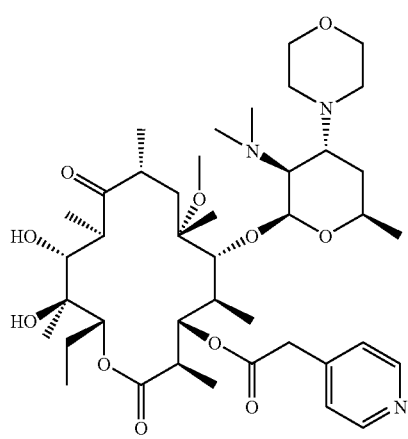 |
| 206 | 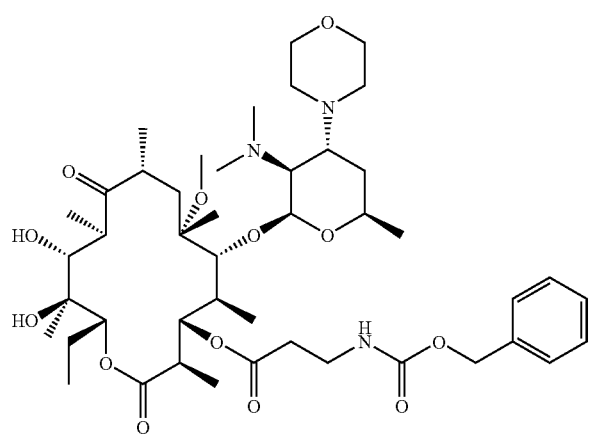 |
| 207 | 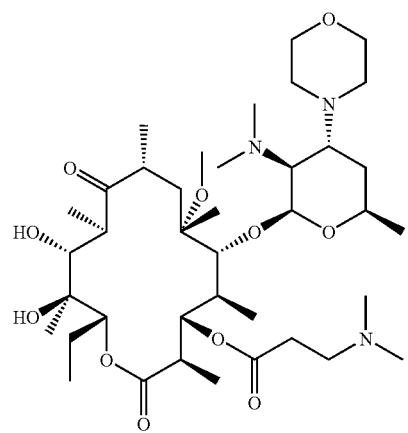 |

TABLE 1-23

| Ex. No. | Structural Formula |
| --- | --- |
| 208 | |
| 209 | |
| 210 | |

TABLE 1-23-continued

| Ex. No. | Structural Formula |
| --- | --- |
| 211 | |
| 212 | |
| 213 | |

TABLE 1-23-continued

| Ex. No. | Structural Formula |
|---|---|
| 214 | |
| 215 | |
| 216 | |

Test Example 1

Inhibitory Activity Against proMMP-9 Protein Production

To 7- to 9-week male C57BL/6J mice (purchased from CLEA Japan, Inc. or Japan SLC, Inc.), Zymosan A (SIGMA) derived from budding yeasts which is adjusted to be 1 mg/ml in a phosphate buffer solution (PBS, 10010-49, Invitrogen) was administered intraperitoneally at 1 ml per mouse to induce peritonitis. Three days later, filter-sterilized cell recovery buffer (2 mM EDTA, 0.5% bovine serum albumin, PBS, pH 7.4) was administered intraperitoneally at 5 ml per mouse to recover peritoneal exudata cells. The cells went through a cell strainer (70 μm nylon, FALCON) and were then washed twice with a Hanks solution (Invitrogen). The cells were suspended in 10% fetal calf serum-containing Dulbecco's modified Eagle's culture medium (Invitrogen). The suspension was seeded on a plate with 48 wells, after 6 hours, the culture medium was completely exchanged. After culturing for another 18 hours, test compounds were added at 0.02 to 20 μM of the final concentration. After 1 hour from the addition of the compounds, a tumor necrosis factor (TNF) α (R & D Systems) was added at 25 ng/ml of the final concentration, and 24 hours later, the culture supernatant was collected. The amount of pro MMP-9 protein in the supernatant was quantified by an enzyme-linked immunosorbent assay (ELISA) (R & D Systems), IC50 values of the test compounds on the increased amount by TNF α stimuli, were calculated by ORIGIN analysis software (trade name: OriginLab). In addition, minimal inhibitory concentration (MIC) of each test compounds (measured bacterium: *Staphylococcus aureus* ATCC29213) was measured. As a comparative agent 1,6-O-methylerythromycin A (clarithromycin) was used. The results are shown in Table 2-1 and 2-2.

TABLE 2-1

| Test Compound | IC50 (μM)* | MIC (μg/mL) |
|---|---|---|
| Comparative Agent 1 | 10.0 | 0.25 |
| Compound of Example 20 | 0.83 | >128 |
| Compound of Example 24 | 0.38 | >64 |
| Compound of Example 31 | 4.08 | >128 |
| Compound of Example 65 | 1.37 | — |
| Compound of Example 89 | 1.59 | >128 |
| Compound of Example 95 | 4.36 | >128 |
| Compound of Example 101 | 0.62 | >128 |
| Compound of Example 104 | 5.00 | >128 |
| Compound of Example 105 | 4.38 | >128 |
| Compound of Example 115 | 3.88 | >128 |
| Compound of Example 116 | 2.79 | >128 |
| Compound of Example 117 | 3.55 | >128 |
| Compound of Example 119 | 4.42 | >128 |
| Compound of Example 122 | 3.06 | >128 |
| Compound of Example 129 | <1.04 | >128 |
| Compound of Example 130 | 1.33 | >128 |
| Compound of Example 131 | 3.33 | >128 |
| Compound of Example 132 | 2.52 | >128 |
| Compound of Example 136 | 2.12 | >128 |
| Compound of Example 138 | 3.95 | >128 |
| Compound of Example 139 | 5.51 | >128 |
| Compound of Example 141 | 2.18 | >128 |
| Compound T of Example 142 | 8.88 | >128 |
| Compound V of Example 147 | 2.61 | >128 |
| Compound W of Example 147 | 6.56 | >128 |
| Compound of Example 148 | 7.68 | >128 |
| Compound of Example 155 | 9.70 | >128 |
| Compound of Example 162 | <1.50 | >128 |
| Compound of Example 164 | 2.77 | >128 |
| Compound of Example 169 | 2.89 | >128 |
| Compound of Example 170 | 1.01 | >128 |

TABLE 2-2

| Test Compound | IC50 (μM)* | MIC (μg/mL) |
|---|---|---|
| Compound of Example 171 | 1.45 | >128 |
| Compound of Example 173 | 4.95 | >128 |
| Compound of Example 174 | 1.70 | >128 |
| Compound of Example 175 | 1.65 | 128 |
| Compound of Example 177 | 4.42 | >128 |
| Compound of Example 178 | 3.10 | >128 |
| Compound of Example 182 | 1.72 | >128 |
| Compound of Example 185 | 2.40 | >128 |
| Compound of Example 186 | 4.01 | >128 |
| Compound of Example 187 | 1.37 | >128 |
| Compound of Example 188 | 3.24 | >128 |
| Compound of Example 189 | 3.38 | >128 |
| Compound of Example 190 | 3.82 | >128 |
| Compound of Example 191 | 1.42 | 128 |
| Compound of Example 192 | 2.46 | >128 |
| Compound of Example 194 | 1.23 | >128 |
| Compound of Example 196 | 2.51 | >128 |
| Compound of Example 198 | 2.88 | >128 |
| Compound of Example 199 | 3.60 | >128 |
| Compound X of Example 200 | 2.03 | >128 |
| Compound Y of Example 200 | 3.02 | >128 |
| Compound of Example 201 | 4.45 | >128 |
| Compound of Example 203 | 5.03 | >128 |
| Compound of Example 209 | 3.47 | >128 |
| Compound of Example 210 | 4.63 | 128 |
| Compound of Example 211 | 2.58 | >128 |
| Compound of Example 212 | 1.78 | >128 |
| Compound of Example 213 | 0.77 | >128 |
| Compound of Example 214 | 2.73 | >128 |
| Compound of Example 215 | 1.21 | >128 |
| Compound of Example 216 | 2.55 | >128 |

*Relative activity when the value of Comparative Agent 1 (IC50 = 10.04 ± 4.11 μM) is 10.

As is clear from the tables, the compounds of the invention have a strong inhibitory activity of MMP-9 production, while the antibacterial activity is weak.

INDUSTRIAL APPLICABILITY

Compounds of the present invention have an excellent inhibitory activity of MMP-9 production, therefore, are useful as a medicine agent with fewer side effects than conventional MMP enzyme activity inhibitors, as a prophylactic and therapeutic drug for oncogenic angiogenesis, chronic rheumatoid arthritis, vascular intimal thickening after a percutaneous coronary transluminal angioplasty, vascular atherosclerosis, hemorrhagic apoplexy, acute myocardial infarction, chronic heart failure, aneurysm, lung cancer metastasis, adult respiratory distress syndrome, asthma, interstitial pulmonary fibrosis, chronic rhinosinusitis, bronchitis or chronic obstructive pulmonary disease (COPD).

The invention claimed is:

1. A compound represented by formula (I) or a pharmaceutically acceptable salt thereof:

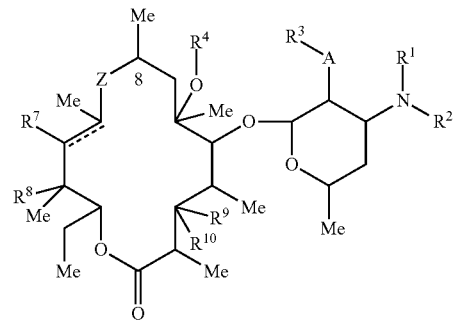

(I)

wherein,
the double line including the dashed line represents a single bond or a double bond;
$R^1$ and $R^2$ each independently represents
a hydrogen atom,
an alkyl group having 1 to 6 carbon atom(s) unsubstituted or substituted with 1 to 3 substituent(s) selected from "an aryl group unsubstituted or substituted with 1 to 5 substituent(s) selected from Substituent Group 1, a heteroaryl group unsubstituted or substituted with 1 to 3 substituent(s) selected from Substituent Group 1, a carboxy group, and an alkoxycarbonyl group having 2 to 7 carbon atoms", wherein Substituent Group 1 consists of a halogen atom, an alkyl group having 1 to 6 carbon atom(s), an alkoxy group having 1 to 6 carbon atom(s), a cyano group, a nitro group, a hydroxy group, a cyclic alkyl group having 3 to 6 carbon atoms including 1 to 3 hetero atom(s) on a ring, and an amino group unsubstituted or substituted with 1 or 2 alkyl group(s) having 1 to 6 carbon atom(s),
an alkyl group having 2 to 6 carbon atoms substituted with 1 to 5 group(s) selected from "an amino group unsubstituted or substituted with 1 or 2 alkyl group(s) having 1 to 6 carbon atoms, a phthalimide group, an alkoxy group having 1 to 6 carbon atom(s), a morpholino group, an aralkyloxy group having 7 to 12 carbon atoms, an alkanoyloxy group having 2 to 6 carbon atoms, a hydroxy group, and a group represented by the formula:

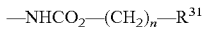

wherein n is an integer of 0 to 6, $R^{31}$ is a hydrogen atom, an amino group unsubstituted or substituted with 1 or 2 alkyl group(s) having 1 to 6 carbon atom(s), an aryl group, or a heteroaryl group",
a cyclic alkenyl group having 4 to 6 carbon atoms unsubstituted or substituted with 1 to 5 substituent(s) selected from "an oxo group, and an amino group unsubstituted or substituted with 1 or 2 alkyl group(s) having 1 to 6 carbon atom(s)",
a group represented by the formula:

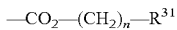

wherein n and $R^{31}$ have the same meanings as defined above,
an alkanoyl group having 2 to 6 carbon atoms,
an alkylsulfonyl group having 1 to 6 carbon atom(s), or
an aryl group unsubstituted or substituted with 1 to 5 substituent(s) selected from Substituent Group 1, or R¹ and R² represent a cyclic structure represented by the formula which is formed together with the nitrogen atom to which each is bonded:

—(CH$_2$)$_p$—Y—(CH$_2$)$_q$— wherein p and q each independently represents an integer of 1 to 3, Y represents an oxygen atom, a group represented by the formula:

—CR$^{39}$R$^{40}$— wherein R$^{39}$ and R$^{40}$ each independently represents a hydrogen atom, a hydroxy group, an alkoxy group having 1 to 6 carbon atom(s), a carboxy group, or an alkoxycarbonyl group having 2 to 7 carbon atoms,
or a group represented by the formula:

—NR$^{21}$— wherein R$^{21}$ represents a hydrogen atom, or an alkyl group having 1 to 6 carbon atom(s) unsubstituted or substituted with 1 to 3 substitutent(s) selected from "an aryl group, a carboxy group, an alkoxycarbonyl group having 2 to 7 carbon atoms, and an amino group unsubstituted or substituted with 1 or 2 alkyl group(s) having 1 to 6 carbon atom(s)";
R³ represents
an alkyl group having 1 to 6 carbon atom(s) unsubstituted or substituted with 1 to 3 group(s) selected from "a halogen atom, a cyano group, a carboxy group, an alkoxycarbonyl group having 2 to 7 carbon atoms, an aralkyloxy group having 7 to 12 carbon atoms, an alkanoyloxy group having 2 to 6 carbon atoms, a hydroxy group, a phthalimide group, an alkylsulfonylamino group having 1 to 6 carbon atom(s), a methanesulfonyloxy group, a toluenesulfonyloxy group, an aryl group unsubstituted or substituted with 1 to 5 group(s) selected from a halogen atom, an alkyl group having 1 to 6 carbon atom(s), an alkoxy group having 1 to 6 carbon atom(s), a cyano group, a nitro group, a hydroxy group, a cyclic alkyl group having 3 to 6 carbon atoms including 1 to 3 hetero atom(s) on a ring, and an amino group substituted with 1 or 2 alkyl group(s) having 1 to 6 atom(s), a heteroaryl group unsubstituted or substituted with 1 to 3 group(s) selected from Substituent Group 1, a group represented by the formula:

—CO—N(—(CH$_2$)$_l$—R$^{36}$)—(CH$_2$)$_m$—R$^{32}$ wherein l and m each independently represents an integer of 0 to 6, R$^{36}$ and R$^{32}$ each independently represents "a hydrogen atom, an amino group unsubstituted or substituted with 1 or 2 alkyl group(s) having 1 to 6 carbon atom(s), an aryl group, or a heteroaryl group", and a group represented by the formula:

—NR$^{41}$R$^{42}$ wherein R$^{41}$ and R$^{42}$ each independently represents a hydrogen atom, an alkyl group having 1 to 6 carbon atom(s), or R$^{41}$ and R$^{42}$ represent a cyclic structure represented by the formula which is formed together with the nitrogen atom to which each is bonded:

—(CH$_2$)$_s$—W—(CH$_2$)$_t$— wherein s and t each independently represents an integer of 1 to 3, W represents an oxygen atom, a group represented by the formula:

—CR$^{43}$R$^{44}$— wherein R$^{43}$ and R$^{44}$ each independently represents a hydrogen atom, a hydroxy group, an alkoxy group having 1 to 6 carbon atom(s), a carboxy group, or an alkoxycarbonyl group having 2 to 7 carbon atoms,
or a group represented by the formula:

—NR$^{45}$— wherein R$^{45}$ represents a hydrogen atom, an alkyl group having 1 to 6 carbon atom(s) unsubstituted or substituted with 1 to 3 substituent(s) selected from "an aryl group, a carboxy group, an alkoxycarbonyl group having 2 to 7 carbon atoms, and an amino group unsubstituted or substituted with 1 or 2 alkyl group(s) having 1 to 6 carbon atom(s)"",
an alkenyl group having 2 to 6 carbon atoms unsubstituted or substituted with 1 to 3 group(s) selected from "a halogen atom, an alkyl group having 1 to 6 carbon atom(s), an alkoxy group having 1 to 6 carbon atom(s), an alkoxycarbonyl group having 2 to 7 carbon atoms, a cyano group, a nitro group, a hydroxy group, an oxo group, and an amino group unsubstituted or substituted with 1 or 2 alkyl group(s) having 1 to 6 carbon atom(s)",
an aryl group unsubstituted or substituted with 1 to 5 group(s) selected from Substituent Group 1, or
a heteroaryl group unsubstituted or substituted with 1 to 3 group(s) selected from Substituent Group 1;
R⁴ represents
a hydrogen atom,
an alkyl group having 1 to 6 carbon atom(s) unsubstituted or substituted with 1 to 3 group(s) selected from Substituent Group 2, wherein Substituent Group 2 consists of a halogen atom, a cyclic alkyl group having 3 to 6 carbon atoms, a hydroxy group, a cyano group, an aminosulfonyl group, an aryl group unsubstituted or substituted with 1 to 5 optional substituent(s), and a heteroaryl group unsubstituted or substituted with 1 to 3 optional substituent(s),
an alkenyl group having 2 to 6 carbon atoms unsubstituted or substituted with 1 to 3 group(s) selected from Substituent Group 2,
an alkynyl group having 2 to 6 carbon atoms unsubstituted or substituted with 1 to 3 group(s) selected from Substituent Group 2, or
an alkanoyl group having 2 to 6 carbon atoms,
Z represents a group represented by the formula:

—CR⁵R⁶—, a group represented by the formula:

—C(=O)—, a group represented by the formula:

—C(=N—NH$_2$)—, a group represented by the formula:

—C(=N—OR$^{12}$)—, wherein R$^{12}$ is a hydrogen atom, an alkanoyl group having 2 to 6 carbon atoms unsubstituted or substituted with 1 to 3 group(s) selected from "a halogen atom, and an amino group unsubstituted or substituted with 1 or 2 alkyl group(s) having 1 to 6 carbon atom(s)", a vinylcarbonyl group, an alkyl group having 1 to 6 carbon atom(s), a cyclic alkyl group having 3 to 6 carbon atoms, an aryl group unsubstituted or substituted with 1 to 5 optional substituent(s), or an aralkyl group having 7 to 12 carbon atoms unsubstituted or substituted with 1 to 5 optional substituent(s), a group represented by the formula:

—NR$^{14}$—CH$_2$— wherein R$^{14}$ represents a hydrogen atom, an alkyl group having 1 to 6 carbon atom(s), an alkanoyl group having 2 to 6 carbon atoms, an alkylsulfonyl group having 1 to 6 carbon atom(s), or a benzyloxycarbonyl group, and the last dash binds to a carbon atom at 8-position of formula (I), or a group represented by the formula:

—CH$_2$—NR$^{14}$— wherein R$^{14}$ has the same meaning as defined above, and the last dash binds to a carbon atom at 8-position of formula (I), one of R$^5$ and R$^6$ is a hydrogen atom while the other one is a group represented by the formula:

—NR$^{13}$R$^{15}$ wherein R$^{13}$ and R$^{15}$ each independently represents a hydrogen atom, an alkyl group having 1 to 6 carbon atom(s), a cyclic alkyl group having 3 to 6 carbon atoms, an alkanoyl group having 2 to 6 carbon atoms, an alkylsulfonyl group having 1 to 6 carbon atom(s), an aryl group unsubstituted or substituted with 1 to 5 optional substituent(s), or an aralkyl group having 7 to 12 carbon atoms unsubstituted or substituted with 1 to 5 optional substituent(s), or R$^{13}$ and R$^{15}$ represent a 5- or 6-membered heterocyclic ring formed together with the nitrogen atom to which each is bonded, or a group represented by the formula:

—OR$^{12}$ wherein R$^{12}$ has the same meaning as defined above;

R$^7$ represents a hydrogen atom with the proviso that the double line including the dashed line is limited to represent a double bond, a hydroxy group, or a group represented by the formula:

—OR$^{22}$ wherein R$^{22}$ represents "an alkyl group having 1 to 6 carbon atom(s), an alkenyl group having 2 to 6 carbon atoms, an alkynyl group having 2 to 6 carbon atoms, or an alkanoyl group having 2 to 6 carbon atoms" unsubstituted or substituted with 1 to 3 group(s) selected from "a halogen atom, an oxo group, an alkyl group having 1 to 6 carbon atom(s), an alkenyl group having 2 to 6 carbon atoms, an alkynyl group having 2 to 6 carbon atoms, a cyano group, an amino group unsubstituted or substituted with 1 or 2 alkyl group(s) having 1 to 6 carbon atom(s), a hydroxy group, a nitro group, a carboxy group, a alkoxy group having 1 to 6 carbon atom(s), an aryl group, and a heteroaryl group";

R$^8$ represents a hydrogen atom or a hydroxy group,

R$^7$ and R$^8$ may represent a cyclic structure represented by formula (II) which is formed together with carbon atoms to which each is bonded:

(II)

wherein R$^{35}$ represents a hydrogen atom, an alkyl group having 1 to 6 carbon atom(s), an aryl group, a heteroaryl group, an alkyl group having 1 to 6 carbon atom(s) substituted with 1 to 3 aryl group(s) or heteroaryl group(s), an alkyl group having 1 to 6 carbon atom(s) substituted with 1 to 3 heteroaryl group(s) substituted with 1 to 3 heteroaryl group(s), an alkoxy group having 1 to 6 carbon atom(s), an alkoxy group having 1 to 6 carbon atom(s) substituted with 1 to 3 aryl group(s) or heteroaryl group(s), an amino group substituted with 1 or 2 alkyl group(s) having 1 to 6 carbon atom(s), or an amino group substituted with 1 or 2 alkyl group(s) having 1 to 6 carbon atom(s) substituted with 1 to 3 aryl group(s) or heteroaryl group(s), or a cyclic structure represented by formula (III) which is formed together with carbon atoms to which each is bonded:

(III)

or R$^7$, R$^8$ and the above-mentioned Z may together represent a cyclic structure represented by formula (IV):

(IV)

R$^9$ represents a hydrogen atom;

R$^{10}$ represents a hydroxy group, a group represented by the formula:

—OR$^{23}$ wherein R$^{23}$ represents an aryl group unsubstituted or substituted with 1 to 5 optional substituent(s), or a heteroaryl group unsubstituted or substituted with 1 to 3 optional substituent(s), a group represented by the formula:

—OCO—R$^{24}$ wherein R$^{24}$ represents a cyclic alkyl group having 3 to 6 carbon atoms unsubstituted or substituted with 1 to 5 optional substituent(s), which may include 1 to 3 hetero atom(s) on a ring, or a group represented by the formula:

—(CH$_2$)$_j$-D-(CH$_2$)$_k$—R$^{25}$ wherein D represents a bond, a hetero atom, or a group represented by the formula:

—NHCO$_2$—

R$^{25}$ represents a hydrogen atom, an aryl group unsubstituted or substituted with 1 to 5 optional substituent(s), a heteroaryl group unsubstituted or substituted with 1 to 3 optional substituent(s), a cyclic alkyl group having 3 to 6 carbon atoms which may include 1 to 3 hetero atom(s) on a ring and be substituted with 1 to 5 optional group(s), a group represented by the formula:

—NR$^{37}$R$^{38}$ wherein $R^{37}$ and $R^{38}$ each independently represents a hydrogen atom, an amino group unsubstituted or substituted with 1 or 2 alkyl group(s) having 1 to 6 carbon atom(s), or "an alkyl group having 1 to 6 carbon atom(s), aryl group, or heteroaryl group" unsubstituted or substituted with 1 to 3 group(s) selected from "a halogen atom, an amino group unsubstituted or substituted with 1 or 2 alkyl group(s) having 1 to 6 carbon atom(s), a cyclic alkyl group having 3 to 6 carbon atoms including 1 to 3 hetero atom(s) on a ring, a hydroxy group, an alkyl group having 1 to 6 carbon atom(s), an alkoxy group having 1 to 6 carbon atom(s), and a nitro group",
a group represented by the formula:

—NHCOR$^{37}$ wherein $R^{37}$ has the same meaning as defined above, a group represented by the formula:

—NHSO$_2$R$^{37}$ wherein $R^{37}$ has the same meaning as defined above, or a group represented by the formula:

—NHCONHR$^{37}$ wherein $R^{37}$ has the same meaning as defined above, and j and k each independently represents an integer of 0 to 6,
a group represented by the formula:

—OCO$_2$R$^{24}$ wherein $R^{24}$ has the same meaning as defined above, a group represented by the formula:

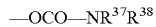
—OCO—NR$^{37}$R$^{38}$ wherein $R^{37}$ and $R^{38}$ have the same meanings as defined above, or a group represented by formula (V):

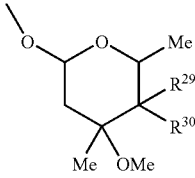

(V)

wherein $R^{29}$ represents a hydrogen atom, $R^{30}$ represents a hydroxy group, an alkoxy group having 1 to 6 carbon atom(s), an alkanoyloxy group having 2 to 6 carbon atoms, an alkanoyloxy group having 2 to 6 carbon atoms substituted with 1 to 3 amino group(s) unsubstituted or substituted with 1 or 2 alkyl group(s) having 1 to 6 carbon atom(s), a cyanomethyloxy group, an aralkyloxy group having 7 to 12 carbon atom(s), an alkoxy group having 1 to 6 carbon atom(s) substituted with 1 to 3 heteroaryl group(s), or a carbamoyloxy group, or $R^{29}$ and $R^{30}$ may together form an oxo group,
$R^9$ and $R^{10}$ may together form an oxo group;
A represents an oxygen atom, or a group represented by the formula:

—NMe-, with the proviso that the following are excluded: a compound in which $R^3$ is a benzyl group or an allyl group and A is an oxygen atom; a compound in which $R^3$ is a methyl group, $R^4$ and $R^9$ are a hydrogen atom, Z is a group represented by the formula —C(=O)—, $R^7$ and $R^8$ are a hydroxy group, $R^{10}$ is a group represented by formula (V), and A is a group represented by the formula —NMe-; a compound in which $R^1$ is a methyl group, $R^2$ is a 2-hydroxyethyl group, $R^3$ is a methyl group, $R^4$ is a hydrogen atom, Z is a group represented by the formula —NMe-CH$_2$—, $R^7$ and $R^8$ are a hydroxy group, $R^9$ is a hydrogen atom, $R^{10}$ is a hydroxy group, and A is a group represented by the formula —NMe-; a compound in which $R^1$ is a methyl group, $R^2$ is a 2-hydroxyethyl group, $R^3$ is a methyl group, $R^4$ is a hydrogen atom, Z is a group represented by the formula —NMe-CH$_2$—, $R^7$ and $R^8$ are a hydroxy group, $R^9$ is a hydrogen atom, $R^{10}$ is a group represented by formula (V), $R^{29}$ is a hydrogen atom, $R^{30}$ is a hydroxy group, and A is a group represented by the formula —NMe-; a compound in which $R^1$ and $R^2$ are a methyl group, $R^3$ is a methyl group, $R^4$ is a hydrogen atom, Z is a group represented by the formula —C(=O)—, $R^7$ and $R^8$ are a hydroxy group, $R^9$ is a hydrogen atom, $R^{10}$ is a group represented by formula (V), $R^{29}$ is a hydrogen atom, $R^{30}$ is a methoxy group, and A is an oxygen atom; and a compound in which $R^1$ and $R^2$ are a methyl group, $R^3$ is an aminophenyl group, $R^4$ is a hydrogen atom, Z is a group represented by the formula —C(=O)—, $R^7$ and $R^8$ are a hydroxy group, $R^9$ is a hydrogen atom, $R^{10}$ is a group represented by formula (V), $R^{29}$ is a hydrogen atom, $R^{30}$ is a methoxy group, and A is an oxygen atom.

2. The compound or the pharmaceutically acceptable salt thereof according to claim 1, wherein,
the double line including the dashed line is a single bond, $R^4$ represents
a hydrogen atom,
an alkyl group having 1 to 6 carbon atom(s) unsubstituted or substituted with 1 to 3 group(s) selected from Substituent Group 2, wherein Substituent Group 2 consists of a halogen atom, a cyclic alkyl group having 3 to 6 carbon atoms, a hydroxy group, a cyano group, an aminosulfonyl group, and "an aryl group or a heteroaryl group" unsubstituted or substituted with 1 to 3 group(s) selected from "a halogen atom, an amino group unsubstituted or substituted with 1 or 2 alkyl group(s) having 1 to 6 carbon atom(s), a cyclic alkyl group having 3 to 6 carbon atom(s) including 1 to 3 hetero atom(s) on a ring, a hydroxy group, an alkyl group having 1 to 6 carbon atom(s), an alkoxy group having 1 to 6 carbon atom(s), an aryl group, a heteroaryl group, and a nitro group",
an alkenyl group having 2 to 6 carbon atoms unsubstituted or substituted with 1 to 3 group(s) selected from Substituent Group 2,
an alkynyl group having 2 to 6 carbon atoms unsubstituted or substituted with 1 to 3 group(s) selected from Substituent Group 2, or
an alkanoyl group having 2 to 6 carbon atoms;
$R^{12}$ is a hydrogen atom, an alkanoyl group having 2 to 6 carbon atoms unsubstituted or substituted with 1 to 3 group(s) selected from "a halogen atom, and an amino group unsubstituted or substituted with 1 or 2 alkyl group(s) having 1 to 6 carbon atom(s)", a vinylcarbonyl group, an alkyl group having 1 to 6 carbon atom(s), a cyclic alkyl group having 3 to 6 carbon atoms, or "an aryl group, or an aralkyl group having 7 to 12 carbon atoms" unsubstituted or substituted with 1 to 5 group(s) selected from "a halogen atom, an amino group unsubstituted or substituted with 1 or 2 alkyl group(s) having 1 to 6 carbon atom(s), a cyclic alkyl group having 3 to 6 carbon atoms including 1 to 3 hetero atom(s) on a ring, a hydroxy group, an alkyl group having 1 to 6 carbon atom(s), an alkoxy group having 1 to 6 carbon atom(s), and a nitro group";

$R^{13}$ and $R^{15}$ each independently represents a hydrogen atom, an alkyl group having 1 to 6 carbon atom(s), a cyclic alkyl group having 3 to 6 carbon atoms, an alkanoyl group having 2 to 6 carbon atoms, an alkylsulfonyl group having 1 to 6 carbon atom(s), or "an aryl group, or an aralkyl group having 7 to 12 carbon atom(s)" unsubstituted or substituted with 1 to 5 group(s) selected from "a halogen atom, an amino group unsubstituted or substituted with 1 or 2 alkyl group(s) having 1 to 6 carbon atom(s), a cyclic alkyl group having 3 to 6 carbon atoms including 1 to 3 hetero atom(s) on a ring, a hydroxy group, an alkyl group having 1 to 6 carbon atom(s), an alkoxy group having 1 to 6 carbon atom(s), and a nitro group", or $R^{13}$ and $R^{15}$ represent a 5- or 6-membered heterocyclic ring formed together with the nitrogen atom to which each is bonded;

$R^{23}$ is "an aryl group or a heteroaryl group" unsubstituted or substituted with 1 to 3 group(s) selected from "a halogen atom, an amino group unsubstituted or substituted with 1 or 2 alkyl group(s) having 1 to 6 carbon atom(s), a cyclic alkyl group having 3 to 6 carbon atoms including 1 to 3 hetero atom(s) on a ring, a hydroxy group, an alkyl group having 1 to 6 carbon atom(s), an alkoxy group having 1 to 6 carbon atom(s), and a nitro group";

$R^{24}$ represents a cyclic alkyl group having 3 to 6 carbon atoms unsubstituted or substituted with 1 to 5 group(s) selected from "a halogen atom, an amino group unsubstituted or substituted with 1 or 2 alkyl group(s) having 1 to 6 carbon atom(s), a cyclic alkyl group having 3 to 6 carbon atoms including 1 to 3 hetero atom(s) on a ring, a hydroxy group, an alkyl group having 1 to 6 carbon atom(s), an alkoxy group having 1 to 6 carbon atom(s), and a nitro group", which may include 1 to 3 hetero atom(s) on a ring, or a group represented by the formula:

—$(CH_2)_j$-D-$(CH_2)_k$—$R^{25}$ wherein D represents a bond, a hetero atom, or a group represented by the formula:

—$NHCO_2$—

$R^{25}$ represents a hydrogen atom, "an aryl group, a heteroaryl group, or a cyclic alkyl group having 3 to 6 carbon atoms which may include 1 to 3 hetero atom(s) on a ring" unsubstituted or substituted with 1 to 3 group(s) selected from "a halogen atom, an amino group unsubstituted or substituted with 1 or 2 alkyl group(s) having 1 to 6 carbon atom(s), a cyclic alkyl group having 3 to 6 carbon atoms including 1 to 3 hetero atom(s) on a ring, a hydroxy group, an alkyl group having 1 to 6 carbon atom(s), an alkoxy group having 1 to 6 carbon atom(s), and a nitro group", a group represented by the formula:

—$NR^{37}R^{38}$ wherein $R^{37}$ and $R^{38}$ each independently represents a hydrogen atom, an amino group unsubstituted or substituted with 1 or 2 alkyl group(s) having 1 to 6 carbon atom(s), or "an alkyl group having 1 to 6 carbon atom(s), an aryl group, or a heteroaryl group" unsubstituted or substituted with 1 to 3 group(s) selected from "a halogen atom, an amino group unsubstituted or substituted with 1 or 2 alkyl group(s) having 1 to 6 carbon atom(s), a cyclic alkyl group having 3 to 6 carbon atoms including 1 to 3 hetero atom(s) on a ring, a hydroxy group, an alkyl group having 1 to 6 carbon atom(s), an alkoxy group having 1 to 6 carbon atom(s), and a nitro group", a group represented by the formula:

—$NHCOR^{37}$ wherein $R^{37}$ has the same meaning as defined above, a group represented by the formula:

—$NHSO_2R^{37}$ wherein $R^{37}$ has the same meaning as defined above, or a group represented by the formula:

—$NHCONHR^{37}$ wherein $R^{37}$ has the same meaning as defined above, j and k each independently represents an integer of 0 to 6.

3. The compound or the pharmaceutically acceptable salt thereof according to claim 1, wherein A is a group represented by the formula:

—NMe-.

4. The compound or the pharmaceutically acceptable salt thereof according to claim 3, wherein $R^3$ is an alkyl group having 1 to 6 carbon atom(s) substituted with an amino group unsubstituted or substituted with 1 or 2 alkyl group(s) having 1 to 6 carbon atom(s), or an alkyl group having 1 to 6 carbon atom(s).

5. The compound or the pharmaceutically acceptable salt thereof according to claim 3, wherein $R^3$ is a methyl group.

6. The compound or the pharmaceutically acceptable salt thereof according to claim 3, wherein $R^1$ and $R^2$ each independently represents a hydrogen atom, an alkyl group having 1 to 6 carbon atom(s) unsubstituted or substituted with 1 to 3 substituent(s) selected from "an aryl group unsubstituted or substituted with 1 to 5 substituent(s) selected from Substituent Group 1, a heteroaryl group unsubstituted or substituted with 1 to 3 substituent(s) selected from Substituent Group 1, a carboxy group, and an alkoxycarbonyl group having 2 to 7 carbon atoms", an alkyl group having 2 to 6 carbon atoms substituted with 1 to 5 group(s) selected from "an amino group unsubstituted or substituted with 1 or 2 alkyl group(s) having 1 to 6 carbon atom(s), a phthalimide group, an alkoxy group having 1 to 6 carbon atom(s), a morpholino group, an aralkyloxy group having 7 to 12 carbon atoms, an alkanoyloxy group having 2 to 6 carbon atoms, a hydroxy group, and a group represented by the formula:

—$NHCO_2$—$(CH_2)_n$—$R^{31}$ wherein n and $R^{31}$ have the same meanings as defined above", an alkanoyl group having 2 to 6 carbon atoms, or an alkylsulfonyl group having 1 to 6 carbon atom(s) or $R^1$ and $R^2$ represent a cyclic structure represented by the formula which is formed together with the nitrogen atom to which each is bonded:

$(CH_2)_p$—Y—$(CH_2)_q$— wherein p, q and Y have the same meanings as defined above.

7. The compound or the pharmaceutically acceptable salt thereof according to claim 3, wherein
$R^1$ represents an alkyl group having 1 to 6 carbon atom(s), $R^2$ represents
a hydrogen atom,
an alkyl group having 1 to 6 carbon atom(s) substituted with a substituent selected from "a phenyl group unsubstituted or substituted with a morpholino group, a pyridyl group, and a carboxy group", or
an alkyl group having 2 to 6 carbon atoms substituted with a group selected from "an amino group unsubstituted or substituted with 1 or 2 alkyl group(s) having 1 to 6 carbon atom(s), and a hydroxy group" or
$R^1$ and $R^2$ represent a cyclic structure represented by the formula which is formed together with the nitrogen atom to which each is bonded:

—$(CH_2)_p$—Y—$(CH_2)_q$— wherein p, q and Y have the same meanings as defined above.

8. The compound or the pharmaceutically acceptable salt thereof according to claim 1, wherein
$R^3$ is an alkyl group having 1 to 6 carbon atom(s), with the proviso that a t-butyl group is excluded and
A is an oxygen atom.

9. The compound or the pharmaceutically acceptable salt thereof according to claim 1, wherein
$R^3$ is a methyl group and
A is an oxygen atom.

10. The compound or the pharmaceutically acceptable salt thereof according to claim 1, wherein
$R^3$ is
an alkyl group having 1 to 6 carbon atom(s) substituted with 1 to 3 group(s) selected from "a halogen atom, a cyano group, a carboxy group, an alkoxycarbonyl group having 2 to 7 carbon atoms, an aralkyloxy group having 7 to 12 carbon atoms, an alkanoyloxy group having 2 to 6 carbon atoms, a hydroxy group, a phthalimide group, an alkylsulfonylamino group having 1 to 6 carbon atom(s), a methanesulfonyloxy group, a toluenesulfonyloxy group, an aryl group unsubstituted or substituted with 1 to 5 group(s) selected from Substituent Group 1, a heteroaryl group unsubstituted or substituted with 1 to 3 group(s) selected from Substituent Group 1, a group represented by the formula:

—CO—N(—$(CH_2)_l$—$R^{36}$)—$(CH_2)_m$—$R^{32}$ wherein l, m, $R^{36}$ and $R^{32}$ have the same meanings as defined above, and a group represented by the formula:

—$NR^{41}R^{42}$ wherein $R^{41}$ and $R^{42}$ have the same meanings as defined above", or
an alkenyl group having 2 to 6 carbon atoms substituted with 1 to 3 group(s) selected from "a halogen atom, an alkyl group having 1 to 6 carbon atom(s), an alkoxy group having 1 to 6 carbon atom(s), an alkoxycarbonyl group having 2 to 7 carbon atoms, a cyano group, a nitro group, a hydroxy group, an oxo group, an amino group unsubstituted or substituted with 1 or 2 alkyl group(s) having 1 to 6 carbon atom(s)", and
A is an oxygen atom.

11. The compound or the pharmaceutically acceptable salt thereof according to claim 1, wherein
$R^3$ is
an alkyl group having 1 to 6 carbon atom(s) substituted with a group selected from "a cyano group, a carboxy group, an alkoxycarbonyl group having 2 to 7 carbon atoms, an aralkyloxy group having 7 to 12 carbon atoms, an alkanoyloxy group having 2 to 6 carbon atoms, a hydroxy group, a phthalimide group, an alkylsulfonylamino group having 1 to 6 carbon atom(s), a phenyl group unsubstituted or substituted with a group selected from "an alkoxy group having 1 to 6 carbon atom(s), a nitro group, and an amino group unsubstituted or substituted with 1 or 2 alkyl group(s) having 1 to 6 carbon atom(s)", a pyridyl group, a group represented by the formula:

—CO—NH—$(CH_2)_2$—$NMe_2$ and a group represented by the formula:

—$NR^{41}R^{42}$ wherein $R^{41}$ and $R^{42}$ have the same meanings as defined above", or
an alkenyl group having 2 to 6 carbon atoms substituted with 1 or 2 group(s) selected from "an alkoxycarbonyl group having 2 to 7 carbon atoms, and an oxo group", and
A is an oxygen atom.

12. The compound or the pharmaceutically acceptable salt thereof according to claim 1, wherein
$R^3$ is
an alkyl group having 2 to 6 carbon atoms substituted with a group selected from "a cyano group, a carboxy group, an alkoxycarbonyl group having 2 to 7 carbon atoms, an alkanoyloxy group having 2 to 6 carbon atoms, a hydroxy group, a phthalimide group, an alkylsulfonylamino group having 1 to 6 carbon atom(s), a phenyl group unsubstituted or substituted with a group selected from "an alkoxy group having 1 to 6 carbon atom(s), a nitro group, and an amino group unsubstituted or substituted with 1 or 2 alkyl group(s) having 1 to 6 carbon atom(s)", a pyridyl group, a group represented by the formula:

—CO—NH—$(CH_2)_2$—$NMe_2$ and a group represented by the formula:

—$NR^{41}R^{42}$ wherein $R^{41}$ and $R^{42}$ have the same meanings as defined above", or
an alkenyl group having 2 to 6 carbon atoms substituted with 1 or 2 group(s) selected from "an alkoxycarbonyl group having 2 to 7 carbon atoms, and an oxo group", and
A is an oxygen atom.

13. The compound or the pharmaceutically acceptable salt thereof according to claim 8, wherein
$R^1$ and $R^2$ each independently represents
a hydrogen atom,
an alkyl group having 1 to 6 carbon atom(s) unsubstituted or substituted with 1 to 3 substituent(s) selected from "an aryl group unsubstituted or substituted with 1 to 5 substituent(s) selected from Substituent Group 1, an heteroaryl group unsubstituted or substituted with 1 to 3 substituent(s) selected from Substituent Group 1, a carboxy group, and an alkoxycarbonyl group having 2 to 7 carbon atoms" with the proviso that when $R^3$ is a methyl group, both $R^1$ and $R^2$ do not represent methyl groups, or an alkyl group having 2 to 6 carbon atoms substituted with 1 to 5 group(s) selected from "an amino group unsubstituted or substituted with 1 or 2 alkyl group(s) having 1 to 6 carbon atom(s), a phthalimide group, an alkoxy group having 1 to 6 carbon atom(s), a morpholino group, an aralkyloxy group having 7 to 12 carbon atoms, an alkanoyloxy group having 2 to 6 carbon atoms, a hydroxy group, and a group represented by the formula:

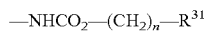
—NHCO$_2$—(CH$_2$)$_n$—R$^{31}$ wherein n and $R^{31}$ have the same meanings as defined above", or $R^1$ and $R^2$ are a cyclic structure represented by the formula which is formed together with the nitrogen atom to which each is bonded:

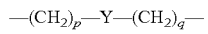
—(CH$_2$)$_p$—Y—(CH$_2$)$_q$— wherein p, q and Y have the same meanings as defined above.

14. The compound or the pharmaceutically acceptable salt thereof according to claim 8, wherein both $R^1$ and $R^2$ represent hydrogen atoms, or $R^1$ represents an alkyl group having 1 to 6 carbon atom(s), $R^2$ represents a hydrogen atom, an alkyl group having 1 to 6 carbon atom(s) unsubstituted or substituted with one "phenyl group substituted with an amino group unsubstituted or substituted with 1 or 2 alkyl group(s) having 1 to 6 carbon atom(s)" with the proviso that when $R^3$ is a methyl group, both $R^1$ and $R^2$ do not represent methyl groups, or an alkyl group having 2 to 6 carbon atoms substituted with 1 or 2 group(s) selected from "an amino group unsubstituted or substituted with 1 or 2 alkyl group(s) having 1 to 6 carbon atom(s), a phthalimide group, an alkoxy group having 1 to 6 carbon atom(s), a morpholino group, an aralkyloxy group having 7 to 12 carbon atoms, an alkanoyloxy group having 2 to 6 carbon atoms, and a hydroxy group", or $R^1$ and $R^2$ are a cyclic structure represented by the formula which is formed together with the nitrogen atom to which each is bonded:

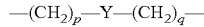
—(CH$_2$)$_p$—Y—(CH$_2$)$_q$— wherein p, q and Y have the same meanings as defined above.

15. The compound or the pharmaceutically acceptable salt thereof according to claim 8, wherein $R^1$ and $R^2$ is each a methyl group.

16. The compound or the pharmaceutically acceptable salt thereof according to claim 8, wherein $R^1$ and $R^2$ is each independently a hydrogen atom, or an alkyl group having 1 to 6 carbon atom(s).

17. The compound or the pharmaceutically acceptable salt thereof according to claim 10, wherein $R^1$ and $R^2$ each independently represents a hydrogen atom, an alkyl group having 1 to 6 carbon atom(s) unsubstituted or substituted with 1 to 3 substituent(s) selected from "an aryl group unsubstituted or substituted with 1 to 5 substituent(s) selected from Substituent Group 1, an heteroaryl group unsubstituted or substituted with 1 to 3 substituent(s) selected from Substituent Group 1, a carboxy group, and an alkoxycarbonyl group having 2 to 7 carbon atoms" with the proviso that when $R^3$ is a methyl group, both $R^1$ and $R^2$ do not represent methyl groups, or an alkyl group having 2 to 6 carbon atoms substituted with 1 to 5 group(s) selected from "an amino group unsubstituted or substituted with 1 or 2 alkyl group(s) having 1 to 6 carbon atom(s), a phthalimide group, an alkoxy group having 1 to 6 carbon atom(s), a morpholino group, an aralkyloxy group having 7 to 12 carbon atoms, an alkanoyloxy group having 2 to 6 carbon atoms, a hydroxy group, and a group represented by the formula:

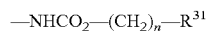
—NHCO$_2$—(CH$_2$)$_n$—R$^{31}$ wherein n and $R^{31}$ have the same meanings as defined above", or $R^1$ and $R^2$ are a cyclic structure represented by the formula which is formed together with the nitrogen atom to which each is bonded:

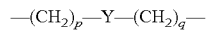
—(CH$_2$)$_p$—Y—(CH$_2$)$_q$— wherein p, q and Y have the same meanings as defined above.

18. The compound or the pharmaceutically acceptable salt thereof according to claim 10, wherein both $R^1$ and $R^2$ represent hydrogen atoms, or $R^1$ represents an alkyl group having 1 to 6 carbon atom(s), $R^2$ represents a hydrogen atom, an alkyl group having 1 to 6 carbon atom(s) unsubstituted or substituted with one "phenyl group substituted with an amino group unsubstituted or substituted with 1 or 2 alkyl group(s) having 1 to 6 carbon atom(s)" with the proviso that when $R^3$ is a methyl group, both $R^1$ and $R^2$ do not represent methyl groups, or an alkyl group having 2 to 6 carbon atoms substituted with 1 or 2 group(s) selected from "an amino group unsubstituted or substituted with 1 or 2 alkyl group(s) having 1 to 6 carbon atom(s), a phthalimide group, an alkoxy group having 1 to 6 carbon atom(s), a morpholino group, an aralkyloxy group having 7 to 12 carbon atoms, an alkanoyloxy group having 2 to 6 carbon atoms, and a hydroxy group", or $R^1$ and $R^2$ are a cyclic structure represented by the formula which is formed together with the nitrogen atom to which each is bonded:

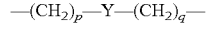
—(CH$_2$)$_p$—Y—(CH$_2$)$_q$— wherein p, q and Y have the same meanings as defined above.

19. The compound or the pharmaceutically acceptable salt thereof according to claim 10, wherein $R^1$ and $R^2$ is each a methyl group.

20. The compound or the pharmaceutically acceptable salt thereof according to claim 10, wherein $R^1$ and $R^2$ is each independently a hydrogen atom, or an alkyl group having 1 to 6 carbon atom(s).

21. The compound or the pharmaceutically acceptable salt thereof according to claim 1, wherein $R^4$ is a methyl group, Z is a group represented by the formula:

—C(=O)—, $R^7$ is a hydroxy group, $R^8$ is a hydrogen atom or a hydroxy group, and $R^9$ is a hydrogen atom.

22. The compound or the pharmaceutically acceptable salt thereof according to claim 1, wherein $R^4$ is a hydrogen atom, an alkyl group having 1 to 6 carbon atom(s), or an alkanoyl group having 2 to 6 carbon atoms, Z is a group represented by the formula:

—NR$^{14}$—CH$_2$—, $R^{14}$ is a hydrogen atom, an alkyl group having 1 to 6 carbon atom(s), or an alkanoyl group having 2 to 6 carbon atoms, $R^7$ is a hydroxy group or an alkanoyloxy group having 2 to 6 carbon atoms, $R^8$ is a hydroxy group, and $R^9$ is a hydrogen atom.

23. The compound or the pharmaceutically acceptable salt thereof according to claim 1, wherein $R^4$ is a hydrogen atom, a methyl group, or an acetyl group, Z is a group represented by the formula:

—NR$^{14}$—CH$_2$—, $R^{14}$ is a hydrogen atom, a methyl group, or an acetyl group, $R^7$ is a hydroxy group, or an acetyloxy group, $R^8$ is a hydroxy group, and $R^9$ is a hydrogen atom.

24. The compound or the pharmaceutically acceptable salt thereof according to claim 1, wherein $R^4$ is a methyl group, Z is a group represented by the formula:

—C(=O)—, $R^7$ and $R^8$ are a cyclic structure represented by formula (II) which is formed together with carbon atoms to which each is bonded, $R^{35}$ is a hydrogen atom, an alkyl group having 1 to 6 carbon atom(s) substituted with 1 to 3 "aryl group(s) or heteroaryl group(s)", or an alkyl group having 1 to 6 carbon atom(s) substituted with 1 to 3 heteroaryl group(s) substituted with 1 to 3 heteroaryl group(s), and $R^9$ is a hydrogen atom.

25. The compound or the pharmaceutically acceptable salt thereof according to claim 1, wherein $R^4$ is a methyl group, Z is a group represented by the formula:

—C(=O)—, $R^7$ and $R^8$ are a cyclic structure represented by formula (II) which is formed together with carbon atoms to which each is bonded, $R^{35}$ is a hydrogen atom, or a 4-(4-(pyridin-3-yl)imidazolyl)butyl group, and $R^9$ is a hydrogen atom.

26. The compound or the pharmaceutically acceptable salt thereof according to claim 1, wherein $R^4$ is a methyl group, Z is a group represented by the formula:

—CR$^5$R$^6$— or a group represented by the formula:

—C(=N—OH)—, one of $R^5$ and $R^6$ is a hydrogen atom while the other one is a group represented by the formula:

—NR$^{13}$R$^{15}$ wherein $R^{13}$ and $R^{15}$ each independently represents a hydrogen atom, an alkyl group having 1 to 6 carbon atom(s), an alkanoyl group having 2 to 6 carbon atoms, or an alkylsulfonyl group having 1 to 6 carbon atom(s), or a group represented by the formula:

—OR$^{12}$ wherein $R^{12}$ is a hydrogen atom, or an alkanoyl group having 2 to 6 carbon atoms unsubstituted or substituted with an amino group unsubstituted or substituted with 1 or 2 alkyl group(s) having 1 to 6 carbon atom(s), $R^7$ is a hydroxy group or a group represented by the formula:

—OR$^{22}$ wherein $R^{22}$ is "an alkyl group having 1 to 6 carbon atom(s) or an alkanoyl group having 2 to 6 carbon atoms" unsubstituted or substituted with an amino group unsubstituted or substituted with 1 or 2 alkyl group(s) having 1 to 6 carbon atom(s), $R^8$ is a hydroxy group, and $R^9$ is a hydrogen atom.

27. The compound or the pharmaceutically acceptable salt thereof according to claim 1, wherein $R^4$ is a methyl group, Z is a group represented by the formula:

—CR$^5$R$^6$— or a group represented by the formula:

—C(=N—OH)—, one of $R^5$ and $R^6$ is a hydrogen atom while the other one is a group represented by the formula:

—NR$^{13}$R$^{15}$ wherein $R^{13}$ and $R^{15}$ each independently represents a hydrogen atom, a methyl group, an acetyl group, or a methanesulfonyl group, or a group represented by the formula:

—OR$^{12}$ wherein $R^{12}$ is a hydrogen atom, or an alkanoyl group having 2 to 6 carbon atoms substituted with an amino group unsubstituted or substituted with 1 or 2 alkyl group(s) having 1 to 6 carbon atom(s), $R^7$ is a hydroxy group, or a group represented by the formula:

—OR$^{22}$ wherein $R^{22}$ is an alkanoyl group having 2 to 6 carbon atoms substituted with an amino group unsubstituted or substituted with 1 or 2 alkyl group(s) having 1 to 6 carbon atom(s), $R^8$ is a hydroxy group, and $R^9$ is a hydrogen atom.

28. The compound or the pharmaceutically acceptable salt thereof according to claim 1, wherein $R^{10}$ is a group represented by formula (V), $R^{29}$ is a hydrogen atom, and $R^{30}$ is a hydroxy group or an alkanoyloxy group having 2 to 6 carbon atoms.

29. The compound or the pharmaceutically acceptable salt thereof according to claim 1, wherein
R$^{10}$ is a group represented by the formula:

—OCO—R$^{24}$ wherein R$^{24}$ is a group represented by the formula:

—(CH$_2$)$_j$-D-(CH$_2$)$_k$—R$^{25}$ wherein D represents a bond, or a group represented by the formula:

—NHCO$_2$—,

R$^{25}$ represents a hydrogen atom, "a phenyl group or a pyridyl group" unsubstituted or substituted with 1 to 3 group(s) selected from "a halogen atom, an amino group unsubstituted or substituted with 1 or 2 alkyl group(s) having 1 to 6 carbon atom(s), a cyclic alkyl group having 3 to 6 carbon atoms including 1 to 3 hetero atom(s) on a ring, a hydroxy group, an alkyl group having 1 to 6 carbon atom(s), an alkoxy group having 1 to 6 carbon atom(s), and a nitro group", a group represented by the formula:

—NR$^{37}$R$^{38}$ wherein R$^{37}$ and R$^{38}$ have the same meanings as defined above, a group represented by the formula:

—NHCOR$^{37}$ wherein R$^{37}$ has the same meaning as defined above, a group represented by the formula:

—NHSO$_2$R$^{37}$ wherein R$^{37}$ has the same meaning as defined above, or a group represented by the formula:

—NHCONHR$^{37}$ wherein R$^{37}$ has the same meaning as defined above, j and k each independently represents an integer of 0 to 2.

30. The compound or the pharmaceutically acceptable salt thereof according to claim 1, wherein
R$^{10}$ is a group represented by the formula:

—OCO—R$^{24}$ wherein R$^{24}$ is a group represented by the formula:

—(CH$_2$)$_j$-D-(CH$_2$)$_k$—R$^{25}$ wherein D represents a bond, or a group represented by the formula:

—NHCO$_2$—,

R$^{25}$ is a hydrogen atom, a phenyl group unsubstituted or substituted with an alkoxy group having 1 to 6 carbon atom(s), a pyridyl group, or a group represented by the formula:

—NR$^{37}$R$^{38}$ wherein R$^{37}$ and R$^{38}$ each independently represents a hydrogen atom, or an alkyl group having 1 to 6 carbon atom(s), j and k each independently represents an integer of 0 to 2.

31. A compound represented by formula (VI) or a pharmaceutically acceptable salt thereof:

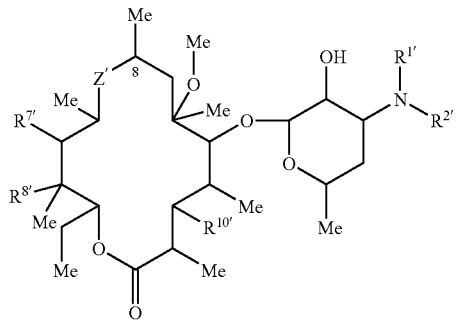

(VI)

wherein
R$^{1'}$ represents a methyl group;
R$^{2'}$ represents
a methyl group substituted with a substituent selected from "a phenyl group unsubstituted or substituted with a substituent selected from "a halogen atom, a methoxy group, a hydroxy group, and a dimethylamino group", and a pyridyl group,"
an ethyl group substituted with a group selected from "an amino group, a dimethylamino group, a phthalimide group, and a benzyloxycarbonylamino group",
a 2-amino-3,4-dioxocyclobut-1-enyl group, or
a phenyl group substituted with a group selected from "a nitro group, an amino group, and a dimethylamino group" or
R$^{1'}$ and R$^{2'}$ may identically represent a pyridylmethyl group or a dimethylaminophenylmethyl group;
Z' represents a group represented by the formula:
—C(=O)—;
R$^{7'}$ is a hydroxy group;
R$^{8'}$ is a hydrogen atom or a hydroxy group,
R$^{7'}$ and R$^{8'}$ may represent a cyclic structure represented by formula (VII) which is formed together with carbon atoms to which each is bonded:

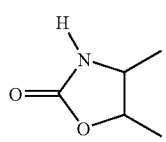

(VII)

or R$^{7'}$, R$^{8'}$, and the above-mentioned Z' may together represent a cyclic structure represented by formula (IV),

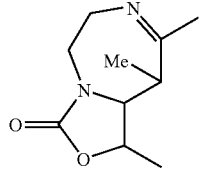

(IV)

R$^{10'}$ represents a hydroxy group, a methoxybenzylcarbonyloxy group, or a group represented by formula (VIII):

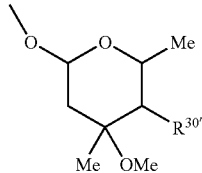

(VIII)

wherein R$^{30'}$ represents a hydroxy group or an acetyloxy group.

* * * * *